US006706738B2

(12) United States Patent
Clark et al.

(10) Patent No.: US 6,706,738 B2
(45) Date of Patent: Mar. 16, 2004

(54) SUBSTITUTED BICYCLIC HETEROARYL COMPOUNDS AND THEIR USE AS INTEGRIN ANTAGONISTS

(75) Inventors: David Edward Clark, Brentwood (GB); Paul Robert Eastwood, Romford (GB); Neil Victor Harris, Tilbury (GB); Clive McCarthy, West Malling (GB); Andrew David Morley, Macclesfield (GB); Stephen Dennis Pickett, Brentwood (GB)

(73) Assignee: Aventis Pharma Limited, Kent (GB)

( * ) Notice: Subject to any disclaimer, the term of this patent is extended or adjusted under 35 U.S.C. 154(b) by 243 days.

(21) Appl. No.: 09/975,721

(22) Filed: Oct. 11, 2001

(65) Prior Publication Data

US 2002/0173506 A1 Nov. 21, 2002

Related U.S. Application Data

(63) Continuation of application No. PCT/GB00/01393, filed on Apr. 12, 2000.
(60) Provisional application No. 60/141,470, filed on Jun. 29, 1999.

(30) Foreign Application Priority Data

Apr. 12, 1999 (GB) .............................................. 9908355

(51) Int. Cl.[7] ..................... A61K 31/443; C07D 413/12
(52) U.S. Cl. ..................... 514/340; 514/339; 546/271.7
(58) Field of Search ................... 546/271.7, 273.4; 514/340, 341

(56) References Cited

U.S. PATENT DOCUMENTS

2002/0137782 A1 * 9/2002 Clark et al. ................. 514/375

FOREIGN PATENT DOCUMENTS

| WO | WO 97/08145 | 3/1997 |
| WO | WO 99/52896 | 10/1999 |

* cited by examiner

Primary Examiner—Alan L. Rotman
Assistant Examiner—Janet L Coppins
(74) Attorney, Agent, or Firm—Ronald G. Ort

(57) ABSTRACT

The invention is directed to physiologically active compounds of general formula (I):

$$R^1Z^1\text{—Het—}L^1\text{—Ar}^1\text{—}L^2\text{—Y} \qquad (I)$$

wherein Het is an optionally substituted, saturated, partially saturated or fully unsaturated 8 to 10 membered bicyclic ring containing at least one heteroatom selected from O, S or N; $R^1$ is optionally substituted aryl, heteroaryl, alkyl, alkenyl, alkynyl, cycloalkyl or heterocycloalkyl; $Z^1$ represents a direct bond, an alkylene chain, $NR^4$, O or $S(O)_n$; $L^1$ is an a —$R^5$—$R^6$— linkage where $R^5$ is alkylene, alkenylene or alkynylene and $R^6$ is a direct bond, cycloalkylene, heterocycloalkylene, arylene, heteroaryldiyl, —C(=$Z^3$)—$NR^4$—, —$NR^4$—C(=$Z^3$)—, —$Z^3$—, —C(=O)—, —C(=$NOR^4$)—, —$NR^4$—, —$NR^4$—C(=$Z^3$)—$NR^4$—, —$SO_2$—$NR^4$—, —$NR^4$—$SO_2$—, —O—C(=O)—, —C(=O)—O—, —$NR^4$—C(=O)—O— or —O—C(=O)—$NR^4$—; $L^2$ is a direct bond; an optionally substituted alkylene, alkenylene, alkynylene, cycloalkenylene, cycloalkylene, heteroaryldiyl, heterocycloalkylene or arylene linkage; a —[C(=O)—N($R^9$)—C($R^4$)($R^{10}$)]$_p$— linkage; a —$Z^4$—$R^{11}$— linkage; a —C(=O)—$CH_2$—C(=O)— linkage; a —$R^{11}$—$Z^4$—$R^{11}$— linkage; or a —$L^3$—$L^4$—$L^5$— linkage; and Y is carboxy or an acid bioisostere; and the corresponding N-oxides, and their prodrugs; and pharmaceutically acceptable salts and solvates (e.g. hydrates) of such compounds and their N-oxides and prodrugs. Such compounds have valuable pharmaceutical properties, in particular the ability to regulate the interaction of VCAM-1 and fibronectin with the integrin VLA-4 (α4β1).

19 Claims, No Drawings

SUBSTITUTED BICYCLIC HETEROARYL COMPOUNDS AND THEIR USE AS INTEGRIN ANTAGONISTS

This application is a continuation of PCT/GB00/01393, filed Apr. 12, 2000, which claims priority from GB Application No. 9908355.2, filed Apr. 12, 1999, and U.S. Provisional Application No. 60/141,470, filed Jun. 29, 1999.

This invention is directed to substituted bicyclic compounds, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, VCAM-1 and vitronectin) and their integrin receptors [e.g. α5β1 (VLA-5), α4β1 (VLA-4) and αVβ3]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called α and β. There are at least fifteen different α-subunits (α1–α9, α-L, α-M, α-X, α-IIb, α-V and α-E) and at least least seven different β (β1–β7) subunits. The integrin family can be subdivided into classes based on the β subunits, which can be associated with one or more α-subunits. The most widely distributed integrins belong to the β1 class, also known as the very late antigens (VLA). The second class of integrins are leukocyte specific receptors and consist of one of three α-subunits (α-L, α-M or α-X) complexed with the β2 protein. The cytoadhesins α-IIbβ3 and α-Vβ3, constitute the third class of integrins.

The present invention principally relates to agents which modulate the interaction of the ligand VCAM-1 with its integrin receptor α4β1 (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin α4β1 mediates both cell-cell and cell-matrix interactions. Cells expressing α4β1 bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-γ, TNF-α, IL-1β and IL-4.

Regulation of α4β1 mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which α4β1 binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-α4 specific monoclonal antibodies significantly inhibited (50–60% reduction in the ear swelling response) the efferent response (P. L. Chisholm et al. J.Immunol., 1993, 23, pages 682–688). In a sheep model of allergic bronchoconstriction, HP1/2, an anti-α4 monoclonal antibody given intravenously or by aerosol, blocked the late response and the development of airway hyperresponsiveness (W. M. Abraham et al. J. Clin. Invest., 1994, 93 pages 776–787).

We have now found a novel group of substituted bicyclic compounds which have valuable pharmaceutical properties, in particular the ability to regulate the interaction of VCAM-1 and fibronectin with the integrin VLA-4 (α4β1).

Thus, in one aspect, the present invention is directed to compounds of general formula (I):

$$R^1Z^1\text{—Het—}L^1\text{—Ar}^1\text{—}L^2\text{—Y} \qquad (I)$$

wherein:

Het: represents a saturated, partially saturated or fully unsaturated 8 to 10 membered bicyclic ring system containing at least one heteroatom selected from O, S or N, optionally substituted by one or more aryl group substituents;

$R^1$ represents aryl, heteroaryl, optionally substituted alkyl, alkenyl or alkynyl where each is optionally substituted by $R^2$, $-Z^2R^3$, $-Z^3H$, $-C(=O)-R^3$, $-NR^4-C(=Z^3)-R^3$, $-NR^4-C(=O)-OR^3$, $-NR^4-SO_2-R^3$, $-SO_2-NY^1Y^2$, $-NY^1Y^2$ or $-C(=Z^3)-NY^1Y^2$, or optionally substituted cycloalkyl or heterocycloalkyl; where each is optionally substituted by $R^3$, $-Z^2R^3$, $-Z^3H$, $-C(=O)-R^3$, $-NR^4-C(=Z^3)-R^3$, $-NR^4-C(=O)-OR^3$, $-NR^4-SO_2-R^3$, $-SO_2-NY^1Y^2$, $-NY^1Y^2$ or $-C(=Z^3)-NY^1Y^2$;

$R^2$ represents aryl, cycloalkyl, cycloalkenyl, heteroaryl, or heterocycloalkyl;

$R^3$ represents alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^4$ represents hydrogen or lower alkyl;

$R^5$ is a direct bond or an alkylene chain, an alkenylene chain or an alkynylene chain;

$R^6$ is a direct bond, cycloalkylene, heterocycloalkylene, arylene, heteroaryldiyl, $-C(=Z^3)-NR^4-$, $-NR^4-C(=Z^3)-$, $-Z^3-$, $-C(=O)-$, $-C(=NOR^4)-$, —NR$^4$—, —NR$^4$—C(=Z$^3$)—NR$^4$—, —SO$_2$—NR$^4$—, —NR$^4$—SO$_2$—, —O—C(=O)—, —C(=O)—O—, —NR$^4$—C(=O)—O— or —O—C(=O)—NR$^4$—;

R$^7$ is hydrogen, alkyl, aryl, arylalkyl, cycloalkyl, cycloalkylalkyl, heteroaryl, heteroarylalkyl, heterocycloalkyl or heterocycloalkylalkyl;

R$^8$ is alkyl, aryl, cycloalkyl, heteroaryl or heterocycloalkyl, or alkyl substituted by aryl, an acidic functional group (or corresponding protected derivative), cycloalkyl, heteroaryl, heterocycloalkyl, —Z$^3$H, —Z$^2$R$^3$, —C(=O)—NY$^3$Y$^4$ or —NY$^3$Y$^4$;

R$^9$ is hydrogen, R$^3$ or alkyl substituted with alkoxy, cycloalkyl, hydroxy, mercapto, alkylthio or —NY$^3$Y$^4$;

R$^{10}$ is hydrogen or a group consisting amino acid side chains and corresponding protected derivatives, an acidic functional group (or corresponding protected derivative), R$^3$, —Z$^2$R$^3$, —C(=O)—R$^3$, or —C(=O)—NY$^3$Y$^4$, or alkyl substituted by an acidic functional group (or corresponding protected derivative) or by R$^3$, —Z$^2$R$^3$, —NY$^3$Y$^4$, —NH—C(=O)—R$^3$, —C(=O)—R$^5$—NH$_2$, —C(=O)—Ar$^2$—NH$_2$, —C(=O)—R$^5$—CO$_2$H, or —C(=O)—NY$^3$Y$^4$;

or R$^9$ and R$^{10}$ together with the atoms to which they attached form a 3- to 6-membered heterocycloalkyl ring;

R$^{11}$ is C$_{1-6}$alkylene, optionally substituted by R$^3$;

R$^{12}$ is alkyl, aryl, arylalkyl, cycloalkyl, cycloalkylalkyl, heteroaryl, heteroarylalkyl, heterocycloalkyl or heterocycloalkylalkyl;

R$^{13}$ is hydrogen, or alkyl optionally substituted by aryl, an acidic functional group (or corresponding protected derivative), cycloalkyl, heteroaryl, heterocycloalkyl, —Z$^3$H, —Z$^2$R$^3$, —C(=O)—NY$^3$Y$^4$ or —NY$^3$Y$^4$;

Ar$^1$ is heteroaryldiyl;

Ar$^2$ is arylene or heteroaryldiyl;

L$^1$ represents a —R$^5$—R$^6$— linkage;

L$^2$ represents:

(i) a direct bond;

(ii) an alkylene, alkenylene, alkynylene, cycloalkenylene, cycloalkylene, heteroaryldiyl, heterocycloalkylene or arylene linkage each optionally substituted by (a) an acidic functional group (or corresponding protected derivative), R$^3$, —Z$^3$H, —Z$^2$R$^8$, —C(=O)—R$^3$, —N(R$^7$)—C(=O)—R$^8$, —N(R$^7$)—C(=O)—OR$^8$, —N(R$^7$)—C(=O)—NR$^4$R$^8$, —N(R$^7$)—SO$_2$—R$^8$, —NY$^3$Y$^4$, or —[C(=O)—N(R$^9$)—C(R$^4$)(R$^{10}$)]$_p$—C(=O)—NY$^3$Y$^4$, or by (b) alkyl substituted by an acidic functional group (or corresponding protected derivative), or by —Z$^3$H, —Z$^2$R$^3$, —C(=O)—NY$^3$Y$^4$ or —NY$^3$Y$^4$;

(iii) a —[C(=O)—N(R$^9$)—C(R$^4$)(R$^{10}$)]$_p$— linkage;

(iv) a —Z$^4$—R$^{11}$— linkage;

(v) a —C(=O)—CH$_2$—C(=O)— linkage;

(vi) a —R$^{11}$—Z$^4$—R$^{11}$— linkage; or (vii) a —L$^3$—L$^4$—L$^5$— linkage;

L$^3$ represents a direct bond and L$^5$ represents an alkylene chain, or

L$^3$ represents an alkylene chain and L$^5$ represents a direct bond or an alkylene chain;

L$^4$ represents a cycloalkylene or heterocycloalkylene linkage;

Y is carboxy or an acid bioisostere;

Y$^1$ and Y$^2$ are independently hydrogen, alkenyl, alkyl, aryl, arylalkyl, cycloalkyl, heteroaryl or heteroarylalkyl; or the group —NY$^1$Y$^2$ may form a cyclic amine;

Y$^3$ and Y$^4$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —NY$^1$Y$^2$, or one or more —CO$_2$R$^7$ or —C(=O)—NY$^1$Y$^2$ groups; or the group —NY$^3$Y$^4$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), R$^8$; (ii) may also contain a further heteroatom selected from O, S, SO$_2$, or NY$^5$; and (iii) may also be fused to additional aryl, heteroaryl, heterocycloalkyl or cycloalkyl rings to form a bicyclic or tricyclic ring system;

Y$^5$ is hydrogen, alkyl, aryl, arylalkyl, —C(=O)—R$^{12}$, —C(=O)—OR$^{12}$ or —SO$_2$R$^{12}$;

Z$^1$ represents a direct bond, an alkylene chain or NR$^4$, O or S(O)$_n$;

Z$^2$ is O or S(O)$_n$;

Z$^3$ is O or S;

Z$^4$ is O, S(O)$_n$, NR$^{13}$, SO$_2$NR$^{13}$, NR$^{13}$C(=O), C(=O)NR$^{13}$ or C(=O); and n is zero or an integer 1 or 2;

p is zero or an integer 1 to 4;

(but excluding compounds where an oxygen, nitrogen or sulphur atom is attached directly to a carbon carbon multiple bond of an alkenyl or alkynyl residue);

and the corresponding N-oxides, and their prodrugs; and pharmaceutically acceptable salts and solvates (e.g. hydrates) of such compounds and their N-oxides and prodrugs.

A particular embodiment of this invention is compounds of formula (I) in which L$^2$ is (i), (ii), (iii), (iv), (v) or (vi).

In the present specification, the term "compounds of the invention", and equivalent expressions, are meant to embrace compounds of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, p283 "Bioisosterism In Drug Design"; Yun, Hwahak Sekye, 1993, 33, p576–579 "Application Of Bioisosterism To New Drug Design"; Zhao, Huaxue Tongbao, 1995, p34–38 "Bioisosteric Replacement And Development Of Lead Compounds In Drug Design"; Graham, Theochem, 1995, 343, p105–109 "Theoretical Studies Applied To Drug Design:ab initio Electronic Distributions In Bioisosteres"). Examples of suitable acid bioisosteres include: —C(=O)—NHOH, —C(=O)—CH$_2$OH, —C(=O)—CH$_2$SH, —C(=O)—NH—CN, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acyl" means an H—CO— or alkyl—CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is $C_{1-4}$ alkyl.

"Alkylsulphonyl" means an alkyl-$SO_2$— group in which the alkyl group is as previously described. Preferred alkylsulphonyl groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$—, $Y^1Y^2N$—$C_{2-6}$alkylene-$Z^1$—, alkylC(=O)—$Y^1N$—, alkyl$SO_2$—$Y^1N$— or alkyl optionally substituted with aryl, heteroaryl, hydroxy, or $Y^1Y^2N$—. When $R^1$ is an optionally substituted aryl group, this may particularly represent optionally substituted phenyl.

"Arylalkenyl" means an aryl-alkenyl- group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl- group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl- group in which the aryl and alkynyl are as previously described. Exemplary arylalkynyl groups include phenylethynyl and 3-phenylbut-2-ynyl.

"Arylene" means an optionally substituted bivalent radical derived from an aryl group. Exemplary arylene groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-$S_2$— group in which the aryl group is as previously described.

"Arylsulphonylcarbamoyl" means an aryl-$S_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryldiyl" means a bivalent radical derived from an aromatic carbocyclic moiety of 5 to about 10 ring members in which one of the ring members is nitrogen and the other ring members are chosen from carbon, oxygen, sulphur, or nitrogen. Examples of azaheteroaryldiyl groups include pyridindiyl, pyrimidindiyl, quinolindiyl, isoquinolindiyl, quinazolindiyl, imidazoldiyl, isoxazoldiyl, isothiazoldiyl, oxazoldiyl, thiazoldiyl and benzimidazoldiyl.

"Cyclic amine" means a 3 to 8 membered monocyclic cycloalkyl ring system where one of the ring carbon atoms is replaced by nitrogen and which (i) may optionally contain an additional heteroatom selected from O, S or $NY^3$ (where $Y^3$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl— group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include $C_{3-8}$ cycloalkyl rings such as cyclopropyl, cyclopentyl, cyclohexyl and cycloheptyl.

"Cycloalkylalkyl" means a cycloalkyl-alkyl— group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzoxazolyl, benzthiazolyl, furyl, imidazolyl, indolyl, indolizinyl, isoxazolyl, isoquinolinyl, isothiazolyl, oxazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl-group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl- alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl— group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulphur, and optionally substituted by one or more "aryl group substituents" as defined above.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-$SO_2$—NH—C(=O)— group in which the heteroaryl group is as previously described.

"Heterocycle" denotes an optionally substituted saturated, partially saturated or fully unsaturated monocyclic organic moiety of 5 or 6 ring members in which one or more of the ring members is/are element(s) other than carbon, for example nitrogen, oxygen or sulphur. Exemplary 5 or 6 membered heterocycles include furyl, imidazolyl, isoxazolyl, isothiazolyl, oxadiazolyl, oxazolyl, oxazinyl, piperidinyl, pyrazinyl, pyridazinyl, pyrazolyl, pyridyl, pyrimidinyl, pyrrolyl, pyrrolidinyl, pyrrolinyl, 1,3,4-thiadiazolyl, thiazolyl, thienyl and triazolyl groups. Optional substituents include one or more "aryl group substituents" as defined above.

"Heterocycloalkyl" means: (i) a cycloalkyl group of about 3 to 7 ring members which contains one or more heteroatoms selected from O, S or NY³; (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or NY⁶ (where Y⁶ is hydrogen, alkyl, arylalkyl, and aryl) and is optionally substituted by oxo, by removing a hydrogen atom from each of two different carbon atoms of the ring, or when NY⁶ is NH by removing a hydrogen atom from one carbon atom of the ring and a hydrogen atom from the NH, or when the ring contains two NY⁶ heteroatoms and NY⁶ is NH by removing a hydrogen atom from both nitrogen atoms.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

Suitable esters of compounds of formula (I) containing both a carboxy group and a hydroxy group within the moiety -L²—Y, include lactones, formed by loss of water between said carboxy and hydroxy groups. Examples of lactones include caprolactones, valerolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations.

Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

R¹ may particularly represent optionally substituted aryl, especially optionally substituted phenyl.

Z¹ may particularly represent NH.

Het may particularly represent

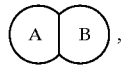, wherein ring

is a 5 or 6 membered heterocycle and ring

is a 5 or 6 membered fully unsaturated heterocycle or a benzene ring, each ring optionally substituted by one or more "aryl group substituents" as defined above, and the two rings are joined together by a carbon-carbon linkage or a carbon-nitrogen linkage.

Ring

may particularly represent a 5 membered heteroaryl ring, optionally substituted by one or more "aryl group substituents" as defined above.

Ring

may particularly represent a benzene ring, optionally substituted by one or more "aryl group substituents" as defined above.

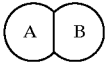

may particularly represent a 9 membered bicyclic system in which rings

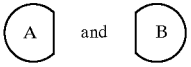

and
are as defined just above and the two rings are joined together by carbon atom linkages.

is preferably benzoxazolyl or benzimidazolyl, in which ring

is optionally substituted by one or more "aryl group substituents" as defined above [examples of particular aryl group substituents include $C_{1-4}$alkyl (e.g. methyl or ethyl), $C_{1-4}$alkoxy (e.g. methoxy), amino, halogen, hydroxy, $C_{1-4}$alkylthio, $C_{1-4}$alkylsulphinyl, $C_{1-4}$alkylsulphonyl, nitro or trifluoromethyl].

$L^1$ may particularly represent a —$R^5$—$R^6$— linkage where $R^5$ represents a straight or branched $C_{1-6}$alkylene chain, especially a straight or branched $C_{1-4}$alkylene chain, and $R^6$ represents —C(=$Z^3$)—N$R^4$—, preferably —C(=O)—N$R^4$—, especially where $R^4$ is hydrogen or lower alkyl (e.g. methyl).

$Ar^1$ may particularly represent azaheteroaryldiyl, especially optionally substituted pyridindiyl, preferably p-pyridindiyl, more preferably pyridin-2,5-diyl. Preferred optional substituents include $C_{1-4}$alkyl, especially methyl, and $C_{1-4}$alkoxy, especially methoxy.

$L^2$ may particularly represent (a) a direct bond (b) an optionally substituted alkylene linkage, especially optionally substituted ethylene (c) an unsubstituted alkenylene linkage, especially vinylene or (d) a —$Z^4$—$R^{11}$— linkage, such as —O—$CH_2$—, —S(O)$_n$—$CH_2$—, —S(O)$_n$—$CH_2$—$CH_2$—, —NH—$CH_2$—. Preferred optional substituents within (b) include lower alkyl (e.g. methyl), aryl, heteroaryl, —$Z^2R^8$, —N($R^7$)—C(=O)—$R^8$, —N($R^7$)—C(=O)—O$R^8$, —N($R^7$)—$SO_2$—$R^8$, —N$Y^3Y^4$, —[C(=O)—N($R^9$)—C($R^4$)($R^{10}$)]$_p$—C(=O)—N$Y^3Y^4$ and alkyl substituted by hydroxy, —O$R^3$, —C(=O)—O$R^3$ or —N$Y^3Y^4$. $L^2$ is more particularly a $C_{1-4}$alkylene linkage (e.g. ethylene) optionally substituted by lower alkyl (e.g. methyl), aryl, heteroaryl, —$Z^2R^8$, —N($R^7$)—C(=O)—$R^8$, —N($R^7$)—C(=O)—O$R^8$, —N($R^7$)—$SO_2$—$R^8$, —N$Y^3Y^4$, —[C(=O)—N($R^9$)—C($R^4$)($R^{10}$)]$_p$—C(=O)—N$Y^3Y^4$ or alkyl substituted by hydroxy, —O$R^3$, —C(=O)—O$R^3$ or —N$Y^3Y^4$. $L^2$ is preferably a group

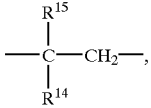

where $R^{15}$ is hydrogen or lower alkyl (e.g. methyl) and $R^{14}$ represents lower alkyl (e.g. methyl), or where $R^{15}$ is hydrogen and $R^{14}$ represents aryl, heteroaryl, —$Z^2R^8$, —N($R^7$)—C(=O)—$R^8$, —N($R^7$)—C(=O)—O$R^8$, —N($R^7$)—$SO_2R^8$, —N$Y^3Y^4$, —[C(=O)—N($R^9$)—C($R^4$)($R^{10}$)]$_p$—C(=O)—N$Y^3Y^4$ or alkyl substituted by hydroxy, —O$R^3$, —C(=O)—O$R^3$ or —N$Y^3Y^4$. $L^2$ is more preferably a group

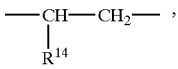

particularly

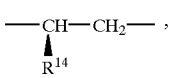

where $R^{14}$ represents lower alkyl (e.g. methyl), —$Z^2R^8$, —N($R^7$)—C(=O)—$R^8$, —N($R^7$)—C(=O)—O$R^8$, —N($R^7$)—$SO_2$—$R^8$, —N$Y^3Y^4$, or alkyl substituted by hydroxy, —O$R^3$, —C(=O)—O$R^3$ or —N$Y^3Y^4$.

Y may particularly represent carboxy.

It is to be understood that this invention covers all appropriate combinations of the particular and preferred groupings referred to herein.

A particular group of compounds of the invention are compounds of formula (Ia):

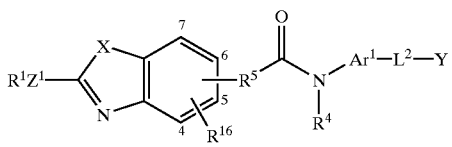 (Ia)

in which $R^1$, $Ar^1$, $R^4$, $R^5$, $L^2$, Y and $Z^1$ are as hereinbefore defined, $R^{16}$ is hydrogen or an aryl group substituent and X is O or $NR^{17}$ (where $R^{17}$ is H or lower alkyl), and their prodrugs and pharmaceutically acceptable salts, and solvates (e.g. hydrates) of compounds of formula (Ia) and their prodrugs.

Compounds of formula (Ia) in which $R^1$ represents optionally substituted aryl, especially optionally substituted phenyl, are preferred. Preferred optional substituents include lower alkyl (e.g. methyl), lower alkyl (e.g. methoxy), halo (e.g. fluoro) and $Y^1Y^2N$— (e.g. dimethylamino). $R^1$ especially represents ortho-tolyl.

Compounds of formula (Ia) in which $R^{16}$ represents hydrogen, $C_{1-4}$alkyl (e.g. methyl or ethyl) or $C_{1-4}$alkoxy (e.g. methoxy) are preferred, especially when attached at the ring 4 position.

Compounds of formula (Ia) in which $Z^1$ represents NH are preferred.

Compounds of formula (Ia) in which $R^5$ represents a straight or branched $C_{1-6}$alkylene chain, especially a straight or branched $C_{1-4}$alkylene chain, more especially methylene, are preferred.

Compounds of formula (Ia) in which $R^4$ represents hydrogen are preferred.

Compounds of formula (Ia) in which $R^4$ represents lower alkyl (e.g. methyl) are also preferred.

Compounds of formula (Ia) in which $Ar^1$ represents an optionally substituted pyridindiyl, especially optionally substituted p-pyridindiyl, more especially pyridin-2,5-diyl, are also preferred. Preferred substituents include $C_{1-4}$alkyl and $C_{1-4}$alkoxy, especially methyl and methoxy.

Compounds of formula (Ia) in which $L^2$ represents an optionally substituted alkylene linkage, especially ethylene or substituted ethylene, are preferred. Preferred optional substituents include lower alkyl (e.g. methyl), aryl, heteroaryl, $-Z^2R^8$, $-N(R^7)-C(=O)-R^8$, $-N(R^7)-C(=O)-OR^8$, $-N(R^7)-SO_2-R^8$, $-NY^3Y^4$, $-[C(=O)-N(R^9)-C(R^4)(R^{10})]_p-C(=O)-NY^3Y^4$ and alkyl substituted by hydroxy, $-OR^3$, $-C(=O)-OR^3$ or $-NY^3Y^4$.

Compounds of formula (Ia) in which $L^2$ is a

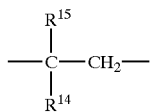

linkage, where $R^{15}$ is hydrogen or lower alkyl (e.g. methyl) and $R^{14}$ represents hydrogen or lower alkyl (e.g. methyl), or where $R^{15}$ is hydrogen and $R^{14}$ represents aryl, heteroaryl, $-Z^2R^8$, $-N(R^7)-C(=O)-R^8$, $-N(R^7)-C(=O)-OR^8$, $-N(R^7)-SO_2-R^8$, $NY^3Y^4$, $-[C(=O)-N(R^9)-C(R^4)(R^{10})]_p-C(=O)-NY^3Y^4$ or alkyl substituted by hydroxy, $-OR^3$, $-C(=O)-OR^3$ or $-NY^3Y^4$ are particularly preferred. Compounds of formula (Ia) in which $L^2$ is a

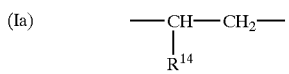

linkage, particularly

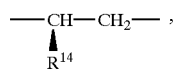

where $R^{14}$ represents lower alkyl (e.g. methyl), aryl, heteroaryl, $-Z^2R^8$, $-N(R^7)-C(=O)-R^8$, $-N(R^7)-C(=O)-OR^8$, $-N(R^7)-SO_2-R^8$, $-NY^3Y^4$, or alkyl substituted by hydroxy, $-OR^3$, $-C(=O)-OR^3$ or $-NY^3Y^4$, are especially preferred.

Compounds of formula (Ia) in which Y represents carboxy are preferred.

The group

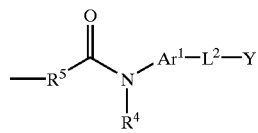

may preferably be attached at the ring 6 position when X is O or NH, or the ring 5 or 6 position when X is $NR^{17}$ and $R^{17}$ is lower alkyl.

A preferred group of compounds of the invention are compounds of formula (Ia) in which:—$R^1$ is optionally substituted phenyl (especially ortho-tolyl); $Z^1$ is NH; X is O; $R^{16}$ is hydrogen, $C_{1-4}$alkyl (e.g. methyl or ethyl) or $C_{1-4}$alkoxy (e.g. methoxy), especially attached to the ring 4 position; $R^5$ is a straight or branched $C_{1-4}$alkylene chain, (especially methylene); $R^4$ is hydrogen or lower alkyl (e.g. methyl); $Ar^1$is optionally substituted pyridindiyl (especially pyridin-2,5-diyl); $L^2$ is a

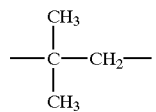

group or preferably a

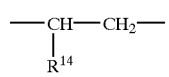

group, particularly

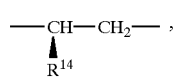

where $R^{14}$ represents hydrogen, lower alkyl (e.g. methyl), aryl, heteroaryl, $-Z^2R^8$, $-N(R^7)-C(=O)-R^8$, $-N(R^7)-C(=O)-OR^8$, $-N(R^7)-SO_2-R^8$, $-NY^3Y^4$, or alkyl substituted by hydroxy, $-OR^3$, $-C(=O)-OR^3$ or $-NY^1Y^2$; Y is carboxy; and the group

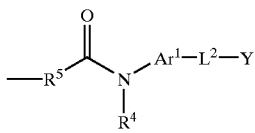

is attached at the ring 6 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ia) in which: $R^1$ is optionally substituted phenyl (especially ortho-tolyl); $Z^1$ is NH; X is $NR^{17}$ (especially NH); $R^{16}$ is hydrogen, $C_{1-4}$alkyl (e.g. methyl or ethyl) or $C_{1-4}$alkoxy (e.g. methoxy), especially attached to the ring 4 position; $R^5$ is a straight or branched $C_{1-4}$alkylene chain, (especially methylene); $R^4$ is hydrogen or lower alkyl (e.g. methyl); $Ar^1$ is optionally substituted pyridindiyl (especially pyridin-2,5-diyl); $L^2$ is a

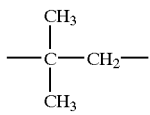

group or preferably a

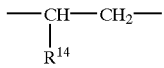

group, particularly

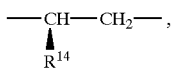

where $R^{14}$ represents hydrogen, lower alkyl (e.g. methyl), aryl, heteroaryl, —$Z^2R^8$, —$N(R^7)$—$C(=O)$—$R^8$, —$N(R^7)$—$C(=O)$—$OR^8$, —$N(R^7)$—$SO_2$—$R^8$, —$NY^3Y^4$, or alkyl substituted by hydroxy, —$OR^3$, —$C(=O)$—$OR^3$ or —$NY^1Y^2$; Y is carboxy; and the group

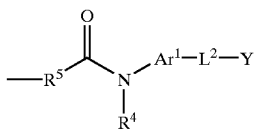

is attached at the ring 5 or 6 position; and the corresponding N-oxides, and their prodrugs; and pharmaceutically acceptable salts and solvates (e.g. hydrates) of such compounds and their N-oxides and prodrugs.

Particular compounds of the invention are selected from the following:
3-{5-[2-(2-phenylamino-benzoxazol-6-yl)-acetylamino]-pyridin-2-yl}-butyric acid;
3-{5-[2-(2-o-tolylamino-benzoxazol-6-yl)-acetylamino]-pyridin-2-yl}-butyric acid;
3-(5-{2-[2-(2-methoxy-phenylamino)-benzoxazol-6-yl]-acetylamino}-pyridin-2-yl)-butyric acid;
3-(5-{2-[2-(2-isopropyl-phenylamino)-benzoxazol-6-yl]-acetylamino}-pyridin-2-yl)-butyric acid;
3-(5-{2-[2-(2,6-dimethyl-phenylamino)-benzoxazol-6-yl]-acetylamino}-pyridin-2-yl)-butyric acid;
3-(5-{2-[2-(3-methoxy-phenylamino)-benzoxazol-6-yl]-acetylamino}-pyridin-2-yl)-butyric acid;
3-(5-{2-[2-(2,3-dimethyl-phenylamino)-benzoxazol-6-yl]-acetylamino}-pyridin-2-yl)-butyric acid;
3-(5-{2-[2-(2,6-diethyl-phenylamino)-benzoxazol-6-yl]-acetylamino}-pyridin-2-yl)-butyric acid;
3-(5-{2-[2-(2-methoxy-5-methyl-phenylamino)-benzoxazol-6-yl]-acetylamino}-pyridin -2-yl)-butyric acid;
3-(5-{2-[2-(pyridin-3-ylamino)-benzoxazol-6-yl]-acetylamino}-pyridin-2-yl)-butyric acid;
3-(5-{2-[2-(2-cyano-phenylamino)-benzoxazol-6-yl]-acetylamino}-pyridin-2-yl)-butyric acid;
3-(5-{2-[2-(pyridin-2-ylamino)-benzoxazol-6-yl]-acetylamino}-pyridin-2-yl)-butyric acid;
3-(5-{2-[2-(2-chloro-phenylamino)-benzoxazol-6-yl]-acetylamino}-pyridin-2-yl)-butyric acid;
3-(5-{methyl-[(2-phenylamino-benzoxazol-6-yl)-acetyl]-amino}-pyridin-2-yl)-butyric acid;
3-(5-{methyl-[(2-o-tolylamino-benzoxazol-6-yl)-acetyl]-amino}-pyridin-2-yl)-butyric acid;
3-[5-({[2-(2-methoxy-phenylamino)-benzoxazol-6-yl]-acetyl}-methyl-amino)-pyridin-2-yl]-butyric acid;
3-[5-({[2-(2-isopropyl-phenylamino)-benzoxazol-6-yl]-acetyl}-methyl-amino)-pyridin-2-yl]-butyric acid;
3-[5-({[2-(2,6-dimethyl-phenylamino)-benzoxazol-6-yl]-acetyl}-methyl-amino)-pyridin-2-yl]butyric acid;
3-[5-({[2-(3-methoxy-phenylamino)-benzoxazol-6-yl]-acetyl}-methyl-amino)-pyridin-2-yl]-butyric acid;
3-[5-({[2-(2,3-dimethyl-phenylamino)-benzoxazol-6-yl]-acetyl}-methyl-amino)-pyridin-2-yl]-butyric acid;
3-[5-({[2-(2,6-diethyl-phenylamino)-benzoxazol-6-yl]-acetyl}-methyl-amino)-pyridin-2-yl]-butyric acid;
3-[5-({[2-(2-methoxy-5-methyl-phenylamino)-benzoxazol-6-yl]-acetyl}-methyl-amino)-pyridin-2-yl]-butyric acid;
3-[5-(methyl-{[2-(pyridin-3-ylamino)-benzoxazol-6-yl]-acetyl}-amino)-pyridin-2-yl]-butyric acid;
3-[5-({[2-(2-cyano-phenylamino)-benzoxazol-6-yl]-acetyl}-methyl-amino)-pyridin-2-yl]-butyric acid;
3-[5-(methyl-{[2-(pyridin-2-ylamino)-benzoxazol-6-yl]-acetyl}-amino)-pyridin-2-yl]-butyric acid;
3-[5-({[2-(2-chloro-phenylamino)-benzoxazol-6-yl]-acetyl}-methyl-amino)-pyridin-2-yl]-butyric acid;
3-{6-[2-(2-phenylamino-benzoxazol-6-yl)-acetylamino]-pyridin-3-yl}-butyric acid;
3-{6-[2-(2-o-tolylamino-benzoxazol-6-yl)-acetylamino]-pyridin-3-yl}-butyric acid;
3-(6-{2-[2-(2-methoxy-phenylamino)-benzoxazol-6-yl]-acetylamino}-pyridin-3-yl)-butyric acid;
3-(6-{2-[2-(2-isopropyl-phenylamino)-benzoxazol-6-yl]-acetylamino}-pyridin-3-yl)-butyric acid;
3-(6-{2-[2-(2,6-dimethyl-phenylamino)-benzoxazol-6-yl]-acetylamino}-pyridin-3-yl)-butyric acid;
3-(6-{2-[2-(3-methoxy-phenylamino)-benzoxazol-6-yl]-acetylamino}-pyridin-3-yl)-butyric acid;
3-(6-{2-[2-(2,3-dimethyl-phenylamino)-benzoxazol-6-yl]-acetylamino}-pyridin-3-yl)-butyric acid;
3-(6-{2-[2-(2,6-diethyl-phenylamino)-benzoxazol-6-yl]-acetylamino}-pyridin-3-yl-butyric acid;
3-(6-{2-[2-(2-methoxy-5-methyl-phenylamino)-benzoxazol-6-yl]-acetylamino}-pyridin -3-yl)-butyric acid;
3-(6-{2-[2-(pyridin-3-ylamino)-benzoxazol-6-yl]-acetylamino}-pyridin-3-yl)-butyric acid;
3-(6-{2-[2-(2-cyano-phenylamino)-benzoxazol-6-yl]-acetylamino}-pyridin-3-yl)-butyric acid;
3-(6-{2-[2-(pyridin-2-ylamino)-benzoxazol-6-yl]-acetylamino}-pyridin-3-yl)-butyric acid;

3-(6-{2-[2-(2-chloro-phenylamino)-benzoxazol-6-yl]-acetylamino}-pyridin-3-yl)-butyric acid;
3-(6-{methyl-[(2-phenylamino-benzoxazol-6-yl)-acetyl]-amino}-pyridin-3-yl)-butyric acid;
3-(6-{methyl-[(2-o-tolylamino-benzoxazol-6-yl)-acetyl]-amino}-pyridin-3-yl)-butyric acid;
3-[6-({[2-(2-methoxy-phenylamino)-benzoxazol-6-yl]-acetyl}-methyl-amino)-pyridin-3-yl]-butyric acid;
3-[6-({[2-(2-isopropyl-phenylamino)-benzoxazol-6-yl]-acetyl}-methyl-amino)-pyridin-3-yl]-butyric acid;
3-[6-({[2-(2,6-dimethyl-phenylamino)-benzoxazol-6-yl]-acetyl}-methyl-amino)-pyridin-3-yl]-butyric acid;
3-[6-({[2-(3-methoxy-phenylamino)-benzoxazol-6-yl]-acetyl}-methyl-amino)-pyridin-3-yl]-butyric acid;
3-[6-({[2-(2,3-dimethyl-phenylamino)-benzoxazol-6-yl]-acetyl}-methyl-amino)-pyridin-3-yl]-butyric acid;
3-[6-({[2-(2,6-diethyl-phenylamino)-benzoxazol-6-yl]-acetyl}-methyl-amino)-pyridin-3-yl]-butyric acid;
3-[6-({[2-(2-methoxy-5-methyl-phenyl amino)-benzoxazol-6-yl]-acetyl}-methyl-amino)-pyridin-3-yl]-butyric acid;
3-[6-(methyl-{[2-(pyridin-3-ylamino)-benzoxazol-6-yl]-acetyl}-amino)-pyridin-3-yl]-butyric acid;
3-[6-({[2-(2-cyano-phenylamino)-benzoxazol-6-yl]-acetyl}-methyl-amino)-pyridin-3-yl]-butyric acid;
3-[6-(methyl-{[2-(pyridin-2-ylamino)-benzoxazol-6-yl]-acetyl}-amino)-pyridin-3-yl]-butyric acid;
3-[6-({[2-(2-chloro-phenylamino)-benzoxazol-6-yl]-acetyl}-methyl-amino)-pyridin-3-yl]-butyric acid;
3-[6-(methyl-{[2-(3-methyl-pyridin-4-ylamino)-benzoxazol-6-yl]-acetyl}-amino)-pyridin-3-yl]-butyric acid;
3-{6-[methyl-({2-[methyl-(3-methyl-pyridin-4-yl)-amino]-benzoxazol-6-yl}-acetyl)-amino]-pyridin-3-yl}-butyric acid;
3-{6-[ethyl-({2-[methyl-(3-methyl-pyridin-4-yl)-amino]-benzoxazol-6-yl}-acetyl)-amino]pyridin-3-yl}-butyric acid;
3-(6-{2-[4-methoxy-2-(3-methyl-pyridin-4-ylamino)-benzoxazol-6-yl]-acetylamino}-pyridin-3-yl)-butyric acid;
3-(6-{2-[7-methoxy-2-(3-methyl-pyridin-4-ylamino)-benzoxazol-6-yl]-acetylamino}-pyridin-3-yl)-butyric acid;
3-(6-{2-{2-[methyl-(3-methyl-pyridin-4-yl)-amino]-benzoxazol-6-yl}-acetylamino)-pyridin-3-yl)-butyric acid;
3-[5-(methyl-{[2-(4-methyl-pyridin-3-ylamino)-benzoxazol-6-yl]-acetyl}-amino)-pyridin-2-yl]-butyric acid;
3-{5-[methyl-({2-[methyl-(4-methyl-pyridin-3-yl)-amino]-benzoxazol-6-yl}-acetyl)-amino]-pyridin-2-yl}-butyric acid;
3-{5-[ethyl-({2-[methyl-(4-methyl-pyridin-3-yl)-amino]-benzoxazol-6-yl}-acetyl)-amino]-pyridin-2-yl}-butyric acid;
b 3-(5-{2-[4-methoxy-2-(4-methyl-pyridin-3-ylamino)-benzoxazol-6-yl]-acetylamino}-pyridin-2-yl)-butyric acid;
3-(5-{2-[7-methoxy-2-(4-methyl-pyridin-3-ylamino)-benzoxazol-6-yl]-acetylamino}-pyridin-2-yl)-butyric acid;
3-[5-(2-{2-[methyl-(4-methyl-pyridin-3-yl)-amino]-benzoxazol-6-yl}-acetylamino)-pyridin-2-yl]-butyric acid;
N-methyl-N-[4-(2-oxo-oxepan-4-yl)-phenyl]-2-(2-o-tolylamino-benzoxazol-6-yl)-acetamide;
N-methyl-2-[2-(methyl-o-tolylamino)-benzoxazol-6-yl]-N-[4-(2-oxo-oxepan4-yl)-phenyl]-acetamide N-ethyl-2-[2-(methyl-o-tolylamino)-benzoxazol-6-yl]-N-[4-(2-oxo-oxepan-4-yl)-phenyl]-acetamide;
2-(4-methoxy-2-o-tolylamino-benzoxazol-6-yl)-N-[4-(2-oxo-oxepan-4-yl)-phenyl]-acetamide;
2-(7-methoxy-2-o-tolylamino-benzoxazol-6-yl)-N-[4-(2-oxo-oxepan-4-yl)-phenyl]-acetamide;
2-[2-(methyl-o-tolylamino)-benzoxazol-6-yl]-N-[4-(2-oxo-oxepan-4-yl)-phenyl]-acetamide
3-{5-[2-(2-phenylamino-3H-benzimidazol-5-yl)-acetylamino]-pyridin-2-yl}-butyric acid;
3-{5-[2-(2-o-tolylamino-3H-benzimidazol-5-yl)-acetylamino]-pyridin-2-yl}-butyric acid;
3-[6-(2-{2-[methyl-(3-methyl-pyridin-4-yl)-amino]-1H-benzimidazol-5-yl}-acetylamino)-pyridin-3-yl]-butyric acid;
3-(6-{2-[3-methyl-2-(3-methyl-pyridin-4-ylamino)-3H-benzimidazol-5-yl]-acetylamino}-pyridin-3-yl)-butyric acid;
3-(6-{2-[1-methyl-2-(3-methyl-pyridin-4-ylamino)-1H-benzimidazol-5-yl]-acetylamino}-pyridin-3-yl)-butyric acid;
3-[6-(methyl-{[2-(3-methyl-pyridin-4-ylamino)-1H-benzimidazol-5-yl]-acetyl}-amino)-pyridin-2-yl]-butyric acid;
3-[6-(ethyl-{[2-(3-methyl-pyridin-4-ylamino)-1H-benzimidazol-5-yl]-acetyl}amino)-pyridin-3-yl]-butyric acid;
3-(6-{2-[7-methoxy-2-(3-methyl-pyridin-4-ylamino)-1H-benzimidazol-5-yl]-acetylamino}-pyridin-3-yl)-butyric acid;
3-(6-{2-[4-methoxy-2-(3-methyl-pyridin-4-ylamino)-1H-benzimidazol-5-yl]-acetylamino}-pyridin-3-yl)-butyric acid;
3-[5-(2-{2-[methyl-(4-methyl-pyridin-3-yl)-amino]-3H-benzimidazol-5-yl}-acetylamino)-pyridin-2-yl]-butyric acid;
3-(5-{2-[3-methyl-2-(4-methyl-pyridin-3-ylamino)-3H-benzimidazol-5-yl]-acetylamino}-pyridin-2-yl)-butyric acid;
3-(5-{2-[1-methyl-2-(4-methyl-pyridin-3-ylamino)-1H-benzimidazol-5-yl]-acetylamino}-pyridin-2-yl)-butyric acid;
3-[5-(methyl-{[2-(4-methyl-pyridin-3-ylamino)-1H-benzimidazol-5-yl]-acetyl}-amino)-pyridin-2-yl]-butyric acid;
3-[5-(ethyl-{[2-(4-methyl-pyridin-3-ylamino)-1H-benzimidazol-5-yl]-acetyl}-amino)-pyridin-2-yl]-butyric acid;
3-(5-{2-[7-methoxy-2-(4-methyl-pyridin-3-ylamino)-2H-benzimidazol-5-yl]-acetylamino}-pyridin-2-yl)-butyric acid;
3-(5-{2-[4-methoxy-2-(4-methyl-pyridin-3-ylamino)-1H-benzimidazol-5-yl]-acetylamino}-pyridin-2-yl)-butyric acid;
2-[2-(methyl-o-tolylamino)-3H-benzimidazol-5-yl]-N-[4-(2-oxo-oxepan-4-yl)-phenyl]-acetamide;
2-(3-methyl-2-o-tolylamino-3H-benzimidazol-5-yl)-N-[4-(2-oxo-oxepan-4-yl)-phenyl]-acetamide;
2-(1-methyl-2-o-tolylamino-1H-benzimidazol-5-yl)-N-[4-(2-oxo-oxepan-4-yl)-phenyl]-acetamide;
N-methyl-N-[4-(2-oxo-oxepan-4-yl)-phenyl]-2-(2-o-tolylamino-3H-benzimidazol-5-yl)-acetamide;
N-ethyl-N-[4-(2-oxo-oxepan-4-yl)-phenyl]-2-(2-o-tolylamino-3H-benzimidazol-5-yl)-acetamide;
2-(7-methoxy-2-o-tolylamino-3H-benzimidazol-5-yl)-N-[4-(2-oxo-oxepan-4-yl)-phenyl]-acetamide;

2-(4-methoxy-2-o-tolylamino-3H-benzimidazol-5-yl)-N-[4-(2-oxo-oxepan-4-yl)-phenyl]-acetamide;

3-{5-[2-(4-methyl-2-o-tolylaminobenzoxazol-6-yl)acetylamino]pyrid-2-yl}butyric acid;

and the corresponding N-oxides, and their prodrugs; and pharmaceutically acceptable salts and solvates (e.g. hydrates) of such compounds and their N-oxides and prodrugs.

Another set of particular compounds of the invention are those selected from the compounds formed by joining the acyl carbon atom (C*) of one of the fragments (A1 to A32) shown in Table 1 to the nitrogen atom (N*) of one of the fragments (B1 to B10) shown in Table 2, and joining the carbon atom (C*) of the phenyl ring in one of the fragments (B1 to B4) shown in Table 2 to the carbon atom (C*) of one of the acidic fragments (C1 to C40) depicted in Table 3.

TABLE 1

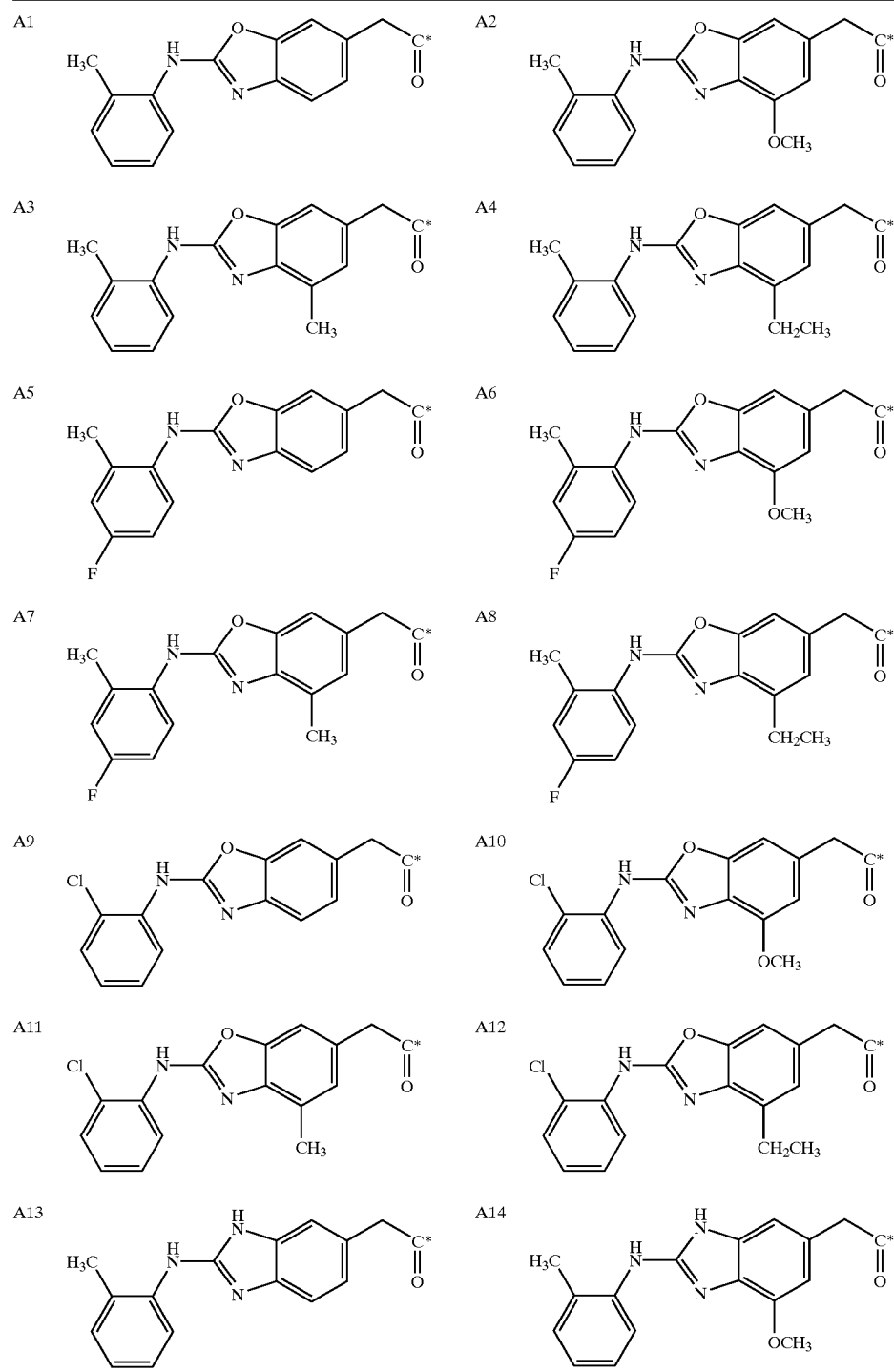

TABLE 1-continued
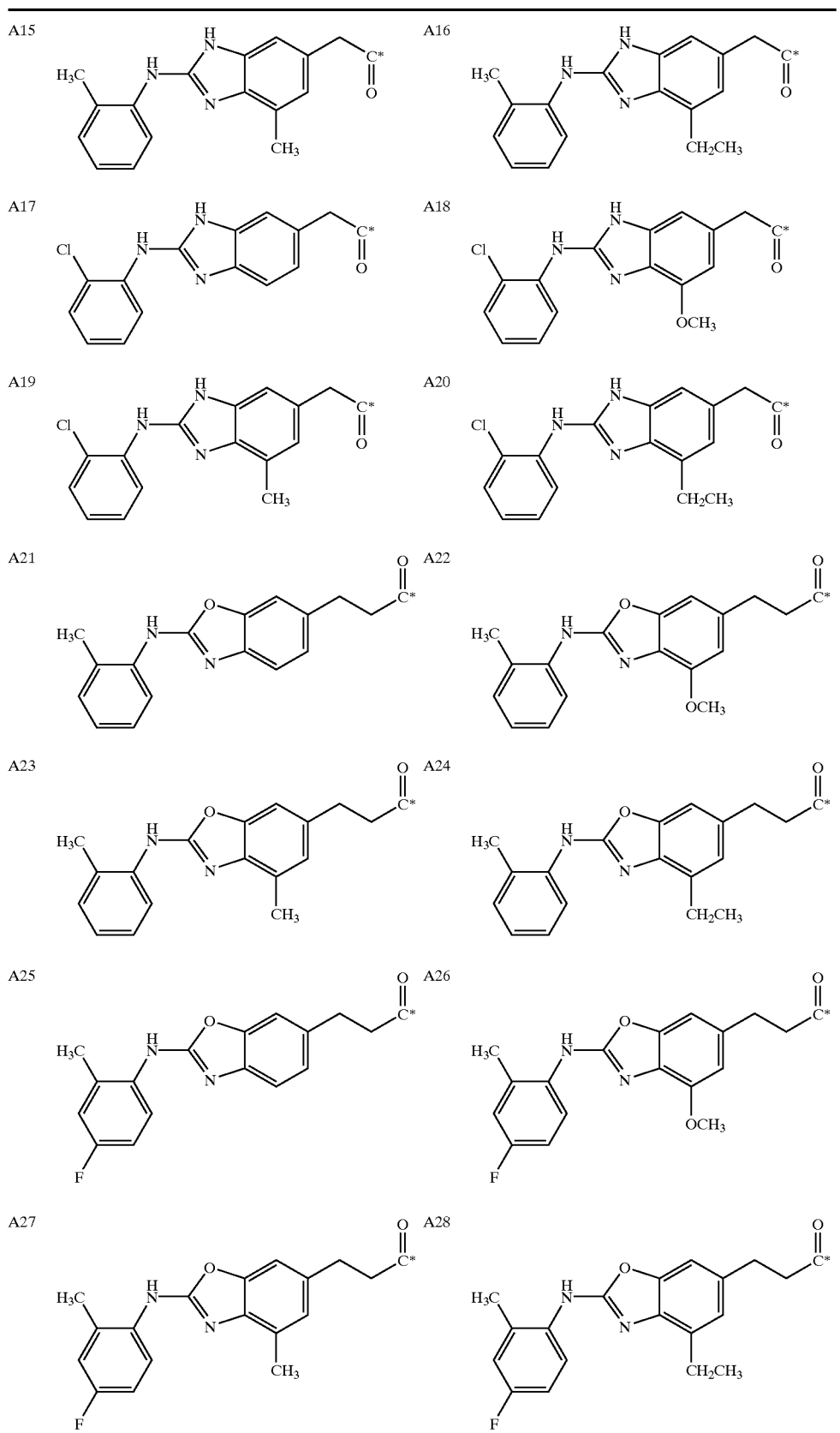

TABLE 1-continued
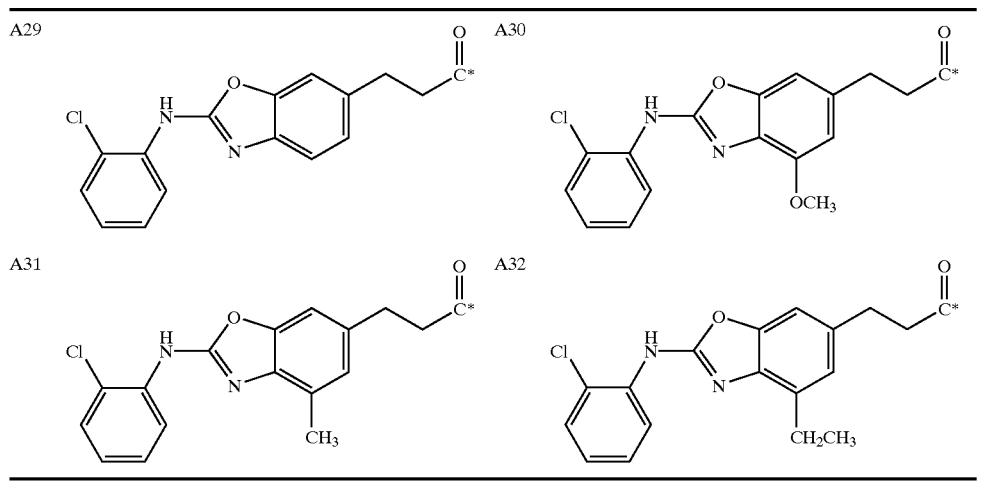
TABLE 2 / TABLE 2-continued
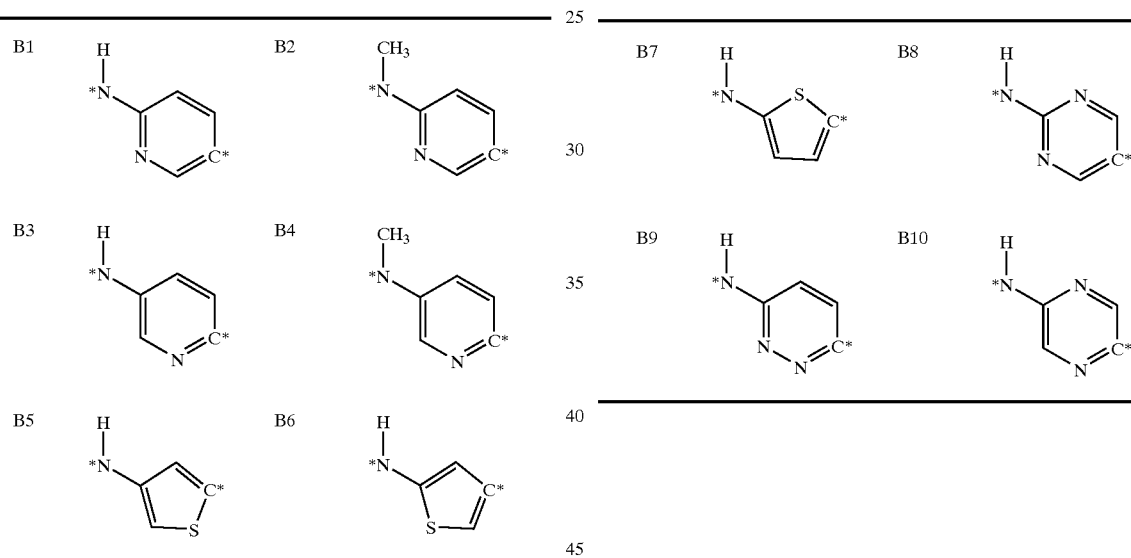
TABLE 3
| C1 | *CH$_2$—CH$_2$—CO$_2$H | C2 | *CH$_2$—CH$_2$—CH$_2$—CO$_2$—H |
|---|---|---|---|
| C3 | *CH—CH$_2$—CO$_2$H<br>\|<br>CH$_3$ | C4 | *CH—CH$_2$—CO$_2$H<br>\|<br>CH$_2$CH$_3$ |
| C5 | *CH—CH$_2$—CO$_2$H<br>\|<br>CH(CH$_3$)$_2$ | C6 | *CH—CH$_2$—CO$_2$H<br>\|<br>CH$_2$CH(CH$_3$)$_2$ |
| C7 | *CH—CH$_2$—CO$_2$H<br>\|<br>C(CH$_3$)$_3$ | C8 | *CH—CH$_2$—CO$_2$H<br>\|<br>CH$_2$C(CH$_3$)$_3$ |

TABLE 3-continued
| | | | |
|---|---|---|---|
| C9 | 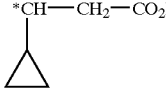 | C10 | 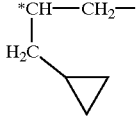 |
| C11 | 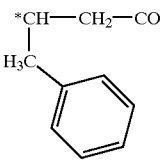 | C12 | 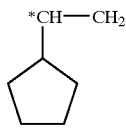 |
| C13 | 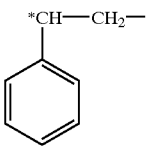 | C14 | 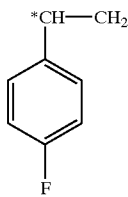 |
| C15 | 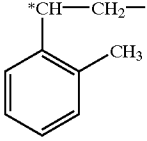 | C16 | 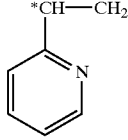 |
| C17 | 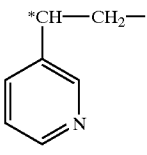 | C18 | 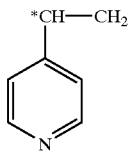 |
| C19 | 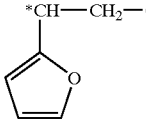 | C20 | 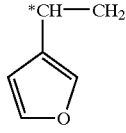 |
| C21 | 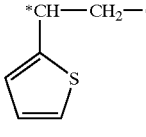 | C22 | 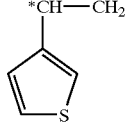 |
| C23 | 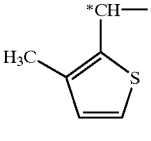 | C24 | 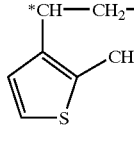 |
| C25 | 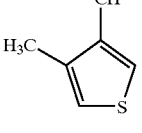 | C26 | 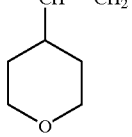 |
| C27 | 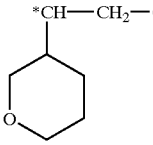 | C28 | 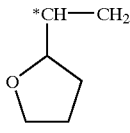 |

TABLE 3-continued
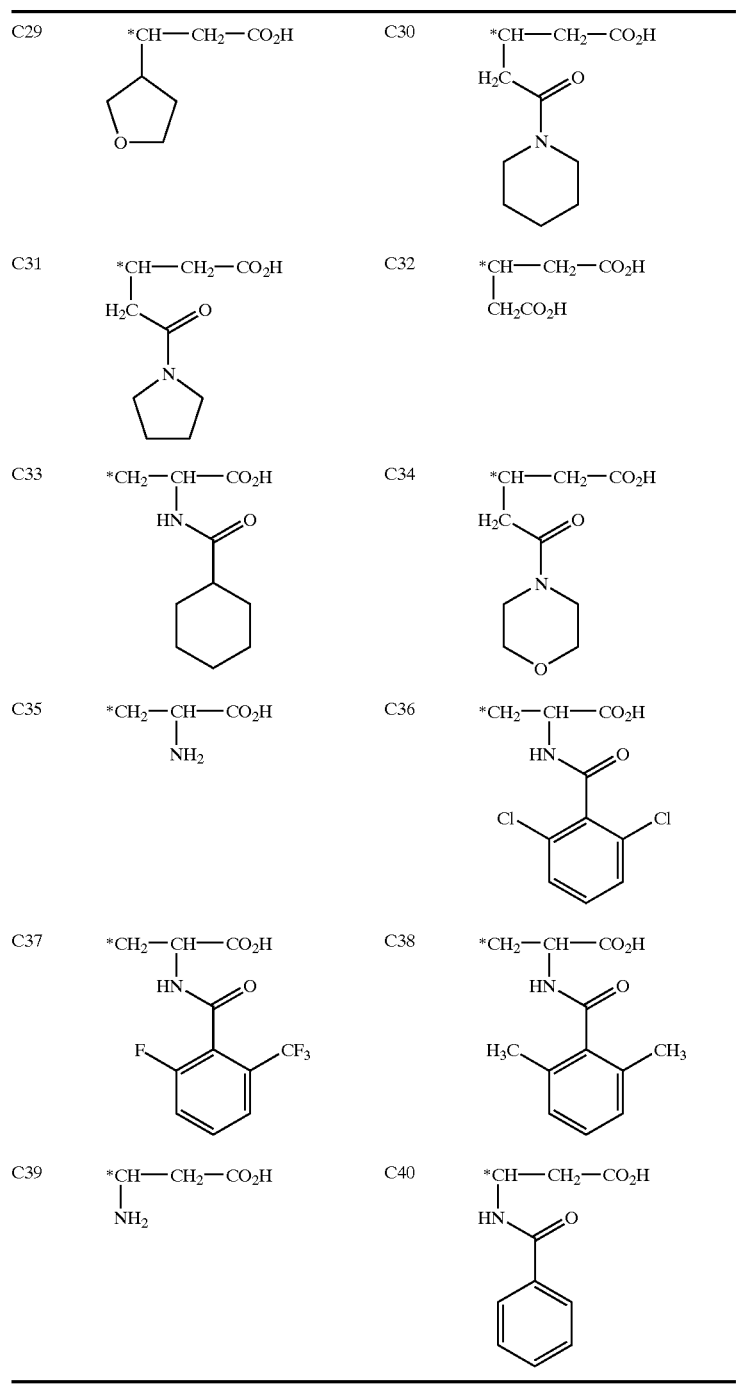
Particularly preferred examples of fragments "A", "B", and "C" are illustrated below:
| | | | | | |
|---|---|---|---|---|---|
| A1-B1-C1; | A3-B1-C2; | A5-B1-C3; | A7-B1-C4; | A9-B1-C5; | A11-B1-C6; |
| A2-B1-C1; | A4-B1-C2; | A6-B1-C3; | A8-B1-C4; | A10-B1-C5; | A12-B1-C6; |
| A3-B1-C1; | A5-B1-C2; | A7-B1-C3; | A9-B1-C4; | A11-B1-C5; | A13-B1-C6; |
| A4-B1-C1; | A6-B1-C2; | A8-B1-C3; | A10-B1-C4; | A12-B1-C5; | A14-B1-C6; |
| A5-B1-C1; | A7-B1-C2; | A9-B1-C3; | A11-B1-C4; | A13-B1-C5; | A15-B1-C6; |
| A6-B1-C1; | A8-B1-C2; | A10-B1-C3; | A12-B1-C4; | A14-B1-C5; | A16-B1-C6; |

| | | | | | |
|---|---|---|---|---|---|
| A7-B1-C1; | A9-B1-C2; | A11-B1-C3; | A13-B1-C4; | A15-B1-C5; | A17-B1-C6; |
| A8-B1-C1; | A10-B1-C2; | A12-B1-C3; | A14-B1-C4; | A16-B1-C5; | A18-B1-C6; |
| A9-B1-C1; | A11-B1-C2; | A13-B1-C3; | A15-B1-C4; | A17-B1-C5; | A19-B1-C6; |
| A10-B1-C1; | A12-B1-C2; | A14-B1-C3; | A16-B1-C4; | A18-B1-C5; | A20-B1-C6; |
| A11-B1-C1; | A13-B1-C2; | A15-B1-C3; | A17-B1-C4; | A19-B1-C5; | A21-B1-C6; |
| A12-B1-C1; | A14-B1-C2; | A16-B1-C3; | A18-B1-C4; | A20-B1-C5; | A22-B1-C6; |
| A13-B1-C1; | A15-B1-C2; | A17-B1-C3; | A19-B1-C4; | A21-B1-C5; | A23-B1-C6; |
| A14-B1-C1; | A16-B1-C2; | A18-B1-C3; | A20-B1-C4; | A22-B1-C5; | A24-B1-C6; |
| A15-B1-C1; | A17-B1-C2; | A19-B1-C3; | A21-B1-C4; | A23-B1-C5; | A25-B1-C6; |
| A16-B1-C1; | A18-B1-C2; | A20-B1-C3; | A22-B1-C4; | A24-B1-C5; | A26-B1-C6; |
| A17-B1-C1; | A19-B1-C2; | A21-B1-C3; | A23-B1-C4; | A25-B1-C5; | A27-B1-C6; |
| A18-B1-C1; | A20-B1-C2; | A22-B1-C3; | A24-B1-C4; | A26-B1-C5; | A28-B1-C6; |
| A19-B1-C1; | A21-B1-C2; | A23-B1-C3; | A25-B1-C4; | A27-B1-C5; | A29-B1-C6; |
| A20-B1-C1; | A22-B1-C2; | A24-B1-C3; | A26-B1-C4; | A28-B1-C5; | A30-B1-C6; |
| A21-B1-C1; | A23-B1-C2; | A25-B1-C3; | A27-B1-C4; | A29-B1-C5; | A31-B1-C6; |
| A22-B1-C1; | A24-B1-C2; | A26-B1-C3; | A28-B1-C4; | A30-B1-C5; | A32-B1-C6; |
| A23-B1-C1; | A25-B1-C2; | A27-B1-C3; | A29-B1-C4; | A31-B1-C5; | A1-B1-C7; |
| A24-B1-C1; | A26-B1-C2; | A28-B1-C3; | A30-B1-C4; | A32-B1-C5; | A2-B1-C7; |
| A25-B1-C1; | A27-B1-C2; | A29-B1-C3; | A31-B1-C4; | A1-B1-C6; | A3-B1-C7; |
| A26-B1-C1; | A28-B1-C2; | A30-B1-C3; | A32-B1-C4; | A2-B1-C6; | A4-B1-C7; |
| A27-B1-C1; | A29-B1-C2; | A31-B1-C3; | A1-B1-C5; | A3-B1-C6; | A5-B1-C7; |
| A28-B1-C1; | A30-B1-C2; | A32-B1-C3; | A2-B1-C5; | A4-B1-C6; | A6-B1-C7; |
| A29-B1-C1; | A31-B1-C2; | A1-B1-C4; | A3-B1-C5; | A5-B1-C6; | A7-B1-C7; |
| A30-B1-C1; | A32-B1-C2; | A2-B1-C4; | A4-B1-C5; | A6-B1-C6; | A8-B1-C7; |
| A31-B1-C1; | A1-B1-C3; | A3-B1-C4; | A5-B1-C5; | A7-B1-C6; | A9-B1-C7; |
| A32-B1-C1; | A2-B1-C3; | A4-B1-C4; | A6-B1-C5; | A8-B1-C6; | A10-B1-C7; |
| A1-B1-C2; | A3-B1-C3; | A5-B1-C4; | A7-B1-C5; | A9-B1-C6; | A11-B1-C7; |
| A2-B1-C2; | A4-B1-C3; | A6-B1-C4; | A8-B1-C5; | A10-B1-C6; | A12-B1-C7; |
| A13-B1-C7; | A16-B1-C8; | A19-B1-C9; | A22-B1-C10; | A25-B1-C11; | A28-B1-C12; |
| A14-B1-C7; | A17-B1-C8; | A20-B1-C9; | A23-B1-C10; | A26-B1-C11; | A29-B1-C12; |
| A15-B1-C7; | A18-B1-C8; | A21-B1-C9; | A24-B1-C10; | A27-B1-C11; | A30-B1-C12; |
| A16-B1-C7; | A19-B1-C8; | A22-B1-C9; | A25-B1-C10; | A28-B1-C11; | A31-B1-C12; |
| A17-B1-C7; | A20-B1-C8; | A23-B1-C9; | A26-B1-C10; | A29-B1-C11; | A32-B1-C12; |
| A18-B1-C7; | A21-B1-C8; | A24-B1-C9; | A27-B1-C10; | A30-B1-C11; | A1-B1-C13; |
| A19-B1-C7; | A22-B1-C8; | A25-B1-C9; | A28-B1-C10; | A31-B1-C11; | A2-B1-C13; |
| A20-B1-C7; | A23-B1-C8; | A26-B1-C9; | A29-B1-C10; | A32-B1-C11; | A3-B1-C13; |
| A21-B1-C7; | A24-B1-C8; | A27-B1-C9; | A30-B1-C10; | A1-B1-C12; | A4-B1-C13; |
| A22-B1-C7; | A25-B1-C8; | A28-B1-C9; | A31-B1-C10; | A2-B1-C12; | A5-B1-C13; |
| A23-B1-C7; | A26-B1-C8; | A29-B1-C9; | A32-B1-C10; | A3-B1-C12; | A6-B1-C13; |
| A24-B1-C7; | A27-B1-C8; | A30-B1-C9; | A1-B1-C11; | A4-B1-C12; | A7-B1-C13; |
| A25-B1-C7; | A28-B1-C8; | A31-B1-C9; | A2-B1-C11; | A5-B1-C12; | A8-B1-C13; |
| A26-B1-C7; | A29-B1-C8; | A32-B1-C9; | A3-B1-C11; | A6-B1-C12; | A9-B1-C13; |
| A27-B1-C7; | A30-B1-C8; | A1-B1-C10; | A4-B1-C11; | A7-B1-C12; | A10-B1-C13; |
| A28-B1-C7; | A31-B1-C8; | A2-B1-C10; | A5-B1-C11; | A8-B1-C12; | A11-B1-C13; |
| A29-B1-C7; | A32-B1-C8; | A3-B1-C10; | A6-B1-C11; | A9-B1-C12; | A12-B1-C13; |
| A30-B1-C7; | A1-B1-C9; | A4-B1-C10; | A7-B1-C11; | A10-B1-C12; | A13-B1-C13; |
| A31-B1-C7; | A2-B1-C9; | A5-B1-C10; | A8-B1-C11; | A11-B1-C12; | A14-B1-C13; |
| A32-B1-C7; | A3-B1-C9; | A6-B1-C10; | A9-B1-C11; | A12-B1-C12; | A15-B1-C13; |
| A1-B1-C8; | A4-B1-C9; | A7-B1-C10; | A10-B1-C11; | A13-B1-C12; | A16-B1-C13; |
| A2-B1-C8; | A5-B1-C9; | A8-B1-C10; | A11-B1-C11; | A14-B1-C12; | A17-B1-C13; |
| A3-B1-C8; | A6-B1-C9; | A9-B1-C10; | A12-B1-C11; | A15-B1-C12; | A18-B1-C13; |
| A4-B1-C8; | A7-B1-C9; | A10-B1-C10; | A13-B1-C11; | A16-B1-C12; | A19-B1-C13; |
| A5-B1-C8; | A8-B1-C9; | A11-B1-C10; | A14-B1-C11; | A17-B1-C12; | A20-B1-C13; |
| A6-B1-C8; | A9-B1-C9; | A12-B1-C10; | A15-B1-C11; | A18-B1-C12; | A21-B1-C13; |
| A7-B1-C8; | A10-B1-C9; | A13-B1-C10; | A16-B1-C11; | A19-B1-C12; | A22-B1-C13; |
| A8-B1-C8; | A11-B1-C9; | A14-B1-C10; | A17-B1-C11; | A20-B1-C12; | A23-B1-C13; |
| A9-B1-C8; | A12-B1-C9; | A15-B1-C10; | A18-B1-C11; | A21-B1-C12; | A24-B1-C13; |
| A10-B1-C8; | A13-B1-C9; | A16-B1-C10; | A19-B1-C11; | A22-B1-C12; | A25-B1-C13; |
| A11-B1-C8; | A14-B1-C9; | A17-B1-C10; | A20-B1-C11; | A23-B1-C12; | A26-B1-C13; |
| A12-B1-C8; | A15-B1-C9; | A18-B1-C10; | A21-B1-C11; | A24-B1-C12; | A27-B1-C13; |
| A13-B1-C8; | A16-B1-C9; | A19-B1-C10; | A22-B1-C11; | A25-B1-C12; | A28-B1-C13; |
| A14-B1-C8; | A17-B1-C9; | A20-B1-C10; | A23-B1-C11; | A26-B1-C12; | A29-B1-C13; |
| A15-B1-C8; | A18-B1-C9; | A21-B1-C10; | A24-B1-C11; | A27-B1-C12; | A30-B1-C13; |
| A31-B1-C13; | A2-B1-C15; | A5-B1-C16; | A8-B1-C17; | A11-B1-C18; | A14-B1-C19; |
| A32-B1-C13; | A3-B1-C15; | A6-B1-C16; | A9-B1-C17; | A12-B1-C18; | A15-B1-C19; |
| A1-B1-C14; | A4-B1-C15; | A7-B1-C16; | A10-B1-C17; | A13-B1-C18; | A16-B1-C19; |
| A2-B1-C14; | A5-B1-C15; | A8-B1-C16; | A11-B1-C17; | A14-B1-C18; | A17-B1-C19; |
| A3-B1-C14; | A6-B1-C15; | A9-B1-C16; | A12-B1-C17; | A15-B1-C18; | A18-B1-C19; |
| A4-B1-C14; | A7-B1-C15; | A10-B1-C16; | A13-B1-C17; | A16-B1-C18; | A19-B1-C19; |
| A5-B1-C14; | A8-B1-C15; | A11-B1-C16; | A14-B1-C17; | A17-B1-C18; | A20-B1-C19; |
| A6-B1-C14; | A9-B1-C15; | A12-B1-C16; | A15-B1-C17; | A18-B1-C18; | A21-B1-C19; |
| A7-B1-C14; | A10-B1-C15; | A13-B1-C16; | A16-B1-C17; | A19-B1-C18; | A22-B1-C19; |
| A8-B1-C14; | A11-B1-C15; | A14-B1-C16; | A17-B1-C17; | A20-B1-C18; | A23-B1-C19; |
| A9-B1-C14; | A12-B1-C15; | A15-B1-C16; | A18-B1-C17; | A21-B1-C18; | A24-B1-C19; |
| A10-B1-C14; | A13-B1-C15; | A16-B1-C16; | A19-B1-C17; | A22-B1-C18; | A25-B1-C19; |
| A11-B1-C14; | A14-B1-C15; | A17-B1-C16; | A20-B1-C17; | A23-B1-C18; | A26-B1-C19; |
| A12-B1-C14; | A15-B1-C15; | A18-B1-C16; | A21-B1-C17; | A24-B1-C18; | A27-B1-C19; |
| A13-B1-C14; | A16-B1-C15; | A19-B1-C16; | A22-B1-C17; | A25-B1-C18; | A28-B1-C19; |
| A14-B1-C14; | A17-B1-C15; | A20-B1-C16; | A23-B1-C17; | A26-B1-C18; | A29-B1-C19; |

-continued

| | | | | | |
|---|---|---|---|---|---|
| A15-B1-C14; | A18-B1-C15; | A21-B1-C16; | A24-B1-C17; | A27-B1-C18; | A30-B1-C19; |
| A16-B1-C14; | A19-B1-C15; | A22-B1-C16; | A25-B1-C17; | A28-B1-C18; | A31-B1-C19; |
| A17-B1-C14; | A20-B1-C15; | A23-B1-C16; | A26-B1-C17; | A29-B1-C18; | A32-B1-C19; |
| A18-B1-C14; | A21-B1-C15; | A24-B1-C16; | A27-B1-C17; | A30-B1-C18; | A1-B1-C20; |
| A19-B1-C14; | A22-B1-C15; | A25-B1-C16; | A28-B1-C17; | A31-B1-C18; | A2-B1-C20; |
| A20-B1-C14; | A23-B1-C15; | A26-B1-C16; | A29-B1-C17; | A32-B1-C18; | A3-B1-C20; |
| A21-B1-C14; | A24-B1-C15; | A27-B1-C16; | A30-B1-C17; | A1-B1-C19; | A4-B1-C20; |
| A22-B1-C14; | A25-B1-C15; | A28-B1-C16; | A31-B1-C17; | A2-B1-C19; | A5-B1-C20; |
| A23-B1-C14; | A26-B1-C15; | A29-B1-C16; | A32-B1-C17; | A3-B1-C19; | A6-B1-C20; |
| A24-B1-C14; | A27-B1-C15; | A30-B1-C16; | A1-B1-C18; | A4-B1-C19; | A7-B1-C20; |
| A25-B1-C14; | A28-B1-C15; | A31-B1-C16; | A2-B1-C18; | A5-B1-C19; | A8-B1-C20; |
| A26-B1-C14; | A29-B1-C15; | A32-B1-C16; | A3-B1-C18; | A6-B1-C19; | A9-B1-C20; |
| A27-B1-C14; | A30-B1-C15; | A1-B1-C17; | A4-B1-C18; | A7-B1-C19; | A10-B1-C20; |
| A28-B1-C14; | A31-B1-C15; | A2-B1-C17; | A5-B1-C18; | A8-B1-C19; | A11-B1-C20; |
| A29-B1-C14; | A32-B1-C15; | A3-B1-C17; | A6-B1-C18; | A9-B1-C19; | A12-B1-C20; |
| A30-B1-C14; | A1-B1-C16; | A4-B1-C17; | A7-B1-C18; | A10-B1-C19; | A13-B1-C20; |
| A31-B1-C14; | A2-B1-C16; | A5-B1-C17; | A8-B1-C18; | A11-B1-C19; | A14-B1-C20; |
| A32-B1-C14; | A3-B1-C16; | A6-B1-C17; | A9-B1-C18; | A12-B1-C19; | A15-B1-C20; |
| A1-B1-C15; | A4-B1-C16; | A7-B1-C17; | A10-B1-C18; | A13-B1-C19; | A16-B1-C20; |
| A17-B1-C20; | A20-B1-C21; | A23-B1-C22; | A26-B1-C23; | A29-B1-C24; | A32-B1-C25; |
| A18-B1-C20; | A21-B1-C21; | A24-B1-C22; | A27-B1-C23; | A30-B1-C24; | A1-B1-C26; |
| A19-B1-C20; | A22-B1-C21; | A25-B1-C22; | A28-B1-C23; | A31-B1-C24; | A2-B1-C26; |
| A20-B1-C20; | A23-B1-C21; | A26-B1-C22; | A29-B1-C23; | A32-B1-C24; | A3-B1-C26; |
| A21-B1-C20; | A24-B1-C21; | A27-B1-C22; | A30-B1-C23; | A1-B1-C25; | A4-B1-C26; |
| A22-B1-C20; | A25-B1-C21; | A28-B1-C22; | A31-B1-C23; | A2-B1-C25; | A5-B1-C26; |
| A23-B1-C20; | A26-B1-C21; | A29-B1-C22; | A32-B1-C23; | A3-B1-C25; | A6-B1-C26; |
| A24-B1-C20; | A27-B1-C21; | A30-B1-C22; | A1-B1-C24; | A4-B1-C25; | A7-B1-C26; |
| A25-B1-C20; | A28-B1-C21; | A31-B1-C22; | A2-B1-C24; | A5-B1-C25; | A8-B1-C26; |
| A26-B1-C20; | A29-B1-C21; | A32-B1-C22; | A3-B1-C24; | A6-B1-C25; | A9-B1-C26; |
| A27-B1-C20; | A30-B1-C21; | A1-B1-C23; | A4-B1-C24; | A7-B1-C25; | A10-B1-C26; |
| A28-B1-C20; | A31-B1-C21; | A2-B1-C23; | A5-B1-C24; | A8-B1-C25; | A11-B1-C26; |
| A29-B1-C20; | A32-B1-C21; | A3-B1-C23; | A6-B1-C24; | A9-B1-C25; | A12-B1-C26; |
| A30-B1-C20; | A1-B1-C22; | A4-B1-C23; | A7-B1-C24; | A10-B1-C25; | A13-B1-C26; |
| A31-B1-C20; | A2-B1-C22; | A5-B1-C23; | A8-B1-C24; | A11-B1-C25; | A14-B1-C26; |
| A32-B1-C20; | A3-B1-C22; | A6-B1-C23; | A9-B1-C24; | A12-B1-C25; | A15-B1-C26; |
| A1-B1-C21; | A4-B1-C22; | A7-B1-C23; | A10-B1-C24; | A13-B1-C25; | A16-B1-C26; |
| A2-B1-C21; | A5-B1-C22; | A8-B1-C23; | A11-B1-C24; | A14-B1-C25; | A17-B1-C26; |
| A3-B1-C21; | A6-B1-C22; | A9-B1-C23; | A12-B1-C24; | A15-B1-C25; | A18-B1-C26; |
| A4-B1-C21; | A7-B1-C22; | A10-B1-C23; | A13-B1-C24; | A16-B1-C25; | A19-B1-C26; |
| A5-B1-C21; | A8-B1-C22; | A11-B1-C23; | A14-B1-C24; | A17-B1-C25; | A20-B1-C26; |
| A6-B1-C21; | A9-B1-C22; | A12-B1-C23; | A15-B1-C24; | A18-B1-C25; | A21-B1-C26; |
| A7-B1-C21; | A10-B1-C22; | A13-B1-C23; | A16-B1-C24; | A19-B1-C25; | A22-B1-C26; |
| A8-B1-C21; | A11-B1-C22; | A14-B1-C23; | A17-B1-C24; | A20-B1-C25; | A23-B1-C26; |
| A9-B1-C21; | A12-B1-C22; | A15-B1-C23; | A18-B1-C24; | A21-B1-C25; | A24-B1-C26; |
| A10-B1-C21; | A13-B1-C22; | A16-B1-C23; | A19-B1-C24; | A22-B1-C25; | A25-B1-C26; |
| A11-B1-C21; | A14-B1-C22; | A17-B1-C23; | A20-B1-C24; | A23-B1-C25; | A26-B1-C26; |
| A12-B1-C21; | A15-B1-C22; | A18-B1-C23; | A21-B1-C24; | A24-B1-C25; | A27-B1-C26; |
| A13-B1-C21; | A16-B1-C22; | A19-B1-C23; | A22-B1-C24; | A25-B1-C25; | A28-B1-C26; |
| A14-B1-C21; | A17-B1-C22; | A20-B1-C23; | A23-B1-C24; | A26-B1-C25; | A29-B1-C26; |
| A15-B1-C21; | A18-B1-C22; | A21-B1-C23; | A24-B1-C24; | A27-B1-C25; | A30-B1-C26; |
| A16-B1-C21; | A19-B1-C22; | A22-B1-C23; | A25-B1-C24; | A28-B1-C25; | A31-B1-C26; |
| A17-B1-C21; | A20-B1-C22; | A23-B1-C23; | A26-B1-C24; | A29-B1-C25; | A32-B1-C26; |
| A18-B1-C21; | A21-B1-C22; | A24-B1-C23; | A27-B1-C24; | A30-B1-C25; | A1-B1-C27; |
| A19-B1-C21; | A22-B1-C22; | A25-B1-C23; | A28-B1-C24; | A31-B1-C25; | A2-B1-C27; |
| A3-B1-C27; | A6-B1-C28; | A9-B1-C29; | A12-B1-C30; | A15-B1-C31; | A18-B1-C32; |
| A4-B1-C27; | A7-B1-C28; | A10-B1-C29; | A13-B1-C30; | A16-B1-C31; | A19-B1-C32; |
| A5-B1-C27; | A8-B1-C28; | A11-B1-C29; | A14-B1-C30; | A17-B1-C31; | A20-B1-C32; |
| A6-B1-C27; | A9-B1-C28; | A12-B1-C29; | A15-B1-C30; | A18-B1-C31; | A21-B1-C32; |
| A7-B1-C27; | A10-B1-C28; | A13-B1-C29; | A16-B1-C30; | A19-B1-C31; | A22-B1-C32; |
| A8-B1-C27; | A11-B1-C28; | A14-B1-C29; | A17-B1-C30; | A20-B1-C31; | A23-B1-C32; |
| A9-B1-C27; | A12-B1-C28; | A15-B1-C29; | A18-B1-C30; | A21-B1-C31; | A24-B1-C32; |
| A10-B1-C27; | A13-B1-C28; | A16-B1-C29; | A19-B1-C30; | A22-B1-C31; | A25-B1-C32; |
| A11-B1-C27; | A14-B1-C28; | A17-B1-C29; | A20-B1-C30; | A23-B1-C31; | A26-B1-C32; |
| A12-B1-C27; | A15-B1-C28; | A18-B1-C29; | A21-B1-C30; | A24-B1-C31; | A27-B1-C32; |
| A13-B1-C27; | A16-B1-C28; | A19-B1-C29; | A22-B1-C30; | A25-B1-C31; | A28-B1-C32; |
| A14-B1-C27; | A17-B1-C28; | A20-B1-C29; | A23-B1-C30; | A26-B1-C31; | A29-B1-C32; |
| A15-B1-C27; | A18-B1-C28; | A21-B1-C29; | A24-B1-C30; | A27-B1-C31; | A30-B1-C32; |
| A16-B1-C27; | A19-B1-C28; | A22-B1-C29; | A25-B1-C30; | A28-B1-C31; | A31-B1-C32; |
| A17-B1-C27; | A20-B1-C28; | A23-B1-C29; | A26-B1-C30; | A29-B1-C31; | A32-B1-C32; |
| A18-B1-C27; | A21-B1-C28; | A24-B1-C29; | A27-B1-C30; | A30-B1-C31; | A1-B1-C33; |
| A19-B1-C27; | A22-B1-C28; | A25-B1-C29; | A28-B1-C30; | A31-B1-C31; | A2-B1-C33; |
| A20-B1-C27; | A23-B1-C28; | A26-B1-C29; | A29-B1-C30; | A32-B1-C31; | A3-B1-C33; |
| A21-B1-C27; | A24-B1-C28; | A27-B1-C29; | A30-B1-C30; | A1-B1-C32; | A4-B1-C33; |
| A22-B1-C27; | A25-B1-C28; | A28-B1-C29; | A31-B1-C30; | A2-B1-C32; | A5-B1-C33; |
| A23-B1-C27; | A26-B1-C28; | A29-B1-C29; | A32-B1-C30; | A3-B1-C32; | A6-B1-C33; |
| A24-B1-C27; | A27-B1-C28; | A30-B1-C29; | A1-B1-C31; | A4-B1-C32; | A7-B1-C33; |
| A25-B1-C27; | A28-B1-C28; | A31-B1-C29; | A2-B1-C31; | A5-B1-C32; | A8-B1-C33; |
| A26-B1-C27; | A29-B1-C28; | A32-B1-C29; | A3-B1-C31; | A6-B1-C32; | A9-B1-C33; |
| A27-B1-C27; | A30-B1-C28; | A1-B1-C30; | A4-B1-C31; | A7-B1-C32; | A10-B1-C33; |

-continued

| | | | | | |
|---|---|---|---|---|---|
| A28-B1-C27; | A31-B1-C28; | A2-B1-C30; | A5-B1-C31; | A8-B1-C32; | A11-B1-C33; |
| A29-B1-C27; | A32-B1-C28; | A3-B1-C30; | A6-B1-C31; | A9-B1-C32; | A12-B1-C33; |
| A30-B1-C27; | A1-B1-C29; | A4-B1-C30; | A7-B1-C31; | A10-B1-C32; | A13-B1-C33; |
| A31-B1-C27; | A2-B1-C29; | A5-B1-C30; | A8-B1-C31; | A11-B1-C32; | A14-B1-C33; |
| A32-B1-C27; | A3-B1-C29; | A6-B1-C30; | A9-B1-C31; | A12-B1-C32; | A15-B1-C33; |
| A1-B1-C28; | A4-B1-C29; | A7-B1-C30; | A10-B1-C31; | A13-B1-C32; | A16-B1-C33; |
| A2-B1-C28; | A5-B1-C29; | A8-B1-C30; | A11-B1-C31; | A14-B1-C32; | A17-B1-C33; |
| A3-B1-C28; | A6-B1-C29; | A9-B1-C30; | A12-B1-C31; | A15-B1-C32; | A18-B1-C33; |
| A4-B1-C28; | A7-B1-C29; | A10-B1-C30; | A13-B1-C31; | A16-B1-C32; | A19-B1-C33; |
| A5-B1-C28; | A8-B1-C29; | A11-B1-C30; | A14-B1-C31; | A17-B1-C32; | A20-B1-C33; |
| A21-B1-C33; | A24-B1-C34; | A27-B1-C35; | A30-B1-C36; | A1-B1-C38; | A4-B1-C39; |
| A22-B1-C33; | A25-B1-C34; | A28-B1-C35; | A31-B1-C36; | A2-B1-C38; | A5-B1-C39; |
| A23-B1-C33; | A26-B1-C34; | A29-B1-C35; | A32-B1-C36; | A3-B1-C38; | A6-B1-C39; |
| A24-B1-C33; | A27-B1-C34; | A30-B1-C35; | A1-B1-C37; | A4-B1-C38; | A7-B1-C39; |
| A25-B1-C33; | A28-B1-C34; | A31-B1-C35; | A2-B1-C37; | A5-B1-C38; | A8-B1-C39; |
| A26-B1-C33; | A29-B1-C34; | A32-B1-C35; | A3-B1-C37; | A6-B1-C38; | A9-B1-C39; |
| A27-B1-C33; | A30-B1-C34; | A1-B1-C36; | A4-B1-C37; | A7-B1-C38; | A10-B1-C39; |
| A28-B1-C33; | A31-B1-C34; | A2-B1-C36; | A5-B1-C37; | A8-B1-C38; | A11-B1-C39; |
| A29-B1-C33; | A32-B1-C34; | A3-B1-C36; | A6-B1-C37; | A9-B1-C38; | A12-B1-C39; |
| A30-B1-C33; | A1-B1-C35; | A4-B1-C36; | A7-B1-C37; | A10-B1-C38; | A13-B1-C39; |
| A31-B1-C33; | A2-B1-C35; | A5-B1-C36; | A8-B1-C37; | A11-B1-C38; | A14-B1-C39; |
| A32-B1-C33; | A3-B1-C35; | A6-B1-C36; | A9-B1-C37; | A12-B1-C38; | A15-B1-C39; |
| A1-B1-C34; | A4-B1-C35; | A7-B1-C36; | A10-B1-C37; | A13-B1-C38; | A16-B1-C39; |
| A2-B1-C34; | A5-B1-C35; | A8-B1-C36; | A11-B1-C37; | A14-B1-C38; | A17-B1-C39; |
| A3-B1-C34; | A6-B1-C35; | A9-B1-C36; | A12-B1-C37; | A15-B1-C38; | A18-B1-C39; |
| A4-B1-C34; | A7-B1-C35; | A10-B1-C36; | A13-B1-C37; | A16-B1-C38; | A19-B1-C39; |
| A5-B1-C34; | A8-B1-C35; | A11-B1-C36; | A14-B1-C37; | A17-B1-C38; | A20-B1-C39; |
| A6-B1-C34; | A9-B1-C35; | A12-B1-C36; | A15-B1-C37; | A18-B1-C38; | A21-B1-C39; |
| A7-B1-C34; | A10-B1-C35; | A13-B1-C36; | A16-B1-C37; | A19-B1-C38; | A22-B1-C39; |
| A8-B1-C34; | A11-B1-C35; | A14-B1-C36; | A17-B1-C37; | A20-B1-C38; | A23-B1-C39; |
| A9-B1-C34; | A12-B1-C35; | A15-B1-C36; | A18-B1-C37; | A21-B1-C38; | A24-B1-C39; |
| A10-B1-C34; | A13-B1-C35; | A16-B1-C36; | A19-B1-C37; | A22-B1-C38; | A25-B1-C39; |
| A11-B1-C34; | A14-B1-C35; | A17-B1-C36; | A20-B1-C37; | A23-B1-C38; | A26-B1-C39; |
| A12-B1-C34; | A15-B1-C35; | A18-B1-C36; | A21-B1-C37; | A24-B1-C38; | A27-B1-C39; |
| A13-B1-C34; | A16-B1-C35; | A19-B1-C36; | A22-B1-C37; | A25-B1-C38; | A28-B1-C39; |
| A14-B1-C34; | A17-B1-C35; | A20-B1-C36; | A23-B1-C37; | A26-B1-C38; | A29-B1-C39; |
| A15-B1-C34; | A18-B1-C35; | A21-B1-C36; | A24-B1-C37; | A27-B1-C38; | A30-B1-C39; |
| A16-B1-C34; | A19-B1-C35; | A22-B1-C36; | A25-B1-C37; | A28-B1-C38; | A31-B1-C39; |
| A17-B1-C34; | A20-B1-C35; | A23-B1-C36; | A26-B1-C37; | A29-B1-C38; | A32-B1-C39; |
| A18-B1-C34; | A21-B1-C35; | A24-B1-C36; | A27-B1-C37; | A30-B1-C38; | A1-B1-C40; |
| A19-B1-C34; | A22-B1-C35; | A25-B1-C36; | A28-B1-C37; | A31-B1-C38; | A2-B1-C40; |
| A20-B1-C34; | A23-B1-C35; | A26-B1-C36; | A29-B1-C37; | A32-B1-C38; | A3-B1-C40; |
| A21-B1-C34; | A24-B1-C35; | A27-B1-C36; | A30-B1-C37; | A1-B1-C39; | A4-B1-C40; |
| A22-B1-C34; | A25-B1-C35; | A28-B1-C36; | A31-B1-C37; | A2-B1-C39; | A5-B1-C40; |
| A23-B1-C34; | A26-B1-C35; | A29-B1-C36; | A32-B1-C37; | A3-B1-C39; | A6-B1-C40; |
| A7-B1-C40; | A10-B2-C1; | A13-B2-C2; | A16-B2-C3; | A19-B2-C4; | A22-B2-C5; |
| A8-B1-C40; | A11-B2-C1; | A14-B2-C2; | A17-B2-C3; | A20-B2-C4; | A23-B2-C5; |
| A9-B1-C40; | A12-B2-C1; | A15-B2-C2; | A18-B2-C3; | A21-B2-C4; | A24-B2-C5; |
| A10-B1-C40; | A13-B2-C1; | A16-B2-C2; | A19-B2-C3; | A22-B2-C4; | A25-B2-C5; |
| A11-B1-C40; | A14-B2-C1; | A17-B2-C2; | A20-B2-C3; | A23-B2-C4; | A26-B2-C5; |
| A12-B1-C40; | A15-B2-C1; | A18-B2-C2; | A21-B2-C3; | A24-B2-C4; | A27-B2-C5; |
| A13-B1-C40; | A16-B2-C1; | A19-B2-C2; | A22-B2-C3; | A25-B2-C4; | A28-B2-C5; |
| A14-B1-C40; | A17-B2-C1; | A20-B2-C2; | A23-B2-C3; | A26-B2-C4; | A29-B2-C5; |
| A15-B1-C40; | A18-B2-C1; | A21-B2-C2; | A24-B2-C3; | A27-B2-C4; | A30-B2-C5; |
| A16-B1-C40; | A19-B2-C1; | A22-B2-C2; | A25-B2-C3; | A28-B2-C4; | A31-B2-C5; |
| A17-B1-C40; | A20-B2-C1; | A23-B2-C2; | A26-B2-C3; | A29-B2-C4; | A32-B2-C5; |
| A18-B1-C40; | A21-B2-C1; | A24-B2-C2; | A27-B2-C3; | A30-B2-C4; | A1-B2-C6; |
| A19-B1-C40; | A22-B2-C1; | A25-B2-C2; | A28-B2-C3; | A31-B2-C4; | A2-B2-C6; |
| A20-B1-C40; | A23-B2-C1; | A26-B2-C2; | A29-B2-C3; | A32-B2-C4; | A3-B2-C6; |
| A21-B1-C40; | A24-B2-C1; | A27-B2-C2; | A30-B2-C3; | A1-B2-C5; | A4-B2-C6; |
| A22-B1-C40; | A25-B2-C1; | A28-B2-C2; | A31-B2-C3; | A2-B2-C5; | A5-B2-C6; |
| A23-B1-C40; | A26-B2-C1; | A29-B2-C2; | A32-B2-C3; | A3-B2-C5; | A6-B2-C6; |
| A24-B1-C40; | A27-B2-C1; | A30-B2-C2; | A1-B2-C4; | A4-B2-C5; | A7-B2-C6; |
| A25-B1-C40; | A28-B2-C1; | A31-B2-C2; | A2-B2-C4; | A5-B2-C5; | A8-B2-C6; |
| A26-B1-C40; | A29-B2-C1; | A32-B2-C2; | A3-B2-C4; | A6-B2-C5; | A9-B2-C6; |
| A27-B1-C40; | A30-B2-C1; | A1-B2-C3; | A4-B2-C4; | A7-B2-C5; | A10-B2-C6; |
| A28-B1-C40; | A31-B2-C1; | A2-B2-C3; | A5-B2-C4; | A8-B2-C5; | A11-B2-C6; |
| A29-B1-C40; | A32-B2-C1; | A3-B2-C3; | A6-B2-C4; | A9-B2-C5; | A12-B2-C6; |
| A30-B1-C40; | A1-B2-C2; | A4-B2-C3; | A7-B2-C4; | A10-B2-C5; | A13-B2-C6; |
| A31-B1-C40; | A2-B2-C2; | A5-B2-C3; | A8-B2-C4; | A11-B2-C5; | A14-B2-C6; |
| A32-B1-C40; | A3-B2-C2; | A6-B2-C3; | A9-B2-C4; | A12-B2-C5; | A15-B2-C6; |
| A1-B2-C1; | A4-B2-C2; | A7-B2-C3; | A10-B2-C4; | A13-B2-C5; | A16-B2-C6; |
| A2-B2-C1; | A5-B2-C2; | A8-B2-C3; | A11-B2-C4; | A14-B2-C5; | A17-B2-C6; |
| A3-B2-C1; | A6-B2-C2; | A9-B2-C3; | A12-B2-C4; | A15-B2-C5; | A18-B2-C6; |
| A4-B2-C1; | A7-B2-C2; | A10-B2-C3; | A13-B2-C4; | A16-B2-C5; | A19-B2-C6; |
| A5-B2-C1; | A8-B2-C2; | A11-B2-C3; | A14-B2-C4; | A17-B2-C5; | A20-B2-C6; |
| A6-B2-C1; | A9-B2-C2; | A12-B2-C3; | A15-B2-C4; | A18-B2-C5; | A21-B2-C6; |
| A7-B2-C1; | A10-B2-C2; | A13-B2-C3; | A16-B2-C4; | A19-B2-C5; | A22-B2-C6; |
| A8-B2-C1; | A11-B2-C2; | A14-B2-C3; | A17-B2-C4; | A20-B2-C5; | A23-B2-C6; |

-continued

| | | | | | |
|---|---|---|---|---|---|
| A9-B2-C1; | A12-B2-C2; | A15-B2-C3; | A18-B2-C4; | A21-B2-C5; | A24-B2-C6; |
| A25-B2-C6; | A28-B2-C7; | A31-B2-C8; | A2-B2-C10; | A5-B2-C11; | A8-B2-C12; |
| A26-B2-C6; | A29-B2-C7; | A32-B2-C8; | A3-B2-C10; | A6-B2-C11; | A9-B2-C12; |
| A27-B2-C6; | A30-B2-C7; | A1-B2-C9; | A4-B2-C10; | A7-B2-C11; | A10-B2-C12; |
| A28-B2-C6; | A31-B2-C7; | A2-B2-C9; | A5-B2-C10; | A8-B2-C11; | A11-B2-C12; |
| A29-B2-C6; | A32-B2-C7; | A3-B2-C9; | A6-B2-C10; | A9-B2-C11; | A12-B2-C12; |
| A30-B2-C6; | A1-B2-C8; | A4-B2-C9; | A7-B2-C10; | A10-B2-C11; | A13-B2-C12; |
| A31-B2-C6; | A2-B2-C8; | A5-B2-C9; | A8-B2-C10; | A11-B2-C11; | A14-B2-C12; |
| A32-B2-C6; | A3-B2-C8; | A6-B2-C9; | A9-B2-C10; | A12-B2-C11; | A15-B2-C12; |
| A1-B2-C7; | A4-B2-C8; | A7-B2-C9; | A10-B2-C10; | A13-B2-C11; | A16-B2-C12; |
| A2-B2-C7; | A5-B2-C8; | A8-B2-C9; | A11-B2-C10; | A14-B2-C11; | A17-B2-C12; |
| A3-B2-C7; | A6-B2-C8; | A9-B2-C9; | A12-B2-C10; | A15-B2-C11; | A18-B2-C12; |
| A4-B2-C7; | A7-B2-C8; | A10-B2-C9; | A13-B2-C10; | A16-B2-C11; | A19-B2-C12; |
| A5-B2-C7; | A8-B2-C8; | A11-B2-C9; | A14-82-C10; | A17-B2-C11; | A20-B2-C12; |
| A6-B2-C7; | A9-B2-C8; | A12-B2-C9; | A15-B2-C10; | A18-B2-C11; | A21-B2-C12; |
| A7-B2-C7; | A10-B2-C8; | A13-B2-C9; | A16-B2-C10; | A19-B2-C11; | A22-B2-C12; |
| A8-B2-C7; | A11-B2-C8; | A14-B2-C9; | A17-B2-C10; | A20-B2-C11; | A23-B2-C12; |
| A9-B2-C7; | A12-B2-C8; | A15-B2-C9; | A18-B2-C10; | A21-B2-C11; | A24-B2-C12; |
| A10-B2-C7; | A13-B2-C8; | A16-B2-C9; | A19-B2-C10; | A22-B2-C11; | A25-B2-C12; |
| A11-B2-C7; | A14-B2-C8; | A17-B2-C9; | A20-B2-C10; | A23-B2-C11; | A26-B2-C12; |
| A12-B2-C7; | A15-B2-C8; | A18-B2-C9; | A21-B2-C10; | A24-B2-C11; | A27-B2-C12; |
| A13-B2-C7; | A16-B2-C8; | A19-B2-C9; | A22-B2-C10; | A25-B2-C11; | A28-B2-C12; |
| A14-B2-C7; | A17-B2-C8; | A20-B2-C9; | A23-B2-C10; | A26-B2-C11; | A29-B2-C12; |
| A15-B2-C7; | A18-B2-C8; | A21-B2-C9; | A24-B2-C10; | A27-B2-C11; | A30-B2-C12; |
| A16-B2-C7; | A19-B2-C8; | A22-B2-C9; | A25-B2-C10; | A28-B2-C11; | A31-B2-C12; |
| A17-B2-C7; | A20-B2-C8; | A23-B2-C9; | A26-B2-C10; | A29-B2-C11; | A32-B2-C12; |
| A18-B2-C7; | A21-B2-C8; | A24-B2-C9; | A27-B2-C10; | A30-B2-C11; | A1-B2-C13; |
| A19-B2-C7; | A22-B2-C8; | A25-B2-C9; | A28-B2-C10; | A31-B2-C11; | A2-B2-C13; |
| A20-B2-C7; | A23-B2-C8; | A26-B2-C9; | A29-B2-C10; | A32-B2-C11; | A3-B2-C13; |
| A21-B2-C7; | A24-B2-C8; | A27-B2-C9; | A30-B2-C10; | A1-B2-C12; | A4-B2-C13; |
| A22-B2-C7; | A25-B2-C8; | A28-B2-C9; | A31-B2-C10; | A2-B2-C12; | A5-B2-C13; |
| A23-B2-C7; | A26-B2-C8; | A29-B2-C9; | A32-B2-C10; | A3-B2-C12; | A6-B2-C13; |
| A24-B2-C7; | A27-B2-C8; | A30-B2-C9; | A1-B2-C11; | A4-B2-C12; | A7-B2-C13; |
| A25-B2-C7; | A28-B2-C8; | A31-B2-C9; | A2-B2-C11; | A5-B2-C12; | A8-B2-C13; |
| A26-B2-C7; | A29-B2-C8; | A32-B2-C9; | A3-B2-C11; | A6-B2-C12; | A9-B2-C13; |
| A27-B2-C7; | A30-B2-C8; | A1-B2-C10; | A4-B2-C11; | A7-B2-C12; | A10-B2-C13; |
| A11-B2-C13; | A14-B2-C14; | A17-B2-C15; | A20-B2-C16; | A23-B2-C17; | A26-B2-C18; |
| A12-B2-C13; | A15-B2-C14; | A18-B2-C15; | A21-B2-C16; | A24-B2-C17; | A27-B2-C18; |
| A13-B2-C13; | A16-B2-C14; | A19-B2-C15; | A22-B2-C16; | A25-B2-C17; | A28-B2-C18; |
| A14-B2-C13; | A17-B2-C14; | A20-B2-C15; | A23-B2-C16; | A26-B2-C17; | A29-B2-C18; |
| A15-B2-C13; | A18-B2-C14; | A21-B2-C15; | A24-B2-C16; | A27-B2-C17; | A30-B2-C18; |
| A16-B2-C13; | A19-B2-C14; | A22-B2-C15; | A25-B2-C16; | A28-B2-C17; | A31-B2-C18; |
| A17-B2-C13; | A20-B2-C14; | A23-B2-C15; | A26-B2-C16; | A29-B2-C17; | A32-B2-C18; |
| A18-B2-C13; | A21-B2-C14; | A24-B2-C15; | A27-B2-C16; | A30-B2-C17; | A1-B2-C19; |
| A19-B2-C13; | A22-B2-C14; | A25-B2-C15; | A28-B2-C16; | A31-B2-C17; | A2-B2-C19; |
| A20-B2-C13; | A23-B2-C14; | A26-B2-C15; | A29-B2-C16; | A32-B2-C17; | A3-B2-C19; |
| A21-B2-C13; | A24-B2-C14; | A27-B2-C15; | A30-B2-C16; | A1-B2-C18; | A4-B2-C19; |
| A22-B2-C13; | A25-B2-C14; | A28-B2-C15; | A31-B2-C16; | A2-B2-C18; | A5-B2-C19; |
| A23-B2-C13; | A26-B2-C14; | A29-B2-C15; | A32-B2-C16; | A3-B2-C18; | A6-B2-C19; |
| A24-B2-C13; | A27-B2-C14; | A30-B2-C15; | A1-B2-C17; | A4-B2-C18; | A7-B2-C19; |
| A25-B2-C13; | A28-B2-C14; | A31-B2-C15; | A2-B2-C17; | A5-B2-C18; | A8-B2-C19; |
| A26-B2-C13; | A29-B2-C14; | A32-B2-C15; | A3-B2-C17; | A6-B2-C18; | A9-B2-C19; |
| A27-B2-C13; | A30-B2-C14; | A1-B2-C16; | A4-B2-C17; | A7-B2-C18; | A10-B2-C19; |
| A28-B2-C13; | A31-B2-C14; | A2-B2-C16; | A5-B2-C17; | A8-B2-C18; | A11-B2-C19; |
| A29-B2-C13; | A32-B2-C14; | A3-B2-C16; | A6-B2-C17; | A9-B2-C18; | A12-B2-C19; |
| A30-B2-C13; | A1-B2-C15; | A4-B2-C16; | A7-B2-C17; | A10-B2-C18; | A13-B2-C19; |
| A31-B2-C13; | A2-B2-C15; | A5-B2-C16; | A8-B2-C17; | A11-B2-C18; | A14-B2-C19; |
| A32-B2-C13; | A3-B2-C15; | A6-B2-C16; | A9-B2-C17; | A12-B2-C18; | A15-B2-C19; |
| A1-B2-C14; | A4-B2-C15; | A7-B2-C16; | A10-B2-C17; | A13-B2-C18; | A16-B2-C19; |
| A2-B2-C14; | A5-B2-C15; | A8-B2-C16; | A11-B2-C17; | A14-B2-C18; | A17-B2-C19; |
| A3-B2-C14; | A6-B2-C15; | A9-B2-C16; | A12-B2-C17; | A15-B2-C18; | A18-B2-C19; |
| A4-B2-C14; | A7-B2-C15; | A10-B2-C16; | A13-B2-C17; | A16-B2-C18; | A19-B2-C19; |
| A5-B2-C14; | A8-B2-C15; | A11-B2-C16; | A14-B2-C17; | A17-B2-C18; | A20-B2-C19; |
| A6-B2-C14; | A9-B2-C15; | A12-B2-C16; | A15-B2-C17; | A18-B2-C18; | A21-B2-C19; |
| A7-B2-C14; | A10-B2-C15; | A13-B2-C16; | A16-B2-C17; | A19-B2-C18; | A22-B2-C19; |
| A8-B2-C14; | A11-B2-C15; | A14-B2-C16; | A17-B2-C17; | A20-B2-C18; | A23-B2-C19; |
| A9-B2-C14; | A12-B2-C15; | A15-B2-C16; | A18-B2-C17; | A21-B2-C18; | A24-B2-C19; |
| A10-B2-C14; | A13-B2-C15; | A16-B2-C16; | A19-B2-C17; | A22-B2-C18; | A25-B2-C19; |
| A11-B2-C14; | A14-B2-C15; | A17-B2-C16; | A20-B2-C17; | A23-B2-C18; | A26-B2-C19; |
| A12-B2-C14; | A15-B2-C15; | A18-B2-C16; | A21-B2-C17; | A24-B2-C18; | A27-B2-C19; |
| A13-B2-C14; | A16-B2-C15; | A19-B2-C16; | A22-B2-C17; | A25-B2-C18; | A28-B2-C19; |
| A29-B2-C19; | A32-B2-C20; | A3-B2-C22; | A6-B2-C23; | A9-B2-C24; | A12-B2-C25; |
| A30-B2-C19; | A1-B2-C21; | A4-B2-C22; | A7-B2-C23; | A10-B2-C24; | A13-B2-C25; |
| A31-B2-C19; | A2-B2-C21; | A5-B2-C22; | A8-B2-C23; | A11-B2-C24; | A14-B2-C25; |
| A32-B2-C19; | A3-B2-C21; | A6-B2-C22; | A9-B2-C23; | A12-B2-C24; | A15-B2-C25; |
| A1-B2-C20; | A4-B2-C21; | A7-B2-C22; | A10-B2-C23; | A13-B2-C24; | A16-B2-C25; |
| A2-B2-C20; | A5-B2-C21; | A8-B2-C22; | A11-B2-C23; | A14-B2-C24; | A17-B2-C25; |
| A3-B2-C20; | A6-B2-C21; | A9-B2-C22; | A12-B2-C23; | A15-B2-C24; | A18-B2-C25; |
| A4-B2-C20; | A7-B2-C21; | A10-B2-C22; | A13-B2-C23; | A16-B2-C24; | A19-B2-C25; |

-continued

| | | | | | |
|---|---|---|---|---|---|
| A5-B2-C20; | A8-B2-C21; | A11-B2-C22; | A14-B2-C23; | A17-B2-C24; | A20-B2-C25; |
| A6-B2-C20; | A9-B2-C21; | A12-B2-C22; | A15-B2-C23; | A18-B2-C24; | A21-B2-C25; |
| A7-B2-C20; | A10-B2-C21; | A13-B2-C22; | A16-B2-C23; | A19-B2-C24; | A22-B2-C25; |
| A8-B2-C20; | A11-B2-C21; | A14-B2-C22; | A17-B2-C23; | A20-B2-C24; | A23-B2-C25; |
| A9-B2-C20; | A12-B2-C21; | A15-B2-C22; | A18-B2-C23; | A21-B2-C24; | A24-B2-C25; |
| A10-B2-C20; | A13-B2-C21; | A16-B2-C22; | A19-B2-C23; | A22-B2-C24; | A25-B2-C25; |
| A11-B2-C20; | A14-B2-C21; | A17-B2-C22; | A20-B2-C23; | A23-B2-C24; | A26-B2-C25; |
| A12-B2-C20; | A15-B2-C21; | A18-B2-C22; | A21-B2-C23; | A24-B2-C24; | A27-B2-C25; |
| A13-B2-C20; | A16-B2-C21; | A19-B2-C22; | A22-B2-C23; | A25-B2-C24; | A28-B2-C25; |
| A14-B2-C20; | A17-B2-C21; | A20-B2-C22; | A23-B2-C23; | A26-B2-C24; | A29-B2-C25; |
| A15-B2-C20; | A18-B2-C21; | A21-B2-C22; | A24-B2-C23; | A27-B2-C24; | A30-B2-C25; |
| A16-B2-C20; | A19-B2-C21; | A22-B2-C22; | A25-B2-C23; | A28-B2-C24; | A31-B2-C25; |
| A17-B2-C20; | A20-B2-C21; | A23-B2-C22; | A26-B2-C23; | A29-B2-C24; | A32-B2-C25; |
| A18-B2-C20; | A21-B2-C21; | A24-B2-C22; | A27-B2-C23; | A30-B2-C24; | A1-B2-C26; |
| A19-B2-C20; | A22-B2-C21; | A25-B2-C22; | A28-B2-C23; | A31-B2-C24; | A2-B2-C26; |
| A20-B2-C20; | A23-B2-C21; | A26-B2-C22; | A29-B2-C23; | A32-B2-C24; | A3-B2-C26; |
| A21-B2-C20; | A24-B2-C21; | A27-B2-C22; | A30-B2-C23; | A1-B2-C25; | A4-B2-C26; |
| A22-B2-C20; | A25-B2-C21; | A28-B2-C22; | A31-B2-C23; | A2-B2-C25; | A5-B2-C26; |
| A23-B2-C20; | A26-B2-C21; | A29-B2-C22; | A32-B2-C23; | A3-B2-C25; | A6-B2-C26; |
| A24-B2-C20; | A27-B2-C21; | A30-B2-C22; | A1-B2-C24; | A4-B2-C25; | A7-B2-C26; |
| A25-B2-C20; | A28-B2-C21; | A31-B2-C22; | A2-B2-C24; | A5-B2-C25; | A8-B2-C26; |
| A26-B2-C20; | A29-B2-C21; | A32-B2-C22; | A3-B2-C24; | A6-B2-C25; | A9-B2-C26; |
| A27-B2-C20; | A30-B2-C21; | A1-B2-C23; | A4-B2-C24; | A7-B2-C25; | A10-B2-C26; |
| A28-B2-C20; | A31-B2-C21; | A2-B2-C23; | A5-B2-C24; | A8-B2-C25; | A11-B2-C26; |
| A29-B2-C20; | A32-B2-C21; | A3-B2-C23; | A6-B2-C24; | A9-B2-C25; | A12-B2-C26; |
| A30-B2-C20; | A1-B2-C22; | A4-B2-C23; | A7-B2-C24; | A10-B2-C25; | A13-B2-C26; |
| A31-B2-C20; | A2-B2-C22; | A5-B2-C23; | A8-B2-C24; | A11-B2-C25; | A14-B2-C26; |
| A15-B2-C26; | A18-B2-C27; | A21-B2-C28; | A24-B2-C29; | A27-B2-C30; | A30-B2-C31; |
| A16-B2-C26; | A19-B2-C27; | A22-B2-C28; | A25-B2-C29; | A28-B2-C30; | A31-B2-C31; |
| A17-B2-C26; | A20-B2-C27; | A23-B2-C28; | A26-B2-C29; | A29-B2-C30; | A32-B2-C31; |
| A18-B2-C26; | A21-B2-C27; | A24-B2-C28; | A27-B2-C29; | A30-B2-C30; | A1-B2-C32; |
| A19-B2-C26; | A22-B2-C27; | A25-B2-C28; | A28-B2-C29; | A31-B2-C30; | A2-B2-C32; |
| A20-B2-C26; | A23-B2-C27; | A26-B2-C28; | A29-B2-C29; | A32-B2-C30; | A3-B2-C32; |
| A21-B2-C26; | A24-B2-C27; | A27-B2-C28; | A30-B2-C29; | A1-B2-C31; | A4-B2-C32; |
| A22-B2-C26; | A25-B2-C27; | A28-B2-C28; | A31-B2-C29; | A2-B2-C31; | A5-B2-C32; |
| A23-B2-C26; | A26-B2-C27; | A29-B2-C28; | A32-B2-C29; | A3-B2-C31; | A6-B2-C32; |
| A24-B2-C26; | A27-B2-C27; | A30-B2-C28; | A1-B2-C30; | A4-B2-C31; | A7-B2-C32; |
| A25-B2-C26; | A28-B2-C27; | A31-B2-C28; | A2-B2-C30; | A5-B2-C31; | A8-B2-C32; |
| A26-B2-C26; | A29-B2-C27; | A32-B2-C28; | A3-B2-C30; | A6-B2-C31; | A9-B2-C32; |
| A27-B2-C26; | A30-B2-C27; | A1-B2-C29; | A4-B2-C30; | A7-B2-C31; | A10-B2-C32; |
| A28-B2-C26; | A31-B2-C27; | A2-B2-C29; | A5-B2-C30; | A8-B2-C31; | A11-B2-C32; |
| A29-B2-C26; | A32-B2-C27; | A3-B2-C29; | A6-B2-C30; | A9-B2-C31; | A12-B2-C32; |
| A30-B2-C26; | A1-B2-C28; | A4-B2-C29; | A7-B2-C30; | A10-B2-C31; | A13-B2-C32; |
| A31-B2-C26; | A2-B2-C28; | A5-B2-C29; | A8-B2-C30; | A11-B2-C31; | A14-B2-C32; |
| A32-B2-C26; | A3-B2-C28; | A6-B2-C29; | A9-B2-C30; | A12-B2-C31; | A15-B2-C32; |
| A1-B2-C27; | A4-B2-C28; | A7-B2-C29; | A10-B2-C30; | A13-B2-C31; | A16-B2-C32; |
| A2-B2-C27; | A5-B2-C28; | A8-B2-C29; | A11-B2-C30; | A14-B2-C31; | A17-B2-C32; |
| A3-B2-C27; | A6-B2-C28; | A9-B2-C29; | A12-B2-C30; | A15-B2-C31; | A18-B2-C32; |
| A4-B2-C27; | A7-B2-C28; | A10-B2-C29; | A13-B2-C30; | A16-B2-C31; | A19-B2-C32; |
| A5-B2-C27; | A8-B2-C28; | A11-B2-C29; | A14-B2-C30; | A17-B2-C31; | A20-B2-C32; |
| A6-B2-C27; | A9-B2-C28; | A12-B2-C29; | A15-B2-C30; | A18-B2-C31; | A21-B2-C32; |
| A7-B2-C27; | A10-B2-C28; | A13-B2-C29; | A16-B2-C30; | A19-B2-C31; | A22-B2-C32; |
| A8-B2-C27; | A11-B2-C28; | A14-B2-C29; | A17-B2-C30; | A20-B2-C31; | A23-B2-C32; |
| A9-B2-C27; | A12-B2-C28; | A15-B2-C29; | A18-B2-C30; | A21-B2-C31; | A24-B2-C32; |
| A10-B2-C27; | A13-B2-C28; | A16-B2-C29; | A19-B2-C30; | A22-B2-C31; | A25-B2-C32; |
| A11-B2-C27; | A14-B2-C28; | A17-B2-C29; | A20-B2-C30; | A23-B2-C31; | A26-B2-C32; |
| A12-B2-C27; | A15-B2-C28; | A18-B2-C29; | A21-B2-C30; | A24-B2-C31; | A27-B2-C32; |
| A13-B2-C27; | A16-B2-C28; | A19-B2-C29; | A22-B2-C30; | A25-B2-C31; | A28-B2-C32; |
| A14-B2-C27; | A17-B2-C28; | A20-B2-C29; | A23-B2-C30; | A26-B2-C31; | A29-B2-C32; |
| A15-B2-C27; | A18-B2-C28; | A21-B2-C29; | A24-B2-C30; | A27-B2-C31; | A30-B2-C32; |
| A16-B2-C27; | A19-B2-C28; | A22-B2-C29; | A25-B2-C30; | A28-B2-C31; | A31-B2-C32; |
| A17-B2-C27; | A20-B2-C28; | A23-B2-C29; | A26-B2-C30; | A29-B2-C31; | A32-B2-C32; |
| A1-B2-C33; | A4-B2-C34; | A7-B2-C35; | A10-B2-C36; | A13-B2-C37; | A16-B2-C38; |
| A2-B2-C33; | A5-B2-C34; | A8-B2-C35; | A11-B2-C36; | A14-B2-C37; | A17-B2-C38; |
| A3-B2-C33; | A6-B2-C34; | A9-B2-C35; | A12-B2-C36; | A15-B2-C37; | A18-B2-C38; |
| A4-B2-C33; | A7-B2-C34; | A10-B2-C35; | A13-B2-C36; | A16-B2-C37; | A19-B2-C38; |
| A5-B2-C33; | A8-B2-C34; | A11-B2-C35; | A14-B2-C36; | A17-B2-C37; | A20-B2-C38; |
| A6-B2-C33; | A9-B2-C34; | A12-B2-C35; | A15-B2-C36; | A18-B2-C37; | A21-B2-C38; |
| A7-B2-C33; | A10-B2-C34; | A13-B2-C35; | A16-B2-C36; | A19-B2-C37; | A22-B2-C38; |
| A8-B2-C33; | A11-B2-C34; | A14-B2-C35; | A17-B2-C36; | A20-B2-C37; | A23-B2-C38; |
| A9-B2-C33; | A12-B2-C34; | A15-B2-C35; | A18-B2-C36; | A21-B2-C37; | A24-B2-C38; |
| A10-B2-C33; | A13-B2-C34; | A16-B2-C35; | A19-B2-C36; | A22-B2-C37; | A25-B2-C38; |
| A11-B2-C33; | A14-B2-C34; | A17-B2-C35; | A20-B2-C36; | A23-B2-C37; | A26-B2-C38; |
| A12-B2-C33; | A15-B2-C34; | A18-B2-C35; | A21-B2-C36; | A24-B2-C37; | A27-B2-C38; |
| A13-B2-C33; | A16-B2-C34; | A19-B2-C35; | A22-B2-C36; | A25-B2-C37; | A28-B2-C38; |
| A14-B2-C33; | A17-B2-C34; | A20-B2-C35; | A23-B2-C36; | A26-B2-C37; | A29-B2-C38; |
| A15-B2-C33; | A18-B2-C34; | A21-B2-C35; | A24-B2-C36; | A27-B2-C37; | A30-B2-C38; |
| A16-B2-C33; | A19-B2-C34; | A22-B2-C35; | A25-B2-C36; | A28-B2-C37; | A31-B2-C38; |
| A17-B2-C33; | A20-B2-C34; | A23-B2-C35; | A26-B2-C36; | A29-B2-C37; | A32-B2-C38; |

-continued

| | | | | | |
|---|---|---|---|---|---|
| A18-B2-C33; | A21-B2-C34; | A24-B2-C35; | A27-B2-C36; | A30-B2-C37; | A1-B2-C39; |
| A19-B2-C33; | A22-B2-C34; | A25-B2-C35; | A28-B2-C36; | A31-B2-C37; | A2-B2-C39; |
| A20-B2-C33; | A23-B2-C34; | A26-B2-C35; | A29-B2-C36; | A32-B2-C37; | A3-B2-C39; |
| A21-B2-C33; | A24-B2-C34; | A27-B2-C35; | A30-B2-C36; | A1-B2-C38; | A4-B2-C39; |
| A22-B2-C33; | A25-B2-C34; | A28-B2-C35; | A31-B2-C36; | A2-B2-C38; | A5-B2-C39; |
| A23-B2-C33; | A26-B2-C34; | A29-B2-C35; | A32-B2-C36; | A3-B2-C38; | A6-B2-C39; |
| A24-B2-C33; | A27-B2-C34; | A30-B2-C35; | A1-B2-C37; | A4-B2-C38; | A7-B2-C39; |
| A25-B2-C33; | A28-B2-C34; | A31-B2-C35; | A2-B2-C37; | A5-B2-C38; | A8-B2-C39; |
| A26-B2-C33; | A29-B2-C34; | A32-B2-C35; | A3-B2-C37; | A6-B2-C38; | A9-B2-C39; |
| A27-B2-C33; | A30-B2-C34; | A1-B2-C36; | A4-B2-C37; | A7-B2-C38; | A10-B2-C39; |
| A28-B2-C33; | A31-B2-C34; | A2-B2-C36; | A5-B2-C37; | A8-B2-C38; | A11-B2-C39; |
| A29-B2-C33; | A32-B2-C34; | A3-B2-C36; | A6-B2-C37; | A9-B2-C38; | A12-B2-C39; |
| A30-B2-C33; | A1-B2-C35; | A4-B2-C36; | A7-B2-C37; | A10-B2-C38; | A13-B2-C39; |
| A31-B2-C33; | A2-B2-C35; | A5-B2-C36; | A8-B2-C37; | A11-B2-C38; | A14-B2-C39; |
| A32-B2-C33; | A3-B2-C35; | A6-B2-C36; | A9-B2-C37; | A12-B2-C38; | A15-B2-C39; |
| A1-B2-C34; | A4-B2-C35; | A7-B2-C36; | A10-B2-C37; | A13-B2-C38; | A16-B2-C39; |
| A2-B2-C34; | A5-B2-C35; | A8-B2-C36; | A11-B2-C37; | A14-B2-C38; | A17-B2-C39; |
| A3-B2-C34; | A6-B2-C35; | A9-B2-C36; | A12-B2-C37; | A15-B2-C38; | A18-B2-C39; |
| A19-B2-C39; | A22-B2-C40; | A25-B3-C1; | A28-B3-C2; | A31-B3-C3; | A2-B3-C5; |
| A20-B2-C39; | A23-B2-C40; | A26-B3-C1; | A29-B3-C2; | A32-B3-C3; | A3-B3-C5; |
| A21-B2-C39; | A24-B2-C40; | A27-B3-C1; | A30-B3-C2; | A1-B3-C4; | A4-B3-C5; |
| A22-B2-C39; | A25-B2-C40; | A28-B3-C1; | A31-B3-C2; | A2-B3-C4; | A5-B3-C5; |
| A23-B2-C39; | A26-B2-C40; | A29-B3-C1; | A32-B3-C2; | A3-B3-C4; | A6-B3-C5; |
| A24-B2-C39; | A27-B2-C40; | A30-B3-C1; | A1-B3-C3; | A4-B3-C4; | A7-B3-C5; |
| A25-B2-C39; | A28-B2-C40; | A31-B3-C1; | A2-B3-C3; | A5-B3-C4; | A8-B3-C5; |
| A26-B2-C39; | A29-B2-C40; | A32-B3-C1; | A3-B3-C3; | A6-B3-C4; | A9-B3-C5; |
| A27-B2-C39; | A30-B2-C40; | A1-B3-C2; | A4-B3-C3; | A7-B3-C4; | A10-B3-C5; |
| A28-B2-C39; | A31-B2-C40; | A2-B3-C2; | A5-B3-C3; | A8-B3-C4; | A11-B3-C5; |
| A29-B2-C39; | A32-B2-C40; | A3-B3-C2; | A6-B3-C3; | A9-B3-C4; | A12-B3-C5; |
| A30-B2-C39; | A1-B3-C1; | A4-B3-C2; | A7-B3-C3; | A10-B3-C4; | A13-B3-C5; |
| A31-B2-C39; | A2-B3-C1; | A5-B3-C2; | A8-B3-C3; | A11-B3-C4; | A14-B3-C5; |
| A32-B2-C39; | A3-B3-C1; | A6-B3-C2; | A9-B3-C3; | A12-B3-C4; | A15-B3-C5; |
| A1-B2-C40; | A4-B3-C1; | A7-B3-C2; | A10-B3-C3; | A13-B3-C4; | A16-B3-C5; |
| A2-B2-C40; | A5-B3-C1; | A8-B3-C2; | A11-B3-C3; | A14-B3-C4; | A17-B3-C5; |
| A3-B2-C40; | A6-B3-C1; | A9-B3-C2; | A12-B3-C3; | A15-B3-C4; | A18-B3-C5; |
| A4-B2-C40; | A7-B3-C1; | A10-B3-C2; | A13-B3-C3; | A16-B3-C4; | A19-B3-C5; |
| A5-B2-C40; | A8-B3-C1; | A11-B3-C2; | A14-B3-C3; | A17-B3-C4; | A20-B3-C5; |
| A6-B2-C40; | A9-B3-C1; | A12-B3-C2; | A15-B3-C3; | A18-B3-C4; | A21-B3-C5; |
| A7-B2-C40; | A10-B3-C1; | A13-B3-C2; | A16-B3-C3; | A19-B3-C4; | A22-B3-C5; |
| A8-B2-C40; | A11-B3-C1; | A14-B3-C2; | A17-B3-C3; | A20-B3-C4; | A23-B3-C5; |
| A9-B2-C40; | A12-B3-C1; | A15-B3-C2; | A18-B3-C3; | A21-B3-C4; | A24-B3-C5; |
| A10-B2-C40; | A13-B3-C1; | A16-B3-C2; | A19-B3-C3; | A22-B3-C4; | A25-B3-C5; |
| A11-B2-C40; | A14-B3-C1; | A17-B3-C2; | A20-B3-C3; | A23-B3-C4; | A26-B3-C5; |
| A12-B2-C40; | A15-B3-C1; | A18-B3-C2; | A21-B3-C3; | A24-B3-C4; | A27-B3-C5; |
| A13-B2-C40; | A16-B3-C1; | A19-B3-C2; | A22-B3-C3; | A25-B3-C4; | A28-B3-C5; |
| A14-B2-C40; | A17-B3-C1; | A20-B3-C2; | A23-B3-C3; | A26-B3-C4; | A29-B3-C5; |
| A15-B2-C40; | A18-B3-C1; | A21-B3-C2; | A24-B3-C3; | A27-B3-C4; | A30-B3-C5; |
| A16-B2-C40; | A19-B3-C1; | A22-B3-C2; | A25-B3-C3; | A28-B3-C4; | A31-B3-C5; |
| A17-B2-C40; | A20-B3-C1; | A23-B3-C2; | A26-B3-C3; | A29-B3-C4; | A32-B3-C5; |
| A18-B2-C40; | A21-B3-C1; | A24-B3-C2; | A27-B3-C3; | A30-B3-C4; | A1-B3-C6; |
| A19-B2-C40; | A22-B3-C1; | A25-B3-C2; | A28-B3-C3; | A31-B3-C4; | A2-B3-C6; |
| A20-B2-C40; | A23-B3-C1; | A26-B3-C2; | A29-B3-C3; | A32-B3-C4; | A3-B3-C6; |
| A21-B2-C40; | A24-B3-C1; | A27-B3-C2; | A30-B3-C3; | A1-B3-C5; | A4-B3-C6; |
| A5-B3-C6; | A8-B3-C7; | A11-B3-C8; | A14-B3-C9; | A17-B3-C10; | A20-B3-C11; |
| A6-B3-C6; | A9-B3-C7; | A12-B3-C8; | A15-B3-C9; | A18-B3-C10; | A21-B3-C11; |
| A7-B3-C6; | A10-B3-C7; | A13-B3-C8; | A16-B3-C9; | A19-B3-C10; | A22-B3-C11; |
| A8-B3-C6; | A11-B3-C7; | A14-B3-C8; | A17-B3-C9; | A20-B3-C10; | A23-B3-C11; |
| A9-B3-C6; | A12-B3-C7; | A15-B3-C8; | A18-B3-C9; | A21-B3-C10; | A24-B3-C11; |
| A10-B3-C6; | A13-B3-C7; | A16-B3-C8; | A19-B3-C9; | A22-B3-C10; | A25-B3-C11; |
| A11-B3-C6; | A14-B3-C7; | A17-B3-C8; | A20-B3-C9; | A23-B3-C10; | A26-B3-C11; |
| A12-B3-C6; | A15-B3-C7; | A18-B3-C8; | A21-B3-C9; | A24-B3-C10; | A27-B3-C11; |
| A13-B3-C6; | A16-B3-C7; | A19-B3-C8; | A22-B3-C9; | A25-B3-C10; | A28-B3-C11; |
| A14-B3-C6; | A17-B3-C7; | A20-B3-C8; | A23-B3-C9; | A26-B3-C10; | A29-B3-C11; |
| A15-B3-C6; | A18-B3-C7; | A21-B3-C8; | A24-B3-C9; | A27-B3-C10; | A30-B3-C11; |
| A16-B3-C6; | A19-B3-C7; | A22-B3-C8; | A25-B3-C9; | A28-B3-C10; | A31-B3-C11; |
| A17-B3-C6; | A20-B3-C7; | A23-B3-C8; | A26-B3-C9; | A29-B3-C10; | A32-B3-C11; |
| A18-B3-C6; | A21-B3-C7; | A24-B3-C8; | A27-B3-C9; | A30-B3-C10; | A1-B3-C12; |
| A19-B3-C6; | A22-B3-C7; | A25-B3-C8; | A28-B3-C9; | A31-B3-C10; | A2-B3-C12; |
| A20-B3-C6; | A23-B3-C7; | A26-B3-C8; | A29-B3-C9; | A32-B3-C10; | A3-B3-C12; |
| A21-B3-C6; | A24-B3-C7; | A27-B3-C8; | A30-B3-C9; | A1-B3-C11; | A4-B3-C12; |
| A22-B3-C6; | A25-B3-C7; | A28-B3-C8; | A31-B3-C9; | A2-B3-C11; | A5-B3-C12; |
| A23-B3-C6; | A26-B3-C7; | A29-B3-C8; | A32-B3-C9; | A3-B3-C11; | A6-B3-C12; |
| A24-B3-C6; | A27-B3-C7; | A30-B3-C8; | A1-B3-C10; | A4-B3-C11; | A7-B3-C12; |
| A25-B3-C6; | A28-B3-C7; | A31-B3-C8; | A2-B3-C10; | A5-B3-C11; | A8-B3-C12; |
| A26-B3-C6; | A29-B3-C7; | A32-B3-C8; | A3-B3-C10; | A6-B3-C11; | A9-B3-C12; |
| A27-B3-C6; | A30-B3-C7; | A1-B3-C9; | A4-B3-C10; | A7-B3-C11; | A10-B3-C12; |
| A28-B3-C6; | A31-B3-C7; | A2-B3-C9; | A5-B3-C10; | A8-B3-C11; | A11-B3-C12; |
| A29-B3-C6; | A32-B3-C7; | A3-B3-C9; | A6-B3-C10; | A9-B3-C11; | A12-B3-C12; |
| A30-B3-C6; | A1-B3-C8; | A4-B3-C9; | A7-B3-C10; | A10-B3-C11; | A13-B3-C12; |

-continued

| | | | | | |
|---|---|---|---|---|---|
| A31-B3-C6; | A2-B3-C8; | A5-B3-C9; | A8-B3-C10; | A11-B3-C11; | A14-B3-C12; |
| A32-B3-C6; | A3-B3-C8; | A6-B3-C9; | A9-B3-C10; | A12-B3-C11; | A15-B3-C12; |
| A1-B3-C7; | A4-B3-C8; | A7-B3-C9; | A10-B3-C10; | A13-B3-C11; | A16-B3-C12; |
| A2-B3-C7; | A5-B3-C8; | A8-B3-C9; | A11-B3-C10; | A14-B3-C11; | A17-B3-C12; |
| A3-B3-C7; | A6-B3-C8; | A9-B3-C9; | A12-B3-C10; | A15-B3-C11; | A18-B3-C12; |
| A4-B3-C7; | A7-B3-C8; | A10-B3-C9; | A13-B3-C10; | A16-B3-C11; | A19-B3-C12; |
| A5-B3-C7; | A8-B3-C8; | A11-B3-C9; | A14-B3-C10; | A17-B3-C11; | A20-B3-C12; |
| A6-B3-C7; | A9-B3-C8; | A12-B3-C9; | A15-B3-C10; | A18-B3-C11; | A21-B3-C12; |
| A7-B3-C7; | A10-B3-C8; | A13-B3-C9; | A16-B3-C10; | A19-B3-C11; | A22-B3-C12; |
| A23-B3-C12; | A26-B3-C13; | A29-B3-C14; | A32-B3-C15; | A3-B3-C17; | A6-B3-C18; |
| A24-B3-C12; | A27-B3-C13; | A30-B3-C14; | A1-B3-C16; | A4-B3-C17; | A7-B3-C18; |
| A25-B3-C12; | A28-B3-C13; | A31-B3-C14; | A2-B3-C16; | A5-B3-C17; | A8-B3-C18; |
| A26-B3-C12; | A29-B3-C13; | A32-B3-C14; | A3-B3-C16; | A6-B3-C17; | A9-B3-C18; |
| A27-B3-C12; | A30-B3-C13; | A1-B3-C15; | A4-B3-C16; | A7-B3-C17; | A10-B3-C18; |
| A28-B3-C12; | A31-B3-C13; | A2-B3-C15; | A5-B3-C16; | A8-B3-C17; | A11-B3-C18; |
| A29-B3-C12; | A32-B3-C13; | A3-B3-C15; | A6-B3-C16; | A9-B3-C17; | A12-B3-C18; |
| A30-B3-C12; | A1-B3-C14; | A4-B3-C15; | A7-B3-C16; | A10-B3-C17; | A13-B3-C18; |
| A31-B3-C12; | A2-B3-C14; | A5-B3-C15; | A8-B3-C16; | A11-B3-C17; | A14-B3-C18; |
| A32-B3-C12; | A3-B3-C14; | A6-B3-C15; | A9-B3-C16; | A12-B3-C17; | A15-B3-C18; |
| A1-B3-C13; | A4-B3-C14; | A7-B3-C15; | A10-B3-C16; | A13-B3-C17; | A16-B3-C18; |
| A2-B3-C13; | A5-B3-C14; | A8-B3-C15; | A11-B3-C16; | A14-B3-C17; | A17-B3-C18; |
| A3-B3-C13; | A6-B3-C14; | A9-B3-C15; | A12-B3-C16; | A15-B3-C17; | A18-B3-C18; |
| A4-B3-C13; | A7-B3-C14; | A10-B3-C15; | A13-B3-C16; | A16-B3-C17; | A19-B3-C18; |
| A5-B3-C13; | A8-B3-C14; | A11-B3-C15; | A14-B3-C16; | A17-B3-C17; | A20-B3-C18; |
| A6-B3-C13; | A9-B3-C14; | A12-B3-C15; | A15-B3-C16; | A18-B3-C17; | A21-B3-C18; |
| A7-B3-C13; | A10-B3-C14; | A13-B3-C15; | A16-B3-C16; | A19-B3-C17; | A22-B3-C18; |
| A8-B3-C13; | A11-B3-C14; | A14-B3-C15; | A17-B3-C16; | A20-B3-C17; | A23-B3-C18; |
| A9-B3-C13; | A12-B3-C14; | A15-B3-C15; | A18-B3-C16; | A21-B3-C17; | A24-B3-C18; |
| A10-B3-C13; | A13-B3-C14; | A16-B3-C15; | A19-B3-C16; | A22-B3-C17; | A25-B3-C18; |
| A11-B3-C13; | A14-B3-C14; | A17-B3-C15; | A20-B3-C16; | A23-B3-C17; | A26-B3-C18; |
| A12-B3-C13; | A15-B3-C14; | A18-B3-C15; | A21-B3-C16; | A24-B3-C17; | A27-B3-C18; |
| A13-B3-C13; | A16-B3-C14; | A19-B3-C15; | A22-B3-C16; | A25-B3-C17; | A28-B3-C18; |
| A14-B3-C13; | A17-B3-C14; | A20-B3-C15; | A23-B3-C16; | A26-B3-C17; | A29-B3-C18; |
| A15-B3-C13; | A18-B3-C14; | A21-B3-C15; | A24-B3-C16; | A27-B3-C17; | A30-B3-C18; |
| A16-B3-C13; | A19-B3-C14; | A22-B3-C15; | A25-B3-C16; | A28-B3-C17; | A31-B3-C18; |
| A17-B3-C13; | A20-B3-C14; | A23-B3-C15; | A26-B3-C16; | A29-B3-C17; | A32-B3-C18; |
| A18-B3-C13; | A21-B3-C14; | A24-B3-C15; | A27-B3-C16; | A30-B3-C17; | A1-B3-C19; |
| A19-B3-C13; | A22-B3-C14; | A25-B3-C15; | A28-B3-C16; | A31-B3-C17; | A2-B3-C19; |
| A20-B3-C13; | A23-B3-C14; | A26-B3-C15; | A29-B3-C16; | A32-B3-C17; | A3-B3-C19; |
| A21-B3-C13; | A24-B3-C14; | A27-B3-C15; | A30-B3-C16; | A1-B3-C18; | A4-B3-C19; |
| A22-B3-C13; | A25-B3-C14; | A28-B3-C15; | A31-B3-C16; | A2-B3-C18; | A5-B3-C19; |
| A23-B3-C13; | A26-B3-C14; | A29-B3-C15; | A32-B3-C16; | A3-B3-C18; | A6-B3-C19; |
| A24-B3-C13; | A27-B3-C14; | A30-B3-C15; | A1-B3-C17; | A4-B3-C18; | A7-B3-C19; |
| A25-B3-C13; | A28-B3-C14; | A31-B3-C15; | A2-B3-C17; | A5-83-C18; | A8-B3-C19; |
| A9-B3-C19; | A12-B3-C20; | A15-B3-C21; | A18-B3-C22; | A21-B3-C23; | A24-B3-C24; |
| A10-B3-C19; | A13-B3-C20; | A16-B3-C21; | A19-B3-C22; | A22-B3-C23; | A25-B3-C24; |
| A11-B3-C19; | A14-B3-C20; | A17-B3-C21; | A20-B3-C22; | A23-B3-C23; | A26-B3-C24; |
| A12-B3-C19; | A15-B3-C20; | A18-B3-C21; | A21-B3-C22; | A24-B3-C23; | A27-B3-C24; |
| A13-B3-C19; | A16-B3-C20; | A19-B3-C21; | A22-B3-C22; | A25-B3-C23; | A28-B3-C24; |
| A14-B3-C19; | A17-B3-C20; | A20-B3-C21; | A23-B3-C22; | A26-B3-C23; | A29-B3-C24; |
| A15-B3-C19; | A18-B3-C20; | A21-B3-C21; | A24-B3-C22; | A27-B3-C23; | A30-B3-C24; |
| A16-B3-C19; | A19-B3-C20; | A22-B3-C21; | A25-B3-C22; | A28-B3-C23; | A31-B3-C24; |
| A17-B3-C19; | A20-B3-C20; | A23-B3-C21; | A26-B3-C22; | A29-B3-C23; | A32-B3-C24; |
| A18-B3-C19; | A21-B3-C20; | A24-B3-C21; | A27-B3-C22; | A30-B3-C23; | A1-B3-C25; |
| A19-B3-C19; | A22-B3-C20; | A25-B3-C21; | A28-B3-C22; | A31-B3-C23; | A2-B3-C25; |
| A20-B3-C19; | A23-B3-C20; | A26-B3-C21; | A29-B3-C22; | A32-B3-C23; | A3-B3-C25; |
| A21-B3-C19; | A24-B3-C20; | A27-B3-C21; | A30-B3-C22; | A1-B3-C24; | A4-B3-C25; |
| A22-B3-C19; | A25-B3-C20; | A28-B3-C21; | A31-B3-C22; | A2-B3-C24; | A5-B3-C25; |
| A23-B3-C19; | A26-B3-C20; | A29-B3-C21; | A32-B3-C22; | A3-B3-C24; | A6-B3-C25; |
| A24-B3-C19; | A27-B3-C20; | A30-B3-C21; | A1-B3-C23; | A4-B3-C24; | A7-B3-C25; |
| A25-B3-C19; | A28-B3-C20; | A31-B3-C21; | A2-B3-C23; | A5-B3-C24; | A8-B3-C25; |
| A26-B3-C19; | A29-B3-C20; | A32-B3-C21; | A3-B3-C23; | A6-B3-C24; | A9-B3-C25; |
| A27-B3-C19; | A30-B3-C20; | A1-B3-C22; | A4-B3-C23; | A7-B3-C24; | A10-B3-C25; |
| A28-B3-C19; | A31-B3-C20; | A2-B3-C22; | A5-B3-C23; | A8-B3-C24; | A11-B3-C25; |
| A29-B3-C19; | A32-B3-C20; | A3-B3-C22; | A6-B3-C23; | A9-B3-C24; | A12-B3-C25; |
| A30-B3-C19; | A1-B3-C21; | A4-B3-C22; | A7-B3-C23; | A10-B3-C24; | A13-B3-C25; |
| A31-B3-C19; | A2-B3-C21; | A5-B3-C22; | A8-B3-C23; | A11-B3-C24; | A14-B3-C25; |
| A32-B3-C19; | A3-B3-C21; | A6-B3-C22; | A9-B3-C23; | A12-B3-C24; | A15-B3-C25; |
| A1-B3-C20; | A4-B3-C21; | A7-B3-C22; | A10-B3-C23; | A13-B3-C24; | A16-B3-C25; |
| A2-B3-C20; | A5-B3-C21; | A8-B3-C22; | A11-B3-C23; | A14-B3-C24; | A17-B3-C25; |
| A3-B3-C20; | A6-B3-C21; | A9-B3-C22; | A12-B3-C23; | A15-B3-C24; | A18-B3-C25; |
| A4-B3-C20; | A7-B3-C21; | A10-B3-C22; | A13-B3-C23; | A16-B3-C24; | A19-B3-C25; |
| A5-B3-C20; | A8-B3-C21; | A11-B3-C22; | A14-B3-C23; | A17-B3-C24; | A20-B3-C25; |
| A6-B3-C20; | A9-B3-C21; | A12-B3-C22; | A15-B3-C23; | A18-B3-C24; | A21-B3-C25; |
| A7-B3-C20; | A10-B3-C21; | A13-B3-C22; | A16-B3-C23; | A19-B3-C24; | A22-B3-C25; |
| A8-B3-C20; | A11-B3-C21; | A14-B3-C22; | A17-B3-C23; | A20-B3-C24; | A23-B3-C25; |
| A9-B3-C20; | A12-B3-C21; | A15-B3-C22; | A18-B3-C23; | A21-B3-C24; | A24-B3-C25; |
| A10-B3-C20; | A13-B3-C21; | A16-B3-C22; | A19-B3-C23; | A22-B3-C24; | A25-B3-C25; |
| A11-B3-C20; | A14-B3-C21; | A17-B3-C22; | A20-B3-C23; | A23-B3-C24; | A26-B3-C25; |

-continued

| | | | | | |
|---|---|---|---|---|---|
| A27-B3-C25; | A30-B3-C26; | A1-B3-C28; | A4-B3-C29; | A7-B3-C30; | A10-B3-C31; |
| A28-B3-C25; | A31-B3-C26; | A2-B3-C28; | A5-B3-C29; | A8-B3-C30; | A11-B3-C31; |
| A29-B3-C25; | A32-B3-C26; | A3-B3-C28; | A6-B3-C29; | A9-B3-C30; | A12-B3-C31; |
| A30-B3-C25; | A1-B3-C27; | A4-B3-C28; | A7-B3-C29; | A10-B3-C30; | A13-B3-C31; |
| A31-B3-C25; | A2-B3-C27; | A5-B3-C28; | A8-B3-C29; | A11-B3-C30; | A14-B3-C31; |
| A32-B3-C25; | A3-B3-C27; | A6-B3-C28; | A9-B3-C29; | A12-B3-C30; | A15-B3-C31; |
| A1-B3-C26; | A4-B3-C27; | A7-B3-C28; | A10-B3-C29; | A13-B3-C30; | A16-B3-C31; |
| A2-B3-C26; | A5-B3-C27; | A8-B3-C28; | A11-B3-C29; | A14-B3-C30; | A17-B3-C31; |
| A3-B3-C26; | A6-B3-C27; | A9-B3-C28; | A12-B3-C29; | A15-B3-C30; | A18-B3-C31; |
| A4-B3-C26; | A7-B3-C27; | A10-B3-C28; | A13-B3-C29; | A16-B3-C30; | A19-B3-C31; |
| A5-B3-C26; | A8-B3-C27; | A11-B3-C28; | A14-B3-C29; | A17-B3-C30; | A20-B3-C31; |
| A6-B3-C26; | A9-B3-C27; | A12-B3-C28; | A15-B3-C29; | A18-B3-C30; | A21-B3-C31; |
| A7-B3-C26; | A10-B3-C27; | A13-B3-C28; | A16-B3-C29; | A19-B3-C30; | A22-B3-C31; |
| A8-B3-C26; | A11-B3-C27; | A14-B3-C28; | A17-B3-C29; | A20-B3-C30; | A23-B3-C31; |
| A9-B3-C26; | A12-B3-C27; | A15-B3-C28; | A18-B3-C29; | A21-B3-C30; | A24-B3-C31; |
| A10-B3-C26; | A13-B3-C27; | A16-B3-C28; | A19-B3-C29; | A22-B3-C30; | A25-B3-C31; |
| A11-B3-C26; | A14-B3-C27; | A17-B3-C28; | A20-B3-C29; | A23-B3-C30; | A26-B3-C31; |
| A12-B3-C26; | A15-B3-C27; | A18-B3-C28; | A21-B3-C29; | A24-B3-C30; | A27-B3-C31; |
| A13-B3-C26; | A16-B3-C27; | A19-B3-C28; | A22-B3-C29; | A25-B3-C30; | A28-B3-C31; |
| A14-B3-C26; | A17-B3-C27; | A20-B3-C28; | A23-B3-C29; | A26-B3-C30; | A29-B3-C31; |
| A15-B3-C26; | A18-B3-C27; | A21-B3-C28; | A24-B3-C29; | A27-B3-C30; | A30-B3-C31; |
| A16-B3-C26; | A19-B3-C27; | A22-B3-C28; | A25-B3-C29; | A28-B3-C30; | A31-B3-C31; |
| A17-B3-C26; | A20-B3-C27; | A23-B3-C28; | A26-B3-C29; | A29-B3-C30; | A32-B3-C31; |
| A18-B3-C26; | A21-B3-C27; | A24-B3-C28; | A27-B3-C29; | A30-B3-C30; | A1-B3-C32; |
| A19-B3-C26; | A22-B3-C27; | A25-B3-C28; | A28-B3-C29; | A31-B3-C30; | A2-B3-C32; |
| A20-B3-C26; | A23-B3-C27; | A26-B3-C28; | A29-B3-C29; | A32-B3-C30; | A3-B3-C32; |
| A21-B3-C26; | A24-B3-C27; | A27-B3-C28; | A30-B3-C29; | A1-B3-C31; | A4-B3-C32; |
| A22-B3-C26; | A25-B3-C27; | A28-B3-C28; | A31-B3-C29; | A2-B3-C31; | A5-B3-C32; |
| A23-B3-C26; | A26-B3-C27; | A29-B3-C28; | A32-B3-C29; | A3-B3-C31; | A6-B3-C32; |
| A24-B3-C26; | A27-B3-C27; | A30-B3-C28; | A1-B3-C30; | A4-B3-C31; | A7-B3-C32; |
| A25-B3-C26; | A28-B3-C27; | A31-B3-C28; | A2-B3-C30; | A5-B3-C31; | A8-B3-C32; |
| A26-B3-C26; | A29-B3-C27; | A32-B3-C28; | A3-B3-C30; | A6-B3-C31; | A9-B3-C32; |
| A27-B3-C26; | A30-B3-C27; | A1-B3-C29; | A4-B3-C30; | A7-B3-C31; | A10-B3-C32; |
| A28-B3-C26; | A31-B3-C27; | A2-B3-C29; | A5-B3-C30; | A8-B3-C31; | A11-B3-C32; |
| A29-B3-C26; | A32-B3-C27; | A3-B3-C29; | A6-B3-C30; | A9-B3-C31; | A12-B3-C32; |
| A13-B3-C32; | A16-B3-C33; | A19-B3-C34; | A22-B3-C35; | A25-B3-C36; | A28-B3-C37; |
| A14-B3-C32; | A17-B3-C33; | A20-B3-C34; | A23-B3-C35; | A26-B3-C36; | A29-B3-C37; |
| A15-B3-C32; | A18-B3-C33; | A21-B3-C34; | A24-B3-C35; | A27-B3-C36; | A30-B3-C37; |
| A16-B3-C32; | A19-B3-C33; | A22-B3-C34; | A25-B3-C35; | A28-B3-C36; | A31-B3-C37; |
| A17-B3-C32; | A20-B3-C33; | A23-B3-C34; | A26-B3-C35; | A29-B3-C36; | A32-B3-C37; |
| A18-B3-C32; | A21-B3-C33; | A24-B3-C34; | A27-B3-C35; | A30-B3-C36; | A1-B3-C38; |
| A19-B3-C32; | A22-B3-C33; | A25-B3-C34; | A28-B3-C35; | A31-B3-C36; | A2-B3-C38; |
| A20-B3-C32; | A23-B3-C33; | A26-B3-C34; | A29-B3-C35; | A32-B3-C36; | A3-B3-C38; |
| A21-B3-C32; | A24-B3-C33; | A27-B3-C34; | A30-B3-C35; | A1-B3-C37; | A4-B3-C38; |
| A22-B3-C32; | A25-B3-C33; | A28-B3-C34; | A31-B3-C35; | A2-B3-C37; | A5-B3-C38; |
| A23-B3-C32; | A26-B3-C33; | A29-B3-C34; | A32-B3-C35; | A3-B3-C37; | A6-B3-C38; |
| A24-B3-C32; | A27-B3-C33; | A30-B3-C34; | A1-B3-C36; | A4-B3-C37; | A7-B3-C38; |
| A25-B3-C32; | A28-B3-C33; | A31-B3-C34; | A2-B3-C36; | A5-B3-C37; | A8-B3-C38; |
| A26-B3-C32; | A29-B3-C33; | A32-B3-C34; | A3-B3-C36; | A6-B3-C37; | A9-B3-C38; |
| A27-B3-C32; | A30-B3-C33; | A1-B3-C35; | A4-B3-C36; | A7-B3-C37; | A10-B3-C38; |
| A28-B3-C32; | A31-B3-C33; | A2-B3-C35; | A5-B3-C36; | A8-B3-C37; | A11-B3-C38; |
| A29-B3-C32; | A32-B3-C33; | A3-B3-C35; | A6-B3-C36; | A9-B3-C37; | A12-B3-C38; |
| A30-B3-C32; | A1-B3-C34; | A4-B3-C35; | A7-B3-C36; | A10-B3-C37; | A13-B3-C38; |
| A31-B3-C32; | A2-B3-C34; | A5-B3-C35; | A8-B3-C36; | A11-B3-C37; | A14-B3-C38; |
| A32-B3-C32; | A3-B3-C34; | A6-B3-C35; | A9-B3-C36; | A12-B3-C37; | A15-B3-C38; |
| A1-B3-C33; | A4-B3-C34; | A7-B3-C35; | A10-B3-C36; | A13-B3-C37; | A16-B3-C38; |
| A2-B3-C33; | A5-B3-C34; | A8-B3-C35; | A11-B3-C36; | A14-B3-C37; | A17-B3-C38; |
| A3-B3-C33; | A6-B3-C34; | A9-B3-C35; | A12-B3-C36; | A15-B3-C37; | A18-B3-C38; |
| A4-B3-C33; | A7-B3-C34; | A10-B3-C35; | A13-B3-C36; | A16-B3-C37; | A19-B3-C38; |
| A5-B3-C33; | A8-B3-C34; | A11-B3-C35; | A14-B3-C36; | A17-B3-C37; | A20-B3-C38; |
| A6-B3-C33; | A9-B3-C34; | A12-B3-C35; | A15-B3-C36; | A18-B3-C37; | A21-B3-C38; |
| A7-B3-C33; | A10-B3-C34; | A13-B3-C35; | A16-B3-C36; | A19-B3-C37; | A22-B3-C38; |
| A8-B3-C33; | A11-B3-C34; | A14-B3-C35; | A17-B3-C36; | A20-B3-C37; | A23-B3-C38; |
| A9-B3-C33; | A12-B3-C34; | A15-B3-C35; | A18-B3-C36; | A21-B3-C37; | A24-B3-C38; |
| A10-B3-C33; | A13-B3-C34; | A16-B3-C35; | A19-B3-C36; | A22-B3-C37; | A25-B3-C38; |
| A11-B3-C33; | A14-B3-C34; | A17-B3-C35; | A20-B3-C36; | A23-B3-C37; | A26-B3-C38; |
| A12-B3-C33; | A15-B3-C34; | A18-B3-C35; | A21-B3-C36; | A24-B3-C37; | A27-B3-C38; |
| A13-B3-C33; | A16-B3-C34; | A19-B3-C35; | A22-B3-C36; | A25-B3-C37; | A28-B3-C38; |
| A14-B3-C33; | A17-B3-C34; | A20-B3-C35; | A23-B3-C36; | A26-B3-C37; | A29-B3-C38; |
| A15-B3-C33; | A18-B3-C34; | A21-B3-C35; | A24-B3-C36; | A27-B3-C37; | A30-B3-C38; |
| A31-B3-C38; | A2-B3-C40; | A5-B4-C1; | A8-B4-C2; | A11-B4-C3; | A14-B4-C4; |
| A32-B3-C38; | A3-B3-C40; | A6-B4-C1; | A9-B4-C2; | A12-B4-C3; | A15-B4-C4; |
| A1-B3-C39; | A4-B3-C40; | A7-B4-C1; | A10-B4-C2; | A13-B4-C3; | A16-B4-C4; |
| A2-B3-C39; | A5-B3-C40; | A8-B4-C1; | A11-B4-C2; | A14-B4-C3; | A17-B4-C4; |
| A3-B3-C39; | A6-B3-C40; | A9-B4-C1; | A12-B4-C2; | A15-B4-C3; | A18-B4-C4; |
| A4-B3-C39; | A7-B3-C40; | A10-B4-C1; | A13-B4-C2; | A16-B4-C3; | A19-B4-C4; |
| A5-B3-C39; | A8-B3-C40; | A11-B4-C1; | A14-B4-C2; | A17-B4-C3; | A20-B4-C4; |
| A6-B3-C39; | A9-B3-C40; | A12-B4-C1; | A15-B4-C2; | A18-B4-C3; | A21-B4-C4; |
| A7-B3-C39; | A10-B3-C40; | A13-B4-C1; | A16-B4-C2; | A19-B4-C3; | A22-B4-C4; |

-continued

| | | | | | |
|---|---|---|---|---|---|
| A8-B3-C39; | A11-B3-C40; | A14-B4-C1; | A17-B4-C2; | A20-B4-C3; | A23-B4-C4; |
| A9-B3-C39; | A12-B3-C40; | A15-B4-C1; | A18-B4-C2; | A21-B4-C3; | A24-B4-C4; |
| A10-B3-C39; | A13-B3-C40; | A16-B4-C1; | A19-B4-C2; | A22-B4-C3; | A25-B4-C4; |
| A11-B3-C39; | A14-B3-C40; | A17-B4-C1; | A20-B4-C2; | A23-B4-C3; | A26-B4-C4; |
| A12-B3-C39; | A15-B3-C40; | A18-B4-C1; | A21-B4-C2; | A24-B4-C3; | A27-B4-C4; |
| A13-B3-C39; | A16-B3-C40; | A19-B4-C1; | A22-B4-C2; | A25-B4-C3; | A28-B4-C4; |
| A14-B3-C39; | A17-B3-C40; | A20-B4-C1; | A23-B4-C2; | A26-B4-C3; | A29-B4-C4; |
| A15-B3-C39; | A18-B3-C40; | A21-B4-C1; | A24-B4-C2; | A27-B4-C3; | A30-B4-C4; |
| A16-B3-C39; | A19-B3-C40; | A22-B4-C1; | A25-B4-C2; | A28-B4-C3; | A31-B4-C4; |
| A17-B3-C39; | A20-B3-C40; | A23-B4-C1; | A26-B4-C2; | A29-B4-C3; | A32-B4-C4; |
| A18-B3-C39; | A21-B3-C40; | A24-B4-C1; | A27-B4-C2; | A30-B4-C3; | A1-B4-C5; |
| A19-B3-C39; | A22-B3-C40; | A25-B4-C1; | A28-B4-C2; | A31-B4-C3; | A2-B4-C5; |
| A20-B3-C39; | A23-B3-C40; | A26-B4-C1; | A29-B4-C2; | A32-B4-C3; | A3-B4-C5; |
| A21-B3-C39; | A24-B3-C40; | A27-B4-C1; | A30-B4-C2; | A1-B4-C4; | A4-B4-C5; |
| A22-B3-C39; | A25-B3-C40; | A28-B4-C1; | A31-B4-C2; | A2-B4-C4; | A5-B4-C5; |
| A23-B3-C39; | A26-B3-C40; | A29-B4-C1; | A32-B4-C2; | A3-B4-C4; | A6-B4-C5; |
| A24-B3-C39; | A27-B3-C40; | A30-B4-C1; | A1-B4-C3; | A4-B4-C4; | A7-B4-C5; |
| A25-B3-C39; | A28-B3-C40; | A31-B4-C1; | A2-B4-C3; | A5-B4-C4; | A8-B4-C5; |
| A26-B3-C39; | A29-B3-C40; | A32-B4-C1; | A3-B4-C3; | A6-B4-C4; | A9-B4-C5; |
| A27-B3-C39; | A30-B3-C40; | A1-B4-C2; | A4-B4-C3; | A7-B4-C4; | A10-B4-C5; |
| A28-B3-C39; | A31-B3-C40; | A2-B4-C2; | A5-B4-C3; | A8-B4-C4; | A11-B4-C5; |
| A29-B3-C39; | A32-B3-C40; | A3-B4-C2; | A6-B4-C3; | A9-B4-C4; | A12-B4-C5; |
| A30-B3-C39; | A1-B4-C1; | A4-B4-C2; | A7-B4-C3; | A10-B4-C4; | A13-B4-C5; |
| A31-B3-C39; | A2-B4-C1; | A5-B4-C2; | A8-B4-C3; | A11-B4-C4; | A14-B4-C5; |
| A32-B3-C39; | A3-B4-C1; | A6-B4-C2; | A9-34-C3; | A12-B4-C4; | A15-B4-C5; |
| A1-B3-C40; | A4-B4-C1; | A7-B4-C2; | A10-B4-C3; | A13-B4-C4; | A16-B4-C5; |
| A17-B4-C5; | A20-B4-C6; | A23-B4-C7; | A26-B4-C8; | A29-B4-C9; | A32-B4-C10; |
| A18-B4-C5; | A21-B4-C6; | A24-B4-C7; | A27-B4-C8; | A30-B4-C9; | A1-B4-C11; |
| A19-B4-C5; | A22-B4-C6; | A25-B4-C7; | A28-B4-C8; | A31-B4-C9; | A2-B4-C11; |
| A20-B4-C5; | A23-B4-C6; | A26-B4-C7; | A29-B4-C8; | A32-B4-C9; | A3-B4-C11; |
| A21-B4-C5; | A24-B4-C6; | A27-B4-C7; | A30-B4-C8; | A1-B4-C10; | A4-B4-C11; |
| A22-B4-C5; | A25-B4-C6; | A28-B4-C7; | A31-B4-C8; | A2-B4-C10; | A5-B4-C11; |
| A23-B4-C5; | A26-B4-C6; | A29-B4-C7; | A32-B4-C8; | A3-B4-C10; | A6-B4-C11; |
| A24-B4-C5; | A27-B4-C6; | A30-B4-C7; | A1-B4-C9; | A4-B4-C10; | A7-B4-C11; |
| A25-B4-C5; | A28-B4-C6; | A31-B4-C7; | A2-B4-C9; | A5-B4-C10; | A8-B4-C11; |
| A26-B4-C5; | A29-B4-C6; | A32-B4-C7; | A3-B4-C9; | A6-B4-C10; | A9-B4-C11; |
| A27-B4-C5; | A30-B4-C6; | A1-B4-C8; | A4-B4-C9; | A7-B4-C10; | A10-B4-C11; |
| A28-B4-C5; | A31-B4-C6; | A2-B4-C8; | A5-B4-C9; | A8-B4-C10; | A11-B4-C11; |
| A29-B4-C5; | A32-B4-C6; | A3-B4-C8; | A6-B4-C9; | A9-B4-C10; | A12-B4-C11; |
| A30-B4-C5; | A1-B4-C7; | A4-B4-C8; | A7-B4-C9; | A10-B4-C10; | A13-B4-C11; |
| A31-B4-C5; | A2-B4-C7; | A5-B4-C8; | A8-B4-C9; | A11-B4-C10; | A14-B4-C11; |
| A32-B4-C5; | A3-B4-C7; | A6-B4-C8; | A9-B4-C9; | A12-B4-C10; | A15-B4-C11; |
| A1-B4-C6; | A4-B4-C7; | A7-B4-C8; | A10-B4-C9; | A13-B4-C10; | A16-B4-C11; |
| A2-B4-C6; | A5-B4-C7; | A8-B4-C8; | A11-B4-C9; | A14-B4-C10; | A17-B4-C11; |
| A3-B4-C6; | A6-B4-C7; | A9-B4-C8; | A12-B4-C9; | A15-B4-C10; | A18-B4-C11; |
| A4-B4-C6; | A7-B4-C7; | A10-B4-C8; | A13-B4-C9; | A16-B4-C10; | A19-B4-C11; |
| A5-B4-C6; | A8-B4-C7; | A11-B4-C8; | A14-B4-C9; | A17-B4-C10; | A20-B4-C11; |
| A6-B4-C6; | A9-B4-C7; | A12-B4-C8; | A15-B4-C9; | A18-B4-C10; | A21-B4-C11; |
| A7-B4-C6; | A10-B4-C7; | A13-B4-C8; | A16-B4-C9; | A19-B4-C10; | A22-B4-C11; |
| A8-B4-C6; | A11-B4-C7; | A14-B4-C8; | A17-B4-C9; | A20-B4-C10; | A23-B4-C11; |
| A9-B4-C6; | A12-B4-C7; | A15-B4-C8; | A18-B4-C9; | A21-B4-C10; | A24-B4-C11; |
| A10-B4-C6; | A13-B4-C7; | A16-B4-C8; | A19-B4-C9; | A22-B4-C10; | A25-B4-C11; |
| A11-B4-C6; | A14-B4-C7; | A17-B4-C8; | A20-B4-C9; | A23-B4-C10; | A26-B4-C11; |
| A12-B4-C6; | A15-B4-C7; | A18-B4-C8; | A21-B4-C9; | A24-B4-C10; | A27-B4-C11; |
| A13-B4-C6; | A16-B4-C7; | A19-B4-C8; | A22-B4-C9; | A25-B4-C10; | A28-B4-C11; |
| A14-B4-C6; | A17-B4-C7; | A20-B4-C8; | A23-B4-C9; | A26-B4-C10; | A29-B4-C11; |
| A15-B4-C6; | A18-B4-C7; | A21-B4-C8; | A24-B4-C9; | A27-B4-C10; | A30-B4-C11; |
| A16-B4-C6; | A19-B4-C7; | A22-B4-C8; | A25-B4-C9; | A28-B4-C10; | A31-B4-C11; |
| A17-B4-C6; | A20-B4-C7; | A23-B4-C8; | A26-B4-C9; | A29-B4-C10; | A32-B4-C11; |
| A18-B4-C6; | A21-B4-C7; | A24-B4-C8; | A27-B4-C9; | A30-B4-C10; | A1-B4-C12; |
| A19-B4-C6; | A22-B4-C7; | A25-B4-C8; | A28-B4-C9; | A31-B4-C10; | A2-B4-C12; |
| A3-B4-C12; | A6-B4-C13; | A9-B4-C14; | A12-B4-C15; | A15-B4-C16; | A18-B4-C17; |
| A4-B4-C12; | A7-B4-C13; | A10-B4-C14; | A13-B4-C15; | A16-B4-C16; | A19-B4-C17; |
| A5-B4-C12; | A8-B4-C13; | A11-B4-C14; | A14-B4-C15; | A17-B4-C16; | A20-B4-C17; |
| A6-B4-C12; | A9-B4-C13; | A12-B4-C14; | A15-B4-C15; | A18-B4-C16; | A21-B4-C17; |
| A7-B4-C12; | A10-B4-C13; | A13-B4-C14; | A16-B4-C15; | A19-B4-C16; | A22-B4-C17; |
| A8-B4-C12; | A11-B4-C13; | A14-B4-C14; | A17-B4-C15; | A20-B4-C16; | A23-B4-C17; |
| A9-B4-C12; | A12-B4-C13; | A15-B4-C14; | A18-B4-C15; | A21-B4-C16; | A24-B4-C17; |
| A10-B4-C12; | A13-B4-C13; | A16-B4-C14; | A19-B4-C15; | A22-B4-C16; | A25-B4-C17; |
| A11-B4-C12; | A14-B4-C13; | A17-B4-C14; | A20-B4-C15; | A23-B4-C16; | A26-B4-C17; |
| A12-B4-C12; | A15-B4-C13; | A18-B4-C14; | A21-B4-C15; | A24-B4-C16; | A27-B4-C17; |
| A13-B4-C12; | A16-B4-C13; | A19-B4-C14; | A22-B4-C15; | A25-B4-C16; | A28-B4-C17; |
| A14-B4-C12; | A17-B4-C13; | A20-B4-C14; | A23-B4-C15; | A26-B4-C16; | A29-B4-C17; |
| A15-B4-C12; | A18-B4-C13; | A21-B4-C14; | A24-B4-C15; | A27-B4-C16; | A30-B4-C17; |
| A16-B4-C12; | A19-B4-C13; | A22-B4-C14; | A25-B4-C15; | A28-B4-C16; | A31-B4-C17; |
| A17-B4-C12; | A20-B4-C13; | A23-B4-C14; | A26-B4-C15; | A29-B4-C16; | A32-B4-C17; |
| A18-B4-C12; | A21-B4-C13; | A24-B4-C14; | A27-B4-C15; | A30-B4-C16; | A1-B4-C18; |
| A19-B4-C12; | A22-B4-C13; | A25-B4-C14; | A28-B4-C15; | A31-B4-C16; | A2-B4-C18; |
| A20-B4-C12; | A23-B4-C13; | A26-B4-C14; | A29-B4-C15; | A32-B4-C16; | A3-B4-C18; |

| | | | | | |
|---|---|---|---|---|---|
| A21-B4-C12; | A24-B4-C13; | A27-B4-C14; | A30-B4-C15; | A1-B4-C17; | A4-B4-C18; |
| A22-B4-C12; | A25-B4-C13; | A28-B4-C14; | A31-B4-C15; | A2-B4-C17; | A5-B4-C18; |
| A23-B4-C12; | A26-B4-C13; | A29-B4-C14; | A32-B4-C15; | A3-B4-C17; | A6-B4-C18; |
| A24-B4-C12; | A27-B4-C13; | A30-B4-C14; | A1-B4-C16; | A4-B4-C17; | A7-B4-C18; |
| A25-B4-C12; | A28-B4-C13; | A31-B4-C14; | A2-B4-C16; | A5-B4-C17; | A8-B4-C18; |
| A26-B4-C12; | A29-B4-C13; | A32-B4-C14; | A3-B4-C16; | A6-B4-C17; | A9-B4-C18; |
| A27-B4-C12; | A30-B4-C13; | A1-B4-C15; | A4-B4-C16; | A7-B4-C17; | A10-B4-C18; |
| A28-B4-C12; | A31-B4-C13; | A2-B4-C15; | A5-B4-C16; | A8-B4-C17; | A11-B4-C18; |
| A29-B4-C12; | A32-B4-C13; | A3-B4-C15; | A6-B4-C16; | A9-B4-C17; | A12-B4-C18; |
| A30-B4-C12; | A1-B4-C14; | A4-B4-C15; | A7-B4-C16; | A10-B4-C17; | A13-B4-C18; |
| A31-B4-C12; | A2-B4-C14; | A5-B4-C15; | A8-B4-C16; | A11-B4-C17; | A14-B4-C18; |
| A32-B4-C12; | A3-B4-C14; | A6-B4-C15; | A9-B4-C16; | A12-B4-C17; | A15-B4-C18; |
| A1-B4-C13; | A4-B4-C14; | A7-B4-C15; | A10-B4-C16; | A13-B4-C17; | A16-B4-C18; |
| A2-B4-C13; | A5-B4-C14; | A8-B4-C15; | A11-B4-C16; | A14-B4-C17; | A17-B4-C18; |
| A3-B4-C13; | A6-B4-C14; | A9-B4-C15; | A12-B4-C16; | A15-B4-C17; | A18-B4-C18; |
| A4-B4-C13; | A7-B4-C14; | A10-B4-C15; | A13-B4-C16; | A16-B4-C17; | A19-B4-C18; |
| A5-B4-C13; | A8-B4-C14; | A11-B4-C15; | A14-B4-C16; | A17-B4-C17; | A20-B4-C18; |
| A21-B4-C18; | A24-B4-C19; | A27-B4-C20; | A30-B4-C21; | A1-B4-C23; | A4-B4-C24; |
| A22-B4-C18; | A25-B4-C19; | A28-B4-C20; | A31-B4-C21; | A2-B4-C23; | A5-B4-C24; |
| A23-B4-C18; | A26-B4-C19; | A29-B4-C20; | A32-B4-C21; | A3-B4-C23; | A6-B4-C24; |
| A24-B4-C18; | A27-B4-C19; | A30-B4-C20; | A1-B4-C22; | A4-B4-C23; | A7-B4-C24; |
| A25-B4-C18; | A28-B4-C19; | A31-B4-C20; | A2-B4-C22; | A5-B4-C23; | A8-B4-C24; |
| A26-B4-C18; | A29-B4-C19; | A32-B4-C20; | A3-B4-C22; | A6-B4-C23; | A9-B4-C24; |
| A27-B4-C18; | A30-B4-C19; | A1-B4-C21; | A4-B4-C22; | A7-B4-C23; | A10-B4-C24; |
| A28-B4-C18; | A31-B4-C19; | A2-B4-C21; | A5-B4-C22; | A8-B4-C23; | A11-B4-C24; |
| A29-B4-C18; | A32-B4-C19; | A3-B4-C21; | A6-B4-C22; | A9-B4-C23; | A12-B4-C24; |
| A30-B4-C18; | A1-B4-C20; | A4-B4-C21; | A7-B4-C22; | A10-B4-C23; | A13-B4-C24; |
| A31-B4-C18; | A2-B4-C20; | A5-B4-C21; | A8-B4-C22; | A11-B4-C23; | A14-B4-C24; |
| A32-B4-C18; | A3-B4-C20; | A6-B4-C21; | A9-B4-C22; | A12-B4-C23; | A15-B4-C24; |
| A1-B4-C19; | A4-B4-C20; | A7-B4-C21; | A10-B4-C22; | A13-B4-C23; | A16-B4-C24; |
| A2-B4-C19; | A5-B4-C20; | A8-B4-C21; | A11-B4-C22; | A14-B4-C23; | A17-B4-C24; |
| A3-B4-C19; | A6-B4-C20; | A9-B4-C21; | A12-B4-C22; | A15-B4-C23; | A18-B4-C24; |
| A4-B4-C19; | A7-B4-C20; | A10-B4-C21; | A13-B4-C22; | A16-B4-C23; | A19-B4-C24; |
| A5-B4-C19; | A8-B4-C20; | A11-B4-C21; | A14-B4-C22; | A17-B4-C23; | A20-B4-C24; |
| A6-B4-C19; | A9-B4-C20; | A12-B4-C21; | A15-B4-C22; | A18-B4-C23; | A21-B4-C24; |
| A7-B4-C19; | A10-B4-C20; | A13-B4-C21; | A16-B4-C22; | A19-B4-C23; | A22-B4-C24; |
| A8-B4-C19; | A11-B4-C20; | A14-B4-C21; | A17-B4-C22; | A20-B4-C23; | A23-B4-C24; |
| A9-B4-C19; | A12-B4-C20; | A15-B4-C21; | A18-B4-C22; | A21-B4-C23; | A24-B4-C24; |
| A10-B4-C19; | A13-B4-C20; | A16-B4-C21; | A19-B4-C22; | A22-B4-C23; | A25-B4-C24; |
| A11-B4-C19; | A14-B4-C20; | A17-B4-C21; | A20-B4-C22; | A23-B4-C23; | A26-B4-C24; |
| A12-B4-C19; | A15-B4-C20; | A18-B4-C21; | A21-B4-C22; | A24-B4-C23; | A27-B4-C24; |
| A13-B4-C19; | A16-B4-C20; | A19-B4-C21; | A22-B4-C22; | A25-B4-C23; | A28-B4-C24; |
| A14-B4-C19; | A17-B4-C20; | A20-B4-C21; | A23-B4-C22; | A26-B4-C23; | A29-B4-C24; |
| A15-B4-C19; | A18-B4-C20; | A11-B4-C21; | A24-B4-C22; | A27-B4-C23; | A30-B4-C24; |
| A16-B4-C19; | A19-B4-C20; | A22-B4-C21; | A25-B4-C22; | A28-B4-C23; | A31-B4-C24; |
| A17-B4-C19; | A20-B4-C20; | A23-B4-C21; | A26-B4-C22; | A29-B4-C23; | A32-B4-C24; |
| A18-B4-C19; | A11-B4-C20; | A24-B4-C21; | A27-B4-C22; | A30-B4-C23; | A1-B4-C25; |
| A19-B4-C19; | A22-B4-C20; | A25-B4-C21; | A28-B4-C22; | A31-B4-C23; | A2-B4-C25; |
| A20-B4-C19; | A23-B4-C20; | A26-B4-C21; | A29-B4-C22; | A32-B4-C23; | A3-B4-C25; |
| A11-B4-C19; | A24-B4-C20; | A27-B4-C21; | A30-B4-C22; | A1-B4-C24; | A4-B4-C25; |
| A22-B4-C19; | A25-B4-C20; | A28-B4-C21; | A31-B4-C22; | A2-B4-C24; | A5-B4-C25; |
| A23-B4-C19; | A26-B4-C20; | A29-B4-C21; | A32-B4-C22; | A3-B4-C24; | A6-B4-C25; |
| A7-B4-C25; | A10-B4-C26; | A13-B4-C27; | A16-B4-C28; | A19-B4-C29; | A22-B4-C30; |
| A8-B4-C25; | A11-B4-C26; | A14-B4-C27; | A17-B4-C28; | A20-B4-C29; | A23-B4-C30; |
| A9-B4-C25; | A12-B4-C26; | A15-B4-C27; | A18-B4-C28; | A21-B4-C29; | A24-B4-C30; |
| A10-B4-C25; | A13-B4-C26; | A16-B4-C27; | A19-B4-C28; | A22-B4-C29; | A25-B4-C30; |
| A11-B4-C25; | A14-B4-C26; | A17-B4-C27; | A20-B4-C28; | A23-B4-C29; | A26-B4-C30; |
| A12-B4-C25; | A15-B4-C26; | A18-B4-C27; | A21-B4-C28; | A24-B4-C29; | A27-B4-C30; |
| A13-B4-C25; | A16-B4-C26; | A19-B4-C27; | A22-B4-C28; | A25-B4-C29; | A28-B4-C30; |
| A14-B4-C25; | A17-B4-C26; | A20-B4-C27; | A23-B4-C28; | A26-B4-C29; | A29-B4-C30; |
| A15-B4-C25; | A18-B4-C26; | A21-B4-C27; | A24-B4-C28; | A27-B4-C29; | A30-B4-C30; |
| A16-B4-C25; | A19-B4-C26; | A22-B4-C27; | A25-B4-C28; | A28-B4-C29; | A31-B4-C30; |
| A17-B4-C25; | A20-B4-C26; | A23-B4-C27; | A26-B4-C28; | A29-B4-C29; | A32-B4-C30; |
| A18-B4-C25; | A21-B4-C26; | A24-B4-C27; | A27-B4-C28; | A30-B4-C29; | A1-B4-C31; |
| A19-B4-C25; | A22-B4-C26; | A25-B4-C27; | A28-B4-C28; | A31-B4-C29; | A2-B4-C31; |
| A20-B4-C25; | A23-B4-C26; | A26-B4-C27; | A29-B4-C28; | A32-B4-C29; | A3-B4-C31; |
| A21-B4-C25; | A24-B4-C26; | A27-B4-C27; | A30-B4-C28; | A1-B4-C30; | A4-B4-C31; |
| A22-B4-C25; | A25-B4-C26; | A28-B4-C27; | A31-B4-C28; | A2-B4-C30; | A5-B4-C31; |
| A23-B4-C25; | A26-B4-C26; | A29-B4-C27; | A32-B4-C28; | A3-B4-C30; | A6-B4-C31; |
| A24-B4-C25; | A27-B4-C26; | A30-B4-C27; | A1-B4-C29; | A4-B4-C30; | A7-B4-C31; |
| A25-B4-C25; | A28-B4-C26; | A31-B4-C27; | A2-B4-C29; | A5-B4-C30; | A8-B4-C31; |
| A26-B4-C25; | A29-B4-C26; | A32-B4-C27; | A3-B4-C29; | A6-B4-C30; | A9-B4-C31; |
| A27-B4-C25; | A30-B4-C26; | A1-B4-C28; | A4-B4-C29; | A7-B4-C30; | A10-B4-C31; |
| A28-B4-C25; | A31-B4-C26; | A2-B4-C28; | A5-B4-C29; | A8-B4-C30; | A11-B4-C31; |
| A29-B4-C25; | A32-B4-C26; | A3-B4-C28; | A6-B4-C29; | A9-B4-C30; | A12-B4-C31; |
| A30-B4-C25; | A1-B4-C27; | A4-B4-C28; | A7-B4-C29; | A10-B4-C30; | A13-B4-C31; |
| A31-B4-C25; | A2-B4-C27; | A5-B4-C28; | A8-B4-C29; | A11-B4-C30; | A14-B4-C31; |
| A32-B4-C25; | A3-B4-C27; | A6-B4-C28; | A9-B4-C29; | A12-B4-C30; | A15-B4-C31; |
| A1-B4-C26; | A4-B4-C27; | A7-B4-C28; | A10-B4-C29; | A13-B4-C30; | A16-B4-C31; |

-continued

| | | | | | |
|---|---|---|---|---|---|
| A2-B4-C26; | A5-B4-C27; | A8-B4-C28; | A11-B4-C29; | A14-B4-C30; | A17-B4-C31; |
| A3-B4-C26; | A6-B4-C27; | A9-B4-C28; | A12-B4-C29; | A15-B4-C30; | A18-B4-C31; |
| A4-B4-C26; | A7-B4-C27; | A10-B4-C28; | A13-B4-C29; | A16-B4-C30; | A19-B4-C31; |
| A5-B4-C26; | A8-B4-C27; | A11-B4-C28; | A14-B4-C29; | A17-B4-C30; | A20-B4-C31; |
| A6-B4-C26; | A9-B4-C27; | A12-B4-C28; | A15-B4-C29; | A18-B4-C30; | A21-B4-C31; |
| A7-B4-C26; | A10-B4-C27; | A13-B4-C28; | A16-B4-C29; | A19-B4-C30; | A22-B4-C31; |
| A8-B4-C26; | A11-B4-C27; | A14-B4-C28; | A17-B4-C29; | A20-B4-C30; | A23-B4-C31; |
| A9-B4-C26; | A12-B4-C27; | A15-B4-C28; | A18-B4-C29; | A21-B4-C30; | A24-B4-C31; |
| A25-B4-C31; | A28-B4-C32; | A31-B4-C33; | A2-B4-C35; | A5-B4-C36; | A8-B4-C37; |
| A26-B4-C31; | A29-B4-C32; | A32-B4-C33; | A3-B4-C35; | A6-B4-C36; | A9-B4-C37; |
| A27-B4-C31; | A30-B4-C32; | A1-B4-C34; | A4-B4-C35; | A7-B4-C36; | A10-B4-C37; |
| A28-B4-C31; | A31-B4-C32; | A2-B4-C34; | A5-B4-C35; | A8-B4-C36; | A11-B4-C37; |
| A29-B4-C31; | A32-B4-C32; | A3-B4-C34; | A6-B4-C35; | A9-B4-C36; | A12-B4-C37; |
| A30-B4-C31; | A1-B4-C33; | A4-B4-C34; | A7-B4-C35; | A10-B4-C36; | A13-B4-C37; |
| A31-B4-C31; | A2-B4-C33; | A5-B4-C34; | A8-B4-C35; | A11-B4-C36; | A14-B4-C37; |
| A32-B4-C31; | A3-B4-C33; | A6-B4-C34; | A9-B4-C35; | A12-B4-C36; | A15-B4-C37; |
| A1-B4-C32; | A4-B4-C33; | A7-B4-C34; | A10-B4-C35; | A13-B4-C36; | A16-B4-C37; |
| A2-B4-C32; | A5-B4-C33; | A8-B4-C34; | A11-B4-C35; | A14-B4-C36; | A17-B4-C37; |
| A3-B4-C32; | A6-B4-C33; | A9-B4-C34; | A12-B4-C35; | A15-B4-C36; | A18-B4-C37; |
| A4-B4-C32; | A7-B4-C33; | A10-B4-C34; | A13-B4-C35; | A16-B4-C36; | A19-B4-C37; |
| A5-B4-C32; | A8-B4-C33; | A11-B4-C34; | A14-B4-C35; | A17-B4-C36; | A20-B4-C37; |
| A6-B4-C32; | A9-B4-C33; | A12-B4-C34; | A15-B4-C35; | A18-B4-C36; | A21-B4-C37; |
| A7-B4-C32; | A10-B4-C33; | A13-B4-C34; | A16-B4-C35; | A19-B4-C36; | A22-B4-C37; |
| A8-B4-C32; | A11-B4-C33; | A14-B4-C34; | A17-B4-C35; | A20-B4-C36; | A23-B4-C37; |
| A9-B4-C32; | A12-B4-C33; | A15-B4-C34; | A18-B4-C35; | A21-B4-C36; | A24-B4-C37; |
| A10-B4-C32; | A13-B4-C33; | A16-B4-C34; | A19-B4-C35; | A22-B4-C36; | A25-B4-C37; |
| A11-B4-C32; | A14-B4-C33; | A17-B4-C34; | A20-B4-C35; | A23-B4-C36; | A26-B4-C37; |
| A12-B4-C32; | A15-B4-C33; | A18-B4-C34; | A21-B4-C35; | A24-B4-C36; | A27-B4-C37; |
| A13-B4-C32; | A16-B4-C33; | A19-B4-C34; | A22-B4-C35; | A25-B4-C36; | A28-B4-C37; |
| A14-B4-C32; | A17-B4-C33; | A20-B4-C34; | A23-B4-C35; | A26-B4-C36; | A29-B4-C37; |
| A15-B4-C32; | A18-B4-C33; | A21-B4-C34; | A24-B4-C35; | A27-B4-C36; | A30-B4-C37; |
| A16-B4-C32; | A19-B4-C33; | A22-B4-C34; | A25-B4-C35; | A28-B4-C36; | A31-B4-C37; |
| A17-B4-C32; | A20-B4-C33; | A23-B4-C34; | A26-B4-C35; | A29-B4-C36; | A32-B4-C37; |
| A18-B4-C32; | A21-B4-C33; | A24-B4-C34; | A27-B4-C35; | A30-B4-C36; | A1-B4-C38; |
| A19-B4-C32; | A22-B4-C33; | A25-B4-C34; | A28-B4-C35; | A31-B4-C36; | A2-B4-C38; |
| A20-B4-C32; | A23-B4-C33; | A26-B4-C34; | A29-B4-C35; | A32-B4-C36; | A3-B4-C38; |
| A21-B4-C32; | A24-B4-C33; | A27-B4-C34; | A30-B4-C35; | A1-B4-C37; | A4-B4-C38; |
| A22-B4-C32; | A25-B4-C33; | A28-B4-C34; | A31-B4-C35; | A2-B4-C37; | A5-B4-C38; |
| A23-B4-C32; | A26-B4-C33; | A29-B4-C34; | A32-B4-C35; | A3-B4-C37; | A6-B4-C38; |
| A24-B4-C32; | A27-B4-C33; | A30-B4-C34; | A1-B4-C36; | A4-B4-C37; | A7-B4-C38; |
| A25-B4-C32; | A28-B4-C33; | A31-B4-C34; | A2-B4-C36; | A5-B4-C37; | A8-B4-C38; |
| A26-B4-C32; | A29-B4-C33; | A32-B4-C34; | A3-B4-C36; | A6-B4-C37; | A9-B4-C38; |
| A27-B4-C32; | A30-B4-C33; | A1-B4-C35; | A4-B4-C36; | A7-B4-C37; | A10-B4-C38; |
| A11-B4-C38; | A14-B4-C39; | A17-B4-C40; | A20-B5-C1; | A23-B5-C2; | A26-B5-C3; |
| A12-B4-C38; | A15-B4-C39; | A18-B4-C40; | A21-B5-C1; | A24-B5-C2; | A27-B5-C3; |
| A13-B4-C38; | A16-B4-C39; | A19-B4-C40; | A22-B5-C1; | A25-B5-C2; | A28-B5-C3; |
| A14-B4-C38; | A17-B4-C39; | A20-B4-C40; | A23-B5-C1; | A26-B5-C2; | A29-B5-C3; |
| A15-B4-C38; | A18-B4-C39; | A21-B4-C40; | A24-B5-C1; | A27-B5-C2; | A30-B5-C3; |
| A16-B4-C38; | A19-B4-C39; | A22-B4-C40; | A25-B5-C1; | A28-B5-C2; | A31-B5-C3; |
| A17-B4-C38; | A20-B4-C39; | A23-B4-C40; | A26-B5-C1; | A29-B5-C2; | A32-B5-C3; |
| A18-B4-C38; | A21-B4-C39; | A24-B4-C40; | A27-B5-C1; | A30-B5-C2; | A1-B5-C4; |
| A19-B4-C38; | A22-B4-C39; | A25-B4-C40; | A28-B5-C1; | A31-B5-C2; | A2-B5-C4; |
| A20-B4-C38; | A23-B4-C39; | A26-B4-C40; | A29-B5-C1; | A32-B5-C2; | A3-B5-C4; |
| A21-B4-C38; | A24-B4-C39; | A27-B4-C40; | A30-B5-C1; | A1-B5-C3; | A4-B5-C4; |
| A22-B4-C38; | A25-B4-C39; | A28-B4-C40; | A31-B5-C1; | A2-B5-C3; | A5-B5-C4; |
| A23-B4-C38; | A26-B4-C39; | A29-B4-C40; | A32-B5-C1; | A3-B5-C3; | A6-B5-C4; |
| A24-B4-C38; | A27-B4-C39; | A30-B4-C40; | A1-B5-C2; | A4-B5-C3; | A7-B5-C4; |
| A25-B4-C38; | A28-B4-C39; | A31-B4-C40; | A2-B5-C2; | A5-B5-C3; | A8-B5-C4; |
| A26-B4-C38; | A29-B4-C39; | A32-B4-C40; | A3-B5-C2; | A6-B5-C3; | A9-B5-C4; |
| A27-B4-C38; | A30-B4-C39; | A1-B5-C1; | A4-B5-C2; | A7-B5-C3; | A10-B5-C4; |
| A28-B4-C38; | A31-B4-C39; | A2-B5-C1; | A5-B5-C2; | A8-B5-C3; | A11-B5-C4; |
| A29-B4-C38; | A32-B4-C39; | A3-B5-C1; | A6-B5-C2; | A9-B5-C3; | A12-B5-C4; |
| A30-B4-C38; | A1-B4-C40; | A4-B5-C1; | A7-B5-C2; | A10-B5-C3; | A13-B5-C4; |
| A31-B4-C38; | A2-B4-C40; | A5-B5-C1; | A8-B5-C2; | A11-B5-C3; | A14-B5-C4; |
| A32-B4-C38; | A3-B4-C40; | A6-B5-C1; | A9-B5-C2; | A12-B5-C3; | A15-B5-C4; |
| A1-B4-C39; | A4-B4-C40; | A7-B5-C1; | A10-B5-C2; | A13-B5-C3; | A16-B5-C4; |
| A2-B4-C39; | A5-B4-C40; | A8-B5-C1; | A11-B5-C2; | A14-B5-C3; | A17-B5-C4; |
| A3-B4-C39; | A6-B4-C40; | A9-B5-C1; | A12-B5-C2; | A15-B5-C3; | A18-B5-C4; |
| A4-B4-C39; | A7-B4-C40; | A10-B5-C1; | A13-B5-C2; | A16-B5-C3; | A19-B5-C4; |
| A5-B4-C39; | A8-B4-C40; | A11-B5-C1; | A14-B5-C2; | A17-B5-C3; | A20-B5-C4; |
| A6-B4-C39; | A9-B4-C40; | A12-B5-C1; | A15-B5-C2; | A18-B5-C3; | A21-B5-C4; |
| A7-B4-C39; | A10-B4-C40; | A13-B5-C1; | A16-B5-C2; | A19-B5-C3; | A22-B5-C4; |
| A8-B4-C39; | A11-B4-C40; | A14-B5-C1; | A17-B5-C2; | A20-B5-C3; | A23-B5-C4; |
| A9-B4-C39; | A12-B4-C40; | A15-B5-C1; | A18-B5-C2; | A21-B5-C3; | A24-B5-C4; |
| A10-B4-C39; | A13-B4-C40; | A16-B5-C1; | A19-B5-C2; | A22-B5-C3; | A25-B5-C4; |
| A11-B4-C39; | A14-B4-C40; | A17-B5-C1; | A20-B5-C2; | A23-B5-C3; | A26-B5-C4; |
| A12-B4-C39; | A15-B4-C40; | A18-B5-C1; | A21-B5-C2; | A24-B5-C3; | A27-B5-C4; |
| A13-B4-C39; | A16-B4-C40; | A19-B5-C1; | A22-B5-C2; | A25-B5-C3; | A28-B5-C4; |
| A29-B5-C4; | A32-B5-C5; | A3-B5-C7; | A6-B5-C8; | A9-B5-C9; | A12-B5-C10; |

-continued

| | | | | | |
|---|---|---|---|---|---|
| A30-B5-C4; | A1-B5-C6; | A4-B5-C7; | A7-B5-C8; | A10-B5-C9; | A13-B5-C10; |
| A31-B5-C4; | A2-B5-C6; | A5-B5-C7; | A8-B5-C8; | A11-B5-C9; | A14-B5-C10; |
| A32-B5-C4; | A3-B5-C6; | A6-B5-C7; | A9-B5-C8; | A12-B5-C9; | A15-B5-C10; |
| A1-B5-C5; | A4-B5-C6; | A7-B5-C7; | A10-B5-C8; | A13-B5-C9; | A16-B5-C10; |
| A2-B5-C5; | A5-B5-C6; | A8-B5-C7; | A11-B5-C8; | A14-B5-C9; | A17-B5-C10; |
| A3-B5-C5; | A6-B5-C6; | A9-B5-C7; | A12-B5-C8; | A15-B5-C9; | A18-B5-C10; |
| A4-B5-C5; | A7-B5-C6; | A10-B5-C7; | A13-B5-C8; | A16-B5-C9; | A19-B5-C10; |
| A5-B5-C5; | A8-B5-C6; | A11-B5-C7; | A14-B5-C8; | A17-B5-C9; | A20-B5-C10; |
| A6-B5-C5; | A9-B5-C6; | A12-B5-C7; | A15-B5-C8; | A18-B5-C9; | A21-B5-C10; |
| A7-B5-C5; | A10-B5-C6; | A13-B5-C7; | A16-B5-C8; | A19-B5-C9; | A22-B5-C10; |
| A8-B5-C5; | A11-B5-C6; | A14-B5-C7; | A17-B5-C8; | A20-B5-C9; | A23-B5-C10; |
| A9-B5-C5; | A12-B5-C6; | A15-B5-C7; | A18-B5-C8; | A21-B5-C9; | A24-B5-C10; |
| A10-B5-C5; | A13-B5-C6; | A16-B5-C7; | A19-B5-C8; | A22-B5-C9; | A25-B5-C10; |
| A11-B5-C5; | A14-B5-C6; | A17-B5-C7; | A20-B5-C8; | A23-B5-C9; | A26-B5-C10; |
| A12-B5-C5; | A15-B5-C6; | A18-B5-C7; | A21-B5-C8; | A24-B5-C9; | A27-B5-C10; |
| A13-B5-C5; | A16-B5-C6; | A19-B5-C7; | A22-B5-C8; | A25-B5-C9; | A28-B5-C10; |
| A14-B5-C5; | A17-B5-C6; | A20-B5-C7; | A23-B5-C8; | A26-B5-C9; | A29-B5-C10; |
| A15-B5-C5; | A18-B5-C6; | A21-B5-C7; | A24-B5-C8; | A27-B5-C9; | A30-B5-C10; |
| A16-B5-C5; | A19-B5-C6; | A22-B5-C7; | A25-B5-C8; | A28-B5-C9; | A31-B5-C10; |
| A17-B5-C5; | A20-B5-C6; | A23-B5-C7; | A26-B5-C8; | A29-B5-C9; | A32-B5-C10; |
| A18-B5-C5; | A21-B5-C6; | A24-B5-C7; | A27-B5-C8; | A30-B5-C9; | A1-B5-C11; |
| A19-B5-C5; | A22-B5-C6; | A25-B5-C7; | A28-B5-C8; | A31-B5-C9; | A2-B5-C11; |
| A20-B5-C5; | A23-B5-C6; | A26-B5-C7; | A29-B5-C8; | A32-B5-C9; | A3-B5-C11; |
| A21-B5-C5; | A24-B5-C6; | A27-B5-C7; | A30-B5-C8; | A1-B5-C10; | A4-B5-C11; |
| A22-B5-C5; | A25-B5-C6; | A28-B5-C7; | A31-B5-C8; | A2-B5-C10; | A5-B5-C11; |
| A23-B5-C5; | A26-B5-C6; | A29-B5-C7; | A32-B5-C8; | A3-B5-C10; | A6-B5-C11; |
| A24-B5-C5; | A27-B5-C6; | A30-B5-C7; | A1-B5-C9; | A4-B5-C10; | A7-B5-C11; |
| A25-B5-C5; | A28-B5-C6; | A31-B5-C7; | A2-B5-C9; | A5-B5-C10; | A8-B5-C11; |
| A26-B5-C5; | A29-B5-C6; | A32-B5-C7; | A3-B5-C9; | A6-B5-C10; | A9-B5-C11; |
| A27-B5-C5; | A30-B5-C6; | A1-B5-C8; | A4-B5-C9; | A7-B5-C10; | A10-B5-C11; |
| A28-B5-C5; | A31-B5-C6; | A2-B5-C8; | A5-B5-C9; | A8-B5-C10; | A11-B5-C11; |
| A29-B5-C5; | A32-B5-C6; | A3-B5-C8; | A6-B5-C9; | A9-B5-C10; | A12-B5-C11; |
| A30-B5-C5; | A1-B5-C7; | A4-B5-C8; | A7-B5-C9; | A10-B5-C10; | A13-B5-C11; |
| A31-B5-C5; | A2-B5-C7; | A5-B5-C8; | A8-B5-C9; | A11-B5-C10; | A14-B5-C11; |
| A15-B5-C11; | A18-B5-C12; | A21-B5-C13; | A24-B5-C14; | A27-B5-C15; | A30-B5-C16; |
| A16-B5-C11; | A19-B5-C12; | A22-B5-C13; | A25-B5-C14; | A28-B5-C15; | A31-B5-C16; |
| A17-B5-C11; | A20-B5-C12; | A23-B5-C13; | A26-B5-C14; | A29-B5-C15; | A32-B5-C16; |
| A18-B5-C11; | A21-B5-C12; | A24-B5-C13; | A27-B5-C14; | A30-B5-C15; | A1-B5-C17; |
| A19-B5-C11; | A22-B5-C12; | A25-B5-C13; | A28-B5-C14; | A31-B5-C15; | A2-B5-C17; |
| A20-B5-C11; | A23-B5-C12; | A26-B5-C13; | A29-B5-C14; | A32-B5-C15; | A3-B5-C17; |
| A21-B5-C11; | A24-B5-C12; | A27-B5-C13; | A30-B5-C14; | A1-B5-C16; | A4-B5-C17; |
| A22-B5-C11; | A25-B5-C12; | A28-B5-C13; | A31-B5-C14; | A2-B5-C16; | A5-B5-C17; |
| A23-B5-C11; | A26-B5-C12; | A29-B5-C13; | A32-B5-C14; | A3-B5-C16; | A6-B5-C17; |
| A24-B5-C11; | A27-B5-C12; | A30-B5-C13; | A1-B5-C15; | A4-B5-C16; | A7-B5-C17; |
| A25-B5-C11; | A28-B5-C12; | A31-B5-C13; | A2-B5-C15; | A5-B5-C16; | A8-B5-C17; |
| A26-B5-C11; | A29-B5-C12; | A32-B5-C13; | A3-B5-C15; | A6-B5-C16; | A9-B5-C17; |
| A27-B5-C11; | A30-B5-C12; | A1-B5-C14; | A4-B5-C15; | A7-B5-C16; | A10-B5-C17; |
| A28-B5-C11; | A31-B5-C12; | A2-B5-C14; | A5-B5-C15; | A8-B5-C16; | A11-B5-C17; |
| A29-B5-C11; | A32-B5-C12; | A3-B5-C14; | A6-B5-C15; | A9-B5-C16; | A12-B5-C17; |
| A30-B5-C11; | A1-B5-C13; | A4-B5-C14; | A7-B5-C15; | A10-B5-C16; | A13-B5-C17; |
| A31-B5-C11; | A2-B5-C13; | A5-B5-C14; | A8-B5-C15; | A11-B5-C16; | A14-B5-C17; |
| A32-B5-C11; | A3-B5-C13; | A6-B5-C14; | A9-B5-C15; | A12-B5-C16; | A15-B5-C17; |
| A1-B5-C12; | A4-B5-C13; | A7-B5-C14; | A10-B5-C15; | A13-B5-C16; | A16-B5-C17; |
| A2-B5-C12; | A5-B5-C13; | A8-B5-C14; | A11-B5-C15; | A14-B5-C16; | A17-B5-C17; |
| A3-B5-C12; | A6-B5-C13; | A9-B5-C14; | A12-B5-C15; | A15-B5-C16; | A18-B5-C17; |
| A4-B5-C12; | A7-B5-C13; | A10-B5-C14; | A13-B5-C15; | A16-B5-C16; | A19-B5-C17; |
| A5-B5-C12; | A8-B5-C13; | A11-B5-C14; | A14-B5-C15; | A17-B5-C16; | A20-B5-C17; |
| A6-B5-C12; | A9-B5-C13; | A12-B5-C14; | A15-B5-C15; | A18-B5-C16; | A21-B5-C17; |
| A7-B5-C12; | A10-B5-C13; | A13-B5-C14; | A16-B5-C15; | A19-B5-C16; | A22-B5-C17; |
| A8-B5-C12; | A11-B5-C13; | A14-B5-C14; | A17-B5-C15; | A20-B5-C16; | A23-B5-C17; |
| A9-B5-C12; | A12-B5-C13; | A15-B5-C14; | A18-B5-C15; | A21-B5-C16; | A24-B5-C17; |
| A10-B5-C12; | A13-B5-C13; | A16-B5-C14; | A19-B5-C15; | A22-B5-C16; | A25-B5-C17; |
| A11-B5-C12; | A14-B5-C13; | A17-B5-C14; | A20-B5-C15; | A23-B5-C16; | A26-B5-C17; |
| A12-B5-C12; | A15-B5-C13; | A18-B5-C14; | A21-B5-C15; | A24-B5-C16; | A27-B5-C17; |
| A13-B5-C12; | A16-B5-C13; | A19-B5-C14; | A22-B5-C15; | A25-B5-C16; | A28-B5-C17; |
| A14-B5-C12; | A17-B5-C13; | A20-B5-C14; | A23-B5-C15; | A26-B5-C16; | A29-B5-C17; |
| A15-B5-C12; | A18-B5-C13; | A21-B5-C14; | A24-B5-C15; | A27-B5-C16; | A30-B5-C17; |
| A16-B5-C12; | A19-B5-C13; | A22-B5-C14; | A25-B5-C15; | A28-B5-C16; | A31-B5-C17; |
| A17-B5-C12; | A20-B5-C13; | A23-B5-C14; | A26-B5-C15; | A29-B5-C16; | A32-B5-C17; |
| A1-B5-C18; | A4-B5-C19; | A7-B5-C20; | A10-B5-C21; | A13-B5-C22; | A16-B5-C23; |
| A2-B5-C18; | A5-B5-C19; | A8-B5-C20; | A11-B5-C21; | A14-B5-C22; | A17-B5-C23; |
| A3-B5-C18; | A6-B5-C19; | A9-B5-C20; | A12-B5-C21; | A15-B5-C22; | A18-B5-C23; |
| A4-B5-C18; | A7-B5-C19; | A10-B5-C20; | A13-B5-C21; | A16-B5-C22; | A19-B5-C23; |
| A5-B5-C18; | A8-B5-C19; | A11-B5-C20; | A14-B5-C21; | A17-B5-C22; | A20-B5-C23; |
| A6-B5-C18; | A9-B5-C19; | A12-B5-C20; | A15-B5-C21; | A18-B5-C22; | A21-B5-C23; |
| A7-B5-C18; | A10-B5-C19; | A13-B5-C20; | A16-B5-C21; | A19-B5-C22; | A22-B5-C23; |
| A8-B5-C18; | A11-B5-C19; | A14-B5-C20; | A17-B5-C21; | A20-B5-C22; | A23-B5-C23; |
| A9-B5-C18; | A12-B5-C19; | A15-B5-C20; | A18-B5-C21; | A21-B5-C22; | A24-B5-C23; |
| A10-B5-C18; | A13-B5-C19; | A16-B5-C20; | A19-B5-C21; | A22-B5-C22; | A25-B5-C23; |

-continued

| | | | | | |
|---|---|---|---|---|---|
| A11-B5-C18; | A14-B5-C19; | A17-B5-C20; | A20-B5-C21; | A23-B5-C22; | A26-B5-C23; |
| A12-B5-C18; | A15-B5-C19; | A18-B5-C20; | A21-B5-C21; | A24-B5-C22; | A27-B5-C23; |
| A13-B5-C18; | A16-B5-C19; | A19-B5-C20; | A22-B5-C21; | A25-B5-C22; | A28-B5-C23; |
| A14-B5-C18; | A17-B5-C19; | A20-B5-C20; | A23-B5-C21; | A26-B5-C22; | A29-B5-C23; |
| A15-B5-C18; | A18-B5-C19; | A21-B5-C20; | A24-B5-C21; | A27-B5-C22; | A30-B5-C23; |
| A16-B5-C18; | A19-B5-C19; | A22-B5-C20; | A25-B5-C21; | A28-B5-C22; | A31-B5-C23; |
| A17-B5-C18; | A20-B5-C19; | A23-B5-C20; | A26-B5-C21; | A29-B5-C22; | A32-B5-C23; |
| A18-B5-C18; | A21-B5-C19; | A24-B5-C20; | A27-B5-C21; | A30-B5-C22; | A1-B5-C24; |
| A19-B5-C18; | A22-B5-C19; | A25-B5-C20; | A28-B5-C21; | A31-B5-C22; | A2-B5-C24; |
| A20-B5-C18; | A23-B5-C19; | A26-B5-C20; | A29-B5-C21; | A32-B5-C22; | A3-B5-C24; |
| A21-B5-C18; | A24-B5-C19; | A27-B5-C20; | A30-B5-C21; | A1-B5-C23; | A4-B5-C24; |
| A22-B5-C18; | A25-B5-C19; | A28-B5-C20; | A31-B5-C21; | A2-B5-C23; | A5-B5-C24; |
| A23-B5-C18; | A26-B5-C19; | A29-B5-C20; | A32-B5-C21; | A3-B5-C23; | A6-B5-C24; |
| A24-B5-C18; | A27-B5-C19; | A30-B5-C20; | A1-B5-C22; | A4-B5-C23; | A7-B5-C24; |
| A25-B5-C18; | A28-B5-C19; | A31-B5-C20; | A2-B5-C22; | A5-B5-C23; | A8-B5-C24; |
| A26-B5-C18; | A29-B5-C19; | A32-B5-C20; | A3-B5-C22; | A6-B5-C23; | A9-B5-C24; |
| A27-B5-C18; | A30-B5-C19; | A1-B5-C21; | A4-B5-C22; | A7-B5-C23; | A10-B5-C24; |
| A28-B5-C18; | A31-B5-C19; | A2-B5-C21; | A5-B5-C22; | A8-B5-C23; | A11-B5-C24; |
| A29-B5-C18; | A32-B5-C19; | A3-B5-C21; | A6-B5-C22; | A9-B5-C23; | A12-B5-C24; |
| A30-B5-C18; | A1-B5-C20; | A4-B5-C21; | A7-B5-C22; | A10-B5-C23; | A13-B5-C24; |
| A31-B5-C18; | A2-B5-C20; | A5-B5-C21; | A8-B5-C22; | A11-B5-C23; | A14-B5-C24; |
| A32-B5-C18; | A3-B5-C20; | A6-B5-C21; | A9-B5-C22; | A12-B5-C23; | A15-B5-C24; |
| A1-B5-C19; | A4-B5-C20; | A7-B5-C21; | A10-B5-C22; | A13-B5-C23; | A16-B5-C24; |
| A2-B5-C19; | A5-B5-C20; | A8-B5-C21; | A11-B5-C22; | A14-B5-C23; | A17-B5-C24; |
| A3-B5-C19; | A6-B5-C20; | A9-B5-C21; | A12-B5-C22; | A15-B5-C23; | A18-B5-C24; |
| A19-B5-C24; | A22-B5-C25; | A25-B5-C26; | A28-B5-C27; | A31-B5-C28; | A2-B5-C30; |
| A20-B5-C24; | A23-B5-C25; | A26-B5-C26; | A29-B5-C27; | A32-B5-C28; | A3-B5-C30; |
| A21-B5-C24; | A24-B5-C25; | A27-B5-C26; | A30-B5-C27; | A1-B5-C29; | A4-B5-C30; |
| A22-B5-C24; | A25-B5-C25; | A28-B5-C26; | A31-B5-C27; | A2-B5-C29; | A5-B5-C30; |
| A23-B5-C24; | A26-B5-C25; | A29-B5-C26; | A32-B5-C27; | A3-B5-C29; | A6-B5-C30; |
| A24-B5-C24; | A27-B5-C25; | A30-B5-C26; | A1-B5-C28; | A4-B5-C29; | A7-B5-C30; |
| A25-B5-C24; | A28-B5-C25; | A31-B5-C26; | A2-B5-C28; | A5-B5-C29; | A8-B5-C30; |
| A26-B5-C24; | A29-B5-C25; | A32-B5-C26; | A3-B5-C28; | A6-B5-C29; | A9-B5-C30; |
| A27-B5-C24; | A30-B5-C25; | A1-B5-C27; | A4-B5-C28; | A7-B5-C29; | A10-B5-C30; |
| A28-B5-C24; | A31-B5-C25; | A2-B5-C27; | A5-B5-C28; | A8-B5-C29; | A11-B5-C30; |
| A29-B5-C24; | A32-B5-C25; | A3-B5-C27; | A6-B5-C28; | A9-B5-C29; | A12-B5-C30; |
| A30-B5-C24; | A1-B5-C26; | A4-B5-C27; | A7-B5-C28; | A10-B5-C29; | A13-B5-C30; |
| A31-B5-C24; | A2-B5-C26; | A5-B5-C27; | A8-B5-C28; | A11-B5-C29; | A14-B5-C30; |
| A32-B5-C24; | A3-B5-C26; | A6-B5-C27; | A9-B5-C28; | A12-B5-C29; | A15-B5-C30; |
| A1-B5-C25; | A4-B5-C26; | A7-B5-C27; | A10-B5-C28; | A13-B5-C29; | A16-B5-C30; |
| A2-B5-C25; | A5-B5-C26; | A8-B5-C27; | A11-B5-C28; | A14-B5-C29; | A17-B5-C30; |
| A3-B5-C25; | A6-B5-C26; | A9-B5-C27; | A12-B5-C28; | A15-B5-C29; | A18-B5-C30; |
| A4-B5-C25; | A7-B5-C26; | A10-B5-C27; | A13-B5-C28; | A16-B5-C29; | A19-B5-C30; |
| A5-B5-C25; | A8-B5-C26; | A11-B5-C27; | A14-B5-C28; | A17-B5-C29; | A20-B5-C30; |
| A6-B5-C25; | A9-B5-C26; | A12-B5-C27; | A15-B5-C28; | A18-B5-C29; | A21-B5-C30; |
| A7-B5-C25; | A10-B5-C26; | A13-B5-C27; | A16-B5-C28; | A19-B5-C29; | A22-B5-C30; |
| A8-B5-C25; | A11-B5-C26; | A14-B5-C27; | A17-B5-C28; | A20-B5-C29; | A23-B5-C30; |
| A9-B5-C25; | A12-B5-C26; | A15-B5-C27; | A18-B5-C28; | A21-B5-C29; | A24-B5-C30; |
| A10-B5-C25; | A13-B5-C26; | A16-B5-C27; | A19-B5-C28; | A22-B5-C29; | A25-B5-C30; |
| A11-B5-C25; | A14-B5-C26; | A17-B5-C27; | A20-B5-C28; | A23-B5-C29; | A26-B5-C30; |
| A12-B5-C25; | A15-B5-C26; | A18-B5-C27; | A21-B5-C28; | A24-B5-C29; | A27-B5-C30; |
| A13-B5-C25; | A16-B5-C26; | A19-B5-C27; | A22-B5-C28; | A25-B5-C29; | A28-B5-C30; |
| A14-B5-C25; | A17-B5-C26; | A20-B5-C27; | A23-B5-C28; | A26-B5-C29; | A29-B5-C30; |
| A15-B5-C25; | A18-B5-C26; | A21-B5-C27; | A24-B5-C28; | A27-B5-C29; | A30-B5-C30; |
| A16-B5-C25; | A19-B5-C26; | A22-B5-C27; | A25-B5-C28; | A28-B5-C29; | A31-B5-C30; |
| A17-B5-C25; | A20-B5-C26; | A23-B5-C27; | A26-B5-C28; | A29-B5-C29; | A32-B5-C30; |
| A18-B5-C25; | A21-B5-C26; | A24-B5-C27; | A27-B5-C28; | A30-B5-C29; | A1-B5-C31; |
| A19-B5-C25; | A22-B5-C26; | A25-B5-C27; | A28-B5-C28; | A31-B5-C29; | A2-B5-C31; |
| A20-B5-C25; | A23-B5-C26; | A26-B5-C27; | A29-B5-C28; | A32-B5-C29; | A3-B5-C31; |
| A21-B5-C25; | A24-B5-C26; | A27-B5-C27; | A30-B5-C28; | A1-B5-C30; | A4-B5-C31; |
| A5-B5-C31; | A8-B5-C32; | A11-B5-C33; | A14-B5-C34; | A17-B5-C35; | A20-B5-C36; |
| A6-B5-C31; | A9-B5-C32; | A12-B5-C33; | A15-B5-C34; | A18-B5-C35; | A21-B5-C36; |
| A7-B5-C31; | A10-B5-C32; | A13-B5-C33; | A16-B5-C34; | A19-B5-C35; | A22-B5-C36; |
| A8-B5-C31; | A11-B5-C32; | A14-B5-C33; | A17-B5-C34; | A20-B5-C35; | A23-B5-C36; |
| A9-B5-C31; | A12-B5-C32; | A15-B5-C33; | A18-B5-C34; | A21-B5-C35; | A24-B5-C36; |
| A10-B5-C31; | A13-B5-C32; | A16-B5-C33; | A19-B5-C34; | A22-B5-C35; | A25-B5-C36; |
| A11-B5-C31; | A14-B5-C32; | A17-B5-C33; | A20-B5-C34; | A23-B5-C35; | A26-B5-C36; |
| A12-B5-C31; | A15-B5-C32; | A18-B5-C33; | A21-B5-C34; | A24-B5-C35; | A27-B5-C36; |
| A13-B5-C31; | A16-B5-C32; | A19-B5-C33; | A22-B5-C34; | A25-B5-C35; | A28-B5-C36; |
| A14-B5-C31; | A17-B5-C32; | A20-B5-C33; | A23-B5-C34; | A26-B5-C35; | A29-B5-C36; |
| A15-B5-C31; | A18-B5-C32; | A21-B5-C33; | A24-B5-C34; | A27-B5-C35; | A30-B5-C36; |
| A16-B5-C31; | A19-B5-C32; | A22-B5-C33; | A25-B5-C34; | A28-B5-C35; | A31-B5-C36; |
| A17-B5-C31; | A20-B5-C32; | A23-B5-C33; | A26-B5-C34; | A29-B5-C35; | A32-B5-C36; |
| A18-B5-C31; | A21-B5-C32; | A24-B5-C33; | A27-B5-C34; | A30-B5-C35; | A1-B5-C37; |
| A19-B5-C31; | A22-B5-C32; | A25-B5-C33; | A28-B5-C34; | A31-B5-C35; | A2-B5-C37; |
| A20-B5-C31; | A23-B5-C32; | A26-B5-C33; | A29-B5-C34; | A32-B5-C35; | A3-B5-C37; |
| A21-B5-C31; | A24-B5-C32; | A27-B5-C33; | A30-B5-C34; | A1-B5-C36; | A4-B5-C37; |
| A22-B5-C31; | A25-B5-C32; | A28-B5-C33; | A31-B5-C34; | A2-B5-C36; | A5-B5-C37; |
| A23-B5-C31; | A26-B5-C32; | A29-B5-C33; | A32-B5-C34; | A3-B5-C36; | A6-B5-C37; |

-continued

| | | | | | |
|---|---|---|---|---|---|
| A24-B5-C31; | A27-B5-C32; | A30-B5-C33; | A1-B5-C35; | A4-B5-C36; | A7-B5-C37; |
| A25-B5-C31; | A28-B5-C32; | A31-B5-C33; | A2-B5-C35; | A5-B5-C36; | A8-B5-C37; |
| A26-B5-C31; | A29-B5-C32; | A32-B5-C33; | A3-B5-C35; | A6-B5-C36; | A9-B5-C37; |
| A27-B5-C31; | A30-B5-C32; | A1-B5-C34; | A4-B5-C35; | A7-B5-C36; | A10-B5-C37; |
| A28-B5-C31; | A31-B5-C32; | A2-B5-C34; | A5-B5-C35; | A8-B5-C36; | A11-B5-C37; |
| A29-B5-C31; | A32-B5-C32; | A3-B5-C34; | A6-B5-C35; | A9-B5-C36; | A12-B5-C37; |
| A30-B5-C31; | A1-B5-C33; | A4-B5-C34; | A7-B5-C35; | A10-B5-C36; | A13-B5-C37; |
| A31-B5-C31; | A2-B5-C33; | A5-B5-C34; | A8-B5-C35; | A11-B5-C36; | A14-B5-C37; |
| A32-B5-C31; | A3-B5-C33; | A6-B5-C34; | A9-B5-C35; | A12-B5-C36; | A15-B5-C37; |
| A1-B5-C32; | A4-B5-C33; | A7-B5-C34; | A10-B5-C35; | A13-B5-C36; | A16-B5-C37; |
| A2-B5-C32; | A5-B5-C33; | A8-B5-C34; | A11-B5-C35; | A14-B5-C36; | A17-B5-C37; |
| A3-B5-C32; | A6-B5-C33; | A9-B5-C34; | A12-B5-C35; | A15-B5-C36; | A18-B5-C37; |
| A4-B5-C32; | A7-B5-C33; | A10-B5-C34; | A13-B5-C35; | A16-B5-C36; | A19-B5-C37; |
| A5-B5-C32; | A8-B5-C33; | A11-B5-C34; | A14-B5-C35; | A17-B5-C36; | A20-B5-C37; |
| A6-B5-C32; | A9-B5-C33; | A12-B5-C34; | A15-B5-C35; | A18-B5-C36; | A21-B5-C37; |
| A7-B5-C32; | A10-B5-C33; | A13-B5-C34; | A16-B5-C35; | A19-B5-C36; | A22-B5-C37; |
| A23-B5-C37; | A26-B5-C38; | A29-B5-C39; | A32-B5-C40; | A3-B6-C2; | A6-B6-C3; |
| A24-B5-C37; | A27-B5-C38; | A30-B5-C39; | A1-B6-C1; | A4-B6-C2; | A7-B6-C3; |
| A25-B5-C37; | A28-B5-C38; | A31-B5-C39; | A2-B6-C1; | A5-B6-C2; | A8-B6-C3; |
| A26-B5-C37; | A29-B5-C38; | A32-B5-C39; | A3-B6-C1; | A6-B6-C2; | A9-B6-C3; |
| A27-B5-C37; | A30-B5-C38; | A1-B5-C40; | A4-B6-C1; | A7-B6-C2; | A10-B6-C3; |
| A28-B5-C37; | A31-B5-C38; | A2-B5-C40; | A5-B6-C1; | A8-B6-C2; | A11-B6-C3; |
| A29-B5-C37; | A32-B5-C38; | A3-B5-C40; | A6-B6-C1; | A9-B6-C2; | A12-B6-C3; |
| A30-B5-C37; | A1-B5-C39; | A4-B5-C40; | A7-B6-C1; | A10-B6-C2; | A13-B6-C3; |
| A31-B5-C37; | A2-B5-C39; | A5-B5-C40; | A8-B6-C1; | A11-B6-C2; | A14-B6-C3; |
| A32-B5-C37; | A3-B5-C39; | A6-B5-C40; | A9-B6-C1; | A12-B6-C2; | A15-B6-C3; |
| A1-B5-C38; | A4-B5-C39; | A7-B5-C40; | A10-B6-C1; | A13-B6-C2; | A16-B6-C3; |
| A2-B5-C38; | A5-B5-C39; | A8-B5-C40; | A11-B6-C1; | A14-B6-C2; | A17-B6-C3; |
| A3-B5-C38; | A6-B5-C39; | A9-B5-C40; | A12-B6-C1; | A15-B6-C2; | A18-B6-C3; |
| A4-B5-C38; | A7-B5-C39; | A10-B5-C40; | A13-B6-C1; | A16-B6-C2; | A19-B6-C3; |
| A5-B5-C38; | A8-B5-C39; | A11-B5-C40; | A14-B6-C1; | A17-B6-C2; | A20-B6-C3; |
| A6-B5-C38; | A9-B5-C39; | A12-B5-C40; | A15-B6-C1; | A18-B6-C2; | A21-B6-C3; |
| A7-B5-C38; | A10-B5-C39; | A13-B5-C40; | A16-B6-C1; | A19-B6-C2; | A22-B6-C3; |
| A8-B5-C38; | A11-B5-C39; | A14-B5-C40; | A17-B6-C1; | A20-B6-C2; | A23-B6-C3; |
| A9-B5-C38; | A12-B5-C39; | A15-B5-C40; | A18-B6-C1; | A21-B6-C2; | A24-B6-C3; |
| A10-B5-C38; | A13-B5-C39; | A16-B5-C40; | A19-B6-C1; | A22-B6-C2; | A25-B6-C3; |
| A11-B5-C38; | A14-B5-C39; | A17-B5-C40; | A20-B6-C1; | A23-B6-C2; | A26-B6-C3; |
| A12-B5-C38; | A15-B5-C39; | A18-B5-C40; | A21-B6-C1; | A24-B6-C2; | A27-B6-C3; |
| A13-B5-C38; | A16-B5-C39; | A19-B5-C40; | A22-B6-C1; | A25-B6-C2; | A28-B6-C3; |
| A14-B5-C38; | A17-B5-C39; | A20-B5-C40; | A23-B6-C1; | A26-B6-C2; | A29-B6-C3; |
| A15-B5-C38; | A18-B5-C39; | A21-B5-C40; | A24-B6-C1; | A27-B6-C2; | A30-B6-C3; |
| A16-B5-C38; | A19-B5-C39; | A22-B5-C40; | A25-B6-C1; | A28-B6-C2; | A31-B6-C3; |
| A17-B5-C38; | A20-B5-C39; | A23-B5-C40; | A26-B6-C1; | A29-B6-C2; | A32-B6-C3; |
| A18-B5-C38; | A21-B5-C39; | A24-B5-C40; | A27-B6-C1; | A30-B6-C2; | A1-B6-C4; |
| A19-B5-C38; | A22-B5-C39; | A25-B5-C40; | A28-B6-C1; | A31-B6-C2; | A2-B6-C4; |
| A20-B5-C38; | A23-B5-C39; | A26-B5-C40; | A29-B6-C1; | A32-B6-C2; | A3-B6-C4; |
| A21-B5-C38; | A24-B5-C39; | A27-B5-C40; | A30-B6-C1; | A1-B6-C3; | A4-B6-C4; |
| A22-B5-C38; | A25-B5-C39; | A28-B5-C40; | A31-B6-C1; | A2-B6-C3; | A5-B6-C4; |
| A23-B5-C38; | A26-B5-C39; | A29-B5-C40; | A32-B6-C1; | A3-B6-C3; | A6-B6-C4; |
| A24-B5-C38; | A27-B5-C39; | A30-B5-C40; | A1-B6-C2; | A4-B6-C3; | A7-B6-C4; |
| A25-B5-C38; | A28-B5-C39; | A31-B5-C40; | A2-B6-C2; | A5-B6-C3; | A8-B6-C4; |
| A9-B6-C4; | A12-B6-C5; | A15-B6-C6; | A18-B6-C7; | A21-B6-C8; | A24-B6-C9; |
| A10-B6-C4; | A13-B6-C5; | A16-B6-C6; | A19-B6-C7; | A22-B6-C8; | A25-B6-C9; |
| A11-B6-C4; | A14-B6-C5; | A17-B6-C6; | A20-B6-C7; | A23-B6-C8; | A26-B6-C9; |
| A12-B6-C4; | A15-B6-C5; | A18-B6-C6; | A21-B6-C7; | A24-B6-C8; | A27-B6-C9; |
| A13-B6-C4; | A16-B6-C5; | A19-B6-C6; | A22-B6-C7; | A25-B6-C8; | A28-B6-C9; |
| A14-B6-C4; | A17-B6-C5; | A20-B6-C6; | A23-B6-C7; | A26-B6-C8; | A29-B6-C9; |
| A15-B6-C4; | A18-B6-C5; | A21-B6-C6; | A24-B6-C7; | A27-B6-C8; | A30-B6-C9; |
| A16-B6-C4; | A19-B6-C5; | A22-B6-C6; | A25-B6-C7; | A28-B6-C8; | A31-B6-C9; |
| A17-B6-C4; | A20-B6-C5; | A23-B6-C6; | A26-B6-C7; | A29-B6-C8; | A32-B6-C9; |
| A18-B6-C4; | A21-B6-C5; | A24-B6-C6; | A27-B6-C7; | A30-B6-C8; | A1-B6-C10; |
| A19-B6-C4; | A22-B6-C5; | A25-B6-C6; | A28-B6-C7; | A31-B6-C8; | A2-B6-C10; |
| A20-B6-C4; | A23-B6-C5; | A26-B6-C6; | A29-B6-C7; | A32-B6-C8; | A3-B6-C10; |
| A21-B6-C4; | A24-B6-C5; | A27-B6-C6; | A30-B6-C7; | A1-B6-C9; | A4-B6-C10; |
| A22-B6-C4; | A25-B6-C5; | A28-B6-C6; | A31-B6-C7; | A2-B6-C9; | A5-B6-C10; |
| A23-B6-C4; | A26-B6-C5; | A29-B6-C6; | A32-B6-C7; | A3-B6-C9; | A6-B6-C10; |
| A24-B6-C4; | A27-B6-C5; | A30-B6-C6; | A1-B6-C8; | A4-B6-C9; | A7-B6-C10; |
| A25-B6-C4; | A28-B6-C5; | A31-B6-C6; | A2-B6-C8; | A5-B6-C9; | A8-B6-C10; |
| A26-B6-C4; | A29-B6-C5; | A32-B6-C6; | A3-B6-C8; | A6-B6-C9; | A9-B6-C10; |
| A27-B6-C4; | A30-B6-C5; | A1-B6-C7; | A4-B6-C8; | A7-B6-C9; | A10-B6-C10; |
| A28-B6-C4; | A31-B6-C5; | A2-B6-C7; | A5-B6-C8; | A8-B6-C9; | A11-B6-C10; |
| A29-B6-C4; | A32-B6-C5; | A3-B6-C7; | A6-B6-C8; | A9-B6-C9; | A12-B6-C10; |
| A30-B6-C4; | A1-B6-C6; | A4-B6-C7; | A7-B6-C8; | A10-B6-C9; | A13-B6-C10; |
| A31-B6-C4; | A2-B6-C6; | A5-B6-C7; | A8-B6-C8; | A11-B6-C9; | A14-B6-C10; |
| A32-B6-C4; | A3-B6-C6; | A6-B6-C7; | A9-B6-C8; | A12-B6-C9; | A15-B6-C10; |
| A1-B6-C5; | A4-B6-C6; | A7-B6-C7; | A10-B6-C8; | A13-B6-C9; | A16-B6-C10; |
| A2-B6-C5; | A5-B6-C6; | A8-B6-C7; | A11-B6-C8; | A14-B6-C9; | A17-B6-C10; |
| A3-B6-C5; | A6-B6-C6; | A9-B6-C7; | A12-B6-C8; | A15-B6-C9; | A18-B6-C10; |
| A4-B6-C5; | A7-B6-C6; | A10-B6-C7; | A13-B6-C8; | A16-B6-C9; | A19-B6-C10; |

-continued

| | | | | | |
|---|---|---|---|---|---|
| A5-B6-C5; | A8-B6-C6; | A11-B6-C7; | A14-B6-C8; | A17-B6-C9; | A20-B6-C10; |
| A6-B6-C5; | A9-B6-C6; | A12-B6-C7; | A15-B6-C8; | A18-B6-C9; | A21-B6-C10; |
| A7-B6-C5; | A10-B6-C6; | A13-B6-C7; | A16-B6-C8; | A19-B6-C9; | A22-B6-C10; |
| A8-B6-C5; | A11-B6-C6; | A14-B6-C7; | A17-B6-C8; | A20-B6-C9; | A23-B6-C10; |
| A9-B6-C5; | A12-B6-C6; | A15-B6-C7; | A18-B6-C8; | A21-B6-C9; | A24-B6-C10; |
| A10-B6-C5; | A13-B6-C6; | A16-B6-C7; | A19-B6-C8; | A22-B6-C9; | A25-B6-C10; |
| A11-B6-C5; | A14-B6-C6; | A17-B6-C7; | A20-B6-C8; | A23-B6-C9; | A26-B6-C10; |
| A27-B6-C10; | A30-B6-C11; | A1-B6-C13; | A4-B6-C14; | A7-B6-C15; | A10-B6-C16; |
| A28-B6-C10; | A31-B6-C11; | A2-B6-C13; | A5-B6-C14; | A8-B6-C15; | A11-B6-C16; |
| A29-B6-C10; | A32-B6-C11; | A3-B6-C13; | A6-B6-C14; | A9-B6-C15; | A12-B6-C16; |
| A30-B6-C10; | A1-B6-C12; | A4-B6-C13; | A7-B6-C14; | A10-B6-C15; | A13-B6-C16; |
| A31-B6-C10; | A2-B6-C12; | A5-B6-C13; | A8-B6-C14; | A11-B6-C15; | A14-B6-C16; |
| A32-B6-C10; | A3-B6-C12; | A6-B6-C13; | A9-B6-C14; | A12-B6-C15; | A15-B6-C16; |
| A1-B6-C11; | A4-B6-C12; | A7-B6-C13; | A10-B6-C14; | A13-B6-C15; | A16-B6-C16; |
| A2-B6-C11; | A5-B6-C12; | A8-B6-C13; | A11-B6-C14; | A14-B6-C15; | A17-B6-C16; |
| A3-B6-C11; | A6-B6-C12; | A9-B6-C13; | A12-B6-C14; | A15-B6-C15; | A18-B6-C16; |
| A4-B6-C11; | A7-B6-C12; | A10-B6-C13; | A13-B6-C14; | A16-B6-C15; | A19-B6-C16; |
| A5-B6-C11; | A8-B6-C12; | A11-B6-C13; | A14-B6-C14; | A17-B6-C15; | A20-B6-C16; |
| A6-B6-C11; | A9-B6-C12; | A12-B6-C13; | A15-B6-C14; | A18-B6-C15; | A21-B6-C16; |
| A7-B6-C11; | A10-B6-C12; | A13-B6-C13; | A16-B6-C14; | A19-B6-C15; | A22-B6-C16; |
| A8-B6-C11; | A11-B6-C12; | A14-B6-C13; | A17-B6-C14; | A20-B6-C15; | A23-B6-C16; |
| A9-B6-C11; | A12-B6-C12; | A15-B6-C13; | A18-B6-C14; | A21-B6-C15; | A24-B6-C16; |
| A10-B6-C11; | A13-B6-C12; | A16-B6-C13; | A19-B6-C14; | A22-B6-C15; | A25-B6-C16; |
| A11-B6-C11; | A14-B6-C12; | A17-B6-C13; | A20-B6-C14; | A23-B6-C15; | A26-B6-C16; |
| A12-B6-C11; | A15-B6-C12; | A18-B6-C13; | A21-B6-C14; | A24-B6-C15; | A27-B6-C16; |
| A13-B6-C11; | A16-B6-C12; | A19-B6-C13; | A22-B6-C14; | A25-B6-C15; | A28-B6-C16; |
| A14-B6-C11; | A17-B6-C12; | A20-B6-C13; | A23-B6-C14; | A26-B6-C15; | A29-B6-C16; |
| A15-B6-C11; | A18-B6-C12; | A21-B6-C13; | A24-B6-C14; | A27-B6-C15; | A30-B6-C16; |
| A16-B6-C11; | A19-B6-C12; | A22-B6-C13; | A25-B6-C14; | A28-B6-C15; | A31-B6-C16; |
| A17-B6-C11; | A20-B6-C12; | A23-B6-C13; | A26-B6-C14; | A29-B6-C15; | A32-B6-C16; |
| A18-B6-C11; | A21-B6-C12; | A24-B6-C13; | A27-B6-C14; | A30-B6-C15; | A1-B6-C17; |
| A19-B6-C11; | A22-B6-C12; | A25-B6-C13; | A28-B6-C14; | A31-B6-C15; | A2-B6-C17; |
| A20-B6-C11; | A23-B6-C12; | A26-B6-C13; | A29-B6-C14; | A32-B6-C15; | A3-B6-C17; |
| A21-B6-C11; | A24-B6-C12; | A27-B6-C13; | A30-B6-C14; | A1-B6-C16; | A4-B6-C17; |
| A22-B6-C11; | A25-B6-C12; | A28-B6-C13; | A31-B6-C14; | A2-B6-C16; | A5-B6-C17; |
| A23-B6-C11; | A26-B6-C12; | A29-B6-C13; | A32-B6-C14; | A3-B6-C16; | A6-B6-C17; |
| A24-B6-C11; | A27-B6-C12; | A30-B6-C13; | A1-B6-C15; | A4-B6-C16; | A7-B6-C17; |
| A25-B6-C11; | A28-B6-C12; | A31-B6-C13; | A2-B6-C15; | A5-B6-C16; | A8-B6-C17; |
| A26-B6-C11; | A29-B6-C12; | A32-B6-C13; | A3-B6-C15; | A6-B6-C16; | A9-B6-C17; |
| A27-B6-C11; | A30-B6-C12; | A1-B6-C14; | A4-B6-C15; | A7-B6-C16; | A10-B6-C17; |
| A28-B6-C11; | A31-B6-C12; | A2-B6-C14; | A5-B6-C15; | A8-B6-C16; | A11-B6-C17; |
| A29-B6-C11; | A32-B6-C12; | A3-B6-C14; | A6-B6-C15; | A9-B6-C16; | A12-B6-C17; |
| A13-B6-C17; | A16-B6-C18; | A19-B6-C19; | A22-B6-C20; | A25-B6-C21; | A28-B6-C22; |
| A14-B6-C17; | A17-B6-C18; | A20-B6-C19; | A23-B6-C20; | A26-B6-C21; | A29-B6-C22; |
| A15-B6-C17; | A18-B6-C18; | A21-B6-C19; | A24-B6-C20; | A27-B6-C21; | A30-B6-C22; |
| A16-B6-C17; | A19-B6-C18; | A22-B6-C19; | A25-B6-C20; | A28-B6-C21; | A31-B6-C22; |
| A17-B6-C17; | A20-B6-C18; | A23-B6-C19; | A26-B6-C20; | A29-B6-C21; | A32-B6-C22; |
| A18-B6-C17; | A21-B6-C18; | A24-B6-C19; | A27-B6-C20; | A30-B6-C21; | A1-B6-C23; |
| A19-B6-C17; | A22-B6-C18; | A25-B6-C19; | A28-B6-C20; | A31-B6-C21; | A2-B6-C23; |
| A20-B6-C17; | A23-B6-C18; | A26-B6-C19; | A29-B6-C20; | A32-B6-C21; | A3-B6-C23; |
| A21-B6-C17; | A24-B6-C18; | A27-B6-C19; | A30-B6-C20; | A1-B6-C22; | A4-B6-C23; |
| A22-B6-C17; | A25-B6-C18; | A28-B6-C19; | A31-B6-C20; | A2-B6-C22; | A5-B6-C23; |
| A23-B6-C17; | A26-B6-C18; | A29-B6-C19; | A32-B6-C20; | A3-B6-C22; | A6-B6-C23; |
| A24-B6-C17; | A27-B6-C18; | A30-B6-C19; | A1-B6-C21; | A4-B6-C22; | A7-B6-C23; |
| A25-B6-C17; | A28-B6-C18; | A31-B6-C19; | A2-B6-C21; | A5-B6-C22; | A8-B6-C23; |
| A26-B6-C17; | A29-B6-C18; | A32-B6-C19; | A3-B6-C21; | A6-B6-C22; | A9-B6-C23; |
| A27-B6-C17; | A30-B6-C18; | A1-B6-C20; | A4-B6-C21; | A7-B6-C22; | A10-B6-C23; |
| A28-B6-C17; | A31-B6-C18; | A2-B6-C20; | A5-B6-C21; | A8-B6-C22; | A11-B6-C23; |
| A29-B6-C17; | A32-B6-C18; | A3-B6-C20; | A6-B6-C21; | A9-B6-C22; | A12-B6-C23; |
| A30-B6-C17; | A1-B6-C19; | A4-B6-C20; | A7-B6-C21; | A10-B6-C22; | A13-B6-C23; |
| A31-B6-C17; | A2-B6-C19; | A5-B6-C20; | A8-B6-C21; | A11-B6-C22; | A14-B6-C23; |
| A32-B6-C17; | A3-B6-C19; | A6-B6-C20; | A9-B6-C21; | A12-B6-C22; | A15-B6-C23; |
| A1-B6-C18; | A4-B6-C19; | A7-B6-C20; | A10-B6-C21; | A13-B6-C22; | A16-B6-C23; |
| A2-B6-C18; | A5-B6-C19; | A8-B6-C20; | A11-B6-C21; | A14-B6-C22; | A17-B6-C23; |
| A3-B6-C18; | A6-B6-C19; | A9-B6-C20; | A12-B6-C21; | A15-B6-C22; | A18-B6-C23; |
| A4-B6-C18; | A7-B6-C19; | A10-B6-C20; | A13-B6-C21; | A16-B6-C22; | A19-B6-C23; |
| A5-B6-C18; | A8-B6-C19; | A11-B6-C20; | A14-B6-C21; | A17-B6-C22; | A20-B6-C23; |
| A6-B6-C18; | A9-B6-C19; | A12-B6-C20; | A15-B6-C21; | A18-B6-C22; | A21-B6-C23; |
| A7-B6-C18; | A10-B6-C19; | A13-B6-C20; | A16-B6-C21; | A19-B6-C22; | A22-B6-C23; |
| A8-B6-C18; | A11-B6-C19; | A14-B6-C20; | A17-B6-C21; | A20-B6-C22; | A23-B6-C23; |
| A9-B6-C18; | A12-B6-C19; | A15-B6-C20; | A18-B6-C21; | A21-B6-C22; | A24-B6-C23; |
| A10-B6-C18; | A13-B6-C19; | A16-B6-C20; | A19-B6-C21; | A22-B6-C22; | A25-B6-C23; |
| A11-B6-C18; | A14-B6-C19; | A17-B6-C20; | A20-B6-C21; | A23-B6-C22; | A26-B6-C23; |
| A12-B6-C18; | A15-B6-C19; | A18-B6-C20; | A21-B6-C21; | A24-B6-C22; | A27-B6-C23; |
| A13-B6-C18; | A16-B6-C19; | A19-B6-C20; | A22-B6-C21; | A25-B6-C22; | A28-B6-C23; |
| A14-B6-C18; | A17-B6-C19; | A20-B6-C20; | A23-B6-C21; | A26-B6-C22; | A29-B6-C23; |
| A15-B6-C18; | A18-B6-C19; | A21-B6-C20; | A24-B6-C21; | A27-B6-C22; | A30-B6-C23; |
| A31-B6-C23; | A2-B6-C25; | A5-B6-C26; | A8-B6-C27; | A11-B6-C28; | A14-B6-C29; |
| A32-B6-C23; | A3-B6-C25; | A6-B6-C26; | A9-B6-C27; | A12-B6-C28; | A15-B6-C29; |

| | | | | | |
|---|---|---|---|---|---|
| A1-B6-C24; | A4-B6-C25; | A7-B6-C26; | A10-B6-C27; | A13-B6-C28; | A16-B6-C29; |
| A2-B6-C24; | A5-B6-C25; | A8-B6-C26; | A11-B6-C27; | A14-B6-C28; | A17-B6-C29; |
| A3-B6-C24; | A6-B6-C25; | A9-B6-C26; | A12-B6-C27; | A15-B6-C28; | A18-B6-C29; |
| A4-B6-C24; | A7-B6-C25; | A10-B6-C26; | A13-B6-C27; | A16-B6-C28; | A19-B6-C29; |
| A5-B6-C24; | A8-B6-C25; | A11-B6-C26; | A14-B6-C27; | A17-B6-C28; | A20-B6-C29; |
| A6-B6-C24; | A9-B6-C25; | A12-B6-C26; | A15-B6-C27; | A18-B6-C28; | A21-B6-C29; |
| A7-B6-C24; | A10-B6-C25; | A13-B6-C26; | A16-B6-C27; | A19-B6-C28; | A22-B6-C29; |
| A8-B6-C24; | A11-B6-C25; | A14-B6-C26; | A17-B6-C27; | A20-B6-C28; | A23-B6-C29; |
| A9-B6-C24; | A12-B6-C25; | A15-B6-C26; | A18-B6-C27; | A21-B6-C28; | A24-B6-C29; |
| A10-B6-C24; | A13-B6-C25; | A16-B6-C26; | A19-B6-C27; | A22-B6-C28; | A25-B6-C29; |
| A11-B6-C24; | A14-B6-C25; | A17-B6-C26; | A20-B6-C27; | A23-B6-C28; | A26-B6-C29; |
| A12-B6-C24; | A15-B6-C25; | A18-B6-C26; | A21-B6-C27; | A24-B6-C28; | A27-B6-C29; |
| A13-B6-C24; | A16-B6-C25; | A19-B6-C26; | A22-B6-C27; | A25-B6-C28; | A28-B6-C29; |
| A14-B6-C24; | A17-B6-C25; | A20-B6-C26; | A23-B6-C27; | A26-B6-C28; | A29-B6-C29; |
| A15-B6-C24; | A18-B6-C25; | A21-B6-C26; | A24-B6-C27; | A27-B6-C28; | A30-B6-C29; |
| A16-B6-C24; | A19-B6-C25; | A22-B6-C26; | A25-B6-C27; | A28-B6-C28; | A31-B6-C29; |
| A17-B6-C24; | A20-B6-C25; | A23-B6-C26; | A26-B6-C27; | A29-B6-C28; | A32-B6-C29; |
| A18-B6-C24; | A21-B6-C25; | A24-B6-C26; | A27-B6-C27; | A30-B6-C28; | A1-B6-C30; |
| A19-B6-C24; | A22-B6-C25; | A25-B6-C26; | A28-B6-C27; | A31-B6-C28; | A2-B6-C30; |
| A20-B6-C24; | A23-B6-C25; | A26-B6-C26; | A29-B6-C27; | A32-B6-C28; | A3-B6-C30; |
| A21-B6-C24; | A24-B6-C25; | A27-B6-C26; | A30-B6-C27; | A1-B6-C29; | A4-B6-C30; |
| A22-B6-C24; | A25-B6-C25; | A28-B6-C26; | A31-B6-C27; | A2-B6-C29; | A5-B6-C30; |
| A23-B6-C24; | A26-B6-C25; | A29-B6-C26; | A32-B6-C27; | A3-B6-C29; | A6-B6-C30; |
| A24-B6-C24; | A27-B6-C25; | A30-B6-C26; | A1-B6-C28; | A4-B6-C29; | A7-B6-C30; |
| A25-B6-C24; | A28-B6-C25; | A31-B6-C26; | A2-B6-C28; | A5-B6-C29; | A8-B6-C30; |
| A26-B6-C24; | A29-B6-C25; | A32-B6-C26; | A3-B6-C28; | A6-B6-C29; | A9-B6-C30; |
| A27-B6-C24; | A30-B6-C25; | A1-B6-C27; | A4-B6-C28; | A7-B6-C29; | A10-B6-C30; |
| A28-B6-C24; | A31-B6-C25; | A2-B6-C27; | A5-B6-C28; | A8-B6-C29; | A11-B6-C30; |
| A29-B6-C24; | A32-B6-C25; | A3-B6-C27; | A6-B6-C28; | A9-B6-C29; | A12-B6-C30; |
| A30-B6-C24; | A1-B6-C26; | A4-B6-C27; | A7-B6-C28; | A10-B6-C29; | A13-B6-C30; |
| A31-B6-C24; | A2-B6-C26; | A5-B6-C27; | A8-B6-C28; | A11-B6-C29; | A14-B6-C30; |
| A32-B6-C24; | A3-B6-C26; | A6-B6-C27; | A9-B6-C28; | A12-B6-C29; | A15-B6-C30; |
| A1-B6-C25; | A4-B6-C26; | A7-B6-C27; | A10-B6-C28; | A13-B6-C29; | A16-B6-C30; |
| A17-B6-C30; | A20-B6-C31; | A23-B6-C32; | A26-B6-C33; | A29-B6-C34; | A32-B6-C35; |
| A18-B6-C30; | A21-B6-C31; | A24-B6-C32; | A27-B6-C33; | A30-B6-C34; | A1-B6-C36; |
| A19-B6-C30; | A22-B6-C31; | A25-B6-C32; | A28-B6-C33; | A31-B6-C34; | A2-B6-C36; |
| A20-B6-C30; | A23-B6-C31; | A26-B6-C32; | A29-B6-C33; | A32-B6-C34; | A3-B6-C36; |
| A21-B6-C30; | A24-B6-C31; | A27-B6-C32; | A30-B6-C33; | A1-B6-C35; | A4-B6-C36; |
| A22-B6-C30; | A25-B6-C31; | A28-B6-C32; | A31-B6-C33; | A2-B6-C35; | A5-B6-C36; |
| A23-B6-C30; | A26-B6-C31; | A29-B6-C32; | A32-B6-C33; | A3-B6-C35; | A6-B6-C36; |
| A24-B6-C30; | A27-B6-C31; | A30-B6-C32; | A1-B6-C34; | A4-B6-C35; | A7-B6-C36; |
| A25-B6-C30; | A28-B6-C31; | A31-B6-C32; | A2-B6-C34; | A5-B6-C35; | A8-B6-C36; |
| A26-B6-C30; | A29-B6-C31; | A32-B6-C32; | A3-B6-C34; | A6-B6-C35; | A9-B6-C36; |
| A27-B6-C30; | A30-B6-C31; | A1-B6-C33; | A4-B6-C34; | A7-B6-C35; | A10-B6-C36; |
| A28-B6-C30; | A31-B6-C31; | A2-B6-C33; | A5-B6-C34; | A8-B6-C35; | A11-B6-C36; |
| A29-B6-C30; | A32-B6-C31; | A3-B6-C33; | A6-B6-C34; | A9-B6-C35; | A12-B6-C36; |
| A30-B6-C30; | A1-B6-C32; | A4-B6-C33; | A7-B6-C34; | A10-B6-C35; | A13-B6-C36; |
| A31-B6-C30; | A2-B6-C32; | A5-B6-C33; | A8-B6-C34; | A11-B6-C35; | A14-B6-C36; |
| A32-B6-C30; | A3-B6-C32; | A6-B6-C33; | A9-B6-C34; | A12-B6-C35; | A15-B6-C36; |
| A1-B6-C31; | A4-B6-C32; | A7-B6-C33; | A10-B6-C34; | A13-B6-C35; | A16-B6-C36; |
| A2-B6-C31; | A5-B6-C32; | A8-B6-C33; | A11-B6-C34; | A14-B6-C35; | A17-B6-C36; |
| A3-B6-C31; | A6-B6-C32; | A9-B6-C33; | A12-B6-C34; | A15-B6-C35; | A18-B6-C36; |
| A4-B6-C31; | A7-B6-C32; | A10-B6-C33; | A13-B6-C34; | A16-B6-C35; | A19-B6-C36; |
| A5-B6-C31; | A8-B6-C32; | A11-B6-C33; | A14-B6-C34; | A17-B6-C35; | A20-B6-C36; |
| A6-B6-C31; | A9-B6-C32; | A12-B6-C33; | A15-B6-C34; | A18-B6-C35; | A21-B6-C36; |
| A7-B6-C31; | A10-B6-C32; | A13-B6-C33; | A16-B6-C34; | A19-B6-C35; | A22-B6-C36; |
| A8-B6-C31; | A11-B6-C32; | A14-B6-C33; | A17-B6-C34; | A20-B6-C35; | A23-B6-C36; |
| A9-B6-C31; | A12-B6-C32; | A15-B6-C33; | A18-B6-C34; | A21-B6-C35; | A24-B6-C36; |
| A10-B6-C31; | A13-B6-C32; | A16-B6-C33; | A19-B6-C34; | A22-B6-C35; | A25-B6-C36; |
| A11-B6-C31; | A14-B6-C32; | A17-B6-C33; | A20-B6-C34; | A23-B6-C35; | A26-B6-C36; |
| A12-B6-C31; | A15-B6-C32; | A18-B6-C33; | A21-B6-C34; | A24-B6-C35; | A27-B6-C36; |
| A13-B6-C31; | A16-B6-C32; | A19-B6-C33; | A22-B6-C34; | A25-B6-C35; | A28-B6-C36; |
| A14-B6-C31; | A17-B6-C32; | A20-B6-C33; | A23-B6-C34; | A26-B6-C35; | A29-B6-C36; |
| A15-B6-C31; | A18-B6-C32; | A21-B6-C33; | A24-B6-C34; | A27-B6-C35; | A30-B6-C36; |
| A16-B6-C31; | A19-B6-C32; | A22-B6-C33; | A25-B6-C34; | A28-B6-C35; | A31-B6-C36; |
| A17-B6-C31; | A20-B6-C32; | A23-B6-C33; | A26-B6-C34; | A29-B6-C35; | A32-B6-C36; |
| A18-B6-C31; | A21-B6-C32; | A24-B6-C33; | A27-B6-C34; | A30-B6-C35; | A1-B6-C37; |
| A19-B6-C31; | A22-B6-C32; | A25-B6-C33; | A28-B6-C34; | A31-B6-C35; | A2-B6-C37; |
| A3-B6-C37; | A6-B6-C38; | A9-B6-C39; | A12-B6-C40; | A15-B7-C1; | A18-B7-C2; |
| A4-B6-C37; | A7-B6-C38; | A10-B6-C39; | A13-B6-C40; | A16-B7-C1; | A19-B7-C2; |
| A5-B6-C37; | A8-B6-C38; | A11-B6-C39; | A14-B6-C40; | A17-B7-C1; | A20-B7-C2; |
| A6-B6-C37; | A9-B6-C38; | A12-B6-C39; | A15-B6-C40; | A18-B7-C1; | A21-B7-C2; |
| A7-B6-C37; | A10-B6-C38; | A13-B6-C39; | A16-B6-C40; | A19-B7-C1; | A22-B7-C2; |
| A8-B6-C37; | A11-B6-C38; | A14-B6-C39; | A17-B6-C40; | A20-B7-C1; | A23-B7-C2; |
| A9-B6-C37; | A12-B6-C38; | A15-B6-C39; | A18-B6-C40; | A21-B7-C1; | A24-B7-C2; |
| A10-B6-C37; | A13-B6-C38; | A16-B6-C39; | A19-B6-C40; | A22-B7-C1; | A25-B7-C2; |
| A11-B6-C37; | A14-B6-C38; | A17-B6-C39; | A20-B6-C40; | A23-B7-C1; | A26-B7-C2; |
| A12-B6-C37; | A15-B6-C38; | A18-B6-C39; | A21-B6-C40; | A24-B7-C1; | A27-B7-C2; |
| A13-B6-C37; | A16-B6-C38; | A19-B6-C39; | A22-B6-C40; | A25-B7-C1; | A28-B7-C2; |

-continued

| | | | | | |
|---|---|---|---|---|---|
| A14-B6-C37; | A17-B6-C38; | A20-B6-C39; | A23-B6-C40; | A26-B7-C1; | A29-B7-C2; |
| A15-B6-C37; | A18-B6-C38; | A21-B6-C39; | A24-B6-C40; | A27-B7-C1; | A30-B7-C2; |
| A16-B6-C37; | A19-B6-C38; | A22-B6-C39; | A25-B6-C40; | A28-B7-C1; | A31-B7-C2; |
| A17-B6-C37; | A20-B6-C38; | A23-B6-C39; | A26-B6-C40; | A29-B7-C1; | A32-B7-C2; |
| A18-B6-C37; | A21-B6-C38; | A24-B6-C39; | A27-B6-C40; | A30-B7-C1; | A1-B7-C3; |
| A19-B6-C37; | A22-B6-C38; | A25-B6-C39; | A28-B6-C40; | A31-B7-C1; | A2-B7-C3; |
| A20-B6-C37; | A23-B6-C38; | A26-B6-C39; | A29-B6-C40; | A32-B7-C1; | A3-B7-C3; |
| A21-B6-C37; | A24-B6-C38; | A27-B6-C39; | A30-B6-C40; | A1-B7-C2; | A4-B7-C3; |
| A22-B6-C37; | A25-B6-C38; | A28-B6-C39; | A31-B6-C40; | A2-B7-C2; | A5-B7-C3; |
| A23-B6-C37; | A26-B6-C38; | A29-B6-C39; | A32-B6-C40; | A3-B7-C2; | A6-B7-C3; |
| A24-B6-C37; | A27-B6-C38; | A30-B6-C39; | A1-B7-C1; | A4-B7-C2; | A7-B7-C3; |
| A25-B6-C37; | A28-B6-C38; | A31-B6-C39; | A2-B7-C1; | A5-B7-C2; | A8-B7-C3; |
| A26-B6-C37; | A29-B6-C38; | A32-B6-C39; | A3-B7-C1; | A6-B7-C2; | A9-B7-C3; |
| A27-B6-C37; | A30-B6-C38; | A1-B6-C40; | A4-B7-C1; | A7-B7-C2; | A10-B7-C3; |
| A28-B6-C37; | A31-B6-C38; | A2-B6-C40; | A5-B7-C1; | A8-B7-C2; | A11-B7-C3; |
| A29-B6-C37; | A32-B6-C38; | A3-B6-C40; | A6-B7-C1; | A9-B7-C2; | A12-B7-C3; |
| A30-B6-C37; | A1-B6-C39; | A4-B6-C40; | A7-B7-C1; | A10-B7-C2; | A13-B7-C3; |
| A31-B6-C37; | A2-B6-C39; | A5-B6-C40; | A8-B7-C1; | A11-B7-C2; | A14-B7-C3; |
| A32-B6-C37; | A3-B6-C39; | A6-B6-C40; | A9-B7-C1; | A12-B7-C2; | A15-B7-C3; |
| A1-B6-C38; | A4-B6-C39; | A7-B6-C40; | A10-B7-C1; | A13-B7-C2; | A16-B7-C3; |
| A2-B6-C38; | A5-B6-C39; | A8-B6-C40; | A11-B7-C1; | A14-B7-C2; | A17-B7-C3; |
| A3-B6-C38; | A6-B6-C39; | A9-B6-C40; | A12-B7-C1; | A15-B7-C2; | A18-B7-C3; |
| A4-B6-C38; | A7-B6-C39; | A10-B6-C40; | A13-B7-C1; | A16-B7-C2; | A19-B7-C3; |
| A5-B6-C38; | A8-B6-C39; | A11-B6-C40; | A14-B7-C1; | A17-B7-C2; | A20-B7-C3; |
| A21-B7-C3; | A24-B7-C4; | A27-B7-C5; | A30-B7-C6; | A1-B7-C8; | A4-B7-C9; |
| A22-B7-C3; | A25-B7-C4; | A28-B7-C5; | A31-B7-C6; | A2-B7-C8; | A5-B7-C9; |
| A23-B7-C3; | A26-B7-C4; | A29-B7-C5; | A32-B7-C6; | A3-B7-C8; | A6-B7-C9; |
| A24-B7-C3; | A27-B7-C4; | A30-B7-C5; | A1-B7-C7; | A4-B7-C8; | A7-B7-C9; |
| A25-B7-C3; | A28-B7-C4; | A31-B7-C5; | A2-B7-C7; | A5-B7-C8; | A8-B7-C9; |
| A26-B7-C3; | A29-B7-C4; | A32-B7-C5; | A3-B7-C7; | A6-B7-C8; | A9-B7-C9; |
| A27-B7-C3; | A30-B7-C4; | A1-B7-C6; | A4-B7-C7; | A7-B7-C8; | A10-B7-C9; |
| A28-B7-C3; | A31-B7-C4; | A2-B7-C6; | A5-B7-C7; | A8-B7-C8; | A11-B7-C9; |
| A29-B7-C3; | A32-B7-C4; | A3-B7-C6; | A6-B7-C7; | A9-B7-C8; | A12-B7-C9; |
| A30-B7-C3; | A1-B7-C5; | A4-B7-C6; | A7-B7-C7; | A10-B7-C8; | A13-B7-C9; |
| A31-B7-C3; | A2-B7-C5; | A5-B7-C6; | A8-B7-C7; | A11-B7-C8; | A14-B7-C9; |
| A32-B7-C3; | A3-B7-C5; | A6-B7-C6; | A9-B7-C7; | A12-B7-C8; | A15-B7-C9; |
| A1-B7-C4; | A4-B7-C5; | A7-B7-C6; | A10-B7-C7; | A13-B7-C8; | A16-B7-C9; |
| A2-B7-C4; | A5-B7-C5; | A8-B7-C6; | A11-B7-C7; | A14-B7-C8; | A17-B7-C9; |
| A3-B7-C4; | A6-B7-C5; | A9-B7-C6; | A12-B7-C7; | A15-B7-C8; | A18-B7-C9; |
| A4-B7-C4; | A7-B7-C5; | A10-B7-C6; | A13-B7-C7; | A16-B7-C8; | A19-B7-C9; |
| A5-B7-C4; | A8-B7-C5; | A11-B7-C6; | A14-B7-C7; | A17-B7-C8; | A20-B7-C9; |
| A6-B7-C4; | A9-B7-C5; | A12-B7-C6; | A15-B7-C7; | A18-B7-C8; | A21-B7-C9; |
| A7-B7-C4; | A10-B7-C5; | A13-B7-C6; | A16-B7-C7; | A19-B7-C8; | A22-B7-C9; |
| A8-B7-C4; | A11-B7-C5; | A14-B7-C6; | A17-B7-C7; | A20-B7-C8; | A23-B7-C9; |
| A9-B7-C4; | A12-B7-C5; | A15-B7-C6; | A18-B7-C7; | A21-B7-C8; | A24-B7-C9; |
| A10-B7-C4; | A13-B7-C5; | A16-B7-C6; | A19-B7-C7; | A22-B7-C8; | A25-B7-C9; |
| A11-B7-C4; | A14-B7-C5; | A17-B7-C6; | A20-B7-C7; | A23-B7-C8; | A26-B7-C9; |
| A12-B7-C4; | A15-B7-C5; | A18-B7-C6; | A21-B7-C7; | A24-B7-C8; | A27-B7-C9; |
| A13-B7-C4; | A16-B7-C5; | A19-B7-C6; | A22-B7-C7; | A25-B7-C8; | A28-B7-C9; |
| A14-B7-C4; | A17-B7-C5; | A20-B7-C6; | A23-B7-C7; | A26-B7-C8; | A29-B7-C9; |
| A15-B7-C4; | A18-B7-C5; | A21-B7-C6; | A24-B7-C7; | A27-B7-C8; | A30-B7-C9; |
| A16-B7-C4; | A19-B7-C5; | A22-B7-C6; | A25-B7-C7; | A28-B7-C8; | A31-B7-C9; |
| A17-B7-C4; | A20-B7-C5; | A23-B7-C6; | A26-B7-C7; | A29-B7-C8; | A32-B7-C9; |
| A18-B7-C4; | A21-B7-C5; | A24-B7-C6; | A27-B7-C7; | A30-B7-C8; | A1-B7-C10; |
| A19-B7-C4; | A22-B7-C5; | A25-B7-C6; | A28-B7-C7; | A31-B7-C8; | A2-B7-C10; |
| A20-B7-C4; | A23-B7-C5; | A26-B7-C6; | A29-B7-C7; | A32-B7-C8; | A3-B7-C10; |
| A21-B7-C4; | A24-B7-C5; | A27-B7-C6; | A30-B7-C7; | A1-B7-C9; | A4-B7-C10; |
| A22-B7-C4; | A25-B7-C5; | A28-B7-C6; | A31-B7-C7; | A2-B7-C9; | A5-B7-C10; |
| A23-B7-C4; | A26-B7-C5; | A29-B7-C6; | A32-B7-C7; | A3-B7-C9; | A6-B7-C10; |
| A7-B7-C10; | A10-B7-C11; | A13-B7-C12; | A16-B7-C13; | A19-B7-C14; | A22-B7-C15; |
| A8-B7-C10; | A11-B7-C11; | A14-B7-C12; | A17-B7-C13; | A20-B7-C14; | A23-B7-C15; |
| A9-B7-C10; | A12-B7-C11; | A15-B7-C12; | A18-B7-C13; | A21-B7-C14; | A24-B7-C15; |
| A10-B7-C10; | A13-B7-C11; | A16-B7-C12; | A19-B7-C13; | A22-B7-C14; | A25-B7-C15; |
| A11-B7-C10; | A14-B7-C11; | A17-B7-C12; | A20-B7-C13; | A23-B7-C14; | A26-B7-C15; |
| A12-B7-C10; | A15-B7-C11; | A18-B7-C12; | A21-B7-C13; | A24-B7-C14; | A27-B7-C15; |
| A13-B7-C10; | A16-B7-C11; | A19-B7-C12; | A22-B7-C13; | A25-B7-C14; | A28-B7-C15; |
| A14-B7-C10; | A17-B7-C11; | A20-B7-C12; | A23-B7-C13; | A26-B7-C14; | A29-B7-C15; |
| A15-B7-C10; | A18-B7-C11; | A21-B7-C12; | A24-B7-C13; | A27-B7-C14; | A30-B7-C15; |
| A16-B7-C10; | A19-B7-C11; | A22-B7-C12; | A25-B7-C13; | A28-B7-C14; | A31-B7-C15; |
| A17-B7-C10; | A20-B7-C11; | A23-B7-C12; | A26-B7-C13; | A29-B7-C14; | A32-B7-C15; |
| A18-B7-C10; | A21-B7-C11; | A24-B7-C12; | A27-B7-C13; | A30-B7-C14; | A1-B7-C16; |
| A19-B7-C10; | A22-B7-C11; | A25-B7-C12; | A28-B7-C13; | A31-B7-C14; | A2-B7-C16; |
| A20-B7-C10; | A23-B7-C11; | A26-B7-C12; | A29-B7-C13; | A32-B7-C14; | A3-B7-C16; |
| A21-B7-C10; | A24-B7-C11; | A27-B7-C12; | A30-B7-C13; | A1-B7-C15; | A4-B7-C16; |
| A22-B7-C10; | A25-B7-C11; | A28-B7-C12; | A31-B7-C13; | A2-B7-C15; | A5-B7-C16; |
| A23-B7-C10; | A26-B7-C11; | A29-B7-C12; | A32-B7-C13; | A3-B7-C15; | A6-B7-C16; |
| A24-B7-C10; | A27-B7-C11; | A30-B7-C12; | A1-B7-C14; | A4-B7-C15; | A7-B7-C16; |
| A25-B7-C10; | A28-B7-C11; | A31-B7-C12; | A2-B7-C14; | A5-B7-C15; | A8-B7-C16; |
| A26-B7-C10; | A29-B7-C11; | A32-B7-C12; | A3-B7-C14; | A6-B7-C15; | A9-B7-C16; |

-continued

| | | | | | |
|---|---|---|---|---|---|
| A27-B7-C10; | A30-B7-C11; | A1-B7-C13; | A4-B7-C14; | A7-B7-C15; | A10-B7-C16; |
| A28-B7-C10; | A31-B7-C11; | A2-B7-C13; | A5-B7-C14; | A8-B7-C15; | A11-B7-C16; |
| A29-B7-C10; | A32-B7-C11; | A3-B7-C13; | A6-B7-C14; | A9-B7-C15; | A12-B7-C16; |
| A30-B7-C10; | A1-B7-C12; | A4-B7-C13; | A7-B7-C14; | A10-B7-C15; | A13-B7-C16; |
| A31-B7-C10; | A2-B7-C12; | A5-B7-C13; | A8-B7-C14; | A11-B7-C15; | A14-B7-C16; |
| A32-B7-C10; | A3-B7-C12; | A6-B7-C13; | A9-B7-C14; | A12-B7-C15; | A15-B7-C16; |
| A1-B7-C11; | A4-B7-C12; | A7-B7-C13; | A10-B7-C14; | A13-B7-C15; | A16-B7-C16; |
| A2-B7-C11; | A5-B7-C12; | A8-B7-C13; | A11-B7-C14; | A14-B7-C15; | A17-B7-C16; |
| A3-B7-C11; | A6-B7-C12; | A9-B7-C13; | A12-B7-C14; | A15-B7-C15; | A18-B7-C16; |
| A4-B7-C11; | A7-B7-C12; | A10-B7-C13; | A13-B7-C14; | A16-B7-C15; | A19-B7-C16; |
| A5-B7-C11; | A8-B7-C12; | A11-B7-C13; | A14-B7-C14; | A17-B7-C15; | A20-B7-C16; |
| A6-B7-C11; | A9-B7-C12; | A12-B7-C13; | A15-B7-C14; | A15-B7-C15; | A21-B7-C16; |
| A7-B7-C11; | A10-B7-C12; | A13-B7-C13; | A16-B7-C14; | A19-B7-C15; | A22-B7-C16; |
| A8-B7-C11; | A11-B7-C12; | A14-B7-C13; | A17-B7-C14; | A20-B7-C15; | A23-B7-C16; |
| A9-B7-C11; | A12-B7-C12; | A15-B7-C13; | A18-B7-C14; | A21-B7-C15; | A24-B7-C16; |
| A25-B7-C16; | A28-B7-C17; | A31-B7-C18; | A2-B7-C20; | A5-B7-C21; | A8-B7-C22; |
| A26-B7-C16; | A29-B7-C17; | A32-B7-C18; | A3-B7-C20; | A6-B7-C21; | A9-B7-C22; |
| A27-B7-C16; | A30-B7-C17; | A1-B7-C19; | A4-B7-C20; | A7-B7-C21; | A10-B7-C22; |
| A28-B7-C16; | A31-B7-C17; | A2-B7-C19; | A5-B7-C20; | A8-B7-C21; | A11-B7-C22; |
| A29-B7-C16; | A32-B7-C17; | A3-B7-C19; | A6-B7-C20; | A9-B7-C21; | A12-B7-C22; |
| A30-B7-C16; | A1-B7-C18; | A4-B7-C19; | A7-B7-C20; | A10-B7-C21; | A13-B7-C22; |
| A31-B7-C16; | A2-B7-C18; | A5-B7-C19; | A8-B7-C20; | A11-B7-C21; | A14-B7-C22; |
| A32-B7-C16; | A3-B7-C18; | A6-B7-C19; | A9-B7-C20; | A12-B7-C21; | A15-B7-C22; |
| A1-B7-C17; | A4-B7-C18; | A7-B7-C19; | A10-B7-C20; | A13-B7-C21; | A16-B7-C22; |
| A2-B7-C17; | A5-B7-C18; | A8-B7-C19; | A11-B7-C20; | A14-B7-C21; | A17-B7-C22; |
| A3-B7-C17; | A6-B7-C18; | A9-B7-C19; | A12-B7-C20; | A15-B7-C21; | A18-B7-C22; |
| A4-B7-C17; | A7-B7-C18; | A10-B7-C19; | A13-B7-C20; | A16-B7-C21; | A19-B7-C22; |
| A5-B7-C17; | A8-B7-C18; | A11-B7-C19; | A14-B7-C20; | A17-B7-C21; | A20-B7-C22; |
| A6-B7-C17; | A9-B7-C18; | A12-B7-C19; | A15-B7-C20; | A18-B7-C21; | A21-B7-C22; |
| A7-B7-C17; | A10-B7-C18; | A13-B7-C19; | A16-B7-C20; | A19-B7-C21; | A22-B7-C22; |
| A8-B7-C17; | A11-B7-C18; | A14-B7-C19; | A17-B7-C20; | A20-B7-C21; | A23-B7-C22; |
| A9-B7-C17; | A12-B7-C18; | A15-B7-C19; | A18-B7-C20; | A21-B7-C21; | A24-B7-C22; |
| A10-B7-C17; | A13-B7-C18; | A16-B7-C19; | A19-B7-C20; | A22-B7-C21; | A25-B7-C22; |
| A11-B7-C17; | A14-B7-C18; | A17-B7-C19; | A20-B7-C20; | A23-B7-C21; | A26-B7-C22; |
| A12-B7-C17; | A15-B7-C18; | A18-B7-C19; | A21-B7-C20; | A24-B7-C21; | A27-B7-C22; |
| A13-B7-C17; | A16-B7-C18; | A19-B7-C19; | A22-B7-C20; | A25-B7-C21; | A28-B7-C22; |
| A14-B7-C17; | A17-B7-C18; | A20-B7-C19; | A23-B7-C20; | A26-B7-C21; | A29-B7-C22; |
| A15-B7-C17; | A18-B7-C18; | A21-B7-C19; | A24-B7-C20; | A27-B7-C21; | A30-B7-C22; |
| A16-B7-C17; | A19-B7-C18; | A22-B7-C19; | A25-B7-C20; | A28-B7-C21; | A31-B7-C22; |
| A17-B7-C17; | A20-B7-C18; | A23-B7-C19; | A26-B7-C20; | A29-B7-C21; | A32-B7-C22; |
| A18-B7-C17; | A21-B7-C18; | A24-B7-C19; | A27-B7-C20; | A30-B7-C21; | A1-B7-C23; |
| A19-B7-C17; | A22-B7-C18; | A25-B7-C19; | A28-B7-C20; | A31-B7-C21; | A2-B7-C23; |
| A20-B7-C17; | A23-B7-C18; | A26-B7-C19; | A29-B7-C20; | A32-B7-C21; | A3-B7-C23; |
| A21-B7-C17; | A24-B7-C18; | A27-B7-C19; | A30-B7-C20; | A1-B7-C22; | A4-B7-C23; |
| A22-B7-C17; | A25-B7-C18; | A28-B7-C19; | A31-B7-C20; | A2-B7-C22; | A5-B7-C23; |
| A23-B7-C17; | A26-B7-C18; | A29-B7-C19; | A32-B7-C20; | A3-B7-C22; | A6-B7-C23; |
| A24-B7-C17; | A27-B7-C18; | A30-B7-C19; | A1-B7-C21; | A4-B7-C22; | A7-B7-C23; |
| A25-B7-C17; | A28-B7-C18; | A31-B7-C19; | A2-B7-C21; | A5-B7-C22; | A8-B7-C23; |
| A26-B7-C17; | A29-B7-C18; | A32-B7-C19; | A3-B7-C21; | A6-B7-C22; | A9-B7-C23; |
| A27-B7-C17; | A30-B7-C18; | A1-B7-C20; | A4-B7-C21; | A7-B7-C22; | A10-B7-C23; |
| A11-B7-C23; | A14-B7-C24; | A17-B7-C25; | A20-B7-C26; | A23-B7-C27; | A26-B7-C28; |
| A12-B7-C23; | A15-B7-C24; | A18-B7-C25; | A21-B7-C26; | A24-B7-C27; | A27-B7-C28; |
| A13-B7-C23; | A16-B7-C24; | A19-B7-C25; | A22-B7-C26; | A25-B7-C27; | A28-B7-C28; |
| A14-B7-C23; | A17-B7-C24; | A20-B7-C25; | A23-B7-C26; | A26-B7-C27; | A29-B7-C28; |
| A15-B7-C23; | A18-B7-C24; | A21-B7-C25; | A24-B7-C26; | A27-B7-C27; | A30-B7-C28; |
| A16-B7-C23; | A19-B7-C24; | A22-B7-C25; | A25-B7-C26; | A28-B7-C27; | A31-B7-C28; |
| A17-B7-C23; | A20-B7-C24; | A23-B7-C25; | A26-B7-C26; | A29-B7-C27; | A32-B7-C28; |
| A18-B7-C23; | A21-B7-C24; | A24-B7-C25; | A27-B7-C26; | A30-B7-C27; | A1-B7-C29; |
| A19-B7-C23; | A22-B7-C24; | A25-B7-C25; | A28-B7-C26; | A31-B7-C27; | A2-B7-C29; |
| A20-B7-C23; | A23-B7-C24; | A26-B7-C25; | A29-B7-C26; | A32-B7-C27; | A3-B7-C29; |
| A21-B7-C23; | A24-B7-C24; | A27-B7-C25; | A30-B7-C26; | A1-B7-C28; | A4-B7-C29; |
| A22-B7-C23; | A25-B7-C24; | A28-B7-C25; | A31-B7-C26; | A2-B7-C28; | A5-B7-C29; |
| A23-B7-C23; | A26-B7-C24; | A29-B7-C25; | A32-B7-C26; | A3-B7-C28; | A6-B7-C29; |
| A24-B7-C23; | A27-B7-C24; | A30-B7-C25; | A1-B7-C27; | A4-B7-C28; | A7-B7-C29; |
| A25-B7-C23; | A28-B7-C24; | A31-B7-C25; | A2-B7-C27; | A5-B7-C28; | A8-B7-C29; |
| A26-B7-C23; | A29-B7-C24; | A32-B7-C25; | A3-B7-C27; | A6-B7-C28; | A9-B7-C29; |
| A27-B7-C23; | A30-B7-C24; | A1-B7-C26; | A4-B7-C27; | A7-B7-C28; | A10-B7-C29; |
| A28-B7-C23; | A31-B7-C24; | A2-B7-C26; | A5-B7-C27; | A8-B7-C28; | A11-B7-C29; |
| A29-B7-C23; | A32-B7-C24; | A3-B7-C26; | A6-B7-C27; | A9-B7-C28; | A12-B7-C29; |
| A30-B7-C23; | A1-B7-C25; | A4-B7-C26; | A7-B7-C27; | A10-B7-C28; | A13-B7-C29; |
| A31-B7-C23; | A2-B7-C25; | A5-B7-C26; | A8-B7-C27; | A11-B7-C28; | A14-B7-C29; |
| A32-B7-C23; | A3-B7-C25; | A6-B7-C26; | A9-B7-C27; | A12-B7-C28; | A15-B7-C29; |
| A1-B7-C24; | A4-B7-C25; | A7-B7-C26; | A10-B7-C27; | A13-B7-C28; | A16-B7-C29; |
| A2-B7-C24; | A5-B7-C25; | A8-B7-C26; | A11-B7-C27; | A14-B7-C28; | A17-B7-C29; |
| A3-B7-C24; | A6-B7-C25; | A9-B7-C26; | A12-B7-C27; | A15-B7-C28; | A18-B7-C29; |
| A4-B7-C24; | A7-B7-C25; | A10-B7-C26; | A13-B7-C27; | A16-B7-C28; | A19-B7-C29; |
| A5-B7-C24; | A8-B7-C25; | A11-B7-C26; | A14-B7-C27; | A17-B7-C28; | A20-B7-C29; |
| A6-B7-C24; | A9-B7-C25; | A12-B7-C26; | A15-B7-C27; | A18-B7-C28; | A21-B7-C29; |
| A7-B7-C24; | A10-B7-C25; | A13-B7-C26; | A16-B7-C27; | A19-B7-C28; | A22-B7-C29; |

-continued

| | | | | | |
|---|---|---|---|---|---|
| A8-B7-C24; | A11-B7-C25; | A14-B7-C26; | A17-B7-C27; | A20-B7-C28; | A23-B7-C29; |
| A9-B7-C24; | A12-B7-C25; | A15-B7-C26; | A18-B7-C27; | A21-B7-C28; | A24-B7-C29; |
| A10-B7-C24; | A13-B7-C25; | A16-B7-C26; | A19-B7-C27; | A22-B7-C28; | A25-B7-C29; |
| A11-B7-C24; | A14-B7-C25; | A17-B7-C26; | A20-B7-C27; | A23-B7-C28; | A26-B7-C29; |
| A12-B7-C24; | A15-B7-C25; | A18-B7-C26; | A21-B7-C27; | A24-B7-C28; | A27-B7-C29; |
| A13-B7-C24; | A16-B7-C25; | A19-B7-C26; | A22-B7-C27; | A25-B7-C28; | A28-B7-C29; |
| A29-B7-C29; | A32-B7-C30; | A3-B7-C32; | A6-B7-C33; | A9-B7-C34; | A12-B7-C35; |
| A30-B7-C29; | A1-B7-C31; | A4-B7-C32; | A7-B7-C33; | A10-B7-C34; | A13-B7-C35; |
| A31-B7-C29; | A2-B7-C31; | A5-B7-C32; | A8-B7-C33; | A11-B7-C34; | A14-B7-C35; |
| A32-B7-C29; | A3-B7-C31; | A6-B7-C32; | A9-B7-C33; | A12-B7-C34; | A15-B7-C35; |
| A1-B7-C30; | A4-B7-C31; | A7-B7-C32; | A10-B7-C33; | A13-B7-C34; | A16-B7-C35; |
| A2-B7-C30; | A5-B7-C31; | A8-B7-C32; | A11-B7-C33; | A14-B7-C34; | A17-B7-C35; |
| A3-B7-C30; | A6-B7-C31; | A9-B7-C32; | A12-B7-C33; | A15-B7-C34; | A18-B7-C35; |
| A4-B7-C30; | A7-B7-C31; | A10-B7-C32; | A13-B7-C33; | A16-B7-C34; | A19-B7-C35; |
| A5-B7-C30; | A8-B7-C31; | A11-B7-C32; | A14-B7-C33; | A17-B7-C34; | A20-B7-C35; |
| A6-B7-C30; | A9-B7-C31; | A12-B7-C32; | A15-B7-C33; | A18-B7-C34; | A21-B7-C35; |
| A7-B7-C30; | A10-B7-C31; | A13-B7-C32; | A16-B7-C33; | A19-B7-C34; | A22-B7-C35; |
| A8-B7-C30; | A11-B7-C31; | A14-B7-C32; | A17-B7-C33; | A20-B7-C34; | A23-B7-C35; |
| A9-B7-C30; | A12-B7-C31; | A15-B7-C32; | A18-B7-C33; | A21-B7-C34; | A24-B7-C35; |
| A10-B7-C30; | A13-B7-C31; | A16-B7-C32; | A19-B7-C33; | A22-B7-C34; | A25-B7-C35; |
| A11-B7-C30; | A14-B7-C31; | A17-B7-C32; | A20-B7-C33; | A23-B7-C34; | A26-B7-C35; |
| A12-B7-C30; | A15-B7-C31; | A18-B7-C32; | A21-B7-C33; | A24-B7-C34; | A27-B7-C35; |
| A13-B7-C30; | A16-B7-C31; | A19-B7-C32; | A22-B7-C33; | A25-B7-C34; | A28-B7-C35; |
| A14-B7-C30; | A17-B7-C31; | A20-B7-C32; | A23-B7-C33; | A26-B7-C34; | A29-B7-C35; |
| A15-B7-C30; | A18-B7-C31; | A21-B7-C32; | A24-B7-C33; | A27-B7-C34; | A30-B7-C35; |
| A16-B7-C30; | A19-B7-C31; | A22-B7-C32; | A25-B7-C33; | A28-B7-C34; | A31-B7-C35; |
| A17-B7-C30; | A20-B7-C31; | A23-B7-C32; | A26-B7-C33; | A29-B7-C34; | A32-B7-C35; |
| A18-B7-C30; | A21-B7-C31; | A24-B7-C32; | A27-B7-C33; | A30-B7-C34; | A1-B7-C36; |
| A19-B7-C30; | A22-B7-C31; | A25-B7-C32; | A28-B7-C33; | A31-B7-C34; | A2-B7-C36; |
| A20-B7-C30; | A23-B7-C31; | A26-B7-C32; | A29-B7-C33; | A32-B7-C34; | A3-B7-C36; |
| A21-B7-C30; | A24-B7-C31; | A27-B7-C32; | A30-B7-C33; | A1-B7-C35; | A4-B7-C36; |
| A22-B7-C30; | A25-B7-C31; | A28-B7-C32; | A31-B7-C33; | A2-B7-C35; | A5-B7-C36; |
| A23-B7-C30; | A26-B7-C31; | A29-B7-C32; | A32-B7-C33; | A3-B7-C35; | A6-B7-C36; |
| A24-B7-C30; | A27-B7-C31; | A30-B7-C32; | A1-B7-C34; | A4-B7-C35; | A7-B7-C36; |
| A25-B7-C30; | A28-B7-C31; | A31-B7-C32; | A2-B7-C34; | A5-B7-C35; | A8-B7-C36; |
| A26-B7-C30; | A29-B7-C31; | A32-B7-C32; | A3-B7-C34; | A6-B7-C35; | A9-B7-C36; |
| A27-B7-C30; | A30-B7-C31; | A1-B7-C33; | A4-B7-C34; | A7-B7-C35; | A10-B7-C36; |
| A28-B7-C30; | A31-B7-C31; | A2-B7-C33; | A5-B7-C34; | A8-B7-C35; | A11-B7-C36; |
| A29-B7-C30; | A32-B7-C31; | A3-B7-C33; | A6-B7-C34; | A9-B7-C35; | A12-B7-C36; |
| A30-B7-C30; | A1-B7-C32; | A4-B7-C33; | A7-B7-C34; | A10-B7-C35; | A13-B7-C36; |
| A31-B7-C30; | A2-B7-C32; | A5-B7-C33; | A8-B7-C34; | A11-B7-C35; | A14-B7-C36; |
| A15-B7-C36; | A18-B7-C37; | A21-B7-C38; | A24-B7-C39; | A27-B7-C40; | A30-B8-C1; |
| A16-B7-C36; | A19-B7-C37; | A22-B7-C38; | A25-B7-C39; | A28-B7-C40; | A31-B8-C1; |
| A17-B7-C36; | A20-B7-C37; | A23-B7-C38; | A26-B7-C39; | A29-B7-C40; | A32-B8-C1; |
| A18-B7-C36; | A21-B7-C37; | A24-B7-C38; | A27-B7-C39; | A30-B7-C40; | A1-B8-C2; |
| A19-B7-C36; | A22-B7-C37; | A25-B7-C38; | A28-B7-C39; | A31-B7-C40; | A2-B8-C2; |
| A20-B7-C36; | A23-B7-C37; | A26-B7-C38; | A29-B7-C39; | A32-B7-C40; | A3-B8-C2; |
| A21-B7-C36; | A24-B7-C37; | A27-B7-C38; | A30-B7-C39; | A1-B8-C1; | A4-B8-C2; |
| A22-B7-C36; | A25-B7-C37; | A28-B7-C38; | A31-B7-C39; | A2-B8-C1; | A5-B8-C2; |
| A23-B7-C36; | A26-B7-C37; | A29-B7-C38; | A32-B7-C39; | A3-B8-C1; | A6-B8-C2; |
| A24-B7-C36; | A27-B7-C37; | A30-B7-C38; | A1-B7-C40; | A4-B8-C1; | A7-B8-C2; |
| A25-B7-C36; | A28-B7-C37; | A31-B7-C38; | A2-B7-C40; | A5-B8-C1; | A8-B8-C2; |
| A26-B7-C36; | A29-B7-C37; | A32-B7-C38; | A3-B7-C40; | A6-B8-C1; | A9-B8-C2; |
| A27-B7-C36; | A30-B7-C37; | A1-B7-C39; | A4-B7-C40; | A7-B8-C1; | A10-B8-C2; |
| A28-B7-C36; | A31-B7-C37; | A2-B7-C39; | A5-B7-C40; | A8-B8-C1; | A11-B8-C2; |
| A29-B7-C36; | A32-B7-C37; | A3-B7-C39; | A6-B7-C40; | A9-B8-C1; | A12-B8-C2; |
| A30-B7-C36; | A1-B7-C38; | A4-B7-C39; | A7-B7-C40; | A10-B8-C1; | A13-B8-C2; |
| A31-B7-C36; | A2-B7-C38; | A5-B7-C39; | A8-B7-C40; | A11-B8-C1; | A14-B8-C2; |
| A32-B7-C36; | A3-B7-C38; | A6-B7-C39; | A9-B7-C40; | A12-B8-C1; | A15-B8-C2; |
| A1-B7-C37; | A4-B7-C38; | A7-B7-C39; | A10-B7-C40; | A13-B8-C1; | A16-B8-C2; |
| A2-B7-C37; | A5-B7-C38; | A8-B7-C39; | A11-B7-C40; | A14-B8-C1; | A17-B8-C2; |
| A3-B7-C37; | A6-B7-C38; | A9-B7-C39; | A12-B7-C40; | A15-B8-C1; | A18-B8-C2; |
| A4-B7-C37; | A7-B7-C38; | A10-B7-C39; | A13-B7-C40; | A16-B8-C1; | A19-B8-C2; |
| A5-B7-C37; | A8-B7-C38; | A11-B7-C39; | A14-B7-C40; | A17-B8-C1; | A20-B8-C2; |
| A6-B7-C37; | A9-B7-C38; | A12-B7-C39; | A15-B7-C40; | A18-B8-C1; | A21-B8-C2; |
| A7-B7-C37; | A10-B7-C38; | A13-B7-C39; | A16-B7-C40; | A19-B8-C1; | A22-B8-C2; |
| A8-B7-C37; | A11-B7-C38; | A14-B7-C39; | A17-B7-C40; | A20-B8-C1; | A23-B8-C2; |
| A9-B7-C37; | A12-B7-C38; | A15-B7-C39; | A18-B7-C40; | A21-B8-C1; | A24-B8-C2; |
| A10-B7-C37; | A13-B7-C38; | A16-B7-C39; | A19-B7-C40; | A22-B8-C1; | A25-B8-C2; |
| A11-B7-C37; | A14-B7-C38; | A17-B7-C39; | A20-B7-C40; | A23-B8-C1; | A26-B8-C2; |
| A12-B7-C37; | A15-B7-C38; | A18-B7-C39; | A21-B7-C40; | A24-B8-C1; | A27-B8-C2; |
| A13-B7-C37; | A16-B7-C38; | A19-B7-C39; | A22-B7-C40; | A25-B8-C1; | A28-B8-C2; |
| A14-B7-C37; | A17-B7-C38; | A20-B7-C39; | A23-B7-C40; | A26-B8-C1; | A29-B8-C2; |
| A15-B7-C37; | A18-B7-C38; | A21-B7-C39; | A24-B7-C40; | A27-B8-C1; | A30-B8-C2; |
| A16-B7-C37; | A19-B7-C38; | A22-B7-C39; | A25-B7-C40; | A28-B8-C1; | A31-B8-C2; |
| A17-B7-C37; | A20-B7-C38; | A23-B7-C39; | A26-B7-C40; | A29-B8-C1; | A32-B8-C2; |
| A1-B8-C3; | A4-B8-C4; | A7-B8-C5; | A10-B8-C6; | A13-B8-C7; | A16-B8-C8; |
| A2-B8-C3; | A5-B8-C4; | A8-B8-C5; | A11-B8-C6; | A14-B8-C7; | A17-B8-C8; |
| A3-B8-C3; | A6-B8-C4; | A9-B8-C5; | A12-B8-C6; | A15-B8-C7; | A18-B8-C8; |

-continued

| | | | | | |
|---|---|---|---|---|---|
| A4-B8-C3; | A7-B8-C4; | A10-B8-C5; | A13-B8-C6; | A16-B8-C7; | A19-B8-C8; |
| A5-B8-C3; | A8-B8-C4; | A11-B8-C5; | A14-B8-C6; | A17-B8-C7; | A20-B8-C8; |
| A6-B8-C3; | A9-B8-C4; | A12-B8-C5; | A15-B8-C6; | A18-B8-C7; | A21-B8-C8; |
| A7-B8-C3; | A10-B8-C4; | A13-B8-C5; | A16-B8-C6; | A19-B8-C7; | A22-B8-C8; |
| A8-B8-C3; | A11-B8-C4; | A14-B8-C5; | A17-B8-C6; | A20-B8-C7; | A23-B8-C8; |
| A9-B8-C3; | A12-B8-C4; | A15-B8-C5; | A18-B8-C6; | A21-B8-C7; | A24-B8-C8; |
| A10-B8-C3; | A13-B8-C4; | A16-B8-C5; | A19-B8-C6; | A22-B8-C7; | A25-B8-C8; |
| A11-B8-C3; | A14-B8-C4; | A17-B8-C5; | A20-B8-C6; | A23-B8-C7; | A26-B8-C8; |
| A12-B8-C3; | A15-B8-C4; | A18-B8-C5; | A21-B8-C6; | A24-B8-C7; | A27-B8-C8; |
| A13-B8-C3; | A16-B8-C4; | A19-B8-C5; | A22-B8-C6; | A25-B8-C7; | A28-B8-C8; |
| A14-B8-C3; | A17-B8-C4; | A20-B8-C5; | A23-B8-C6; | A26-B8-C7; | A29-B8-C8; |
| A15-B8-C3; | A18-B8-C4; | A21-B8-C5; | A24-B8-C6; | A27-B8-C7; | A30-B8-C8; |
| A16-B8-C3; | A19-B8-C4; | A22-B8-C5; | A25-B8-C6; | A28-B8-C7; | A31-B8-C8; |
| A17-B8-C3; | A20-B8-C4; | A23-B8-C5; | A26-B8-C6; | A29-B8-C7; | A32-B8-C8; |
| A18-B8-C3; | A21-B8-C4; | A24-B8-C5; | A27-B8-C6; | A30-B8-C7; | A1-B8-C9; |
| A19-B8-C3; | A22-B8-C4; | A25-B8-C5; | A28-B8-C6; | A31-B8-C7; | A2-B8-C9; |
| A20-B8-C3; | A23-B8-C4; | A26-B8-C5; | A29-B8-C6; | A32-B8-C7; | A3-B8-C9; |
| A21-B8-C3; | A24-B8-C4; | A27-B8-C5; | A30-B8-C6; | A1-B8-C8; | A4-B8-C9; |
| A22-B8-C3; | A25-B8-C4; | A28-B8-C5; | A31-B8-C6; | A2-B8-C8; | A5-B8-C9; |
| A23-B8-C3; | A26-B8-C4; | A29-B8-C5; | A32-B8-C6; | A3-B8-C8; | A6-B8-C9; |
| A24-B8-C3; | A27-B8-C4; | A30-B8-C5; | A1-B8-C7; | A4-B8-C8; | A7-B8-C9; |
| A25-B8-C3; | A28-B8-C4; | A31-B8-C5; | A2-B8-C7; | A5-B8-C8; | A8-B8-C9; |
| A26-B8-C3; | A29-B8-C4; | A32-B8-C5; | A3-B8-C7; | A6-B8-C8; | A9-B8-C9; |
| A27-B8-C3; | A30-B8-C4; | A1-B8-C6; | A4-B8-C7; | A7-B8-C8; | A10-B8-C9; |
| A28-B8-C3; | A31-B8-C4; | A2-B8-C6; | A5-B8-C7; | A8-B8-C8; | A11-B8-C9; |
| A29-B8-C3; | A32-B8-C4; | A3-B8-C6; | A6-B8-C7; | A9-B8-C8; | A12-B8-C9; |
| A30-B8-C3; | A1-B8-C5; | A4-B8-C6; | A7-B8-C7; | A10-B8-C8; | A13-B8-C9; |
| A31-B8-C3; | A2-B8-C5; | A5-B8-C6; | A8-B8-C7; | A11-B8-C8; | A14-B8-C9; |
| A32-B8-C3; | A3-B8-C5; | A6-B8-C6; | A9-B8-C7; | A12-B8-C8; | A15-B8-C9; |
| A1-B8-C4; | A4-B8-C5; | A7-B8-C6; | A10-B8-C7; | A13-B8-C8; | A16-B8-C9; |
| A2-B8-C4; | A5-B8-C5; | A8-B8-C6; | A11-B8-C7; | A14-B8-C8; | A17-B8-C9; |
| A3-B8-C4; | A6-B8-C5; | A9-B8-C6; | A12-B8-C7; | A15-B8-C8; | A18-B8-C9; |
| A19-B8-C9; | A22-B8-C10; | A25-B8-C11; | A28-B8-C12; | A31-B8-C13; | A2-B8-C15; |
| A20-B8-C9; | A23-B8-C10; | A26-B8-C11; | A29-B8-C12; | A32-B8-C13; | A3-B8-C15; |
| A21-B8-C9; | A24-B8-C10; | A27-B8-C11; | A30-B8-C12; | A1-B8-C14; | A4-B8-C15; |
| A22-B8-C9; | A25-B8-C10; | A28-B8-C11; | A31-B8-C12; | A2-B8-C14; | A5-B8-C15; |
| A23-B8-C9; | A26-B8-C10; | A29-B8-C11; | A32-B8-C12; | A3-B8-C14; | A6-B8-C15; |
| A24-B8-C9; | A27-B8-C10; | A30-B8-C11; | A1-B8-C13; | A4-B8-C14; | A7-B8-C15; |
| A25-B8-C9; | A28-B8-C10; | A31-B8-C11; | A2-B8-C13; | A5-B8-C14; | A8-B8-C15; |
| A26-B8-C9; | A29-B8-C10; | A32-B8-C11; | A3-B8-C13; | A6-B8-C14; | A9-B8-C15; |
| A27-B8-C9; | A30-B8-C10; | A1-B8-C12; | A4-B8-C13; | A7-B8-C14; | A10-B8-C15; |
| A28-B8-C9; | A31-B8-C10; | A2-B8-C12; | A5-B8-C13; | A8-B8-C14; | A11-B8-C15; |
| A29-B8-C9; | A32-B8-C10; | A3-B8-C12; | A6-B8-C13; | A9-B8-C14; | A12-B8-C15; |
| A30-B8-C9; | A1-B8-C11; | A4-B8-C12; | A7-B8-C13; | A10-B8-C14; | A13-B8-C15; |
| A31-B8-C9; | A2-B8-C11; | A5-B8[]C12; | A8-B8-C13; | A11-B8-C14; | A14-B8-C15; |
| A32-B8-C9; | A3-B8-C11; | A6-B8-C12; | A9-B8-C13; | A12-B8-C14; | A15-B8-C15; |
| A1-B8-C10; | A4-B8-C11; | A7-B8-C12; | A10-B8-C13; | A13-B8-C14; | A16-B8-C15; |
| A2-B8-C10; | A5-B8-C11; | A8-B8-C12; | A11-B8-C13; | A14-B8-C14; | A17-B8-C15; |
| A3-B8-C10; | A6-B8-C11; | A9-B8-C12; | A12-B8-C13; | A15-B8-C14; | A18-B8-C15; |
| A4-B8-C10; | A7-B8-C11; | A10-B8-C12; | A13-B8-C13; | A16-B8-C14; | A19-B8-C15; |
| A5-B8-C10; | A8-B8-C11; | A11-B8-C12; | A14-B8-C13; | A17-B8-C14; | A20-B8-C15; |
| A6-B8-C10; | A9-B8-C11; | A12-B8-C12; | A15-B8-C13; | A18-B8-C14; | A21-B8-C15; |
| A7-B8-C10; | A10-B8-C11; | A13-B8-C12; | A16-B8-C13; | A19-B8-C14; | A22-B8-C15; |
| A8-B8-C10; | A11-B8-C11; | A14-B8-C12; | A17-B8-C13; | A20-B8-C14; | A23-B8-C15; |
| A9-B8-C10; | A12-B8-C11; | A15-B8-C12; | A18-B8-C13; | A21-B8-C14; | A24-B8-C15; |
| A10-B8-C10; | A13-B8-C11; | A16-B8-C12; | A19-B8-C13; | A22-B8-C14; | A25-B8-C15; |
| A11-B8-C10; | A14-B8-C11; | A17-B8-C12; | A20-B8-C13; | A23-B8-C14; | A26-B8-C15; |
| A12-B8-C10; | A15-B8-C11; | A18-B8-C12; | A21-B8-C13; | A24-B8-C14; | A27-B8-C15; |
| A13-B8-C10; | A16-B8-C11; | A19-B8-C12; | A22-B8-C13; | A25-B8-C14; | A28-B8-C15; |
| A14-B8-C10; | A17-B8-C11; | A20-B8-C12; | A23-B8-C13; | A26-B8-C14; | A29-B8-C15; |
| A15-B8-C10; | A18-B8-C11; | A21-B8-C12; | A24-B8-C13; | A27-B8-C14; | A30-B8-C15; |
| A16-B8-C10; | A19-B8-C11; | A22-B8-C12; | A25-B8-C13; | A28-B8-C14; | A31-B8-C15; |
| A17-B8-C10; | A20-B8-C11; | A23-B8-C12; | A26-B8-C13; | A29-B8-C14; | A32-B8-C15; |
| A18-B8-C10; | A21-B8-C11; | A24-B8-C12; | A27-B8-C13; | A30-B8-C14; | A1-B8-C16; |
| A19-B8-C10; | A22-B8-C11; | A25-B8-C12; | A28-B8-C13; | A31-B8-C14; | A2-B8-C16; |
| A20-B8-C10; | A23-B8-C11; | A26-B8-C12; | A29-B8-C13; | A32-B8-C14; | A3-B8-C16; |
| A21-B8-C10; | A24-B8-C11; | A27-B8-C12; | A30-B8-C13; | A1-B8-C15; | A4-B8-C16; |
| A5-B8-C16; | A8-B8-C17; | A11-B8-C18; | A14-B8-C19; | A17-B8-C20; | A20-B8-C21; |
| A6-B8-C16; | A9-B8-C17; | A12-B8-C18; | A15-B8-C19; | A18-B8-C20; | A21-B8-C21; |
| A7-B8-C16; | A10-B8-C17; | A13-B8-C18; | A16-B8-C19; | A19-B8-C20; | A22-B8-C21; |
| A8-B8-C16; | A11-B8-C17; | A14-B8-C18; | A17-B8-C19; | A20-B8-C20; | A23-B8-C21; |
| A9-B8-C16; | A12-B8-C17; | A15-B8-C18; | A18-B8-C19; | A21-B8-C20; | A24-B8-C21; |
| A10-B8-C16; | A13-B8-C17; | A16-B8-C18; | A19-B8-C19; | A22-B8-C20; | A25-B8-C21; |
| A11-B8-C16; | A14-B8-C17; | A17-B8-C18; | A20-B8-C19; | A23-B8-C20; | A26-B8-C21; |
| A12-B8-C16; | A15-B8-C17; | A18-B8-C18; | A21-B8-C19; | A24-B8-C20; | A27-B8-C21; |
| A13-B8-C16; | A16-B8-C17; | A19-B8-C18; | A22-B8-C19; | A25-B8-C20; | A28-B8-C21; |
| A14-B8-C16; | A17-B8-C17; | A20-B8-C18; | A23-B8-C19; | A26-B8-C20; | A29-B8-C21; |
| A15-B8-C16; | A18-B8-C17; | A21-B8-C18; | A24-B8-C19; | A27-B8-C20; | A30-B8-C21; |
| A16-B8-C16; | A19-B8-C17; | A22-B8-C18; | A25-B8-C19; | A28-B8-C20; | A31-B8-C21; |

-continued

| | | | | | |
|---|---|---|---|---|---|
| A17-B8-C16; | A20-B8-C17; | A23-B8-C18; | A26-B8-C19; | A29-B8-C20; | A32-B8-C21; |
| A18-B8-C16; | A21-B8-C17; | A24-B8-C18; | A27-B8-C19; | A30-B8-C20; | A1-B8-C22; |
| A19-B8-C16; | A22-B8-C17; | A25-B8-C18; | A28-B8-C19; | A31-B8-C20; | A2-B8-C22; |
| A20-B8-C16; | A23-B8-C17; | A26-B8-C18; | A29-B8-C19; | A32-B8-C20; | A3-B8-C22; |
| A21-B8-C16; | A24-B8-C17; | A27-B8-C18; | A30-B8-C19; | A1-B8-C21; | A4-B8-C22; |
| A22-B8-C16; | A25-B8-C17; | A28-B8-C18; | A31-B8-C19; | A2-B8-C21; | A5-B8-C22; |
| A23-B8-C16; | A26-B8-C17; | A29-B8-C18; | A32-B8-C19; | A3-B8-C21; | A6-B8-C22; |
| A24-B8-C16; | A27-B8-C17; | A30-B8-C18; | A1-B8-C20; | A4-B8-C21; | A7-B8-C22; |
| A25-B8-C16; | A28-B8-C17; | A31-B8-C18; | A2-B8-C20; | A5-B8-C21; | A8-B8-C22; |
| A26-B8-C16; | A29-B8-C17; | A32-B8-C18; | A3-B8-C20; | A6-B8-C21; | A9-B8-C22; |
| A27-B8-C16; | A30-B8-C17; | A1-B8-C19; | A4-B8-C20; | A7-B8-C21; | A10-B8-C22; |
| A28-B8-C16; | A31-B8-C17; | A2-B8-C19; | A5-B8-C20; | A8-B8-C21; | A11-B8-C22; |
| A29-B8-C16; | A32-B8-C17; | A3-B8-C19; | A6-B8-C20; | A9-B8-C21; | A12-B8-C22; |
| A30-B8-C16; | A1-B8-C18; | A4-B8-C19; | A7-B8-C20; | A10-B8-C21; | A13-B8-C22; |
| A31-B8-C16; | A2-B8-C18; | A5-B8-C19; | A8-B8-C20; | A11-B8-C21; | A14-B8-C22; |
| A32-B8-C16; | A3-B8-C18; | A6-B8-C19; | A9-B8-C20; | A12-B8-C21; | A15-B8-C22; |
| A1-B8-C17; | A4-B8-C18; | A7-B8-C19; | A10-B8-C20; | A13-B8-C21; | A16-B8-C22; |
| A2-B8-C17; | A5-B8-C18; | A8-B8-C19; | A11-B8-C20; | A14-B8-C21; | A17-B8-C22; |
| A3-B8-C17; | A6-B8-C18; | A9-B8-C19; | A12-B8-C20; | A15-B8-C21; | A18-B8-C22; |
| A4-B8-C17; | A7-B8-C18; | A10-B8-C19; | A13-B8-C20; | A16-B8-C21; | A19-B8-C22; |
| A5-B8-C17; | A8-B8-C18; | A11-B8-C19; | A14-B8-C20; | A17-B8-C21; | A20-B8-C22; |
| A6-B8-C17; | A9-B8-C18; | A12-B8-C19; | A15-B8-C20; | A18-B8-C21; | A21-B8-C22; |
| A7-B8-C17; | A10-B8-C18; | A13-B8-C19; | A16-B8-C20; | A19-B8-C21; | A22-B8-C22; |
| A23-B8-C22; | A26-B8-C23; | A29-B8-C24; | A32-B8-C25; | A3-B8-C27; | A6-B8-C28; |
| A24-B8-C22; | A27-B8-C23; | A30-B8-C24; | A1-B8-C26; | A4-B8-C27; | A7-B8-C28; |
| A25-B8-C22; | A28-B8-C23; | A31-B8-C24; | A2-B8-C26; | A5-B8-C27; | A8-B8-C28; |
| A26-B8-C22; | A29-B8-C23; | A32-B8-C24; | A3-B8-C26; | A6-B8-C27; | A9-B8-C28; |
| A27-B8-C22; | A30-B8-C23; | A1-B8-C25; | A4-B8-C26; | A7-B8-C27; | A10-B8-C28; |
| A28-B8-C22; | A31-B8-C23; | A2-B8-C25; | A5-B8-C26; | A8-B8-C27; | A11-B8-C28; |
| A29-B8-C22; | A32-B8-C23; | A3-B8-C25; | A6-B8-C26; | A9-B8-C27; | A12-B8-C28; |
| A30-B8-C22; | A1-B8-C24; | A4-B8-C25; | A7-B8-C26; | A10-B8-C27; | A13-B8-C28; |
| A31-B8-C22; | A2-B8-C24; | A5-B8-C25; | A8-B8-C26; | A11-B8-C27; | A14-B8-C28; |
| A32-B8-C22; | A3-B8-C24; | A6-B8-C25; | A9-B8-C26; | A12-B8-C27; | A15-B8-C28; |
| A1-B8-C23; | A4-B8-C24; | A7-B8-C25; | A10-B8-C26; | A13-B8-C27; | A16-B8-C28; |
| A2-B8-C23; | A5-B8-C24; | A8-B8-C25; | A11-B8-C26; | A14-B8-C27; | A17-B8-C28; |
| A3-B8-C23; | A6-B8-C24; | A9-B8-C25; | A12-B8-C26; | A15-B8-C27; | A18-B8-C28; |
| A4-B8-C23; | A7-B8-C24; | A10-B8-C25; | A13-B8-C26; | A16-B8-C27; | A19-B8-C28; |
| A5-B8-C23; | A8-B8-C24; | A11-B8-C25; | A14-B8-C26; | A17-B8-C27; | A20-B8-C28; |
| A6-B8-C23; | A9-B8-C24; | A12-B8-C25; | A15-B8-C26; | A18-B8-C27; | A21-B8-C28; |
| A7-B8-C23; | A10-B8-C24; | A13-B8-C25; | A16-B8-C26; | A19-B8-C27; | A22-B8-C28; |
| A8-B8-C23; | A11-B8-C24; | A14-B8-C25; | A17-B8-C26; | A20-B8-C27; | A23-B8-C28; |
| A9-B8-C23; | A12-B8-C24; | A15-B8-C25; | A18-B8-C26; | A21-B8-C27; | A24-B8-C28; |
| A10-B8-C23; | A13-B8-C24; | A16-B8-C25; | A19-B8-C26; | A22-B8-C27; | A25-B8-C28; |
| A11-B8-C23; | A14-B8-C24; | A17-B8-C25; | A20-B8-C26; | A23-B8-C27; | A26-B8-C28; |
| A12-B8-C23; | A15-B8-C24; | A18-B8-C25; | A21-B8-C26; | A24-B8-C27; | A27-B8-C28; |
| A13-B8-C23; | A16-B8-C24; | A19-B8-C25; | A22-B8-C26; | A25-B8-C27; | A28-B8-C28; |
| A14-B8-C23; | A17-B8-C24; | A20-B8-C25; | A23-B8-C26; | A26-B8-C27; | A29-B8-C28; |
| A15-B8-C23; | A18-B8-C24; | A21-B8-C25; | A24-B8-C26; | A27-B8-C27; | A30-B8-C28; |
| A16-B8-C23; | A19-B8-C24; | A22-B8-C25; | A25-B8-C26; | A28-B8-C27; | A31-B8-C28; |
| A17-B8-C23; | A20-B8-C24; | A23-B8-C25; | A26-B8-C26; | A29-B8-C27; | A32-B8-C28; |
| A18-B8-C23; | A21-B8-C24; | A24-B8-C25; | A27-B8-C26; | A30-B8-C27; | A1-B8-C29; |
| A19-B8-C23; | A22-B8-C24; | A25-B8-C25; | A28-B8-C26; | A31-B8-C27; | A2-B8-C29; |
| A20-B8-C23; | A23-B8-C24; | A26-B8-C25; | A29-B8-C26; | A32-B8-C27; | A3-B8-C29; |
| A21-B8-C23; | A24-B8-C24; | A27-B8-C25; | A30-B8-C26; | A1-B8-C28; | A4-B8-C29; |
| A22-B8-C23; | A25-B8-C24; | A28-B8-C25; | A31-B8-C26; | A2-B8-C28; | A5-B8-C29; |
| A23-B8-C23; | A26-B8-C24; | A29-B8-C25; | A32-B8-C26; | A3-B8-C28; | A6-B8-C29; |
| A24-B8-C23; | A27-B8-C24; | A30-B8-C25; | A1-B8-C27; | A4-B8-C28; | A7-B8-C29; |
| A25-B8-C23; | A28-B8-C24; | A31-B8-C25; | A2-B8-C27; | A5-B8-C28; | A8-B8-C29; |
| A9-B8-C29; | A12-B8-C30; | A15-B8-C31; | A18-B8-C32; | A21-B8-C33; | A24-B8-C34; |
| A10-B8-C29; | A13-B8-C30; | A16-B8-C31; | A19-B8-C32; | A22-B8-C33; | A25-B8-C34; |
| A11-B8-C29; | A14-B8-C30; | A17-B8-C31; | A20-B8-C32; | A23-B8-C33; | A26-B8-C34; |
| A12-B8-C29; | A15-B8-C30; | A18-B8-C31; | A21-B8-C32; | A24-B8-C33; | A27-B8-C34; |
| A13-B8-C29; | A16-B8-C30; | A19-B8-C31; | A22-B8-C32; | A25-B8-C33; | A28-B8-C34; |
| A14-B8-C29; | A17-B8-C30; | A20-B8-C31; | A23-B8-C32; | A26-B8-C33; | A29-B8-C34; |
| A15-B8-C29; | A18-B8-C30; | A21-B8-C31; | A24-B8-C32; | A27-B8-C33; | A30-B8-C34; |
| A16-B8-C29; | A19-B8-C30; | A22-B8-C31; | A25-B8-C32; | A28-B8-C33; | A31-B8-C34; |
| A17-B8-C29; | A20-B8-C30; | A23-B8-C31; | A26-B8-C32; | A29-B8-C33; | A32-B8-C34; |
| A18-B8-C29; | A21-B8-C30; | A24-B8-C31; | A27-B8-C32; | A30-B8-C33; | A1-B8-C35; |
| A19-B8-C29; | A22-B8-C30; | A25-B8-C31; | A28-B8-C32; | A31-B8-C33; | A2-B8-C35; |
| A20-B8-C29; | A23-B8-C30; | A26-B8-C31; | A29-B8-C32; | A32-B8-C33; | A3-B8-C35; |
| A21-B8-C29; | A24-B8-C30; | A27-B8-C31; | A30-B8-C32; | A1-B8-C34; | A4-B8-C35; |
| A22-B8-C29; | A25-B8-C30; | A28-B8-C31; | A31-B8-C32; | A2-B8-C34; | A5-B8-C35; |
| A23-B8-C29; | A26-B8-C30; | A29-B8-C31; | A32-B8-C32; | A3-B8-C34; | A6-B8-C35; |
| A24-B8-C29; | A27-B8-C30; | A30-B8-C31; | A1-B8-C33; | A4-B8-C34; | A7-B8-C35; |
| A25-B8-C29; | A28-B8-C30; | A31-B8-C31; | A2-B8-C33; | A5-B8-C34; | A8-B8-C35; |
| A26-B8-C29; | A29-B8-C30; | A32-B8-C31; | A3-B8-C33; | A6-B8-C34; | A9-B8-C35; |
| A27-B8-C29; | A30-B8-C30; | A1-B8-C32; | A4-B8-C33; | A7-B8-C34; | A10-B8-C35; |
| A28-B8-C29; | A31-B8-C30; | A2-B8-C32; | A5-B8-C33; | A8-B8-C34; | A11-B8-C35; |
| A29-B8-C29; | A32-B8-C30; | A3-B8-C32; | A6-B8-C33; | A9-B8-C34; | A12-B8-C35; |

-continued

| | | | | | |
|---|---|---|---|---|---|
| A30-B8-C29; | A1-B8-C31; | A4-B8-C32; | A7-B8-C33; | A10-B8-C34; | A13-B8-C35; |
| A31-B8-C29; | A2-B8-C31; | A5-B8-C32; | A8-B8-C33; | A11-B8-C34; | A14-B8-C35; |
| A32-B8-C29; | A3-B8-C31; | A6-B8-C32; | A9-B8-C33; | A12-B8-C34; | A15-B8-C35; |
| A1-B8-C30; | A4-B8-C31; | A7-B8-C32; | A10-B8-C33; | A13-B8-C34; | A16-B8-C35; |
| A2-B8-C30; | A5-B8-C31; | A8-B8-C32; | A11-B8-C33; | A14-B8-C34; | A17-B8-C35; |
| A3-B8-C30; | A6-B8-C31; | A9-B8-C32; | A12-B8-C33; | A15-B8-C34; | A18-B8-C35; |
| A4-B8-C30; | A7-B8-C31; | A10-B8-C32; | A13-B8-C33; | A16-B8-C34; | A19-B8-C35; |
| A5-B8-C30; | A8-B8-C31; | A11-B8-C32; | A14-B8-C33; | A17-B8-C34; | A20-B8-C35; |
| A6-B8-C30; | A9-B8-C31; | A12-B8-C32; | A15-B8-C33; | A18-B8-C34; | A21-B8-C35; |
| A7-B8-C30; | A10-B8-C31; | A13-B8-C32; | A16-B8-C33; | A19-B8-C34; | A22-B8-C35; |
| A8-B8-C30; | A11-B8-C31; | A14-B8-C32; | A17-B8-C33; | A20-B8-C34; | A23-B8-C35; |
| A9-B8-C30; | A12-B8-C31; | A15-B8-C32; | A18-B8-C33; | A21-B8-C34; | A24-B8-C35; |
| A10-B8-C30; | A13-B8-C31; | A16-B8-C32; | A19-B8-C33; | A22-B8-C34; | A25-B8-C35; |
| A11-B8-C30; | A14-B8-C31; | A17-B8-C32; | A20-B8-C33; | A23-B8-C34; | A26-B8-C35; |
| A27-B8-C35; | A30-B8-C36; | A1-B8-C38; | A4-B8-C39; | A7-B8-C40; | A10-B9-C1; |
| A28-B8-C35; | A31-B8-C36; | A2-B8-C38; | A5-B8-C39; | A8-B8-C40; | A11-B9-C1; |
| A29-B8-C35; | A32-B8-C36; | A3-B8-C38; | A6-B8-C39; | A9-B8-C40; | A12-B9-C1; |
| A30-B8-C35; | A1-B8-C37; | A4-B8-C38; | A7-B8-C39; | A10-B8-C40; | A13-B9-C1; |
| A31-B8-C35; | A2-B8-C37; | A5-B8-C38; | A8-B8-C39; | A11-B8-C40; | A14-B9-C1; |
| A32-B8-C35; | A3-B8-C37; | A6-B8-C38; | A9-B8-C39; | A12-B8-C40; | A15-B9-C1; |
| A1-B8-C36; | A4-B8-C37; | A7-B8-C38; | A10-B8-C39; | A13-B8-C40; | A16-B9-C1; |
| A2-B8-C36; | A5-B8-C37; | A8-B8-C38; | A11-B8-C39; | A14-B8-C40; | A17-B9-C1; |
| A3-B8-C36; | A6-B8-C37; | A9-B8-C38; | A12-B8-C39; | A15-B8-C40; | A18-B9-C1; |
| A4-B8-C36; | A7-B8-C37; | A10-B8-C38; | A13-B8-C39; | A16-B8-C40; | A19-B9-C1; |
| A5-B8-C36; | A8-B8-C37; | A11-B8-C38; | A14-B8-C39; | A17-B8-C40; | A20-B9-C1; |
| A6-B8-C36; | A9-B8-C37; | A12-B8-C38; | A15-B8-C39; | A18-B8-C40; | A21-B9-C1; |
| A7-B8-C36; | A10-B8-C37; | A13-B8-C38; | A16-B8-C39; | A19-B8-C40; | A22-B9-C1; |
| A8-B8-C36; | A11-B8-C37; | A14-B8-C38; | A17-B8-C39; | A20-B8-C40; | A23-B9-C1; |
| A9-B8-C36; | A12-B8-C37; | A15-B8-C38; | A18-B8-C39; | A21-B8-C40; | A24-B9-C1; |
| A10-B8-C36; | A13-B8-C37; | A16-B8-C38; | A19-B8-C39; | A22-B8-C40; | A25-B9-C1; |
| A11-B8-C36; | A14-B8-C37; | A17-B8-C38; | A20-B8-C39; | A23-B8-C40; | A26-B9-C1; |
| A12-B8-C36; | A15-B8-C37; | A18-B8-C38; | A21-B8-C39; | A24-B8-C40; | A27-B9-C1; |
| A13-B8-C36; | A16-B8-C37; | A19-B8-C38; | A22-B8-C39; | A25-B8-C40; | A28-B9-C1; |
| A14-B8-C36; | A17-B8-C37; | A20-B8-C38; | A23-B8-C39; | A26-B8-C40; | A29-B9-C1; |
| A15-B8-C36; | A18-B8-C37; | A21-B8-C38; | A24-B8-C39; | A27-B8-C40; | A30-B9-C1; |
| A16-B8-C36; | A19-B8-C37; | A22-B8-C38; | A25-B8-C39; | A28-B8-C40; | A31-B9-C1; |
| A17-B8-C36; | A20-B8-C37; | A23-B8-C38; | A26-B8-C39; | A29-B8-C40; | A32-B9-C1; |
| A18-B8-C36; | A21-B8-C37; | A24-B8-C38; | A27-B8-C39; | A30-B8-C40; | A1-B9-C2; |
| A19-B8-C36; | A22-B8-C37; | A25-B8-C38; | A28-B8-C39; | A31-B8-C40; | A2-B9-C2; |
| A20-B8-C36; | A23-B8-C37; | A26-B8-C38; | A29-B8-C39; | A32-B8-C40; | A3-B9-C2; |
| A21-B8-C36; | A24-B8-C37; | A27-B8-C38; | A30-B8-C39; | A1-B9-C1; | A4-B9-C2; |
| A22-B8-C36; | A25-B8-C37; | A28-B8-C38; | A31-B8-C39; | A2-B9-C1; | A5-B9-C2; |
| A23-B8-C36; | A26-B8-C37; | A29-B8-C38; | A32-B8-C39; | A3-B9-C1; | A6-B9-C2; |
| A24-B8-C36; | A27-B8-C37; | A30-B8-C38; | A1-B8-C40; | A4-B9-C1; | A7-B9-C2; |
| A25-B8-C36; | A28-B8-C37; | A31-B8-C38; | A2-B8-C40; | A5-B9-C1; | A8-B9-C2; |
| A26-B8-C36; | A29-B8-C37; | A32-B8-C38; | A3-B8-C40; | A6-B9-C1; | A9-B9-C2; |
| A27-B8-C36; | A30-B8-C37; | A1-B8-C39; | A4-B8-C40; | A7-B9-C1; | A10-B9-C2; |
| A28-B8-C36; | A31-B8-C37; | A2-B8-C39; | A5-B8-C40; | A8-B9-C1; | A11-B9-C2; |
| A29-B8-C36; | A32-B8-C37; | A3-B8-C39; | A6-B8-C40; | A9-B9-C1; | A12-B9-C2; |
| A13-B9-C2; | A16-B9-C3; | A19-B9-C4; | A22-B9-C5; | A25-B9-C6; | A28-B9-C7; |
| A14-B9-C2; | A17-B9-C3; | A20-B9-C4; | A23-B9-C5; | A26-B9-C6; | A29-B9-C7; |
| A15-B9-C2; | A18-B9-C3; | A21-B9-C4; | A24-B9-C5; | A27-B9-C6; | A30-B9-C7; |
| A16-B9-C2; | A19-B9-C3; | A22-B9-C4; | A25-B9-C5; | A28-B9-C6; | A31-B9-C7; |
| A17-B9-C2; | A20-B9-C3; | A23-B9-C4; | A26-B9-C5; | A29-B9-C6; | A32-B9-C7; |
| A18-B9-C2; | A21-B9-C3; | A24-B9-C4; | A27-B9-C5; | A30-B9-C6; | A1-B9-C8; |
| A19-B9-C2; | A22-B9-C3; | A25-B9-C4; | A28-B9-C5; | A31-B9-C6; | A2-B9-C8; |
| A20-B9-C2; | A23-B9-C3; | A26-B9-C4; | A29-B9-C5; | A32-B9-C6; | A3-B9-C8; |
| A21-B9-C2; | A24-B9-C3; | A27-B9-C4; | A30-B9-C5; | A1-B9-C7; | A4-B9-C8; |
| A22-B9-C2; | A25-B9-C3; | A28-B9-C4; | A31-B9-C5; | A2-B9-C7; | A5-B9-C8; |
| A23-B9-C2; | A26-B9-C3; | A29-B9-C4; | A32-B9-C5; | A3-B9-C7; | A6-B9-C8; |
| A24-B9-C2; | A27-B9-C3; | A30-B9-C4; | A1-B9-C6; | A4-B9-C7; | A7-B9-C8; |
| A25-B9-C2; | A28-B9-C3; | A31-B9-C4; | A2-B9-C6; | A5-B9-C7; | A8-B9-C8; |
| A26-B9-C2; | A29-B9-C3; | A32-B9-C4; | A3-B9-C6; | A6-B9-C7; | A9-B9-C8; |
| A27-B9-C2; | A30-B9-C3; | A1-B9-C5; | A4-B9-C6; | A7-B9-C7; | A10-B9-C8; |
| A28-B9-C2; | A31-B9-C3; | A2-B9-C5; | A5-B9-C6; | A8-B9-C7; | A11-B9-C8; |
| A29-B9-C2; | A32-B9-C3; | A3-B9-C5; | A6-B9-C6; | A9-B9-C7; | A12-B9-C8; |
| A30-B9-C2; | A1-B9-C4; | A4-B9-C5; | A7-B9-C6; | A10-B9-C7; | A13-B9-C8; |
| A31-B9-C2; | A2-B9-C4; | A5-B9-C5; | A8-B9-C6; | A11-B9-C7; | A14-B9-C8; |
| A32-B9-C2; | A3-B9-C4; | A6-B9-C5; | A9-B9-C6; | A12-B9-C7; | A15-B9-C8; |
| A1-B9-C3; | A4-B9-C4; | A7-B9-C5; | A10-B9-C6; | A13-B9-C7; | A16-B9-C8; |
| A2-B9-C3; | A5-B9-C4; | A8-B9-C5; | A11-B9-C6; | A14-B9-C7; | A17-B9-C8; |
| A3-B9-C3; | A6-B9-C4; | A9-B9-C5; | A12-B9-C6; | A15-B9-C7; | A18-B9-C8; |
| A4-B9-C3; | A7-B9-C4; | A10-B9-C5; | A13-B9-C6; | A16-B9-C7; | A19-B9-C8; |
| A5-B9-C3; | A8-B9-C4; | A11-B9-C5; | A14-B9-C6; | A17-B9-C7; | A20-B9-C8; |
| A6-B9-C3; | A9-B9-C4; | A12-B9-C5; | A15-B9-C6; | A18-B9-C7; | A21-B9-C8; |
| A7-B9-C3; | A10-B9-C4; | A13-B9-C5; | A16-B9-C6; | A19-B9-C7; | A22-B9-C8; |
| A8-B9-C3; | A11-B9-C4; | A14-B9-C5; | A17-B9-C6; | A20-B9-C7; | A23-B9-C8; |
| A9-B9-C3; | A12-B9-C4; | A15-B9-C5; | A18-B9-C6; | A21-B9-C7; | A24-B9-C8; |
| A10-B9-C3; | A13-B9-C4; | A16-B9-C5; | A19-B9-C6; | A22-B9-C7; | A25-B9-C8; |

-continued

| | | | | | |
|---|---|---|---|---|---|
| A11-B9-C3; | A14-B9-C4; | A17-B9-C5; | A20-B9-C6; | A23-B9-C7; | A26-B9-C8; |
| A12-B9-C3; | A15-B9-C4; | A18-B9-C5; | A21-B9-C6; | A24-B9-C7; | A27-B9-C8; |
| A13-B9-C3; | A16-B9-C4; | A19-B9-C5; | A22-B9-C6; | A25-B9-C7; | A28-B9-C8; |
| A14-B9-C3; | A17-B9-C4; | A20-B9-C5; | A23-B9-C6; | A26-B9-C7; | A29-B9-C8; |
| A15-B9-C3; | A18-B9-C4; | A21-B9-C5; | A24-B9-C6; | A27-B9-C7; | A30-B9-C8; |
| A31-B9-C8; | A2-B9-C10; | A5-B9-C11; | A8-B9-C12; | A11-B9-C13; | A14-B9-C14; |
| A32-B9-C8; | A3-B9-C10; | A6-B9-C11; | A9-B9-C12; | A12-B9-C13; | A15-B9-C14; |
| A1-B9-C9; | A4-B9-C10; | A7-B9-C11; | A10-B9-C12; | A13-B9-C13; | A16-B9-C14; |
| A2-B9-C9; | A5-B9-C10; | A8-B9-C11; | A11-B9-C12; | A14-B9-C13; | A17-B9-C14; |
| A3-B9-C9; | A6-B9-C10; | A9-B9-C11; | A12-B9-C12; | A15-B9-C13; | A18-B9-C14; |
| A4-B9-C9; | A7-B9-C10; | A10-B9-C11; | A13-B9-C12; | A16-B9-C13; | A19-B9-C14; |
| A5-B9-C9; | A8-B9-C10; | A11-B9-C11; | A14-B9-C12; | A17-B9-C13; | A20-B9-C14; |
| A6-B9-C9; | A9-B9-C10; | A12-B9-C11; | A15-B9-C12; | A18-B9-C13; | A21-B9-C14; |
| A7-B9-C9; | A10-B9-C10; | A13-B9-C11; | A16-B9-C12; | A19-B9-C13; | A22-B9-C14; |
| A8-B9-C9; | A11-B9-C10; | A14-B9-C11; | A17-B9-C12; | A20-B9-C13; | A23-B9-C14; |
| A9-B9-C9; | A12-B9-C10; | A15-B9-C11; | A18-B9-C12; | A21-B9-C13; | A24-B9-C14; |
| A10-B9-C9; | A13-B9-C10; | A16-B9-C11; | A19-B9-C12; | A22-B9-C13; | A25-B9-C14; |
| A11-B9-C9; | A14-B9-C10; | A17-B9-C11; | A20-B9-C12; | A23-B9-C13; | A26-B9-C14; |
| A12-B9-C9; | A15-B9-C10; | A18-B9-C11; | A21-B9-C12; | A24-B9-C13; | A27-B9-C14; |
| A13-B9-C9; | A16-B9-C10; | A19-B9-C11; | A22-B9-C12; | A25-B9-C13; | A28-B9-C14; |
| A14-B9-C9; | A17-B9-C10; | A20-B9-C11; | A23-B9-C12; | A26-B9-C13; | A29-B9-C14; |
| A15-B9-C9; | A18-B9-C10; | A21-B9-C11; | A24-B9-C12; | A27-B9-C13; | A30-B9-C14; |
| A16-B9-C9; | A19-B9-C10; | A22-B9-C11; | A25-B9-C12; | A28-B9-C13; | A31-B9-C14; |
| A17-B9-C9; | A20-B9-C10; | A23-B9-C11; | A26-B9-C12; | A29-B9-C13; | A32-B9-C14; |
| A18-B9-C9; | A21-B9-C10; | A24-B9-C11; | A27-B9-C12; | A30-B9-C13; | A1-B9-C15; |
| A19-B9-C9; | A22-B9-C10; | A25-B9-C11; | A28-B9-C12; | A31-B9-C13; | A2-B9-C15; |
| A20-B9-C9; | A23-B9-C10; | A26-B9-C11; | A29-B9-C12; | A32-B9-C13; | A3-B9-C15; |
| A21-B9-C9; | A24-B9-C10; | A27-B9-C11; | A30-B9-C12; | A1-B9-C14; | A4-B9-C15; |
| A22-B9-C9; | A25-B9-C10; | A28-B9-C11; | A31-B9-C12; | A2-B9-C14; | A5-B9-C15; |
| A23-B9-C9; | A26-B9-C10; | A29-B9-C11; | A32-B9-C12; | A3-B9-C14; | A6-B9-C15; |
| A24-B9-C9; | A27-B9-C10; | A30-B9-C11; | A1-B9-C13; | A4-B9-C14; | A7-B9-C15; |
| A25-B9-C9; | A28-B9-C10; | A31-B9-C11; | A2-B9-C13; | A5-B9-C14; | A8-B9-C15; |
| A26-B9-C9; | A29-B9-C10; | A32-B9-C11; | A3-B9-C13; | A6-B9-C14; | A9-B9-C15; |
| A27-B9-C9; | A30-B9-C10; | A1-B9-C12; | A4-B9-C13; | A7-B9-C14; | A10-B9-C15; |
| A28-B9-C9; | A31-B9-C10; | A2-B9-C12; | A5-B9-C13; | A8-B9-C14; | A11-B9-C15; |
| A29-B9-C9; | A32-B9-C10; | A3-B9-C12; | A6-B9-C13; | A9-B9-C14; | A12-B9-C15; |
| A30-B9-C9; | A1-B9-C11; | A4-B9-C12; | A7-B9-C13; | A10-B9-C14; | A13-B9-C15; |
| A31-B9-C9; | A2-B9-C11; | A5-B9-C12; | A8-B9-C13; | A11-B9-C14; | A14-B9-C15; |
| A32-B9-C9; | A3-B9-C11; | A6-B9-C12; | A9-B9-C13; | A12-B9-C14; | A15-B9-C15; |
| A1-B9-C10; | A4-B9-C11; | A7-B9-C12; | A10-B9-C13; | A13-B9-C14; | A16-B9-C15; |
| A17-B9-C15; | A20-B9-C16; | A23-B9-C17; | A26-B9-C18; | A29-B9-C19; | A32-B9-C20; |
| A18-B9-C15; | A21-B9-C16; | A24-B9-C17; | A27-B9-C18; | A30-B9-C19; | A1-B9-C21; |
| A19-B9-C15; | A22-B9-C16; | A25-B9-C17; | A28-B9-C18; | A31-B9-C19; | A2-B9-C21; |
| A20-B9-C15; | A23-B9-C16; | A26-B9-C17; | A29-B9-C18; | A32-B9-C19; | A3-B9-C21; |
| A21-B9-C15; | A24-B9-C16; | A27-B9-C17; | A30-B9-C18; | A1-B9-C20; | A4-B9-C21; |
| A22-B9-C15; | A25-B9-C16; | A28-B9-C17; | A31-B9-C18; | A2-B9-C20; | A5-B9-C21; |
| A23-B9-C15; | A26-B9-C16; | A29-B9-C17; | A32-B9-C18; | A3-B9-C20; | A6-B9-C21; |
| A24-B9-C15; | A27-B9-C16; | A30-B9-C17; | A1-B9-C19; | A4-B9-C20; | A7-B9-C21; |
| A25-B9-C15; | A28-B9-C16; | A31-B9-C17; | A2-B9-C19; | A5-B9-C20; | A8-B9-C21; |
| A26-B9-C15; | A29-B9-C16; | A32-B9-C17; | A3-B9-C19; | A6-B9-C20; | A9-B9-C21; |
| A27-B9-C15; | A30-B9-C16; | A1-B9-C18; | A4-B9-C19; | A7-B9-C20; | A10-B9-C21; |
| A28-B9-C15; | A31-B9-C16; | A2-B9-C18; | A5-B9-C19; | A8-B9-C20; | A11-B9-C21; |
| A29-B9-C15; | A32-B9-C16; | A3-B9-C18; | A6-B9-C19; | A9-B9-C20; | A12-B9-C21; |
| A30-B9-C15; | A1-B9-C17; | A4-B9-C18; | A7-B9-C19; | A10-B9-C20; | A13-B9-C21; |
| A31-B9-C15; | A2-B9-C17; | A5-B9-C18; | A8-B9-C19; | A11-B9-C20; | A14-B9-C21; |
| A32-B9-C15; | A3-B9-C17; | A6-B9-C18; | A9-B9-C19; | A12-B9-C20; | A15-B9-C21; |
| A1-B9-C16; | A4-B9-C17; | A7-B9-C18; | A10-B9-C19; | A13-B9-C20; | A16-B9-C21; |
| A2-B9-C16; | A5-B9-C17; | A8-B9-C18; | A11-B9-C19; | A14-B9-C20; | A17-B9-C21; |
| A3-B9-C16; | A6-B9-C17; | A9-B9-C18; | A12-B9-C19; | A15-B9-C20; | A18-B9-C21; |
| A4-B9-C16; | A7-B9-C17; | A10-B9-C18; | A13-B9-C19; | A16-B9-C20; | A19-B9-C21; |
| A5-B9-C16; | A8-B9-C17; | A11-B9-C18; | A14-B9-C19; | A17-B9-C20; | A20-B9-C21; |
| A6-B9-C16; | A9-B9-C17; | A12-B9-C18; | A15-B9-C19; | A18-B9-C20; | A21-B9-C21; |
| A7-B9-C16; | A10-B9-C17; | A13-B9-C18; | A16-B9-C19; | A19-B9-C20; | A22-B9-C21; |
| A8-B9-C16; | A11-B9-C17; | A14-B9-C18; | A17-B9-C19; | A20-B9-C20; | A23-B9-C21; |
| A9-B9-C16; | A12-B9-C17; | A15-B9-C18; | A18-B9-C19; | A21-B9-C20; | A24-B9-C21; |
| A10-B9-C16; | A13-B9-C17; | A16-B9-C18; | A19-B9-C19; | A22-B9-C20; | A25-B9-C21; |
| A11-B9-C16; | A14-B9-C17; | A17-B9-C18; | A20-B9-C19; | A23-B9-C20; | A26-B9-C21; |
| A12-B9-C16; | A15-B9-C17; | A18-B9-C18; | A21-B9-C19; | A24-B9-C20; | A27-B9-C21; |
| A13-B9-C16; | A16-B9-C17; | A19-B9-C18; | A22-B9-C19; | A25-B9-C20; | A28-B9-C21; |
| A14-B9-C16; | A17-B9-C17; | A20-B9-C18; | A23-B9-C19; | A26-B9-C20; | A29-B9-C21; |
| A15-B9-C16; | A18-B9-C17; | A21-B9-C18; | A24-B9-C19; | A27-B9-C20; | A30-B9-C21; |
| A16-B9-C16; | A19-B9-C17; | A22-B9-C18; | A25-B9-C19; | A28-B9-C20; | A31-B9-C21; |
| A17-B9-C16; | A20-B9-C17; | A23-B9-C18; | A26-B9-C19; | A29-B9-C20; | A32-B9-C21; |
| A18-B9-C16; | A21-B9-C17; | A24-B9-C18; | A27-B9-C19; | A30-B9-C20; | A1-B9-C22; |
| A19-B9-C16; | A22-B9-C17; | A25-B9-C18; | A28-B9-C19; | A31-B9-C20; | A2-B9-C22; |
| A3-B9-C22; | A6-B9-C23; | A9-B9-C24; | A12-B9-C25; | A15-B9-C26; | A18-B9-C27; |
| A4-B9-C22; | A7-B9-C23; | A10-B9-C24; | A13-B9-C25; | A16-B9-C26; | A19-B9-C27; |
| A5-B9-C22; | A8-B9-C23; | A11-B9-C24; | A14-B9-C25; | A17-B9-C26; | A20-B9-C27; |
| A6-B9-C22; | A9-B9-C23; | A12-B9-C24; | A15-B9-C25; | A18-B9-C26; | A21-B9-C27; |

-continued

| | | | | | |
|---|---|---|---|---|---|
| A7-B9-C22; | A10-B9-C23; | A13-B9-C24; | A16-B9-C25; | A19-B9-C26; | A22-B9-C27; |
| A8-B9-C22; | A11-B9-C23; | A14-B9-C24; | A17-B9-C25; | A20-B9-C26; | A23-B9-C27; |
| A9-B9-C22; | A12-B9-C23; | A15-B9-C24; | A18-B9-C25; | A21-B9-C26; | A24-B9-C27; |
| A10-B9-C22; | A13-B9-C23; | A16-B9-C24; | A19-B9-C25; | A22-B9-C26; | A25-B9-C27; |
| A11-B9-C22; | A14-B9-C23; | A17-B9-C24; | A20-B9-C25; | A23-B9-C26; | A26-B9-C27; |
| A12-B9-C22; | A15-B9-C23; | A18-B9-C24; | A21-B9-C25; | A24-B9-C26; | A27-B9-C27; |
| A13-B9-C22; | A16-B9-C23; | A19-B9-C24; | A22-B9-C25; | A25-B9-C26; | A28-B9-C27; |
| A14-B9-C22; | A17-B9-C23; | A20-B9-C24; | A23-B9-C25; | A26-B9-C26; | A29-B9-C27; |
| A15-B9-C22; | A18-B9-C23; | A21-B9-C24; | A24-B9-C25; | A27-B9-C26; | A30-B9-C27; |
| A16-B9-C22; | A19-B9-C23; | A22-B9-C24; | A25-B9-C25; | A28-B9-C26; | A31-B9-C27; |
| A17-B9-C22; | A20-B9-C23; | A23-B9-C24; | A26-B9-C25; | A29-B9-C26; | A32-B9-C27; |
| A18-B9-C22; | A21-B9-C23; | A24-B9-C24; | A27-B9-C25; | A30-B9-C26; | A1-B9-C28; |
| A19-B9-C22; | A22-B9-C23; | A25-B9-C24; | A28-B9-C25; | A31-B9-C26; | A2-B9-C28; |
| A20-B9-C22; | A23-B9-C23; | A26-B9-C24; | A29-B9-C25; | A32-B9-C26; | A3-B9-C28; |
| A21-B9-C22; | A24-B9-C23; | A27-B9-C24; | A30-B9-C25; | A1-B9-C27; | A4-B9-C28; |
| A22-B9-C22; | A25-B9-C23; | A28-B9-C24; | A31-B9-C25; | A2-B9-C27; | A5-B9-C28; |
| A23-B9-C22; | A26-B9-C23; | A29-B9-C24; | A32-B9-C25; | A3-B9-C27; | A6-B9-C28; |
| A24-B9-C22; | A27-B9-C23; | A30-B9-C24; | A1-B9-C26; | A4-B9-C27; | A7-B9-C28; |
| A25-B9-C22; | A28-B9-C23; | A31-B9-C24; | A2-B9-C26; | A5-B9-C27; | A8-B9-C28; |
| A26-B9-C22; | A29-B9-C23; | A32-B9-C24; | A3-B9-C26; | A6-B9-C27; | A9-B9-C28; |
| A27-B9-C22; | A30-B9-C23; | A1-B9-C25; | A4-B9-C26; | A7-B9-C27; | A10-B9-C28; |
| A28-B9-C22; | A31-B9-C23; | A2-B9-C25; | A5-B9-C26; | A8-B9-C27; | A11-B9-C28; |
| A29-B9-C22; | A32-B9-C23; | A3-B9-C25; | A6-B9-C26; | A9-B9-C27; | A12-B9-C28; |
| A30-B9-C22; | A1-B9-C24; | A4-B9-C25; | A7-B9-C26; | A10-B9-C27; | A13-B9-C28; |
| A31-B9-C22; | A2-B9-C24; | A5-B9-C25; | A8-B9-C26; | A11-B9-C27; | A14-B9-C28; |
| A32-B9-C22; | A3-B9-C24; | A6-B9-C25; | A9-B9-C26; | A12-B9-C27; | A15-B9-C28; |
| A1-B9-C23; | A4-B9-C24; | A7-B9-C25; | A10-B9-C26; | A13-B9-C27; | A16-B9-C28; |
| A2-B9-C23; | A5-B9-C24; | A8-B9-C25; | A11-B9-C26; | A14-B9-C27; | A17-B9-C28; |
| A3-B9-C23; | A6-B9-C24; | A9-B9-C25; | A12-B9-C26; | A15-B9-C27; | A18-B9-C28; |
| A4-B9-C23; | A7-B9-C24; | A10-B9-C25; | A13-B9-C26; | A16-B9-C27; | A19-B9-C28; |
| A5-B9-C23; | A8-B9-C24; | A11-B9-C25; | A14-B9-C26; | A17-B9-C27; | A20-B9-C28; |
| A21-B9-C28; | A24-B9-C29; | A27-B9-C30; | A30-B9-C31; | A1-B9-C33; | A4-B9-C34; |
| A22-B9-C28; | A25-B9-C29; | A28-B9-C30; | A31-B9-C31; | A2-B9-C33; | A5-B9-C34; |
| A23-B9-C28; | A26-B9-C29; | A29-B9-C30; | A32-B9-C31; | A3-B9-C33; | A6-B9-C34; |
| A24-B9-C28; | A27-B9-C29; | A30-B9-C30; | A1-B9-C32; | A4-B9-C33; | A7-B9-C34; |
| A25-B9-C28; | A28-B9-C29; | A31-B9-C30; | A2-B9-C32; | A5-B9-C33; | A8-B9-C34; |
| A26-B9-C28; | A29-B9-C29; | A32-B9-C30; | A3-B9-C32; | A6-B9-C33; | A9-B9-C34; |
| A27-B9-C28; | A30-B9-C29; | A1-B9-C31; | A4-B9-C32; | A7-B9-C33; | A10-B9-C34; |
| A28-B9-C28; | A31-B9-C29; | A2-B9-C31; | A5-B9-C32; | A8-B9-C33; | A11-B9-C34; |
| A29-B9-C28; | A32-B9-C29; | A3-B9-C31; | A6-B9-C32; | A9-B9-C33; | A12-B9-C34; |
| A30-B9-C28; | A1-B9-C30; | A4-B9-C31; | A7-B9-C32; | A10-B9-C33; | A13-B9-C34; |
| A31-B9-C28; | A2-B9-C30; | A5-B9-C31; | A8-B9-C32; | A11-B9-C33; | A14-B9-C34; |
| A32-B9-C28; | A3-B9-C30; | A6-B9-C31; | A9-B9-C32; | A12-B9-C33; | A15-B9-C34; |
| A1-B9-C29; | A4-B9-C30; | A7-B9-C31; | A10-B9-C32; | A13-B9-C33; | A16-B9-C34; |
| A2-B9-C29; | A5-B9-C30; | A8-B9-C31; | A11-B9-C32; | A14-B9-C33; | A17-B9-C34; |
| A3-B9-C29; | A6-B9-C30; | A9-B9-C31; | A12-B9-C32; | A15-B9-C33; | A18-B9-C34; |
| A4-B9-C29; | A7-B9-C30; | A10-B9-C31; | A13-B9-C32; | A16-B9-C33; | A19-B9-C34; |
| A5-B9-C29; | A8-B9-C30; | A11-B9-C31; | A14-B9-C32; | A17-B9-C33; | A20-B9-C34; |
| A6-B9-C29; | A9-B9-C30; | A12-B9-C31; | A15-B9-C32; | A18-B9-C33; | A21-B9-C34; |
| A7-B9-C29; | A10-B9-C30; | A13-B9-C31; | A16-B9-C32; | A19-B9-C33; | A22-B9-C34; |
| A8-B9-C29; | A11-B9-C30; | A14-B9-C31; | A17-B9-C32; | A20-B9-C33; | A23-B9-C34; |
| A9-B9-C29; | A12-B9-C30; | A15-B9-C31; | A18-B9-C32; | A21-B9-C33; | A24-B9-C34; |
| A10-B9-C29; | A13-B9-C30; | A16-B9-C31; | A19-B9-C32; | A22-B9-C33; | A25-B9-C34; |
| A11-B9-C29; | A14-B9-C30; | A17-B9-C31; | A20-B9-C32; | A23-B9-C33; | A26-B9-C34; |
| A12-B9-C29; | A15-B9-C30; | A18-B9-C31; | A21-B9-C32; | A24-B9-C33; | A27-B9-C34; |
| A13-B9-C29; | A16-B9-C30; | A19-B9-C31; | A22-B9-C32; | A25-B9-C33; | A28-B9-C34; |
| A14-B9-C29; | A17-B9-C30; | A20-B9-C31; | A23-B9-C32; | A26-B9-C33; | A29-B9-C34; |
| A15-B9-C29; | A18-B9-C30; | A21-B9-C31; | A24-B9-C32; | A27-B9-C33; | A30-B9-C34; |
| A16-B9-C29; | A19-B9-C30; | A22-B9-C31; | A25-B9-C32; | A28-B9-C33; | A31-B9-C34; |
| A17-B9-C29; | A20-B9-C30; | A23-B9-C31; | A26-B9-C32; | A29-B9-C33; | A32-B9-C34; |
| A18-B9-C29; | A21-B9-C30; | A24-B9-C31; | A27-B9-C32; | A30-B9-C33; | A1-B9-C35; |
| A19-B9-C29; | A22-B9-C30; | A25-B9-C31; | A28-B9-C32; | A31-B9-C33; | A2-B9-C35; |
| A20-B9-C29; | A23-B9-C30; | A26-B9-C31; | A29-B9-C32; | A32-B9-C33; | A3-B9-C35; |
| A21-B9-C29; | A24-B9-C30; | A27-B9-C31; | A30-B9-C32; | A1-B9-C34; | A4-B9-C35; |
| A22-B9-C29; | A25-B9-C30; | A28-B9-C31; | A31-B9-C32; | A2-B9-C34; | A5-B9-C35; |
| A23-B9-C29; | A26-B9-C30; | A29-B9-C31; | A32-B9-C32; | A3-B9-C34; | A6-B9-C35; |
| A7-B9-C35; | A10-B9-C36; | A13-B9-C37; | A16-B9-C38; | A19-B9-C39; | A22-B9-C40; |
| A8-B9-C35; | A11-B9-C36; | A14-B9-C37; | A17-B9-C38; | A20-B9-C39; | A23-B9-C40; |
| A9-B9-C35; | A12-B9-C36; | A15-B9-C37; | A18-B9-C38; | A21-B9-C39; | A24-B9-C40; |
| A10-B9-C35; | A13-B9-C36; | A16-B9-C37; | A19-B9-C38; | A22-B9-C39; | A25-B9-C40; |
| A11-B9-C35; | A14-B9-C36; | A17-B9-C37; | A20-B9-C38; | A23-B9-C39; | A26-B9-C40; |
| A12-B9-C35; | A15-B9-C36; | A18-B9-C37; | A21-B9-C38; | A24-B9-C39; | A27-B9-C40; |
| A13-B9-C35; | A16-B9-C36; | A19-B9-C37; | A22-B9-C38; | A25-B9-C39; | A28-B9-C40; |
| A14-B9-C35; | A17-B9-C36; | A20-B9-C37; | A23-B9-C38; | A26-B9-C39; | A29-B9-C40; |
| A15-B9-C35; | A18-B9-C36; | A21-B9-C37; | A24-B9-C38; | A27-B9-C39; | A30-B9-C40; |
| A16-B9-C35; | A19-B9-C36; | A22-B9-C37; | A25-B9-C38; | A28-B9-C39; | A31-B9-C40; |
| A17-B9-C35; | A20-B9-C36; | A23-B9-C37; | A26-B9-C38; | A29-B9-C39; | A32-B9-C40; |
| A18-B9-C35; | A21-B9-C36; | A24-B9-C37; | A27-B9-C38; | A30-B9-C39; | A1-B10-C1; |
| A19-B9-C35; | A22-B9-C36; | A25-B9-C37; | A28-B9-C38; | A31-B9-C39; | A2-B10-C1; |

| | | | | | |
|---|---|---|---|---|---|
| A20-B9-C35; | A23-B9-C36; | A26-B9-C37; | A29-B9-C38; | A32-B9-C39; | A3-B10-C1; |
| A21-B9-C35; | A24-B9-C36; | A27-B9-C37; | A30-B9-C38; | A1-B9-C40; | A4-B10-C1; |
| A22-B9-C35; | A25-B9-C36; | A28-B9-C37; | A31-B9-C38; | A2-B9-C40; | A5-B10-C1; |
| A23-B9-C35; | A26-B9-C36; | A29-B9-C37; | A32-B9-C38; | A3-B9-C40; | A6-B10-C1; |
| A24-B9-C35; | A27-B9-C36; | A30-B9-C37; | A1-B9-C39; | A4-B9-C40; | A7-B10-C1; |
| A25-B9-C35; | A28-B9-C36; | A31-B9-C37; | A2-B9-C39; | A5-B9-C40; | A8-B10-C1; |
| A26-B9-C35; | A29-B9-C36; | A32-B9-C37; | A3-B9-C39; | A6-B9-C40; | A9-B10-C1; |
| A27-B9-C35; | A30-B9-C36; | A1-B9-C38; | A4-B9-C39; | A7-B9-C40; | A10-B10-C1; |
| A28-B9-C35; | A31-B9-C36; | A2-B9-C38; | A5-B9-C39; | A8-B9-C40; | A11-B10-C1; |
| A29-B9-C35; | A32-B9-C36; | A3-B9-C38; | A6-B9-C39; | A9-B9-C40; | A12-B10-C1; |
| A30-B9-C35; | A1-B9-C37; | A4-B9-C38; | A7-B9-C39; | A10-B9-C40; | A13-B10-C1; |
| A31-B9-C35; | A2-B9-C37; | A5-B9-C38; | A8-B9-C39; | A11-B9-C40; | A14-B10-C1; |
| A32-B9-C35; | A3-B9-C37; | A6-B9-C38; | A9-B9-C39; | A12-B9-C40; | A15-B10-C1; |
| A1-B9-C36; | A4-B9-C37; | A7-B9-C38; | A10-B9-C39; | A13-B9-C40; | A16-B10-C1; |
| A2-B9-C36; | A5-B9-C37; | A8-B9-C38; | A11-B9-C39; | A14-B9-C40; | A17-B10-C1; |
| A3-B9-C36; | A6-B9-C37; | A9-B9-C38; | A12-B9-C39; | A15-B9-C40; | A18-B10-C1; |
| A4-B9-C36; | A7-B9-C37; | A10-B9-C38; | A13-B9-C39; | A16-B9-C40; | A19-B10-C1; |
| A5-B9-C36; | A8-B9-C37; | A11-B9-C38; | A14-B9-C39; | A17-B9-C40; | A20-B10-C1; |
| A6-B9-C36; | A9-B9-C37; | A12-B9-C38; | A15-B9-C39; | A18-B9-C40; | A21-B10-C1; |
| A7-B9-C36; | A10-B9-C37; | A13-B9-C38; | A16-B9-C39; | A19-B9-C40; | A22-B10-C1; |
| A8-B9-C36; | A11-B9-C37; | A14-B9-C38; | A17-B9-C39; | A20-B9-C40; | A23-B10-C1; |
| A9-B9-C36; | A12-B9-C37; | A15-B9-C38; | A18-B9-C39; | A21-B9-C40; | A24-B10-C1; |
| A25-B10-C1; | A28-B10-C2; | A31-B10-C3; | A2-B10-C5; | A5-B10-C6; | A8-B10-C7; |
| A26-B10-C1; | A29-B10-C2; | A32-B10-C3; | A3-B10-C5; | A6-B10-C6; | A9-B10-C7; |
| A27-B10-C1; | A30-B10-C2; | A1-B10-C4; | A4-B10-C5; | A7-B10-C6; | A10-B10-C7; |
| A28-B10-C1; | A31-B10-C2; | A2-B10-C4; | A5-B10-C5; | A8-B10-C6; | A11-B10-C7; |
| A29-B10-C1; | A32-B10-C2; | A3-B10-C4; | A6-B10-C5; | A9-B10-C6; | A12-B10-C7; |
| A30-B10-C1; | A1-B10-C3; | A4-B10-C4; | A7-B10-C5; | A10-B10-C6; | A13-B10-C7; |
| A31-B10-C1; | A2-B10-C3; | A5-B10-C4; | A8-B10-C5; | A11-B10-C6; | A14-B10-C7; |
| A32-B10-C1; | A3-B10-C3; | A6-B10-C4; | A9-B10-C5; | A12-B10-C6; | A15-B10-C7; |
| A1-B10-C2; | A4-B10-C3; | A7-B10-C4; | A10-B10-C5; | A13-B10-C6; | A16-B10-C7; |
| A2-B10-C2; | A5-B10-C3; | A8-B10-C4; | A11-B10-C5; | A14-B10-C6; | A17-B10-C7; |
| A3-B10-C2; | A6-B10-C3; | A9-B10-C4; | A12-B10-C5; | A15-B10-C6; | A18-B10-C7; |
| A4-B10-C2; | A7-B10-C3; | A10-B10-C4; | A13-B10-C5; | A16-B10-C6; | A19-B10-C7; |
| A5-B10-C2; | A8-B10-C3; | A11-B10-C4; | A14-B10-C5; | A17-B10-C6; | A20-B10-C7; |
| A6-B10-C2; | A9-B10-C3; | A12-B10-C4; | A15-B10-C5; | A18-B10-C6; | A21-B10-C7; |
| A7-B10-C2; | A10-B10-C3; | A13-B10-C4; | A16-B10-C5; | A19-B10-C6; | A22-B10-C7; |
| A8-B10-C2; | A11-B10-C3; | A14-B10-C4; | A17-B10-C5; | A20-B10-C6; | A23-B10-C7; |
| A9-B10-C2; | A12-B10-C3; | A15-B10-C4; | A18-B10-C5; | A21-B10-C6; | A24-B10-C7; |
| A10-B10-C2; | A13-B10-C3; | A16-B10-C4; | A19-B10-C5; | A22-B10-C6; | A25-B10-C7; |
| A11-B10-C2; | A14-B10-C3; | A17-B10-C4; | A20-B10-C5; | A23-B10-C6; | A26-B10-C7; |
| A12-B10-C2; | A15-B10-C3; | A18-B10-C4; | A21-B10-C5; | A24-B10-C6; | A27-B10-C7; |
| A13-B10-C2; | A16-B10-C3; | A19-B10-C4; | A22-B10-C5; | A25-B10-C6; | A28-B10-C7; |
| A14-B10-C2; | A17-B10-C3; | A20-B10-C4; | A23-B10-C5; | A26-B10-C6; | A29-B10-C7; |
| A15-B10-C2; | A18-B10-C3; | A21-B10-C4; | A24-B10-C5; | A27-B10-C6; | A30-B10-C7; |
| A16-B10-C2; | A19-B10-C3; | A22-B10-C4; | A25-B10-C5; | A28-B10-C6; | A31-B10-C7; |
| A17-B10-C2; | A20-B10-C3; | A23-B10-C4; | A26-B10-C5; | A29-B10-C6; | A32-B10-C7; |
| A18-B10-C2; | A21-B10-C3; | A24-B10-C4; | A27-B10-C5; | A30-B10-C6; | A1-B10-C8; |
| A19-B10-C2; | A22-B10-C3; | A25-B10-C4; | A28-B10-C5; | A31-B10-C6; | A2-B10-C8; |
| A20-B10-C2; | A23-B10-C3; | A26-B10-C4; | A29-B10-C5; | A32-B10-C6; | A3-B10-C8; |
| A21-B10-C2; | A24-B10-C3; | A27-B10-C4; | A30-B10-C5; | A1-B10-C7; | A4-B10-C8; |
| A22-B10-C2; | A25-B10-C3; | A28-B10-C4; | A31-B10-C5; | A2-B10-C7; | A5-B10-C8; |
| A23-B10-C2; | A26-B10-C3; | A29-B10-C4; | A32-B10-C5; | A3-B10-C7; | A6-B10-C8; |
| A24-B10-C2; | A27-B10-C3; | A30-B10-C4; | A1-B10-C6; | A4-B10-C7; | A7-B10-C8; |
| A25-B10-C2; | A28-B10-C3; | A31-B10-C4; | A2-B10-C6; | A5-B10-C7; | A8-B10-C8; |
| A26-B10-C2; | A29-B10-C3; | A32-B10-C4; | A3-B10-C6; | A6-B10-C7; | A9-B10-C8; |
| A27-B10-C2; | A30-B10-C3; | A1-B10-C5; | A4-B10-C6; | A7-B10-C7; | A10-B10-C8; |
| A11-B10-C8; | A14-B10-C9; | A17-B10-C10; | A20-B10-C11; | A23-B10-C12; | A26-B10-C13; |
| A12-B10-C8; | A15-B10-C9; | A18-B10-C10; | A21-B10-C11; | A24-B10-C12; | A27-B10-C13; |
| A13-B10-C8; | A16-B10-C9; | A19-B10-C10; | A22-B10-C11; | A25-B10-C12; | A28-B10-C13; |
| A14-B10-C8; | A17-B10-C9; | A20-B10-C10; | A23-B10-C11; | A26-B10-C12; | A29-B10-C13; |
| A15-B10-C8; | A18-B10-C9; | A21-B10-C10; | A24-B10-C11; | A27-B10-C12; | A30-B10-C13; |
| A16-B10-C8; | A19-B10-C9; | A22-B10-C10; | A25-B10-C11; | A28-B10-C12; | A31-B10-C13; |
| A17-B10-C8; | A20-B10-C9; | A23-B10-C10; | A26-B10-C11; | A29-B10-C12; | A32-B10-C13; |
| A18-B10-C8; | A21-B10-C9; | A24-B10-C10; | A27-B10-C11; | A30-B10-C12; | A1-B10-C14; |
| A19-B10-C8; | A22-B10-C9; | A25-B10-C10; | A28-B10-C11; | A31-B10-C12; | A2-B10-C14; |
| A20-B10-C8; | A23-B10-C9; | A26-B10-C10; | A29-B10-C11; | A32-B10-C12; | A3-B10-C14; |
| A21-B10-C8; | A24-B10-C9; | A27-B10-C10; | A30-B10-C11; | A1-B10-C13; | A4-B10-C14; |
| A22-B10-C8; | A25-B10-C9; | A28-B10-C10; | A31-B10-C11; | A2-B10-C13; | A5-B10-C14; |
| A23-B10-C8; | A26-B10-C9; | A29-B10-C10; | A32-B10-C11; | A3-B10-C13; | A6-B10-C14; |
| A24-B10-C8; | A27-B10-C9; | A30-B10-C10; | A1-B10-C12; | A4-B10-C13; | A7-B10-C14; |
| A25-B10-C8; | A28-B10-C9; | A31-B10-C10; | A2-B10-C12; | A5-B10-C13; | A8-B10-C14; |
| A26-B10-C8; | A29-B10-C9; | A32-B10-C10; | A3-B10-C12; | A6-B10-C13; | A9-B10-C14; |
| A27-B10-C8; | A30-B10-C9; | A1-B10-C11; | A4-B10-C12; | A7-B10-C13; | A10-B10-C14; |
| A28-B10-C8; | A31-B10-C9; | A2-B10-C11; | A5-B10-C12; | A8-B10-C13; | A11-B10-C14; |
| A29-B10-C8; | A32-B10-C9; | A3-B10-C11; | A6-B10-C12; | A9-B10-C13; | A12-B10-C14; |
| A30-B10-C8; | A1-B10-C10; | A4-B10-C11; | A7-B10-C12; | A10-B10-C13; | A13-B10-C14; |
| A31-B10-C8; | A2-B10-C10; | A5-B10-C11; | A8-B10-C12; | A11-B10-C13; | A14-B10-C14; |
| A32-B10-C8; | A3-B10-C10; | A6-B10-C11; | A9-B10-C12; | A12-B10-C13; | A15-B10-C14; |

-continued

| | | | | | |
|---|---|---|---|---|---|
| A1-B10-C9; | A4-B10-C10; | A7-B10-C11; | A10-B10-C12; | A13-B10-C13; | A16-B10-C14; |
| A2-B10-C9; | A5-B10-C10; | A8-B10-C11; | A11-B10-C12; | A14-B10-C13; | A17-B10-C14; |
| A3-B10-C9; | A6-B10-C10; | A9-B10-C11; | A12-B10-C12; | A15-B10-C13; | A18-B10-C14; |
| A4-B10-C9; | A7-B10-C10; | A10-B10-C11; | A13-B10-C12; | A16-B10-C13; | A19-B10-C14; |
| A5-B10-C9; | A8-B10-C10; | A11-B10-C11; | A14-B10-C12; | A17-B10-C13; | A20-B10-C14; |
| A6-B10-C9; | A9-B10-C10; | A12-B10-C11; | A15-B10-C12; | A18-B10-C13; | A21-B10-C14; |
| A7-B10-C9; | A10-B10-C10; | A13-B10-C11; | A16-B10-C12; | A19-B10-C13; | A22-B10-C14; |
| A8-B10-C9; | A11-B10-C10; | A14-B10-C11; | A17-B10-C12; | A20-B10-C13; | A23-B10-C14; |
| A9-B10-C9; | A12-B10-C10; | A15-B10-C11; | A18-B10-C12; | A21-B10-C13; | A24-B10-C14; |
| A10-B10-C9; | A13-B10-C10; | A16-B10-C11; | A19-B10-C12; | A22-B10-C13; | A25-B10-C14; |
| A11-B10-C9; | A14-B10-C10; | A17-B10-C11; | A20-B10-C12; | A23-B10-C13; | A26-B10-C14; |
| A12-B10-C9; | A15-B10-C10; | A18-B10-C11; | A21-B10-C12; | A24-B10-C13; | A27-B10-C14; |
| A13-B10-C9; | A16-B10-C10; | A19-B10-C11; | A22-B10-C12; | A25-B10-C13; | A28-B10-C14; |
| A29-B10-C14; | A32-B10-C15; | A3-B10-C17; | A6-B10-C18; | A9-B10-C19; | A12-B10-C20; |
| A30-B10-C14; | A1-B10-C16; | A4-B10-C17; | A7-B10-C18; | A10-B10-C19; | A13-B10-C20; |
| A31-B10-C14; | A2-B10-C16; | A5-B10-C17; | A8-B10-C18; | A11-B10-C19; | A14-B10-C20; |
| A32-B10-C14; | A3-B10-C16; | A6-B10-C17; | A9-B10-C18; | A12-B10-C19; | A15-B10-C20; |
| A1-B10-C15; | A4-B10-C16; | A7-B10-C17; | A10-B10-C18; | A13-B10-C19; | A16-B10-C20; |
| A2-B10-C15; | A5-B10-C16; | A8-B10-C17; | A11-B10-C18; | A14-B10-C19; | A17-B10-C20; |
| A3-B10-C15; | A6-B10-C16; | A9-B10-C17; | A12-B10-C18; | A15-B10-C19; | A18-B10-C20; |
| A4-B10-C15; | A7-B10-C16; | A10-B10-C17; | A13-B10-C18; | A16-B10-C19; | A19-B10-C20; |
| A5-B10-C15; | A8-B10-C16; | A11-B10-C17; | A14-B10-C18; | A17-B10-C19; | A20-B10-C20; |
| A6-B10-C15; | A9-B10-C16; | A12-B10-C17; | A15-B10-C18; | A18-B10-C19; | A21-B10-C20; |
| A7-B10-C15; | A10-B10-C16; | A13-B10-C17; | A16-B10-C18; | A19-B10-C19; | A22-B10-C20; |
| A8-B10-C15; | A11-B10-C16; | A14-B10-C17; | A17-B10-C18; | A20-B10-C19; | A23-B10-C20; |
| A9-B10-C15; | A12-B10-C16; | A15-B10-C17; | A18-B10-C18; | A21-B10-C19; | A24-B10-C20; |
| A10-B10-C15; | A13-B10-C16; | A16-B10-C17; | A19-B10-C18; | A22-B10-C19; | A25-B10-C20; |
| A11-B10-C15; | A14-B10-C16; | A17-B10-C17; | A20-B10-C18; | A23-B10-C19; | A26-B10-C20; |
| A12-B10-C15; | A15-B10-C16; | A18-B10-C17; | A21-B10-C18; | A24-B10-C19; | A27-B10-C20; |
| A13-B10-C15; | A16-B10-C16; | A19-B10-C17; | A22-B10-C18; | A25-B10-C19; | A28-B10-C20; |
| A14-B10-C15; | A17-B10-C16; | A20-B10-C17; | A23-B10-C18; | A26-B10-C19; | A29-B10-C20; |
| A15-B10-C15; | A18-B10-C16; | A21-B10-C17; | A24-B10-C18; | A27-B10-C19; | A30-B10-C20; |
| A16-B10-C15; | A19-B10-C16; | A22-B10-C17; | A25-B10-C18; | A28-B10-C19; | A31-B10-C20; |
| A17-B10-C15; | A20-B10-C16; | A23-B10-C17; | A26-B10-C18; | A29-B10-C19; | A32-B10-C20; |
| A18-B10-C15; | A21-B10-C16; | A24-B10-C17; | A27-B10-C18; | A30-B10-C19; | A1-B10-C21; |
| A19-B10-C15; | A22-B10-C16; | A25-B10-C17; | A28-B10-C18; | A31-B10-C19; | A2-B10-C21; |
| A20-B10-C15; | A23-B10-C16; | A26-B10-C17; | A29-B10-C18; | A32-B10-C19; | A3-B10-C21; |
| A21-B10-C15; | A24-B10-C16; | A27-B10-C17; | A30-B10-C18; | A1-B10-C20; | A4-B10-C21; |
| A22-B10-C15; | A25-B10-C16; | A28-B10-C17; | A31-B10-C18; | A2-B10-C20; | A5-B10-C21; |
| A23-B10-C15; | A26-B10-C16; | A29-B10-C17; | A32-B10-C18; | A3-B10-C20; | A6-B10-C21; |
| A24-B10-C15; | A27-B10-C16; | A30-B10-C17; | A1-B10-C19; | A4-B10-C20; | A7-B10-C21; |
| A25-B10-C15; | A28-B10-C16; | A31-B10-C17; | A2-B10-C19; | A5-B10-C20; | A8-B10-C21; |
| A26-B10-C15; | A29-B10-C16; | A32-B10-C17; | A3-B10-C19; | A6-B10-C20; | A9-B10-C21; |
| A27-B10-C15; | A30-B10-C16; | A1-B10-C18; | A4-B10-C19; | A7-B10-C20; | A10-B10-C21; |
| A28-B10-C15; | A31-B10-C16; | A2-B10-C18; | A5-B10-C19; | A8-B10-C20; | A11-B10-C21; |
| A29-B10-C15; | A32-B10-C16; | A3-B10-C18; | A6-B10-C19; | A9-B10-C20; | A12-B10-C21; |
| A30-B10-C15; | A1-B10-C17; | A4-B10-C18; | A7-B10-C19; | A10-B10-C20; | A13-B10-C21; |
| A31-B10-C15; | A2-B10-C17; | A5-B10-C18; | A8-B10-C19; | A11-B10-C20; | A14-B10-C21; |
| A15-B10-C21; | A18-B10-C22; | A21-B10-C23; | A24-B10-C24; | A27-B10-C25; | A30-B10-C26; |
| A16-B10-C21; | A19-B10-C22; | A22-B10-C23; | A25-B10-C24; | A28-B10-C25; | A31-B10-C26; |
| A17-B10-C21; | A20-B10-C22; | A23-B10-C23; | A26-B10-C24; | A29-B10-C25; | A32-B10-C26; |
| A18-B10-C21; | A21-B10-C22; | A24-B10-C23; | A27-B10-C24; | A30-B10-C25; | A1-B10-C27; |
| A19-B10-C21; | A22-B10-C22; | A25-B10-C23; | A28-B10-C24; | A31-B10-C25; | A2-B10-C27; |
| A20-B10-C21; | A23-B10-C22; | A26-B10-C23; | A29-B10-C24; | A32-B10-C25; | A3-B10-C27; |
| A21-B10-C21; | A24-B10-C22; | A27-B10-C23; | A30-B10-C24; | A1-B10-C26; | A4-B10-C27; |
| A22-B10-C21; | A25-B10-C22; | A28-B10-C23; | A31-B10-C24; | A2-B10-C26; | A5-B10-C27; |
| A23-B10-C21; | A26-B10-C22; | A29-B10-C23; | A32-B10-C24; | A3-B10-C26; | A6-B10-C27; |
| A24-B10-C21; | A27-B10-C22; | A30-B10-C23; | A1-B10-C25; | A4-B10-C26; | A7-B10-C27; |
| A25-B10-C21; | A28-B10-C22; | A31-B10-C23; | A2-B10-C25; | A5-B10-C26; | A8-B10-C27; |
| A26-B10-C21; | A29-B10-C22; | A32-B10-C23; | A3-B10-C25; | A6-B10-C26; | A9-B10-C27; |
| A27-B10-C21; | A30-B10-C22; | A1-B10-C24; | A4-B10-C25; | A7-B10-C26; | A10-B10-C27; |
| A28-B10-C21; | A31-B10-C22; | A2-B10-C24; | A5-B10-C25; | A8-B10-C26; | A11-B10-C27; |
| A29-B10-C21; | A32-B10-C22; | A3-B10-C24; | A6-B10-C25; | A9-B10-C26; | A12-B10-C27; |
| A30-B10-C21; | A1-B10-C23; | A4-B10-C24; | A7-B10-C25; | A10-B10-C26; | A13-B10-C27; |
| A31-B10-C21; | A2-B10-C23; | A5-B10-C24; | A8-B10-C25; | A11-B10-C26; | A14-B10-C27; |
| A32-B10-C21; | A3-B10-C23; | A6-B10-C24; | A9-B10-C25; | A12-B10-C26; | A15-B10-C27; |
| A1-B10-C22; | A4-B10-C23; | A7-B10-C24; | A10-B10-C25; | A13-B10-C26; | A16-B10-C27; |
| A2-B10-C22; | A5-B10-C23; | A8-B10-C24; | A11-B10-C25; | A14-B10-C26; | A17-B10-C27; |
| A3-B10-C22; | A6-B10-C23; | A9-B10-C24; | A12-B10-C25; | A15-B10-C26; | A18-B10-C27; |
| A4-B10-C22; | A7-B10-C23; | A10-B10-C24; | A13-B10-C25; | A16-B10-C26; | A19-B10-C27; |
| A5-B10-C22; | A8-B10-C23; | A11-B10-C24; | A14-B10-C25; | A17-B10-C26; | A20-B10-C27; |
| A6-B10-C22; | A9-B10-C23; | A12-B10-C24; | A15-B10-C25; | A18-B10-C26; | A21-B10-C27; |
| A7-B10-C22; | A10-B10-C23; | A13-B10-C24; | A16-B10-C25; | A19-B10-C26; | A22-B10-C27; |
| A8-B10-C22; | A11-B10-C23; | A14-B10-C24; | A17-B10-C25; | A20-B10-C26; | A23-B10-C27; |
| A9-B10-C22; | A12-B10-C23; | A15-B10-C24; | A18-B10-C25; | A21-B10-C26; | A24-B10-C27; |
| A10-B10-C22; | A13-B10-C23; | A16-B10-C24; | A19-B10-C25; | A22-B10-C26; | A25-B10-C27; |
| A11-B10-C22; | A14-B10-C23; | A17-B10-C24; | A20-B10-C25; | A23-B10-C26; | A26-B10-C27; |
| A12-B10-C22; | A15-B10-C23; | A18-B10-C24; | A21-B10-C25; | A24-B10-C26; | A27-B10-C27; |
| A13-B10-C22; | A16-B10-C23; | A19-B10-C24; | A22-B10-C25; | A25-B10-C26; | A28-B10-C27; |

-continued

| | | | | | |
|---|---|---|---|---|---|
| A14-B10-C22; | A17-B10-C23; | A20-B10-C24; | A23-B10-C25; | A26-B10-C26; | A29-B10-C27; |
| A15-B10-C22; | A18-B10-C23; | A21-B10-C24; | A24-B10-C25; | A27-B10-C26; | A30-B10-C27; |
| A16-B10-C22; | A19-B10-C23; | A22-B10-C24; | A25-B10-C25; | A28-B10-C26; | A31-B10-C27; |
| A17-B10-C22; | A20-B10-C23; | A23-B10-C24; | A26-B10-C25; | A29-B10-C26; | A32-B10-C27; |
| A1-B10-C28; | A4-B10-C29; | A7-B10-C30; | A10-B10-C31; | A13-B10-C32; | A16-B10-C33; |
| A2-B10-C28; | A5-B10-C29; | A8-B10-C30; | A11-B10-C31; | A14-B10-C32; | A17-B10-C33; |
| A3-B10-C28; | A6-B10-C29; | A9-B10-C30; | A12-B10-C31; | A15-B10-C32; | A18-B10-C33; |
| A4-B10-C28; | A7-B10-C29; | A10-B10-C30; | A13-B10-C31; | A16-B10-C32; | A19-B10-C33; |
| A5-B10-C28; | A8-B10-C29; | A11-B10-C30; | A14-B10-C31; | A17-B10-C32; | A20-B10-C33; |
| A6-B10-C28; | A9-B10-C29; | A12-B10-C30; | A15-B10-C31; | A18-B10-C32; | A21-B10-C33; |
| A7-B10-C28; | A10-B10-C29; | A13-B10-C30; | A16-B10-C31; | A19-B10-C32; | A22-B10-C33; |
| A8-B10-C28; | A11-B10-C29; | A14-B10-C30; | A17-B10-C31; | A20-B10-C32; | A23-B10-C33; |
| A9-B10-C28; | A12-B10-C29; | A15-B10-C30; | A18-B10-C31; | A21-B10-C32; | A24-B10-C33; |
| A10-B10-C28; | A13-B10-C29; | A16-B10-C30; | A19-B10-C31; | A22-B10-C32; | A25-B10-C33; |
| A11-B10-C28; | A14-B10-C29; | A17-B10-C30; | A20-B10-C31; | A23-B10-C32; | A26-B10-C33; |
| A12-B10-C28; | A15-B10-C29; | A18-B10-C30; | A21-B10-C31; | A24-B10-C32; | A27-B10-C33; |
| A13-B10-C28; | A16-B10-C29; | A19-B10-C30; | A22-B10-C31; | A25-B10-C32; | A28-B10-C33; |
| A14-B10-C28; | A17-B10-C29; | A20-B10-C30; | A23-B10-C31; | A26-B10-C32; | A29-B10-C33; |
| A15-B10-C28; | A18-B10-C29; | A21-B10-C30; | A24-B10-C31; | A27-B10-C32; | A30-B10-C33; |
| A16-B10-C28; | A19-B10-C29; | A22-B10-C30; | A25-B10-C31; | A28-B10-C32; | A31-B10-C33; |
| A17-B10-C28; | A20-B10-C29; | A23-B10-C30; | A26-B10-C31; | A29-B10-C32; | A32-B10-C33; |
| A18-B10-C28; | A21-B10-C29; | A24-B10-C30; | A27-B10-C31; | A30-B10-C32; | A1-B10-C34; |
| A19-B10-C28; | A22-B10-C29; | A25-B10-C30; | A28-B10-C31; | A31-B10-C32; | A2-B10-C34; |
| A20-B10-C28; | A23-B10-C29; | A26-B10-C30; | A29-B10-C31; | A32-B10-C32; | A3-B10-C34; |
| A21-B10-C28; | A24-B10-C29; | A27-B10-C30; | A30-B10-C31; | A1-B10-C33; | A4-B10-C34; |
| A22-B10-C28; | A25-B10-C29; | A28-B10-C30; | A31-B10-C31; | A2-B10-C33; | A5-B10-C34; |
| A23-B10-C28; | A26-B10-C29; | A29-B10-C30; | A32-B10-C31; | A3-B10-C33; | A6-B10-C34; |
| A24-B10-C28; | A27-B10-C29; | A30-B10-C30; | A1-B10-C32; | A4-B10-C33; | A7-B10-C34; |
| A25-B10-C28; | A28-B10-C29; | A31-B10-C30; | A2-B10-C32; | A5-B10-C33; | A8-B10-C34; |
| A26-B10-C28; | A29-B10-C29; | A32-B10-C30; | A3-B10-C32; | A6-B10-C33; | A9-B10-C34; |
| A27-B10-C28; | A30-B10-C29; | A1-B10-C31; | A4-B10-C32; | A7-B10-C33; | A10-B10-C34; |
| A28-B10-C28; | A31-B10-C29; | A2-B10-C31; | A5-B10-C32; | A8-B10-C33; | A11-B10-C34; |
| A29-B10-C28; | A32-B10-C29; | A3-B10-C31; | A6-B10-C32; | A9-B10-C33; | A12-B10-C34; |
| A30-B10-C28; | A1-B10-C30; | A4-B10-C31; | A7-B10-C32; | A10-B10-C33; | A13-B10-C34; |
| A31-B10-C28; | A2-B10-C30; | A5-B10-C31; | A8-B10-C32; | A11-B10-C33; | A14-B10-C34; |
| A32-B10-C28; | A3-B10-C30; | A6-B10-C31; | A9-B10-C32; | A12-B10-C33; | A15-B10-C34; |
| A1-B10-C29; | A4-B10-C30; | A7-B10-C31; | A10-B10-C32; | A13-B10-C33; | A16-B10-C34; |
| A2-B10-C29; | A5-B10-C30; | A8-B10-C31; | A11-B10-C32; | A14-B10-C33; | A17-B10-C34; |
| A3-B10-C29; | A6-B10-C30; | A9-B10-C31; | A12-B10-C32; | A15-B10-C33; | A18-B10-C34; |
| A19-B10-C34; | A22-B10-C35; | A25-B10-C36; | A28-B10-C37; | A31-B10-C38; | A2-B10-C40; |
| A20-B10-C34; | A23-B10-C35; | A26-B10-C36; | A29-B10-C37; | A32-B10-C38; | A3-B10-C40; |
| A21-B10-C34; | A24-B10-C35; | A27-B10-C36; | A30-B10-C37; | A1-B10-C39; | A4-B10-C40; |
| A22-B10-C34; | A25-B10-C35; | A28-B10-C36; | A31-B10-C37; | A2-B10-C39; | A5-B10-C40; |
| A23-B10-C34; | A26-B10-C35; | A29-B10-C36; | A32-B10-C37; | A3-B10-C39; | A6-B10-C40; |
| A24-B10-C34; | A27-B10-C35; | A30-B10-C36; | A1-B10-C38; | A4-B10-C39; | A7-B10-C40; |
| A25-B10-C34; | A28-B10-C35; | A31-B10-C36; | A2-B10-C38; | A5-B10-C39; | A8-B10-C40; |
| A26-B10-C34; | A29-B10-C35; | A32-B10-C36; | A3-B10-C38; | A6-B10-C39; | A9-B10-C40; |
| A27-B10-C34; | A30-B10-C35; | A1-B10-C37; | A4-B10-C38; | A7-B10-C39; | A10-B10-C40; |
| A28-B10-C34; | A31-B10-C35; | A2-B10-C37; | A5-B10-C38; | A8-B10-C39; | A11-B10-C40; |
| A29-B10-C34; | A32-B10-C35; | A3-B10-C37; | A6-B10-C38; | A9-B10-C39; | A12-B10-C40; |
| A30-B10-C34; | A1-B10-C36; | A4-B10-C37; | A7-B10-C38; | A10-B10-C39; | A13-B10-C40; |
| A31-B10-C34; | A2-B10-C36; | A5-B10-C37; | A8-B10-C38; | A11-B10-C39; | A14-B10-C40; |
| A32-B10-C34; | A3-B10-C36; | A6-B10-C37; | A9-B10-C38; | A12-B10-C39; | A15-B10-C40; |
| A1-B10-C35; | A4-B10-C36; | A7-B10-C37; | A10-B10-C38; | A13-B10-C39; | A16-B10-C40; |
| A2-B10-C35; | A5-B10-C36; | A8-B10-C37; | A11-B10-C38; | A14-B10-C39; | A17-B10-C40; |
| A3-B10-C35; | A6-B10-C36; | A9-B10-C37; | A12-B10-C38; | A15-B10-C39; | A18-B10-C40; |
| A4-B10-C35; | A7-B10-C36; | A10-B10-C37; | A13-B10-C38; | A16-B10-C39; | A19-B10-C40; |
| A5-B10-C35; | A8-B10-C36; | A11-B10-C37; | A14-B10-C38; | A17-B10-C39; | A20-B10-C40; |
| A6-B10-C35; | A9-B10-C36; | A12-B10-C37; | A15-B10-C38; | A18-B10-C39; | A21-B10-C40; |
| A7-B10-C35; | A10-B10-C36; | A13-B10-C37; | A16-B10-C38; | A19-B10-C39; | A22-B10-C40; |
| A8-B10-C35; | A11-B10-C36; | A14-B10-C37; | A17-B10-C38; | A20-B10-C39; | A23-B10-C40; |
| A9-B10-C35; | A12-B10-C36; | A15-B10-C37; | A18-B10-C38; | A21-B10-C39; | A24-B10-C40; |
| A10-B10-C35; | A13-B10-C36; | A16-B10-C37; | A19-B10-C38; | A22-B10-C39; | A25-B10-C40; |
| A11-B10-C35; | A14-B10-C36; | A17-B10-C37; | A20-B10-C38; | A23-B10-C39; | A26-B10-C40; |
| A12-B10-C35; | A15-B10-C36; | A18-B10-C37; | A21-B10-C38; | A24-B10-C39; | A27-B10-C40; |
| A13-B10-C35; | A16-B10-C36; | A19-B10-C37; | A22-B10-C38; | A25-B10-C39; | A28-B10-C40; |
| A14-B10-C35; | A17-B10-C36; | A20-B10-C37; | A23-B10-C38; | A26-B10-C39; | A29-B10-C40; |
| A15-B10-C35; | A18-B10-C36; | A21-B10-C37; | A24-B10-C38; | A27-B10-C39; | A30-B10-C40; |
| A16-B10-C35; | A19-B10-C36; | A22-B10-C37; | A25-B10-C38; | A28-B10-C39; | A31-B10-C40; |
| A17-B10-C35; | A20-B10-C36; | A23-B10-C37; | A26-B10-C38; | A29-B10-C39; | A32-B10-C40; |
| A18-B10-C35; | A21-B10-C36; | A24-B10-C37; | A27-B10-C38; | A30-B10-C39; | |
| A19-B10-C35; | A22-B10-C36; | A25-B10-C37; | A28-B10-C38; | A31-B10-C39; | |
| A20-B10-C35; | A23-B10-C36; | A26-B10-C37; | A29-B10-C38; | A32-B10-C39; | |
| A21-B10-C35; | A24-B10-C36; | A27-B10-C37; | A30-B10-C38; | A1-B10-C40; | |

Thus, for example, in the above list the compound denoted as A1-B1-C1 is the product of the combination of group A1 in Table 1 and B1 in Table 2 and C1 in Table 3, namely

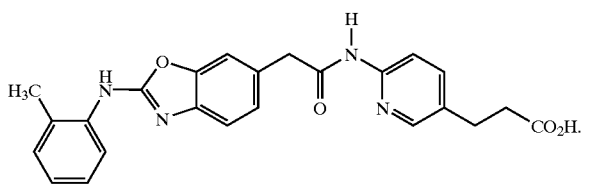

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I) wherein Het, $R^1$, $Ar^1$, $L^1$, $L^2$ and $Z^1$ are as hereinbefore defined, and Y is carboxy may be prepared by hydrolysis of esters of formula (I) wherein Het, $R^1$, $Ar^1$, $L^1$, $L^2$ and $Z^1$ are as hereinbefore defined and where the Y is a —$CO_2R^{18}$ group (in which $R^{18}$ is alkyl, alkenyl or arylalkyl). The hydrolysis may conveniently be carried out by alkaline hydrolysis using a base, such as an alkali metal hydroxide (e.g. sodium hydroxide or lithium hydroxide) or an alkali metal carbonate (e.g. potassium carbonate) in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) wherein Het, $R^1$, $Ar^1$, $L^1$, $L^2$ and $Z^1$ are as hereinbefore defined, and Y is carboxy may be prepared by acid catalysed removal of the tert-butyl group of tert-butyl esters of formula (I) wherein Het, $R^1$, $Ar^1$, $L^1$, $L^2$ and $Z^1$ are as hereinbefore defined and Y is a —$CO_2R^{18}$ group (in which $R^{18}$ is tert-butyl), using standard reaction conditions, for example reaction with trifluoroacetic acid at a temperature at about room temperature.

As another example compounds of formula (I) wherein Het, $R^1$, $Ar^1$, $L^1$, $L^2$ and $Z^1$ are as hereinbefore defined and Y is carboxy may be prepared by hydrogenation of compounds of formula (I) wherein Het, $R^1$, $Ar^1$, $L^1$, $L^2$ and $Z^1$ are as hereinbefore defined and Y is a —$CO_2R^{18}$ group (in which $R^{18}$ is benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

Esters of formula (I) wherein Het, $R^1$, $Ar^1$, $L^2$ and $Z^1$ are as hereinbefore defined $L^1$ is a —$R^5$—$R^6$— linkage (in which $R^5$ is as hereinbefore defined and $R^6$ is —C(=O)—$NR^4$— and Y is a —$CO_2R^{18}$ group (in which $R^{18}$ is as hereinbefore defined) may be prepared by reaction of compounds of formula (II):

$$R^1Z^1\text{—Het—}R^5\text{—C(=O)—}X^1 \qquad (II)$$

wherein Het, $R^1$, $R^5$ and $Z^1$ are as hereinbefore and $X^1$ is a hydroxy group or a halogen, preferably chlorine, atom, with amines of formula (III):

$$R^4\text{—NH—}Ar^1\text{—}L^2\text{—}CO_2R^{18} \qquad (III)$$

wherein $R^4$, $Ar^1$, $R^{18}$ and $L^2$ are as hereinbefore defined. When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and diisopropylethylamine (or triethylamine) in dimethylformamide (or tetrahydrofuran), at room temperature. When $X^1$ is a halogen atom the acylation reaction may be carried out with the aid of a base, such pyridine, preferably in a solvent such as tetrahydrofuran and at a temperature at about room temperature.

Esters of formula (I) wherein Het, $R^1$, $Ar^1$, $L^2$ and $Z^1$ are as hereinbefore defined $L^1$ is a —$R^5$—$R^6$— linkage [in which $R^5$ is as hereinbefore defined, and $R^6$ is —$NR^4$—C(=O)— (where $R^4$ is as hereinbefore defined)] and Y is a —$CO_2R^{18}$ group (in which $R^{18}$ is as hereinbefore defined) may be prepared by reaction of compounds of formula (IV):

$$R^1Z^1\text{—Het—}R^5\text{—}NHR^4 \qquad (IV)$$

wherein Het, $R^1$, $R^4$, $R^5$ and $Z^1$ are as hereinbefore, with compounds of formula (V):

$$X^2\text{—C(=O)—}Ar^1L^2\text{—}CO_2R^{18} \qquad (V)$$

wherein $Ar^1$, $R^{18}$ and $L^2$ are as hereinbefore defined and $X^2$ is a hydroxy group or a halogen, preferably chlorine, atom, using procedures described hereinbefore for coupling acids or acid halides with amines.

Esters of formula (I) wherein Het, $R^1$, $Ar^1$, $L^2$ and $Z^1$ are as hereinbefore defined, $L^1$ is a —$R^5$—$R^6$— linkage (in which $R^5$ is as hereinbefore defined and $R^6$ is —O—) and Y is a —$CO_2R^{18}$ group (in which $R^{18}$ is as hereinbefore defined) may be prepared by reaction of compounds of formula (VI):

$$R^1Z^1\text{—Het—}R^5\text{—OH} \qquad (VI)$$

wherein Het, $R^1$, $R^5$ and $Z^1$ are as hereinbefore defined with compounds of formula (VII):

$$HZ^3—Ar^1—L^2CO_2R^{18} \qquad (VII)$$

wherein $Ar^1$, $R^{18}$ and $L^2$ are as hereinbefore defined and $Z^3$ is O, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Alternatively esters of formula (I) wherein Het, $R^1$, $Ar^1$, $L^2$ and $Z^1$ are as hereinbefore defined, $L^1$ is a —$R^5$—$R^6$— linkage (in which $R^5$ is as hereinbefore defined and $R^6$ is —O—) and Y is a —$CO_2R^{18}$ group (in which $R^{18}$ is as hereinbefore defined) may be prepared by alkylation of compounds of formula (VII), wherein $Ar^1$, $R^{18}$ and $L^2$ are as hereinbefore defined and $Z^3$ is O with the appropriate alkyl bromides of formula (VIII):

$$R^1Z^1—Het—R^5—X^3 \qquad (VIII)$$

Het, $R^1$, $R^5$ and $Z^1$ are as hereinbefore defined and $X^3$ is a halogen, preferably bromo, atom using standard alkylation conditions. The alkylation may for example be carried out in the presence of a base, such as an alkali metal carbonate, e.g. potassium carbonate, or alkali metal hydride, e.g. sodium hydride, in dimethylformamide, or dimethyl sulphoxide, at a temperature from about 0° C. to about 100° C.

Esters of formula (I) wherein Het, $R^1$, $Ar^1$, $L^2$ and $Z^1$ are as hereinbefore defined, $L^1$ is a —$R^5$—$R^6$— linkage (in which $R^5$ is as hereinbefore defined and $R^6$ is —S—) and Y is a —$CO_2R^{18}$ group (in which $R^{18}$ is as hereinbefore defined) may be similarly prepared by alkylation of compounds of formula (VII) wherein $Ar^1$, $R^{18}$ and $L^2$ are as hereinbefore defined and $Z^3$ is S.

Esters of formula (I) wherein Het, $R^1$, $Ar^1$, $L^2$ and $Z^1$ are as hereinbefore defined, $L^1$ is a —$R^5$—$R^6$— linkage [in which $R^5$ is as hereinbefore defined and $R^6$ is —$NR^4$— (where $R^4$ is as hereinbefore defined)] and Y is a —$CO_2R^{18}$ group (in which $R^{18}$ is as hereinbefore defined) may be similarly prepared by alkylation of compounds of formula (III), wherein $Ar^1$, $R^4$, $R^{18}$ and $L^2$ are as hereinbefore defined.

Esters of formula (I) wherein Het, $R^1$, $Ar^1$, $L^2$ and $Z^1$ are as hereinbefore defined, $L^1$ is a —$R^5$—$R^6$— linkage [in which $R^5$ is alkylene and $R^6$ is —C(=O)—] and Y is a —$CO_2R^{18}$ group (in which $R^{18}$ is as hereinbefore defined) may be prepared by reaction of acid chlorides of formula (II) wherein Het, $R^1$ and $Z^1$ are as hereinbefore defined, $X^1$ is chloro and $R^5$ is alkylene, with compounds of formula (IX):

$$Br—Ar^1—L^2—CO_2R^{18} \qquad (IX)$$

wherein $R^{18}$, $Ar^1$ and $L^2$ are as hereinbefore defined, by the application or adaptation of the methodology described by R. D. Rieke et al, Synth.Commun., 1995, 23, pages 3923–3930.

Esters of formula (I) wherein Het, $R^1$, $Ar^1$, $L^2$ and $Z^1$ are as hereinbefore defined, $L^1$ is a —$R^5$—$R^6$— linkage [in which $R^5$ is as hereinbefore defined and $R^6$ is —$NR^4$—C(=O)—NH— (where $R^4$ is as hereinbefore defined)] and Y is a —$CO_2R^{18}$ group (in which $R^{18}$ is as hereinbefore defined) may be prepared by reaction of compounds of formula (IV) wherein Het, $R^1$, $R^4$, $R^5$ and $Z^1$ are as hereinbefore defined, with isocyanates of formula (X):

$$O=C=N—Ar^1—L^2—CO_2R^{18} \qquad (X)$$

wherein $Ar^1$, $R^{18}$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I) wherein Het, $R^1$, $Ar^1$, $L^2$ and $Z^1$ are as hereinbefore defined, $L^1$ is a —$R^5$—$R^6$— linkage [in which $R^5$ is as hereinbefore defined and $R^6$ is —NH—C(=O)—$NR^4$— (where $R^4$ is as hereinbefore defined)] and Y is a —$CO_2R^{18}$ group (in which $R^{18}$ is as hereinbefore defined) may be similarly prepared by reaction of amines of formula (III) wherein $Ar^1$, $R^4$, $R^{18}$ and $L^2$ are as hereinbefore defined with compounds of formula (XI):

$$R^1Z^1—Het—R^5—N=C=O \qquad (XI)$$

wherein Het, $R^1$, $R^5$ and $Z^1$ are as hereinbefore defined.

Esters of formula (I) wherein Het, $R^1$, $Ar^1$, $L^2$ and $Z^1$ are as hereinbefore defined, $L^1$ is a —$R^5$—$R^6$— linkage [in which $R^5$ is as hereinbefore defined and $R^6$ is —$SO_2$—$NR^4$— (where $R^4$ is as hereinbefore defined)] and Y is a —$CO_2R^{18}$ group (in which $R^{18}$ is as hereinbefore defined) may be prepared by reaction of compounds of formula (XII):

$$R^1Z^1—Het—R^5—SO_2Cl \qquad (XII)$$

wherein Het, $R^1$, $R^5$ and Z1 are as hereinbefore defined, with amines of formula (III) wherein Ar1, $R^4$, $R^{18}$ and $L^2$ are as hereinbefore defined. The reaction is preferably carried out with the aid of a base, such as a tertiary amine, for example triethylamine, preferably in a solvent such as tetrahydrofuran and at a temperature at about room temperature.

Esters of formula (I) wherein Het, $R^1$, $Ar^1$, $L^1$, $L^2$ and $Z^1$ are as hereinbefore defined, $L^1$ is a —$R^5$—$R^6$— linkage [in which $R^5$ is as hereinbefore defined and $R^6$ is —$NR^4$—$SO_2$— (where $R^4$ is as hereinbefore defined)] and Y is a —$CO_2R^{18}$ group (in which $R^{18}$ is as hereinbefore defined) may be similarly prepared by reaction of compounds of formula (IV) wherein Het, $R^1$, $R^5$, $R^4$ and $Z^1$ are as hereinbefore defined with sulphonyl chlorides of formula (XIII):

$$Cl—SO_2—Ar^1—L^2—CO_2R^{18} \qquad (XIII)$$

wherein $Ar^1$, $R^{18}$ and $L^2$ are as hereinbefore defined.

Esters of formula (I) wherein Het, $R^1$, $Ar^1$, $L^2$ and $Z^1$ are as hereinbefore defined, $L^1$ is a —$R^5$—$^6$— linkage [in which $R^5$ is as hereinbefore defined and $R^6$ is —O—C(=O)—] and Y is a —$CO_2R^{18}$ group (where $R^{18}$ is as hereinbefore defined) may be prepared by O-acylation of compounds of formula (VI) wherein Het, $R^1$, $R^5$, and $Z^1$ are as hereinbefore defined with compounds of formula (V) wherein $Ar^1$, $R^{18}$ and $L^2$ are as hereinbefore defined and $X^2$ is a chlorine atom. The reaction may be carried using standard O-acylation conditions, for example reaction in the presence of a base, such as triethylamine or pyridine, at a temperature from about 0° C. to about room temperature.

Esters of formula (I) wherein Het, $R^1$, $Ar^1$, $L^2$ and $Z^1$ are as hereinbefore defined, $L^1$ is a —$R^5$—$^6$— linkage [in which $R^5$ is as hereinbefore defined and $R^6$ is —C(=O)—O—] and Y is a —$CO_2R^{18}$ group (where $R^{18}$ is as hereinbefore defined) may be similarly prepared by O-acylation of compounds of formula (VII) wherein $Ar^1$, $R^{18}$ and $L^2$ are as hereinbefore defined and $Z^3$ is O with compounds of formula (II) wherein Het, $R^1$, $R^5$ and $Z^1$ are as hereinbefore defined and $X^1$ is a chlorine atom.

Esters of formula (I) wherein Het, $R^1$, $Ar^1$, $L^1$, $L^2$ and $Z^1$ are as hereinbefore defined, $L^1$ is a —$R^5$—$^6$— linkage (in which $R^5$ is as hereinbefore defined and $R^6$ is —O—C(=O)—NH—) and Y is a —$CO_2R^{18}$ group (where $R^{18}$ is as hereinbefore defined) may be prepared by reaction of compounds of formula (VI) wherein Het, $R^1$, $R^5$ and $Z^1$ are as hereinbefore defined with isocyanates of formula (X) wherein $Ar^1$, $R^{18}$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I) wherein Het, $R^1$, $Ar^1$, $L^1$, $L^2$ and $Z^1$ are as hereinbefore defined, $L^1$ is a —$R^5$—$^6$— linkage [in which $R^5$ is as hereinbefore defined and $R^6$ is —NH—C(=O)—O—] and Y is a —$CO_2R^{18}$ group (where $R^{18}$ is as hereinbefore defined) may be similarly prepared by reaction of isocyanates of formula (XI) wherein Het, $R^1$, $R^5$ and $Z^1$ are as hereinbefore defined with compounds of formula (VII) wherein $Ar^1$, $R^{18}$ and $L^2$ are as hereinbefore defined and $Z^3$ is O.

Esters of formula (I) wherein Het, $R^1$, $Ar^1$, $L^2$ and $Z^1$ are as hereinbefore defined, $L^1$ is a —$R^5$—$^6$— linkage (in which $R^6$ is a direct bond and $R^5$ is a straight or branched chain $C_{2-6}$alkenylene chain where the carbon-carbon double bond is directly attached to the phenyl ring containing the —$L^2$—Y group) and Y is a —$CO_2R^{18}$ group (where $R^{18}$ is as hereinbefore defined) may be prepared by reaction of compounds of formula (XIV):

$$H—C(=O)—Ar^1—L^2—CO_2R^{18} \quad (XIV)$$

wherein $Ar^1$, $R^{18}$ and $L^2$ are as hereinbefore defined, with an appropriate phosphorane (or phosphonate ester) of formula (XV):

$$R^1Z^1—Het—R^5—X^4 \quad (XV)$$

wherein Het, $R^1$ and $Z^1$ are as hereinbefore defined, $R^5$ is a straight or branched chain $C_{1-5}$alkylene chain and $X^4$ is =$PPh_3^+Br^-$ (or —$P(-O)(OEt)_2$), using standard Wittig (or Horner-Wadsworth-Emmons) coupling procedures (for example those described in Tetrahedron Organic Chemistry Series Volume 11, Organic Synthesis Based On Name Reactions and Unnamed Reactions, Editors, J. E. Balwin and P. D. Magnus, pages 181 and 421).

Esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^1$ is an alkylene linkage substituted by —$NY^3Y^4$ (in which one of $Y^3$ and $Y^4$ is hydrogen and the other is alkyl, or alkyl substituted by alkoxy, aryl, cyano, cycloalkyl, heteroaryl, heterocycloalkyl, hydroxy, oxo, —$NY^1Y^2$, or one or more —$CO_2R^7$ or —C(=O)—$NY^1Y^2$ groups), may be prepared by reaction of esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is an alkylene linkage substituted by —$NH_2$, with aldehydes of formula (XVI):

$$R^{19}—CHO \quad (XVI)$$

wherein $R^{19}$ is hydrogen or alkyl, or alkyl substituted by alkoxy, aryl, cyano, cycloalkyl, heteroaryl, heterocycloalkyl, hydroxy, oxo, —$NY^1Y^2$, or one or more —$CO_2R^7$ or —C(=O)—$NY^1Y^2$ groups in the presence of sodium cyanoborohydride. The reaction may be conveniently carried out in methanol, optionally in the presence of sodium acetate and 4 Å molecular sieves, and at a temperature at about room temperature.

Esters of formula (I), wherein Het, $R^1$, $Ar^1$, $L^1$ and $Z^1$ are as hereinbefore defined, and Y is a —$CO_2R^{18}$ group (where $R^{18}$ is as hereinbefore defined) and $L^2$ contains a —$N(R^7)$—C(=O)—$R^8$ group, may be prepared by reaction of amines of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ contains a —$NH(R^7)$ group, with compounds of formula (XVII):

$$R^8—C(=O)—X^5 \quad (XVII)$$

wherein $R^8$ is as hereinbefore defined and $X^5$ is a hydroxy group or a halogen, preferably chlorine, atom. When $X^5$ is a hydroxy group the reaction may be carried out using standard peptide coupling procedures as described hereinbefore. When $X^5$ is a halogen atom the reaction may be carried out with the aid of a base, such pyridine, preferably in a solvent such as tetrahydrofuran and at a temperature at about room temperature.

Esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ contains a —$N(R^7)$—C(=O)—$OR^8$ group, may be prepared by reaction of amines of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ contains a —$NH(R^7)$ group, with the appropriate chloroformate, e.g. ethyl (or benzyl) chloroformate compounds, according to standard reaction conditions.

Esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ contains a —$N(R^7)$—$SO_2$—$R^8$ group, may be prepared by reaction of amines of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ contains a —$NH(R^7)$ group, with the appropriate sulphonyl chloride, e.g. an aryl(or heteroaryl)sulphonyl chloride, such as phenyl(or pyridyl) sulphonyl chloride, according to standard reaction conditions.

Esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a

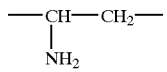

$$—CH—CH_2—$$
$$\phantom{xx}|$$
$$\phantom{xx}NH_2$$

linkage, may be prepared by hydrogenation of esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a

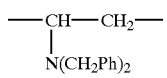

$$—CH—CH_2—$$
$$\phantom{xx}|$$
$$\phantom{xx}N(CH_2Ph)_2$$

linkage. The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a

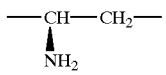

linkage, may be similarly prepared by hydrogenation of esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a

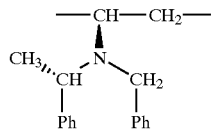

linkage.

Esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a

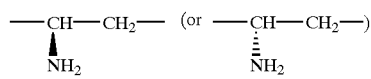

linkage, may also be obtained following standard recrystallisation of salts of the racemic mixture, for example recrystallisation of the tartrate salt.

Esters of formula (I), wherein Het, $R^1$, $Ar^1$, $L^1$ and $Z^1$ are as hereinbefore defined, and Y is a —$CO_2R^{18}$ group (where $R^{18}$ is as hereinbefore defined) and $L^2$ is a

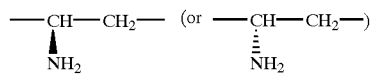

linkage, may also be obtained by the application of standard enzymatic resolution procedures for example those described by Soloshonok, V. A., et.al., Tetrahedron: Asymmetry 6 (1995) 7, 1601–1610.

Esters of formula (I) wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a

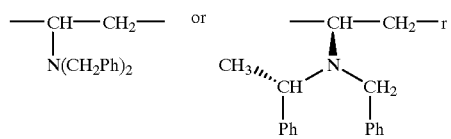

linkage, may be prepared by reaction of esters of formula (I), wherein Het, $R^1$, $Ar^1$, $L^1$ and $Z^1$ are as hereinbefore defined, Y is a —$CO_2R^{18}$ group (where $R^{18}$ is as hereinbefore defined) and $L^2$ is a —CH=CH— linkage, with an alkali metal hydride, such as sodium hydride, in an inert solvent, e.g. tetrahydrofuran, and at a temperature at about room temperature, and subsequent reaction with the anion derived from treating dibenzylamine, or (S)—N-benzyl-α-methylbenzylamine, with butyllithium, at a temperature at about −78° C.

Lactones of formula (I) wherein Het, $R^1$, $Ar^1$, $L^1$ and $Z^1$ are as hereinbefore defined and the moiety—$L^2$—Y is

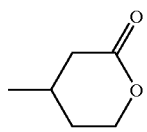

may be prepared by the selective reduction (using for example a borane derivative or lithium borohydride) of compounds of formula (I) wherein Het, $R^1$, $Ar^1$, $L^1$ and $Z^1$ are as hereinbefore defined and the moiety —$L^2$—Y is

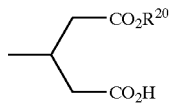

in which $R^{20}$ is lower alkyl, followed by spontaneous cyclisation of the intermediate hydroxy compound. The reduction can be achieved by the application or adaptation of the procedures described by C. J. Francis and J. Bryan Jones, J. Chem. Soc, Chem. Commun., 1984, (9), 579–58, J. Hiratake et al, J. Chem. Soc, Perkin Trans, 1987, 1(5), 1053–8 or L. K. P. Lam et al, J. Org. Chem. (1986), 51(11), 2047–50.

Lactones of formula (I) wherein Het, $R^1$, $Ar^1$, $L^1$ and $Z^1$ are as hereinbefore defined and the moiety—$L^2$—Y is

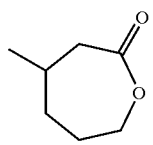

may be similarly prepared from compounds of formula (I) wherein Het, $R^1$, $Ar^1$, $L^1$ and $Z^1$ are as hereinbefore defined and the moiety —$L^2$—Y is

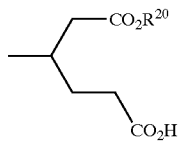

in which $R^{20}$ is lower alkyl.

Lactones of formula (I) wherein Het, $R^1$, $Ar^1$, $L^1$ and $Z^1$ are as hereinbefore defined and the moiety—$L^2$—Y is

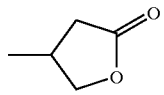

may be similarly prepared from compounds of formula (I) wherein Het, $R^1$, $Ar^1$, $L^1$ and $Z^1$ are as hereinbefore defined and the moiety —$L^2$—Y is

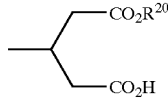

in which $R^{20}$ is lower alkyl.

Compounds of formula (I) wherein Het, $R^1$, $Ar^1$, $R^5$, $L^2$ and $Z^1$ are as hereinbefore defined, and Y is carboxy, represented by formula (XVIII), may be prepared using resin technology as shown in scheme 1.

SCHEME 1

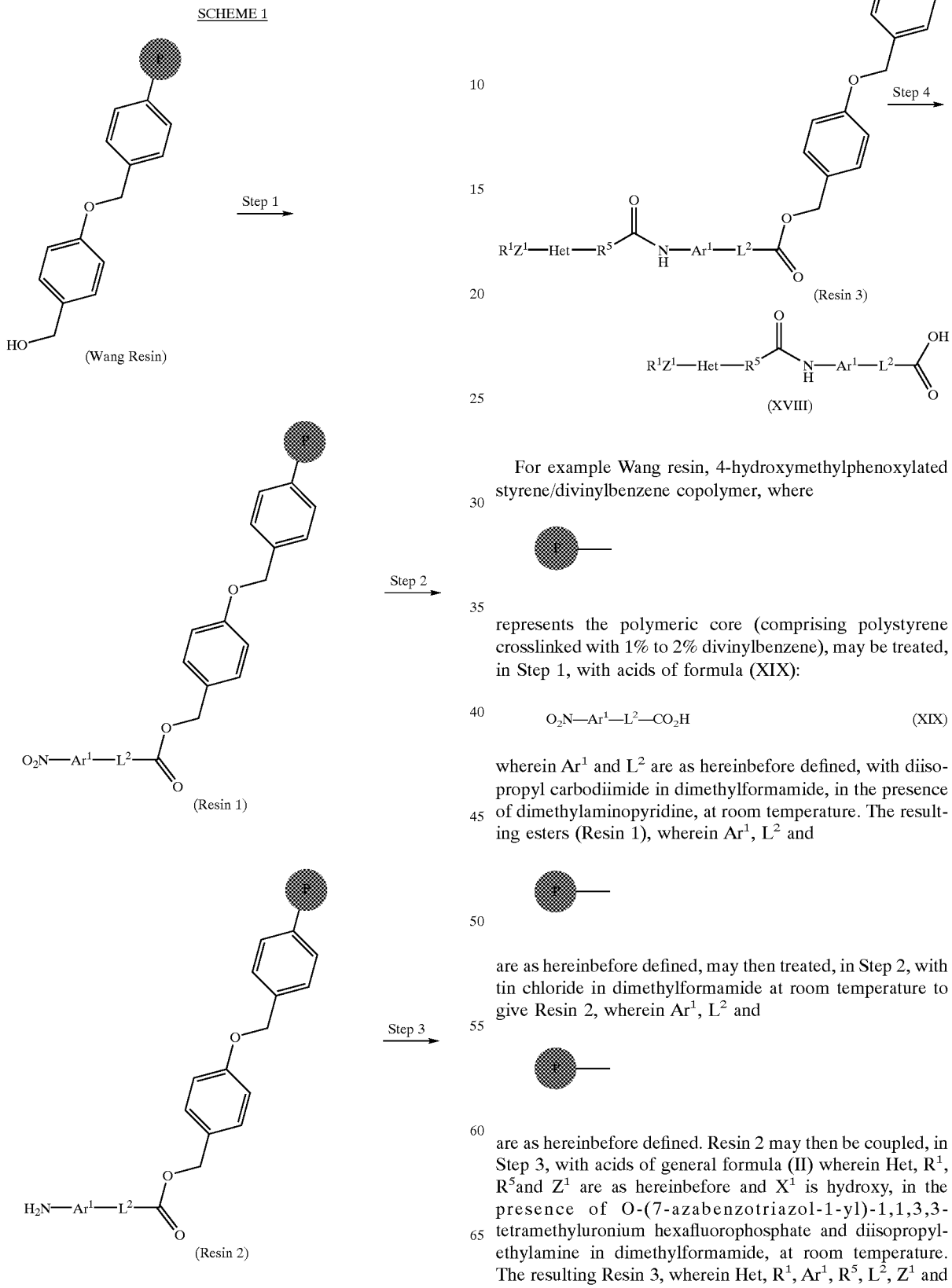

For example Wang resin, 4-hydroxymethylphenoxylated styrene/divinylbenzene copolymer, where represents the polymeric core (comprising polystyrene crosslinked with 1% to 2% divinylbenzene), may be treated, in Step 1, with acids of formula (XIX):

$$O_2N—Ar^1—L^2—CO_2H \qquad (XIX)$$

wherein $Ar^1$ and $L^2$ are as hereinbefore defined, with diisopropyl carbodiimide in dimethylformamide, in the presence of dimethylaminopyridine, at room temperature. The resulting esters (Resin 1), wherein $Ar^1$, $L^2$ and are as hereinbefore defined, may then treated, in Step 2, with tin chloride in dimethylformamide at room temperature to give Resin 2, wherein $Ar^1$, $L^2$ and are as hereinbefore defined. Resin 2 may then be coupled, in Step 3, with acids of general formula (II) wherein Het, $R^1$, $R^5$ and $Z^1$ are as hereinbefore and $X^1$ is hydroxy, in the presence of O-(7-azabenzotriazol-1-yl)-1,1,3,3-tetramethyluronium hexafluorophosphate and diisopropylethylamine in dimethylformamide, at room temperature. The resulting Resin 3, wherein Het, $R^1$, $Ar^1$, $R^5$, $L^2$, $Z^1$ and

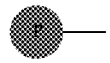

are as hereinbefore defined, may then be treated, in Step 4, with trifluoroacetic acid in an inert solvent such as dichloromethane, at room temperature, to liberate the acids of general formula (XVIII), wherein Het, $R^1$, $Ar^1$, $R^5$, $L^2$ and $Z^1$ are as hereinbefore defined.

Compounds of formula (Ia) wherein $R^1$, $R^5$, $R^{16}$, $Ar^1$ and $L^2$ are as hereinbefore defined, $R^4$ is hydrogen, X is O, $Z^1$ is NH and Y is carboxy, represented by formula (XX), may be prepared using resin technology as shown in scheme 2.

SCHEME 2

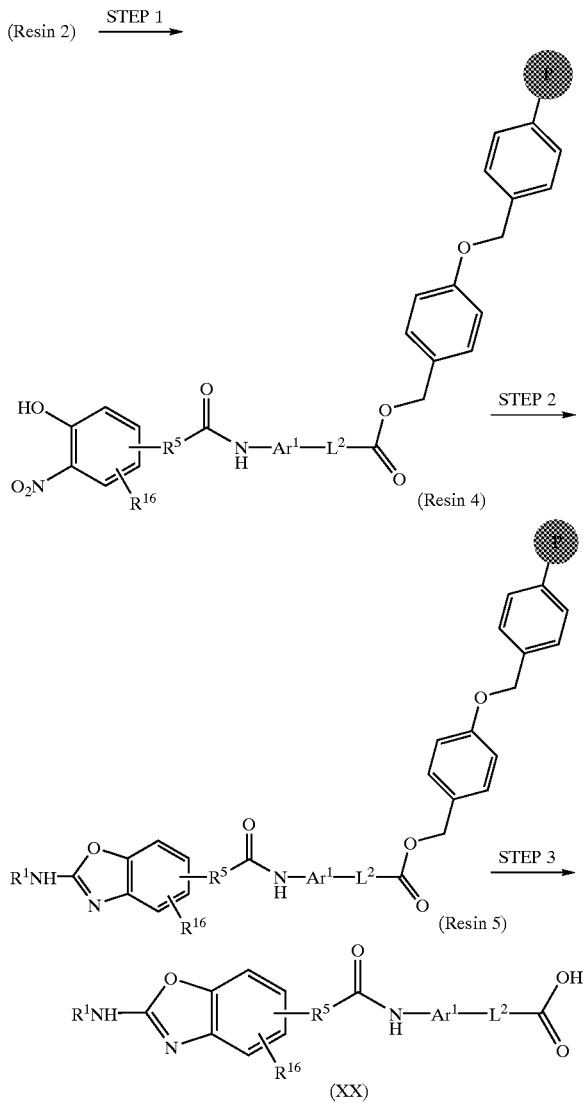

For example Resin 2 wherein $Ar^1$, $L^2$, and

are as hereinbefore defined may be coupled, in Step 1, with acids of general formula (XXI):

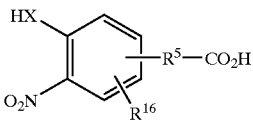

wherein $R^5$ is as hereinbefore defined and X is O, in the presence of O-(7-azabenzotriazol-1-yl)-1,1,3,3-tetramethyluronium hexafluorophosphate and diisopropyl-ethylamine in dimethylformamide, at room temperature to give Resin 4 wherein $R^5$, $R^{16}$, $Ar^1$, $L^2$ and

are as hereinbefore defined. Resin 4 may then be treated with tin chloride in dimethylformamide at room temperature followed treatment with isothiocyanates of formula (XXII):

wherein $R^1$ is as hereinbefore defined, in dimethylformamide at room temperature and then treatment with diisopropylcarbodiimide in dimethylformamide at 75° C. The resulting Resin 5, wherein $R^1$, $R^{16}$, $Ar^1$, $R^5$, $L^2$ and

are as hereinbefore defined, may then be treated, in Step 3, with trifluoroacetic acid in an inert solvent such as dichloromethane, at room temperature, to liberate the acids of general formula (XX), wherein $R^1$, $R^{16}$, $Ar^1$, $R^5$ and $L^2$ are as hereinbefore defined.

Esters of formula (Ia) wherein $R^1$, $R^4$, $R^5$, $Ar^1$ and $L^2$ are as hereinbefore defined, X is O, $Z^1$ is NH and Y is a —$CO_2R^{18}$ group (in which $R^{18}$ is as hereinbefore defined) may be prepared by reaction of compounds of formula (XXIII):

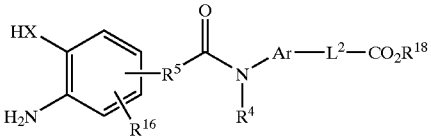

wherein $R^4$, $R^5$, $R^{16}$, $R^{18}$, $Ar^1$ and $L^2$ are as hereinbefore defined, with isothiocyanates of formula (XXII) wherein $R^1$ is as hereinbefore defined in dimethylformamide at room temperature followed by treatment with diisopropylcarbodiimide in dimethylformamide at 75° C.

According to a further feature of the present invention, compounds of the invention may be prepared by interconversion of other compounds of the invention.

For example compounds of formula (I) wherein Het, $R^1$, Art, $L^1$, $L^2$ and $Z^1$ are as hereinbefore defined and Y is —C(=O)—NHOH, may be prepared by reaction of compounds of formula (I) wherein Het, $R^1$, $Ar^1$, $L^1$, $L^2$ and $Z^1$ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) wherein Het, $R^1$, $Ar^1$, $L^1$, $Z^1$ and Y are as hereinbefore defined and $L^2$ is an optionally substituted alkylene linkage, may be prepared by hydrogenation of the corresponding compounds of formula (I) in which $L^2$ is the corresponding optionally substituted alkenylene linkage. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I) wherein Het, $R^1$, $Ar^1$, $L^2$, $Z^1$ and Y are as hereinbefore described and $L^1$ is a —$R^5$—$^6$— linkage where $R^5$ is a straight or branched chain $C_{2-6}$alkylene chain and $R^6$ is a direct bond, may be similarly prepared by hydrogenation of the corresponding compounds of formula (I) in which $L^1$ is a —$R^5$—$^6$— linkage where $R^5$ is a straight or branched chain $C_{2-6}$alkenylene chain and $R^6$ is a direct bond.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

Compounds of this invention can be regenerated from their acid addition salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Acids of formula (II) wherein $R^1$ and $R^5$ are as hereinbefore defined, Het is

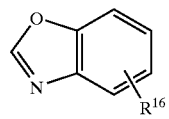

(in which $R^{16}$ is as hereinbefore defined), $Z^1$ is NH and $X^1$ is hydroxy may be prepared by reaction of compounds of formula (XXIV):

(XXIV)

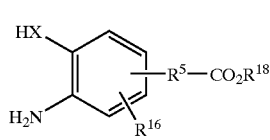

wherein $R^5$ and $R^{16}$ are as hereinbefore defined, $R^{18}$ is lower alkyl and X is O, with isothiocyanates of formula (XXII) wherein $R^1$ is as hereinbefore defined in ethanol and at room temperature, followed by reaction with a carbodiimide, such as dicyclohexylcarbodiimide or diisopropylcarbodiimide, in ethanol and at a temperature from about room temperature to about reflux temperature, followed by subsequent hydrolysis using standard conditions, for example those described hereinbefore.

Acids of formula (II) wherein $R^1$ and $R^5$ are as hereinbefore defined, Het is

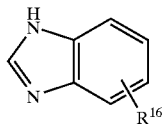

(in which $R^{16}$ is as hereinbefore defined), $Z^1$ is NH and $X^1$ is hydroxy may be similarly prepared from compounds of formula (XXIV) wherein $R^5$ and $R^{16}$ are as hereinbefore defined, $R^{18}$ is lower alkyl and X is NH.

Acid chlorides of formula (II) wherein Het, $R^1$, $R^5$ and $Z^1$ are as hereinbefore defined and $X^1$ is a chlorine atom may be prepared from the corresponding acids of formula (II) wherein Het, $R^1$, $R^5$ and $Z^1$ are as hereinbefore defined and $X^1$ is hydroxy, by the application of standard procedures for the conversion of acids to acid chlorides for example by reaction with oxalyl chloride.

Acid chlorides of formula (V) wherein $Ar^1$, $R^{18}$ and $L^2$ are as hereinbefore defined and $X^2$ is a chlorine atom may be similarly prepared from the corresponding acids of formula (V) wherein $Ar^1$, $R^{18}$ and $L^2$ are as hereinbefore defined and $X^2$ is hydroxy.

Compounds of formula (III) wherein $Ar^1$, $R^{18}$ and $L^2$ are as hereinbefore defined and $R^4$ is methyl may be prepared by treatment of the corresponding compounds of formula (III) wherein $Ar^1$, $R^{18}$ and $L^2$ are as hereinbefore defined and $R^4$ is hydrogen with formic acetic anhydride followed by reduction with lithium aluminium hydride according to the procedure described by L. G. Humber et al, J Med. Chem., 1971, 14, page 982.

Compounds of formula (IV) wherein Het, $R^1$, $R^5$ and $Z^1$ are as hereinbefore defined and $R^4$ is methyl may be similarly prepared by reacting compounds of formula (IV) wherein Het, $R^1$, $R^5$ and $Z^1$ are as hereinbefore defined and $R^4$ is hydrogen.

Compounds of formula (III) wherein $Ar^1$, $R^{18}$ and $L^2$ are as hereinbefore defined and $R^4$ is hydrogen may be prepared by reduction of the corresponding nitro compounds of formula (XXV):

$$O_2N-Ar^1-L^2-CO_2R^{18} \quad (XXV)$$

wherein $R^{18}$, $Ar^1$ and $L^2$ are as hereinbefore defined. The reduction may be carried out using standard procedures for example (i) by treatment with ammonium formate and palladium on charcoal in ethanol at a temperature at about 50° C. or (ii) by treatment with iron powder and ammonium chloride, in aqueous ethanol at a temperature at about reflux.

Compounds of formula (XXIII) wherein $R^4$, $R^5$, $R^{16}$, $R^{18}$, $Ar^1$ and $L^2$ are as hereinbefore defined, may be similarly prepared by reduction of compounds of formula (XXVI):

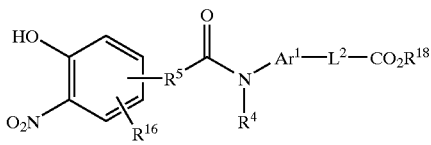

(XXVI)

wherein $R^4$, $R^5$, $R^{16}$, $R^{18}$, $Ar^1$ and $L^2$ are as hereinbefore defined.

Compounds of formula (XXIV) wherein $R^5$, $R^{16}$, $R^{18}$ are as hereinbefore defined and X is O may be similarly prepared by reduction of compounds of formula (XXVII):

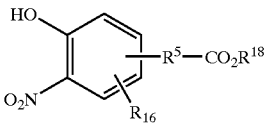

(XXVII)

wherein $R^5$, $R^{16}$, $R^{18}$ are as hereinbefore defined.

Compounds of formula (XXIV) wherein $R^5$, $R^{16}$, $R^{18}$ are as hereinbefore defined and X is NH may be similarly prepared by reduction of compounds of formula (XXVIII):

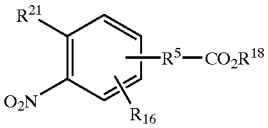

(XXVIII)

wherein $R^5$, $R^{16}$, $R^{18}$ are as hereinbefore defined and $R^{21}$ is $NH_2$ or $NO_2$.

Compounds of formula (III) wherein $Ar^1$ and $R^{18}$ are as hereinbefore defined, $R^4$ is hydrogen and $L^2$ is alkylene (e.g. —CH($CH_3$)—$CH_2$—) may be prepared by hydrogenation of compounds of formula (XXV) wherein $R^{18}$ and $Ar^1$ as hereinbefore defined and $L^2$ is the corresponding alkenylene chain (e.g. —C($CH_3$)=CH—) using standard conditions, for example those described hereinbefore.

Compounds of formula (IV) wherein Het, $R^1$, $R^5$ and $Z^1$ are as hereinbefore defined and $R^4$ is hydrogen may be prepared by reaction of compounds of formula (VIII) wherein Het, $R^1$, $R^5$ and $Z^1$ are as hereinbefore defined and $X^3$ is bromo with phthalimide potassium salt in dimethylformamide followed by reaction with hydrazine hydrate in ethanol (for example using the conditions described by O. Diouf et al., Heterocycles, 1995, 41, page 1219–1233).

Compounds of formula (VI) wherein Het, $R^1$ and $Z^1$ are as hereinbefore defined and $R^5$ is methylene (or a $C_{2-6}$ straight or branched alkylene chain), may be prepared by reduction of esters of formula (XXIX):

$$R^1Z^1-Het-R^{22}-CO_2R^{18} \quad (XXIX)$$

wherein Het, $R^1$ and $Z^1$ are as hereinbefore defined, $R^{18}$ is alkyl and $R^{22}$ is a direct bond (or a $C_{1-5}$ straight or branched alkylene chain). The reduction may conveniently be carried out with diisobutylaluminium hydride in an inert solvent, such as tetrahydrofuran, at a temperature from about −78° C. to about room temperature. The reduction may also be carried out with lithium aluminium hydride in an inert solvent, such as an ether, for example diethyl ether, at a temperature from about room temperature to about reflux.

Compounds of formula (VII) wherein $R^{18}$, $Ar^1$ and $L^2$ are as hereinbefore defined and $Z^3$ is O may be prepared from the corresponding acids of formula (XXX):

$$HZ^3-Ar^1-L^2-CO_2H \quad (XXX)$$

wherein $Ar^1$ and $L^2$ are as hereinbefore defined and $Z^3$ is O, by standard esterification procedures for example reaction with a lower alkyl alcohol (e.g. methanol) in the presence of an acid catalyst, such as hydrogen chloride or sulphuric acid.

Compounds of formula (VIII) wherein Het, $R^1$ and $Z^1$ are as hereinbefore defined, $R^5$ is an alkylene chain and $X^3$ is bromo may be prepared by reaction of compounds of formula (VI) wherein Het, $R^1$ and $Z^1$ are as hereinbefore defined, $R^5$ is an alkylene chain with phosphorus tribromide in an inert solvent such as carbon tetrachloride and at a temperature at about room temperature.

Compounds of formula (X) wherein $R^{18}$, $Ar^1$ and $L^2$ are as hereinbefore defined may be prepared from compounds of formula (III) wherein $R^{18}$, $Ar^1$ and $L^2$ are as hereinbefore defined and $R^4$ is hydrogen with phosgene following standard reaction conditions for the conversion of amines to isocyanates.

Compounds of formula (XI) wherein Het, $R^1$, $R^5$ and $Z^1$ are as hereinbefore defined may be similarly prepared from compounds of formula (IV) wherein Het, $R^1$, $R^5$ and $Z^1$ are as hereinbefore defined and $R^4$ is hydrogen.

Compounds of formula (XII) wherein Het, $R^1$, $R^5$ and $Z^1$ are as hereinbefore defined may be prepared from compounds of formula (VIII) wherein Het, $R^1$, $R^5$ and $Z^1$ are as hereinbefore defined and $X^3$ is bromo by reaction with sodium sulphite followed by phosphorus trichloride according to the described by P. N. Culshaw and J. C. Walton, J. Chem. Soc., Perkin Trans II, 1991, 8, pages1201–1208.

Compounds of formula (XIII) wherein $R^{18}$, $Ar^1$ and $L^2$ are as hereinbefore defined may be prepared from compounds of formula (III) wherein $R^{18}$, $Ar^1$ and $L^2$ are as hereinbefore defined and $R^4$ is hydrogen by application or adaptation of the procedures described by J. A. Diaz and S. Vega J. Heterocycl. Chem., 1994, 31, pages 93–96 for the conversion of aminopyrazoles to the corresponding pyrazolylsulphonyl chlorides.

Compounds of formula (XV) wherein Het, $R^1$ and $Z^1$ are as hereinbefore defined, $R^5$ is a straight or branched chain $C_{1-5}$alkylene chain and $X^4$ is $=PPh_3^+Br^-$ may be prepared by reaction of compounds of formula (VIII) wherein Het, $R^1$ and $Z^1$ are as hereinbefore defined, $R^5$ is a straight or branched chain $C_{1-5}$alkylene chain and $X^3$ is a bromine atom by reaction with triphenylphosphine in an inert solvent and at a temperature from about room temperature to about reflux temperature of the solvent.

Compounds of formula (XIX) wherein $Ar^1$ and $L^2$ are as hereinbefore defined may be prepared by hydrolysis of the corresponding esters of formula (XXV) using standard conditions as described hereinbefore.

Compounds of formula (XIX) wherein $Ar^1$is as defined hereinbefore and $L^2$ is

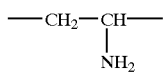

may be prepared by standard methodology for the preparation of α-amino acids aside for example those described in Organic Syntheses Based On Name Reactions and Unnamed Reactions, A. Hassner and C. Stumer, Pergamon, pages 275 and 374.

Compounds of formula (XIX) wherein $Ar^1$ is as defined hereinbefore and $L^2$ is

may also be prepared by reaction of compounds of formula (XXXI):

wherein $Ar^1$ is as hereinbefore defined and $X^6$ is a bromine or chlorine atom with the anion derived from reaction of (2R)-(−)-2,5-dihydro-3,6-dimethoxy-2-isopropylpyrazine with butyllithium according to the method described by D. L. Boger and D. Yohannes, J. Org. Chem. [JOCEAH], 1990, 55, for the preparation of compound 31 on page 6010.

Compounds of formula (XXV) wherein $Ar^1$ is as hereinbefore defined and $L^2$ contains an alkenylene, alkynylene or cycloalkenylene in which the aliphatic carbon-carbon multiple bond is attached directly to the phenyl moiety in formula (I), may be prepared by coupling of compounds of formula (XXXII):

wherein $Ar^1$ is as hereinbefore defined and $X^7$ is a halogen, preferably bromine or iodine, atom with a compound of formula (XXXIII):

wherein $R^{18}$ is as hereinbefore defined and $R^{23}$ is alkenyl, alkynyl or cycloalkenyl. When $X^7$ is a bromine or iodine atom the reaction may be conveniently carried out in the presence of tetrabutylammonium bromide, a palladium catalyst, such as tetrakis(tri-o-tolylphosphine)-palladium(0), and a tertiary amine, such as triethylamine, in an inert solvent, such as dimethylformamide, and at a temperature up to about 100° C. This reaction is particularly suitable for the preparation of compounds of formula (XXV) in which $L^2$ is vinylene or $-C(CH_3)=CH-$. When $X^7$ is a chlorine atom the reaction may be conveniently carried out in the presence of sodium iodide, nickel bromide, palladium(0) bis (dibenzylideneacetone), a triarylphosphine, such as tri-o-tolylphosphine, and a tertiary amine, such as tributylamine, at a temperature up to about 110° C.

Compounds of formula (XXV) wherein $Ar^1$ is pyridindiyl, $R^{18}$ is alkyl and $L^2$ is $-C(R^{24})=C(R^{25})-$ (in which $R^{24}$ and $R^{25}$ are independently hydrogen or alkyl) may be prepared by reaction of compounds of formula (XXXIV):

wherein $Ar^1$ is as hereinbefore defined and $R^{24}$ is hydrogen or alkyl, with a dialkylphosphonoacetate of formula (XXXV):

wherein $R^{18}$ is as hereinbefore defined, $R^{25}$ is hydrogen or alkyl and $R^{26}$ is a $C_{1-4}$alkyl group, in the presence of a base such as an alkali metal alkoxide (for example potassium t-butoxide), or an alkali metal hydride (for example sodium hydride). The reaction is preferably carried out in a solvent such as dimethylformamide or tetrahydrofuran.

Compounds of formula (XXVI) wherein $R^4$, $R^5$, $R^{16}$, $R^{18}$, $Ar^1$ and $L^2$ are as hereinbefore defined may be prepared by coupling of amines of formula (III) wherein $R^4$, $R^{18}$, $Ar^1$ and $L^2$ are as hereinbefore defined with acids of formula (XXI) wherein $R^5$ and $R^{16}$ are as hereinbefore defined and X is O using standard peptide coupling conditions as described hereinbefore. This reaction is preferably carried with the hydroxy group HX- suitably protected.

Compounds of formula (XXVII) wherein $R^5$, $R^{16}$, $R^{18}$ and $Ar^1$ are as hereinbefore defined may be prepared by reaction of compounds of formula (XXXVI):

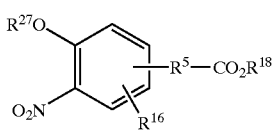

(XXXVI)

wherein $R^5$, $R^{16}$ and $R^{18}$ are as hereinbefore defined and $R^{27}$ is a suitable protecting group, such as alkyl- or arylcarbonyl, with a base, such as lithium hydroxide at a temperature at about room temperature. This method is particularly suitable for the preparation of compounds of formula (XXVII) where $R^5$ is methylene, $R^{16}$ is lower alkyl and $R^{18}$ is tertiary butyl.

Acids of formula (XXX) wherein $Ar^1$ and $L^2$ are as hereinbefore defined and $Z^3$ is O may be prepared by the application or adaptation of procedures described by A. G. Meyers and J. L. Gleason, J.Org.Chem., 1996, 61, pages 813–815. This methodology is particularly suitable for compounds where $Ar^1$ is pyridindiyl.

Acids of formula (XXX) wherein $Ar^1$ and $L^2$ are as hereinbefore defined and $Z^3$ is O may also be prepared by the application or adaptation of procedures described by S. R. Schow et al, J.Org.Chem., 1994, 59, pages 6850–6852. This methodology is particularly suitable for compounds where $Ar^1$ is pyridindiyl.

Compounds of formula (XXXVI) wherein $R^5$, $R^{18}$ are as hereinbefore defined, $R^{16}$ is a lower alkyl group attached to the ring position adjacent to the nitro group and $R^{27}$ is a suitable protecting group, such as alkyl- or arylcarbonyl, may be prepared by reaction of compounds of formula (XXXVII):

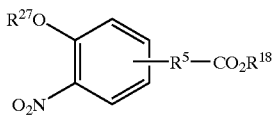

(XXXVII)

wherein $R^5$, $R^{18}$ are as hereinbefore defined and $R^{27}$ is a suitable protecting group, such as alkyl- or arylcarbonyl, with a lower alkyl magnesium halide, such as methyl magnesium chloride, in an inert solvent, such as tetrahydrofuran, and at a temperature at about −15° C.

Intermediates of formulae (XXIII) and (XXVI) are novel compounds and, as such, they and their processes described herein for their preparation constitute further features of the present invention.

The present invention is further exemplified but not limited by the following illustrative Examples and Reference Examples.

High Pressure Liquid Chromatography (HPLC) conditions for determination of retention times ($R_T$) were: 15 cm Hypersil Elite C-18 column, ELS detector; solvent acetonitrile/water gradient (both buffered with 0.5% trifluoroacetic acid): 20% acetonitrile for 3 minutes; than ramp up to 80% over the next 12 minutes; maintain at 80% acetonitrile for 3 minutes; then ramp back to 20% acetonitrile over 0.5 minutes (total run time 20 minutes).

High Pressure Liquid Chromatography/Mass Spectrometry (LC-MS) conditions for determination of retention times ($R_T$) were as follows: 3 micron Luna C18 (2) HPLC column (30 mm×4.6 mm) operated under gradient elution conditions with mixtures of (A) water containing 0.1% formic acid and (B) acetonitrile containing 0.1% formic acid as the mobile phase gradient: 0.00 minutes, 95% A:5% B; 0.50 minutes, 95% A:5% B; 4.50 minutes, 5% A:95% B; 5.00 minutes, 5% A:95% B; 5.50 minute 95% A:5% B; flow rate 2 ml/minute with approximately 200 µl/minute split to the Mass Spectrometer; injection volume 10–40 µl; in line Diode Array (220–450 nm), in line Evaporative light scattering (ELS) detection ELS—temperature 50° C., Gain 8—1.8 ml/minute; Source temperature 150° C.

Mass spectra (MS) were recorded on a Micromass Platform LC mass spectrometer fitted with an Electrospray source and an HP1100 liquid chromatograph; using a mixture of acetonitrile and water (1:1, v/v) as the mobile phase, a flow rate of 0.3 ml/minute, an injection volume of 20 µl, a run time of 2.0 minutes, a scan range of 150–850 Daltons Positive/Negative, a scan time of 2.0 seconds, an ESI voltage of 3.5 Kv, an ESI pressure of 20 n/m2 Nitrogen. The ions quoted are positive ions.

Thin layer chromatography (TLC) was carried out on Merck silica (silica gel 60$F_{254}$) plates.

EXAMPLE 1

(3RS)-3-{5-[2-(2-o-Tolylamino-benzoxazol-6-yl)-acetylamino]-pyrid-2-yl}-butyric acid A solution of (3RS)-3-{5-[2-(2-o-tolylamino-benzoxazol-6-yl)-acetylamino]-pyrid-2-yl}-butyric acid ethyl ester (0.3 g, Reference Example 1) in methanol (4 mL) was treated with aqueous sodium hydroxide solution (1.5 mL, 1M) and left to stand in a water bath at 40° C. for three hours. The mixture was partially evaporated, diluted with more water and partially evaporated again. The residue was diluted with water (10 mL) and washed with diethyl ether (10 mL). The pH of the aqueous phase was adjusted to 7 by addition of dilute hydrochloric acid. The resulting white solid was filtered then dried and then triturated with boiling acetonitrile to give the title compound (0.06 g) as a white powder, m.p. 195–196° C. (with decomposition). MS: 445 (MH⁺).

EXAMPLE 2

(3RS)-3-{5-[2-(2-o-Tolylamino-3H-benzimidazol-5-yl)-acetylamino]-pyridin-2-yl}-butyric acid trifluoroacetate A solution of ethyl (3RS)-3-(5-amino-pyrid-2-yl)butyrate (200 mg, Reference Example 5) and {1-[(2-trimethylsilylethoxy)methyl]-2-o-tolylamino-5-benzimidazolyl}acetic acid (390 mg, Reference Example 7) in dimethylformamide was treated with O-(7-azabenzotriazol-1-yl)-1,1,3,3-tetramethyluronium hexafluorophosphate (380 mg) and then with diisopropylethylamine (260 mg). After standing at room temperature for 2 hours the mixture was partitioned between ethyl acetate (100 mL) and water (50 mL). The layers were separated and the organic layer was dried then evaporated. The residue was subjected to flash chromatography on silica eluting with ethyl acetate. The major component (350 mg) was dissolved in methanol (10 mL) and the solution was treated with aqueous sodium hydroxide solution (3 mL, 1M). After standing at room temperature for 4 hours the mixture was evaporated to low bulk, then diluted with water (20 mL) and then treated with acetic acid until a white precipitate formed. The white precipitate was extracted into ethyl acetate. The solution was dried and then evaporated to give a white gum (40 mg) which was dissolved in trifluoroacetic acid (5 mL). After standing at room temperature for 2 hours the solution was evaporated to give the title compound (21 mg) as a light yellow foam. HPLC: $R_T$=4.63 minutes (100%). MS (ES positive): 444 (MH⁺).

EXAMPLE 3

(3RS)-3-{5-[2-(4-Methyl-2-o-tolylamino-benzoxazol-6-yl)acetylamino]pyrid-2-yl}butyric acid A stirred solution of 2-(4-methyl-2-o-tolylamino-benzoxazol-6-yl)acetic acid (0.13 g, Reference Example 9)

in dimethylformamide (5 mL) was treated with O-(7-azabenzotriazol-1-yl)-1,1,3,3-tetramethyluronium hexafluorophosphate (0.166 g), diisopropylethylamine (0.153 mL) and then with a solution of ethyl (3RS)-3-(4-aminopyrid-2-yl)butyrate (0.091 g, Reference Example 5) in dimethylformamide (5 mL). After stirring for 1 hour and then standing at room temperature over night the reaction mixture was diluted with water and then extracted with t-butyl methyl ether. The extracts were dried over magnesium sulphate and then evaporated to give (3RS)-3-{5-[2-(4-methyl-2-o-tolylamino-benzoxazol-6-yl)acetylamino]pyrid-2-yl}butyric acid ethyl ester as a gum. A solution of this gum in ethanol was treated with aqueous lithium hydroxide solution (1M) and after stirring at room temperature for 1 hour the mixture was partially evaporated. The residue was acidified to pH 6–7 by addition of concentrated hydrochloric acid. This mixture was extracted with ethyl acetate. The extracts were dried over magnesium sulphate and then evaporated to give the title compound (0.012 g) as a cream solid. MS (ES negative): 457(MH−).

EXAMPLE 4

(a) (RS) 3-{5-[2-(2-Phenylamino-benzoxazol-6-yl)-acetylamino]-pyridin-2-yl}-butyric acid A solution of (RS) methyl 3-{5-[2-(4-amino-3-hydroxy-phenyl)-acetylamino]-pyridin-2-yl}-butyrate (41.2 mg, Reference Example 24) in ethanol (1 mL) was treated with a solution of phenyl isothiocyanate (16.23 mg) in ethanol (2 mL). The mixture allowed to stand at room temperature for 48 hours, then heated at 70° C. for 16 hours and then evaporated. The residue, (RS) methyl 3-{5-[2-(3-hydroxy-4-(3-phenylthioureido)-phenyl)-acetylamino]-pyridin-2-yl}-butyrate, was dissolved in dry dimethylformamide (1 mL) and the solution was treated with a solution of dicyclohexylcarbodiimide (74.2 mg) in dry dimethylformamide (2 mL). This mixture was heated at 70° C. for 12 hours and then evaporated. The residue was dissolved in methanol (2 mL) and the solution was treated with aqueous sodium hydroxide (600 μL, 1M). After shaking for 24 hours the mixture was filtered and the filtrate was acidified with aqueous acetic acid (1 mL, 1M). The precipitate was filtered and dissolved in dimethylformamide. This solution was evaporated and the residue was subjected to reversed phase HPLC on a Hypersil Elite C18 column (100 mm×21 mm) using 0.05% TFA in acetonitrile water to give the title compound. LC-MS: $R_T$=2.36 minutes; MS (ES+): 431 (MH+).

(b) By proceeding in a similar manner to Example 4(a) but using 2-chlorophenyl isothiocyanate there was prepared (RS) 3-(5-{2-[2-(2-chloro-phenylamino)-benzoxazol-6-yl]-acetylamino}-pridin-2-yl)-butyric acid. LC-MS: $R_T$=2.52 minutes; MS (ES+): 465, 467 (MH+).

(c) By proceeding in a similar manner to Example 4(a) but using 2-o-tolyl isothiocyanate there was prepared (RS) 3-{5-[2-(2-o-tolylamino-benzoxazol-6-yl)-acetylamino]-pyridin-2-yl}-butyric acid. LC-MS: $R_T$=2.37 minutes; MS (ES+): 445 (MH+).

(d) By proceeding in a similar manner to Example 4(a) but using 2-methoxyphenyl isothiocyanate there was prepared (RS) 3-(5-{2-[2-(2-methoxy-phenylamino)-benzoxazol-6-yl]-acetylamino}-pyridin-2-yl)-butyric acid. LC-MS: $R_T$=2.45 minutes; MS (ES+): 461 (MH+).

(e) By proceeding in a similar manner to Example 4(a) but using (RS) methyl 3-{6-[2-(4-amino-3-hydroxy-phenyl)-acetylamino]-pyridin-3-yl}-butyrate (Reference Example 1) there was prepared (RS) 3-{6-[2-(2phenylamino-benzoxazol-6-yl)-acetylamino]-pyridin-3-yl}-butyric acid. LC-MS: $R_T$=2.37 minutes; MS (ES+): 431 (MH+).

(f) By proceeding in a similar manner to Example 4(a) but using (RS) methyl 3-{6-[2-(4-amino-3-hydroxy-phenyl)-acetylamino]-pyridin-3-yl}-butyrate (Reference Example 14) and 2-chlorophenyl isothiocyanate there was prepared (RS) 3-(6-{2-[2-(2-chloro-phenylamino)-benzoxazol-6-yl]-acetylamino}-pyridin-3-yl)-butyric acid. LC-MS: $R_T$=2.52 minutes; MS (ES+): 465, 467 (MH+).

(g) By proceeding in a similar manner to Example 4(a) but using (RS) methyl 3-{6-[2-(4-amino-3-hydroxy-phenyl)-acetylamino]-pyridin-3-yl}-butyrate (Reference Example 14) and 2-o-tolyl isothiocyanate there was prepared (RS) 3-{6-[2-(2-o-tolylamino-benzoxazol-6-yl)-acetylamino]-pyridin-3-yl}-butyric acid. LC-MS: $R_T$=2.37 minutes; MS (ES+): 445 (MH+).

(h) By proceeding in a similar manner to Example 4(a) but using (RS) methyl 3-{6-[2-(4-amino-3-hydroxy-phenyl)-acetylamino]-pyridin-3-yl}-butyrate (Reference Example 14) and 2-methoxyphenyl isothiocyanate there was prepared (RS) 3-(6-{2-[2-(2-methoxy-phenylamino)-benzoxazol-6-yl]-acetylamino}-pyridin-3-yl)-butyric acid. LC-MS: $R_T$=2.46 minutes; MS (ES+): 461 (MH+).

(i) By proceeding in a similar manner to Example 4(a) but using (RS) methyl 3-{6-[2-(4-amino-3-hydroxy-phenyl)-acetylamino]-pyridin-3-yl}-butyrate (Reference Example 14) and 3-methoxyphenyl isothiocyanate there was prepared (RS) 3-(6-{2-[2-(3-methoxy-phenylamino)-benzoxazol-6-yl]-acetylamino}-pridin-3-yl)-butyric acid. LC-MS: $R_T$=2.42 minutes; MS (ES+): 461 (MH+).

Reference Example 1

(3RS)-3-{5-[2-(2-o-Tolylamino-benzoxazol-6-yl)-acetylamino]-pyrid-2-yl}-butyric acid ethyl ester A stirred solution of 2-o-tolylamino-benzoxazol-6-acetic acid (0.42 g, Reference Example 2) in dimethylformamide (15 mL) was treated with O-(7-azabenzotriazol-1-yl)-1,1,3,3-tetramethyluronium hexafluorophosphate (0.57 g), then with diisopropylethylamine (0.4 g) and then with a solution of ethyl (3RS)-3-(5-aminopyrid-2-yl)butyrate (0.3 g, Reference Example 5) in dimethylformamide (5 mL). The mixture was stirred at room temperature for 5 hours then left to stand over night and then evaporated to low bulk. The residue was partitioned between water and ethyl acetate. The organic phase was washed with dilute acetic acid, then with water, then with aqueous bicarbonate solution (5%), then with water, then with brine, then dried and then evaporated. The residue was subjected to flash chromatography on silica eluting with ethyl acetate to give the title compound (0.5 g) as a colourless glass. TLC: $R_F$=0.36 (eluting with ethyl acetate). MS: 473 (MH+).

Reference Example 2

2-o-Tolylamino-benzoxazole-6-acetic acid

A mixture of ethyl 4-amino-3-hydroxy-phenylacetate (3.3 g, Reference Example 3) and o-tolylisothiocyanate (2.5 mL) in ethanol (150 mL) was stirred at room temperature for about 2 hours. After standing at room temperature overnight the mixture was evaporated and the residue was subjected to flash chromatography on silica eluting with a mixture of pentane and ethyl acetate (7:3, v/v) to give a yellow foam. A solution of this material in ethanol (150 mL) was treated with dicyclohexylcarbodiimide (3.0 g) and the mixture was heated at reflux temperature for 2 hours. The mixture was evaporated and the residue subjected to short column chromatography on silica eluting with a mixture of 5–10% tert-butyl methyl ether in dichloromethane to remove dicyclohexylurea. The resulting light yellow oil was dissolved in ethanol (100 mL) and the solution was treated with sodium hydroxide solution (15 mL, 1M) then heated at reflux temperature for 2 hours. The reaction mixture was evaporated and the residue was dissolved in water. The solution was washed with ethyl acetate and the aqueous layer was acidified to pH 1 by addition of concentrated hydrochloric acid. The resulting white precipitate was collected by filtration, then washed thoroughly with water, and then dried to give the title compound (1.8 g) as a white solid.

Reference Example 3

Ethyl 4-amino-3-hydroxy-phenylacetate

A solution of ethyl 3-hydroxy-4-nitrophenylacetate (5.0 g, Reference Example 4) was dissolved in ethanol (approximately 200 mL) was treated with ammonium formate (approximately 20 g). The mixture was warmed to 50° C. and then treated cautiously with palladium on charcoal (approximately 1 g, 5%)—effervescence was observed. After 30 minutes the mixture was filtered hot through a pad of celite and the filtrate was concentrated to give the title compound (3.3 g) as a black solid.

Reference Example 4

Ethyl 3-hydroxy-4-nitrophenylacetate

A solution of 3-hydroxy-4-nitrophenylacetic acid (4.0 g, prepared according to the procedure described by Meyer et al, J.Med.Chem., 1997, 40, pages 1049–1062) in ethanol (approximately 100 mL) was treated with concentrated hydrochloric acid (5–8 drops) was heated at reflux temperature for 3 hours then evaporated. The residue was dissolved in tert-butyl methylether and the solution was washed with saturated aqueous sodium bicarbonate solution, then with water, then dried, and then evaporated to give the title compound (5.0 g) as a light yellow solid.

Reference Example 5

Ethyl (3RS)-3-(5-aminopyrid-2-yl)butyrate

A mixture of ethyl (E,Z)-(5-nitropyrid-2-yl)but-2-enoate (11.0 g, Reference Example 6), ethanol (450 ml) and 5% palladium on charcoal (2.0 g) was stirred at ambient temperature under an atmosphere of hydrogen for 7 hours then left to stand over night. The reaction mixture was filtered through a short pad of diatomaceous earth. The filtrate was evaporated to give the title compound (9.7 g) as a colourless oil. TLC: $R_F$=0.28 (eluting with ethyl acetate).

Reference Example 6

Ethyl (E,Z)-(5-nitropyrid-2-yl)but-2-enoate

A stirred suspension of sodium hydride (4.4 g, 60% dispersion in mineral oil) in anhydrous tetrahydrofuran (250 mL), under an inert atmosphere, was treated dropwise with a solution of triethyl phosphonoacetate (28.0 g) in anhydrous tetrahydrofuran (150 mL) and the mixture stirred until hydrogen evolution had ceased (~1 hour). The mixture was then treated dropwise with a solution of 2-acetyl-5-nitropyridine (12.2 g prepared according the procedure described in J. Chem. Soc. 1971, 772) in anhydrous tetrahydrofuran (150 mL). After one hour the reaction mixture was treated with ethyl acetate and saturated ammonium chloride solution. The organic phase was dried over magnesium sulphate then evaporated. The residue was subjected to flash chromatography on silica gel eluting with dichloromethane to give the title compound (16.7 g) as a white solid. TLC: $R_F$=0.66 and 0.72 for the Z and E isomers (eluting with ethyl acetate).

Reference Example 7

{1-[(2-Trimethylsilylethoxy)methyl]-2-o-tolylamino-5-benzimidazolyl}acetic acid

A solution of ethyl (2-o-tolylamino-3H-benzimidazol-5-yl)acetate (5 g, Reference Example 8) in tetrahydrofuran (200 mL) was treated with sodium hydride (0.71 g, 60% dispersion in mineral oil) under nitrogen with stirring at room temperature. On completion of the addition the mixture was stirred at room temperature for a further 30 minutes and then treated with (2-trimethylsilylethoxy)methyl chloride (2.95 g). After stirring at room temperature for a further 1 hour the mixture was evaporated to low bulk and the residue was partitioned between ethyl acetate (500 mL) and water (500 mL). The organic phase was separated then dried and then evaporated. The residue was subjected to flash chromatography on silica eluting with a mixture of pentane and ether (3:2, v/v). The material (5.2 g) from chromatography was dissolved in methanol (100 mL) and the solution was treated with aqueous sodium hydroxide solution (30 mL, 1M). After standing at room temperature for 4 hours the mixture was evaporated to low bulk and then diluted with water (50 mL). The mixture was acidified by addition of acetic acid to give a white gum which was decanted from which the aqueous mother liquors. The gum was washed once by decantation with a little water and then triturated with the minimum of ethanol to give the title compound (910 mg) as a white solid. Evaporation of the ethanol solution gave a further quantity of the title compound (3.0 g) as an orange foam.

Reference Example 8

Ethyl (2-o-tolylamino-3H-benzimidazol-5-yl)acetate

A mixture of ethyl 3,4-diaminophenylacetate (5.8 g, prepared according to the procedure of Mederski et al, Bioorg Med Chem Left, 1998, 8, pages 17–22) and o-tolylisothiocyanate (4.9 g) in ethanol (100 mL) was kept at room temperature overnight then treated with diisopropylcarbodiimide (7.6 g). The mixture was stirred at reflux for 5 hours then evaporated. The residue was subjected to flash chromatography on silica eluting with a mixture of 10% methanol and ether (1:9, v/v) to give the title compound (5.2 g) as a yellow gum.

Reference Example 9

2-(4-Methyl-2-o-tolylamino-benzoxazol-6-yl)acetic acid

A mixture of t-butyl 4-amino-3-hydroxy-5-methyl-phenylacetate (0.38 g, Reference Example 10) in ethanol (10 mL) and o-tolylisothiocyanate (0.24 g) was stirred for 7 hours, then left to stand over night and then evaporated. The residue was dissolved in ethanol (10 mL) and the solution was treated with dicyclohexylcarbodiimide (0.36 g). This mixture was heated at reflux temperature for 2 hours and then evaporated. The residual gum was dissolved in dichloromethane (15 mL) and the solution was treated with trifluoroacetic acid (4.75 mL). After standing at room temperature for 3 hours the mixture was evaporated and the residue was dissolved in diethyl ether. This solution was extracted twice with saturated sodium bicarbonate solution and the pH of the combined aqueous extracts was adjusted to 1–2 by addition of dilute hydrochloric acid. This solution was then extracted with ethyl acetate and the extract was washed with brine, then dried and then evaporated to give the title compound (0.33 g) as a pale yellow solid.

Reference Example 10 t-Butyl 4-amino-3-hydroxy-5-methyl-phenylacetate

A solution of t-butyl 3-hydroxy-5-methyl-4-nitrophenylacetate (0.47 g, Reference Example 11) in ethanol (25 mL) was treated with palladium on charcoal (approximately 0.08 g, 10%) and stirred under a hydrogen atmosphere. After 4 hours the mixture was filtered through a pad of celite and the filtrate was evaporated to give the title compound (0.38 g) as a green oil.

Reference Example 11 t-Butyl 3-hydroxy-5-methyl-4-nitrophenylacetate

A solution of t-butyl 3-acetoxy-5-methyl-4-nitrophenylacetate (0.5 g, Reference Example 12) in methanol (6 mL) was treated with lithium hydroxide (0.2 g) in water (1.5 mL). After stirring for 2 hours the mixture was carefully acidified to pH 5 and then treated with ethyl acetate and sodium chloride. The organic layer was evaporated and the residue was dissolved in dichloromethane. This solution was dried and then evaporated to give the title compound (0.45 g) as a yellow green oil.

Reference Example 12 t-Butyl 3-acetoxy-5-methyl-4-nitrophenylacetate

A stirred solution of t-butyl 3-acetoxy-4-nitrophenylacetate (8.0 g, Reference Example 13) in tetrahydrofuran (350 mL) at −15° C. under argon was treated dropwise with methyl magnesium chloride solution in diethyl ether (7mL, 3M) and after 2 hours a further aliquot of methyl magnesium chloride solution in diethyl ether (7 mL, 3M). After stirring for a further 1 hour the reaction mixture was treated with 2,3-dichloro-5,6-dicyano-1,4-benzoquinone (10.4 g), then stirred at room temperature overnight, then partially evaporated and then treated with dichloromethane. The mixture was washed with water, then dried and then evaporated. The residue was subjected to flash chromatography on silica eluting with dichloromethane to give the title compound (1.66 g) as a yellow oil.

Reference Example 13 t-Butyl 3-acetoxy-4-nitrophenylacetate

A stirred suspension of 3-acetoxy-4-nitrobenzoic acid (10.5 g) in dichloromethane (100 mL) was treated with oxalyl chloride (33 mL) and then dimethylformamide (2 drops). After stirring at room temperature over night the mixture was evaporated. The residue was dissolved in acetonitrile (100 mL) and this solution was added dropwise to a stirred mixture of trimethylsilyldiazomethane (25 mL, 2M in hexanes) and triethylamine (5.05 g) in acetonitrile (50 mL) at 0° C. under nitrogen and stirring at 0° C. was continued overnight. The mixture was evaporated and then partitioned between ethyl acetate and saturated sodium bicarbonate solution. The organic phase was dried and then evaporated. The residue was dissolved in refluxing t-butanol and then treated dropwise with a solution of silver benzoate (2.8 g) in triethylamine (15 mL) over 30 minutes. After standing for 30 minutes the cooled reaction mixture was evaporated and then partitioned between ethyl acetate and hydrochloric acid (1M). The organic phase was washed with saturated sodium bicarbonate solution, then dried and then evaporated to give the title compound (10.6 g) as a viscous brown oil.

Reference Example 14

(RS) Methyl 3-{6-[2-(4-amino-3-hydroxy-phenyl)-acetylamino]-pyridin-3-yl}-butyrate Ammonium formate (1.7 g) and 10% palladium on charcoal were added to a solution of (RS) methyl 3-{6-[2-(3-hydroxy-4-nitrophenyl)-acetylamino]-pyridin-3-yl}-butanoate (180 mg, Reference Example 15) in ethanol (15 mL). The mixture was stirred at 60° C. for 1 hour, then cooled to room temperature and then filtered through a pad of diatomaceous earth. The filter pad was washed with ethanol. The combined filtrate and washings were evaporated and the residue was dissolved in ethyl acetate. This solution was washed with water, then dried over magnesium sulphate and then evaporated to give the title compound (134 mg) as a pale brown oil which was used without further purification.

Reference Example 15

(RS) Methyl 3-{6-[2-(3-hydroxy-4-nitrophenyl)-acetylamino]-pyridin-3-yl}-butanoate A solution of (RS) Methyl 3-{6-[2-(3-acetoxy-4-nitrophenyl)-acetylamino]-pyridin-3-yl}-butanoate (1.5 g, Reference Example 16) in dichloromethane (50 mL) was treated with a piperidine (5.0 mL). After stirring at room temperature for 1.5 hours the reaction mixture was washed with aqueous acetic acid (1M), then and dried over magnesium sulphate and then evaporated. The residual light brown oil was subjected to flash chromatography on silica eluting with a mixture of ethyl acetate and pentane (1:1, v/v) to give the title compound (1.26 g) as a pale yellow solid.

Reference Example 16

(RS) Methyl 3-{6-[2-(3-acetoxy-4-nitrophenyl)-acetylamino]-pyridin-3-yl}-butanoate A solution of (RS) methyl 3-(6-amino-pyrid-3-yl)-butanoate (3.26 g, Reference Example 19) in dichloromethane (20 mL) at 10° C. was treated dropwise with a solution of (3-acetoxy-4-nitrophenyl)-acetyl chloride (4.32 g, Reference Example 17) in dichloromethane (30 mL) over 5 minutes. The mixture was stirred at 10° C. for a further 5 minutes then treated dropwise with triethylamine (2.47 mL) over 5 minutes. The resulting dark solution was stirred at room temperature for 1 hour, then left to stand overnight, then subjected to flash chromatography on silica eluting with a mixture of ethyl acetate and pentane (3:2, v/v) to give the title compound (5.9 g) as a viscous gum.

Reference Example 17

(3-Acetoxy-4-nitro-phenyl)acetyl chloride

A solution of (3-acetoxy-4-nitro-phenyl)acetic acid (2.0 g, Reference Example 18) in dichloromethane (20 mL) was treated with a solution of oxalyl chloride in dichloromethane (4.4 mL, 2M) and then with dry dimethylformamide (1 drop). After a vigorous effervescence the mixture was stirred at room temperature for 4 hours, then evaporated to give the title compound as a viscous oil which was used immediately without further purification.

Reference Example 18

(3-Acetoxy-4-nitro-phenyl)acetic acid

A stirred mixture of (3-hydroxy-4-nitro-phenyl)acetic acid (1 2.0 g), aqueous sodium hydroxide (152.3 mL, 1M) and diethyl ether (150 mL), cooled to 0° C. in an ice salt bath, was treated dropwise with acetic anhydride (8.1 g) at a rate to maintain the temperature at 0° C. When the addition was complete the mixture was stirred at 0° C. for a further 2 hours then acidified with dilute hydrochloric acid and then extracted with ethyl acetate. The extracts were dried over magnesium sulphate and then evaporated to give the title compound (12.6 g) as an oil.

Reference Example 19

(RS) Methyl 3-(6-amino-pyrid-3-yl)-butanoate

A solution of (RS) 3-(6-amino-pyrid-3-yl)-butanoic acid hydrochloride (12.0 g, Reference Example 20) in methanol (300 mL) was treated with concentrated sulphuric acid (3.0 mL) then heated at reflux temperature for 8 hours. The reaction mixture was concentrated, then basefied with 5% aqueous sodium bicarbonate and then extracted with ethyl acetate . The extracts were washed with water, then with brine, then dried over magnesium sulphate and then evaporated to give the title compound (7.6 g) as a yellow oil.

Reference Example 20

(RS) 3-(6-Amino-pyrid-3-yl)-butanoic acid hydrochloride

A solution of (RS) ethyl 3-(6-acetylamino-pyrid-3-yl)-butanoate (25.56 g, Reference Example 21) in aqueous hydrochloric acid (500 mL, 6M) was heated at 100° C. for 3.5 hours, then cooled and then evaporated to give the title compound as a crystalline solid.

Reference Example 21

(RS) Ethyl 3-(6-acetylamino-pyrid-3-yl)-butanoate

A solution of (E/Z) ethyl 3-(6-acetylamino-pyrid-3yl)-but-2-enoate (27.3 g, Reference Example 22) in ethanol (500 mL) was hydrogenated (3bar hydrogen pressure) at 50° C. using 10% palladium on charcoal (1.0 g) as catalyst. After 48 h, the mixture was degassed, filtered through a pad of diatomaceous earth and the pad rinsed through with ethanol. The filtrate was evaporated to give the title compound as an oil.

Reference Example 22

(E/Z) Ethyl 3-(6-acetylamino-pyrid-3-yl)-but-2-enoate

A mixture of N-(5-bromopyrid-2-yl)acetamide (31.4 g, Reference Example 23), ethyl crotonate (37.0 mL), triethylamine (33 mL), tetrakis(tri-o-tolylphosphine)palladium(0) and tetrabutylammonium bromide (9.36 g) in dimethylformamide (250 mL) was heated at 100° C. under an argon atmosphere for 48 hours. The reaction mixture was cooled and then evaporated. The residue was partitioned between ethyl acetate and water and the organic phase was washed with brine, then dried over magnesium sulphate and then evaporated. The resulting light brown solid was subjected to flash chromatography on silica eluting with a mixture of pentane and ethyl acetate (7:3, v/v) to give the title compound (27.3 g) as a pale yellow solid.

Reference Example 23

N-(5-Bromopyrid-2-yl)acetamide

Acetic anhydride (27.4 mL) was added to a stirred suspension of 2-amino-5-bromopyridine (10.0 g) in acetic acid (40 mL). The mixture was heated at reflux for 4 hours, then cooled to room temperature and then poured into water (200 mL). The resulting solid was collected, washed three times with water (300 ml) and then dried in vacuo at 70° C., affording the title compound as a white solid (10.9 g).

Reference Example 24

(RS) Methyl 3-{5-[2-(4-amino-3-hydroxy-phenyl)-acetylamino]-pyridin-2-yl}-butanoate A solution of (RS) methyl 3-{5-[2-(3-hydroxy-4-nitrophenyl)-acetylamino]-pyridin-2-yl}-butanoate (2.0 g, Reference Example 25) in ethanol (80 mL), at 60° C., was treated with ammonium formate (4.0 g) and 10% palladium on charcoal (0.5 g). After stirring at 60° C. for 1 hour the reaction mixture was cooled and then filtered. The filtrate was evaporated and the residue was dissolved in ethyl acetate. This solution was washed twice with water, then dried over magnesium sulphate and then evaporated to give the title compound (1.37 g) as an oil.

Reference Example 25

(RS) Methyl 3-{5-[2-(3-hydroxy-4-nitrophenyl)-acetylamino]-pyridin-2-yl}-butanoate (RS) 3-{5-[2-(3-hydroxy-4-nitrophenyl)-acetylamino]-pyridin-2-yl}-butanoic acid (2.1 g, Reference Example 26) in methanol (80 mL) was treated with concentrated sulphuric acid (0.5 mL). The mixture was heated at reflux temperature for 24 hours, then cooled, then concentrated to low volume and then diluted with ethyl acetate. This solution was washed with 5% aqueous sodium bicarbonate, then with water, then dried over magnesium sulphate and then evaporated to give the title compound (2.0 g) as an oil.

Reference Example 26

(RS) 3-{5-[2-(3-Hydroxy-4-nitrophenyl)-acetylamino]-pyridin-2-yl}-butanoic acid

A solution of (RS) ethyl 3-{5-[2-(3-acetoxy-4-nitrophenyl)-acetylamino]-pyridin-2-yl}-butanoate (6.18 g, Reference Example 27) in methanol (100 mL) was treated with a solution of sodium hydroxide (3.5 g) in water (20 mL). The mixture was heated at 50° C. for 5 hours and then evaporated. The residue was dissolved in water and the resulting solution was washed with ethyl acetate, then acidified to pH 5 by addition of glacial acetic acid and then extracted with ethyl acetate. The extracts were washed with water, then dried over magnesium sulphate and then evaporated. The residual dark oil was subjected to flash chromatography on silica eluting with ethyl acetate to give the title compound (2.1 g) as a brown solid.

Reference Example 27

(RS) Ethyl 3-{5-[2-(3-acetoxy-4-nitrophenyl)-acetylamino]-pyridin-2-yl}-butanoate A solution of O-(7-azabenzotriazol-1-yl)-1,1,3,3-tetramethyluronium hexafluorophosphate (10.95 g) in dry dimethylformamide (20 mL) was added to a solution of (RS) ethyl 3-(5-aminopyrid-2-yl)butanoate (3.0 g, Reference Example 5), diisopropylethylamine (10 mL) and (3-acetoxy-4-nitro-phenyl)acetic acid (6.89 g, Reference Example 17) in dimethylformamide (90 mL) under a nitrogen atmosphere. After stirring at 30° C. for 24 hours the reaction mixture was evaporated and the residue was partitioned between ethyl acetate and 5% aqueous sodium bicarbonate. The organic phase was washed with water, then with brine, then dried over magnesium sulphate, then treated with decolourising charcoal followed by filtration and evaporation of the filtrate to give the title compound as a dark oil.

In vitro and In vivo Test Procedures

1. Inhibitory Effects of Compounds on VLA4 Dependent Cell Adhesion to Fibronectin and VCAM 1.1 Metabolic Labelling of RAMOS Cells RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 µCi/100 mls of [$^3$H]-methionine (Amersham, UK) for 18 hours at 37° C.

1.2 96 Well Plate Preparation for Adhesion Assay

Cytostar plates (Amersham, UK) were coated with 50 µl/well of either 3 µg/ml human soluble VCAM-1 (R&D Systems Ltd, UK) or 28.8 µg/ml human tissue Fibronectin (Sigma, UK). In control non-specific binding wells 50 µl phosphate buffered saline was added. The plates were then left to dry in an incubator at 25° C., overnight. The next day the plates were blocked with 200 µl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 µl/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 µl/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 500 µl/well of cells in 3.6% dimethyl sulphoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB} - C_{NS}) - (C_I - C_{NS})]/(C_{TB} - C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Particular compounds of the invention inhibit cell adhesion to fibronectin and VCAM-1 with $IC_{50}$s in the range 100 micromolar to 10 nanomolar. Preferred compounds of the invention inhibit cell adhesion to fibronectin with $IC_{50}$s in the range 100 nanomolar to 10 nanomolar.

2. Inhibition of Antigen-induced Airway Inflammation in the Mouse and Rat 2.1 Sensitization of the Animals Rats (Brown Norway, Harland Olac, UK) are sensitized on days 0, 12 and 21 with ovalbumin (100 µg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 µg, i.p.) administered with aluminium hydroxide adjuvant (20 mg, i.p.) in saline (0.2 ml, i.p.).

2.2 Antigen Challenge

Rats are challenged on any one day between days 28–38, while mice are challenged on any one day between days 20–30.

The animals are challenged by exposure for 30 minutes (rats) or 1 hour (mice) to an aerosol of ovalbumin (10 g/1) generated by an ultrasonic nebulizer (deVilbiss Ultraneb, US) and passed into an exposure chamber.

2.3 Treatment Protocols

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (HAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giernza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where p<0.05 no statistical significance existed.

What is claimed is:

1. A compound of general formula (Ia):

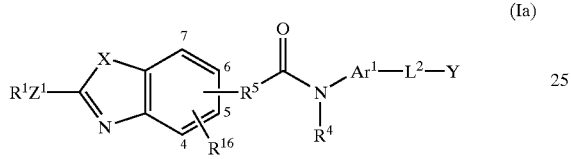

(Ia)

wherein:
- $R^1$ represents aryl, heteroaryl, optionally substituted alkyl, alkenyl or alkynyl where each is optionally substituted by $R^2$, —$Z^2R^3$, —$Z^3H$, —C(=O)—$R^3$, —$NR^4$—C(=$Z^3$)—$R^3$, —$NR^4$—C(=O)—$OR^3$, —$NR^4$—$SO_2$—$R^3$, —$SO_2$—$NY^1Y^2$, —$NY^1Y^2$ or —C(=$Z^3$)—$NY^1Y^2$, or optionally substituted cycloalkyl or heterocycloalkyl where each is optionally substituted by $R^3$, —$Z^2R^3$, —$Z^3H$, —C(=O)—$R^3$, —$NR^4$—C(=$Z^3$)—$R^3$, —$NR^4$—C(=O)—$OR^3$, —$NR^4$—$SO_2$—$R^3$, —$SO_2$—$NY^1Y^2$, —$NY^1Y^2$ or —C(=$Z^3$)—$NY^1Y^2$;
- $R^2$ represents aryl, cycloalkyl, cycloalkenyl, heteroaryl, or heterocycloalkyl;
- $R^3$ represents alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;
- $R^4$ represents hydrogen or lower alkyl;
- $R^5$ is a direct bond or an alkylene chain, an alkenylene chain or an alkynylene chain;
- $R^7$ is hydrogen, alkyl, aryl, arylalkyl, cycloalkyl, cycloalkylalkyl, heteroaryl, heteroarylalkyl, heterocycloalkyl or heterocycloalkylalkyl;
- $R^8$ is alkyl, aryl, cycloalkyl, heteroaryl or heterocycloalkyl, or alkyl substituted by aryl, an acidic functional group (or corresponding protected derivative), cycloalkyl, heteroaryl, heterocycloalkyl, —$Z^3H$, —$Z^2R^3$, —C(=O)—$NY^3Y^4$ or —$NY^3Y^4$;
- $R^9$ is hydrogen, $R^3$ or alkyl substituted with alkoxy, cycloalkyl, hydroxy, mercapto, alkylthio or —$NY^3Y^4$;
- $R^{10}$ is hydrogen or a group consisting amino acid side chains and corresponding protected derivatives, an acidic functional group or corresponding protected derivative, $R^3$, —$Z^2R^3$, —C(=O)—$R^3$, or —C(=O)—$NY^3Y^4$, or alkyl substituted by an acidic functional group or corresponding protected derivative or by $R^3$, —$Z^2R^3$, —$NY^3Y^4$, —NH—C(=O)—$R^3$, —C(=O)—$R^5$—$NH_2$, —C(=O)—$Ar^2$—$NH_2$, —C(=O)—$R^5$—$CO_2H$, or —C(=O)—$NY^3Y^4$;
- or $R^9$ and $R^{10}$ together with the atoms to which they attached form a 3- to 6-membered heterocycloalkyl ring;
- $R^{11}$ is $C_{1-6}$alkylene, optionally substituted by $R^3$;
- $R^{12}$ is alkyl, aryl, arylalkyl, cycloalkyl, cycloalkylalkyl, heteroaryl, heteroarylalkyl, heterocycloalkyl or heterocycloalkylalkyl;
- $R^{13}$ is hydrogen, or alkyl optionally substituted by aryl, an acidic functional group or corresponding protected derivative, cycloalkyl, heteroaryl, heterocycloalkyl, —$Z^3H$, —$Z^2R^3$, —C(=O)—$NY^3Y^4$ or —$NY^3Y^4$;
- $R^{16}$ is hydrogen, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^1Y^2N$—, $Y^1Y^2NCO$—, $Y^1Y^2NSO_2$—, $Y^1Y^2N$—$C_{2-6}$alkylene—$Z^1$—, alkylC(=O)—$Y^1N$—, alkyl$SO_2$—$Y^1N$— or alkyl optionally substituted with aryl, heteroaryl, hydroxy, or $Y^1Y^2N$—
- $Ar^1$ is pyridyl;
- $Ar^2$ is arylene or heteroaryldiyl;
- $L^2$ represents:
  - (i) a direct bond;
  - (ii) an alkylene, alkenylene, alkynylene, cycloalkenylene, heteroaryldiyl, hetrocycloalkylene or arylene linkage each optionally substituted by (a) an acidic functional group (or corresponding protected derivative), $R^3$, —$Z^3H$, —$Z^2R^8$, —C(=O)—$R^3$, —N($R^7$)—C(=O)—$R^8$, —N($R^7$)—C(=O)—$OR^8$, —N($R^7$)—C(=O)—$NR^4R^8$, —N($R^7$)—$SO^2$—$R^8$, —$NY^3Y^4$, or —[C(=O)—N($R^9$)—C($R^4$)($R^{10}$)]$_p$—C(=O)—$NY^3Y^4$, or by (b) alkyl substituted by an acidic functional group (or corresponding protected derivative), or by —$Z^3H$, —$Z^2R^3$, —C(=O)—$NY^3Y^4$ or —$NY^3Y^4$;
  - (iii) a —[C(=O)—N($R^9$)—C($R^4$)($R^{10}$)]$_p$— linkage
  - (iv) a —$Z^4$—$R^{11}$— linkage;
  - (v) a —C(=O)—$CH_2$—C(=O)— linkage;
  - (vi) a —$R^{11}$—$Z^4$—$R^{11}$— linkage; or
  - (vii) a —$L^3$—$L^4$—$L^5$— linkage;
- $L^3$ represents a direct bond and $L^5$ represents an alkylene chain, or
- $L^3$ represents an alkylene chain $L^5$ represents a direct bond or an alkylene chain;
- $L^4$ represents a cycloalkylene or heterocycloalkylene linkage;
- X is O;
- Y is carboxy or an acid bioisostere;
- $Y^1$ and $Y^2$ are independently hydrogen, alkenyl, alkyl, aryl, arylalkyl, cycloalkyl, heteroaryl or heteroarylalkyl; or the group—$NY^1Y^2$ may form a cyclic amine;
- $Y^3$ and $Y^4$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO_2R^7$ or —$C(=O)$—$NY^1Y^2$groups; or the group —$NY^3Y^4$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof) or $R^8$; (ii) may also contain a further heteroatom selected from O, S, $SO_2$, or $NY^5$; and (iii) may also be fused to additional aryl, heteroaryl, heterocycloalkyl or cycloalkyl rings to form a bicyclic or tricyclic ring system;

$Y^5$ is hydrogen, alkyl, aryl, arylalkyl, —$C(=O)$—$R^{12}$, —$C(=O)$—$OR^{12}$ or —$SO_2R^{12}$;

$Z^1$ represents a direct bond, an alkylene chain or $NR^4$, O or $S(O)_n$;

$Z^2$ is O or $S(O)_n$;

$Z^3$ is O or S;

$Z^4$ is O, $S(O)_n$, $NR^{13}$, $SO_2NR^{13}$, $NR^{13}C(=O)$, $C(=O)$ $NR^{13}$ or $C(=O)$; and n is zero or an integer 1 or 2;

p is zero or an integer 1 to 4;

and the corresponding N-oxides, and their prodrugs; and pharmaceutically acceptable salts and solvates of such compounds and their N-oxides and prodrugs; but excluding compounds where an oxygen, nitrogen or sulphur atom is attached directly to a carbon carbon multiple bond of an alkenyl or alkynyl residue.

2. A compound according to claim 1 in which $L^2$ represents:

(i) a direct bond;

(ii) an alkylene, alkenylene, alkynylene, cycloalkenylene, cycloalkylene, heteroaryldiyl, heterocycloalkylene or arylene linkage each optionally substituted by (a) an acidic functional group (or corresponding protected derivative), $R^3$, —$Z^3H$, —$Z^2R^8$, —$C(=O)$—$R^3$, —$N(R^7)$—$C(=O)$—$R^8$, —$N(R^7)$—$C(=O)$—$OR^8$, —$N(R^7)$—$C(=O)$—$NR^4R^8$, —$N(R^7)$—$SO_2$—$R^8$, —$NY^3Y^4$, or —$[C(=O)$—$N(R^9)$—$C(R^4)(R^{10})]_p$—$C(=O)$—$NY^3Y^4$, or by (b) alkyl substituted by an acidic functional group (or corresponding protected derivative), or by —$Z^3H$, —$Z^2R^3$, —$C(=O)$—$NY^3Y^4$ or —$NY^3Y^4$;

(iii) a —$[C(=O)$—$N(R^9)$—$C(R^4)(R^{10})]_p$— linkage;

(iv) a —$Z^4$—$R^{11}$— linkage;

(v) a —$C(=O)$—$CH_2$—$C(=O)$— linkage; or (vi) a —$R^{11}$—$Z^4$—$R^{11}$— linkage.

3. A compound according to claim 1 in which $R^1$ represents optionally substituted phenyl.

4. A compound according to claim 1 in which $Z^1$ represents NH.

5. A compound according to claim 1 in which $Ar^1$ represents optionally substituted pyridin-2,5-diyl.

6. A compound according to claim 1 in which $Ar^1$ represents unsubstituted pyridin-2,5-diyl.

7. A compound according to claim 1 in which $L^2$ represents a $C_{1-4}$alkylene linkage optionally substituted by $C_{1-4}$alkyl, aryl, heteroaryl, —$Z^2R^8$, —$N(R^7)$—$C(=O)$—$R^8$, —$N(R^7)$—$C(=O)$—$OR^8$, —$N(R^7)$—$SO_2$—$R^8$, —$NY^3Y^4$, —$[C(=O)$—$N(R^9)$—$C(R^4)(R^{10})]_p$—$C(=O)$—$NY^3Y^4$ or alkyl substituted by hydroxy, —$OR^3$, —$C(=O)$—$OR^3$ or —$NY^3Y^4$.

8. A compound according to claim 7 in which $L^2$ represents ethylene optionally substituted by $C_{1-4}$alkyl, aryl, heteroaryl, —$Z^2R^8$, —$N(R^7)$—$C(=O)$—$R^8$, —$N(R^7)$—$C(=O)$—$OR^8$, —$N(R^7)$—$SO_2$—$R^8$, —$NY^3Y^4$, —$[C(=O)$—$N(R^9)$—$C(R^4)(R^{10})]_p$—$C(=O)$—$NY^3Y^4$ or alkyl substituted by hydroxy, —$OR^3$, —$C(=O)$—$OR^3$ or —$NY^3Y^4$.

9. A compound according to claim 8 in which $L^2$ is a group

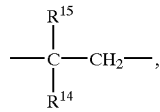

where $R^{15}$ is hydrogen or $C_{1-4}$alkyl and $R^{14}$ represents $C_{1-4}$alkyl, or where $R^{15}$ is hydrogen and $R^{14}$ represents aryl, heteroaryl, —$Z^2R^8$, —$N(R^7)$—$C(=O)$—$R^8$, —$N(R^7)$—$C(=O)$—$OR^8$, —$N(R^7)$—$SO_2$—$R^8$, —$NY^3Y^4$, —$[C(=O)$—$N(R^9)$—$C(R^4)(R^{10})]_p$—$C(=O)$—$NY^3Y^4$ or alkyl substituted by hydroxy, —$OR^3$, —$C(=O)$—$OR^3$ or —$NY^3Y^4$.

10. A compound according to claim 9 in which $L^2$ is a group

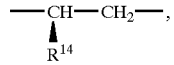

where $R^{14}$ represents $C_{1-4}$alkyl, —$Z^2R^8$, —$N(R^7)$—$C(=O)$—$R^8$, —$N(R^7)$—$C(=O)$—$OR^8$, —$N(R^7)$—$SO_2$—$R^8$, —$NY^3Y^4$, or alkyl substituted by hydroxy, —$OR^3$, —$C(=O)$—$OR^3$ or —$NY^3Y^4$.

11. A compound according to any claim in which Y is carboxy.

12. A compound according to claim 1 in which $R^{16}$ represents hydrogen, $C_{1-4}$ alkyl or $C_{1-4}$ alkoxy.

13. A compound according to claim 1 in which the group

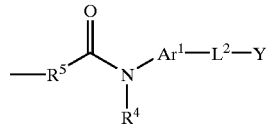

is attached at the ring 6 position.

14. A compound according to claim 1 selected from the group consisting of:

(3RS)-3-{5-[2-(2-o-tolylamino-benzoxazol-6-yl)-acetylamino]-pyrid-2-yl}-butyric acid;

(3RS)-3-{5-[2-(4-methyl-2-o-tolylamino-benzoxazol-6-yl)acetylamino]pyrid-2-yl}butyric acid;

(RS) 3-{5-[2-(2-phenylamino-benzoxazol-6-yl)-acetylamino]-pyridin-2-yl}-butyric acid;

(RS) 3-(5-{2-[2-(2-chloro-phenylamino)-benzoxazol-6-yl]-acetylamino}-pyridin-2-yl)-butyric acid;

(RS) 3-{5-[2-(2-o-tolylamino-benzoxazol-6-yl)-acetylamino]-pyridin-2-yl}-butyric acid;

(RS) 3-(5-{2-[2-(2-methoxy-phenylamino)-benzoxazol-6-yl]-acetylamino}-pyridin-2-yl)-butyric acid;

(RS) 3-{6-[2-(2-phenylamino-benzoxazol-6-yl)-acetylamino]-pyridin-3-yl }-butyric acid;

(RS) 3-(6-{2-[2-(2-chloro-phenylamino)-benzoxazol-6-yl]-acetylamino}-pyridin-3-yl)-butyric acid;

(RS) 3-{6-[2-(2-o-tolylamino-benzoxazol-6-yl)-acetylamino]-pyridin-3-yl }-butyric acid;

(RS) 3-(6-{2-[2-(2-methoxy-phenylamino)-benzoxazol-6-yl]-acetylamino}-pyridin-3-yl)-butyric acid; and (RS) 3-(6-{2-[2-(3-methoxy-phenylamino)-benzoxazol-6-yl]-acetylamino}-pyridin-3-yl)-butyric acid.

15. A pharmaceutical composition comprising an effective amount of a compound according to claim 1 or a corresponding N-oxide or prodrug, or a pharmaceutically acceptable salt or solvate of such a compound or an N-oxide prodrug thereof, in association with a pharmaceutically acceptable carrier or excipient.

16. A method for the treatment of a human or non-human animal patient suffering from, or subject to, a condition which can be ameliorated by the administration of an inhibitor of α4β1 mediated cell adhesion comprising administering to said patient an effective amount of a compound according to claim 1 or a corresponding N-oxide or prodrug, or a pharmaceutically acceptable salt or solvate of such a compound or an N-oxide or prodrug thereof.

17. A method for the treatment of a patient suffering from, or subject to, asthma comprising administering to said patient an effective amount of a compound according to claim 1 or a corresponding N-oxide or prodrug, or a pharmaceutically acceptable salt or solvate of such a compound or an N-oxide or prodrug thereof.

18. A method for the treatment of a human or non-human animal patient suffering from, or subject to, a condition which can be ameliorated by the administration of an inhibitor of α4β1 mediated cell adhesion comprising administering to said patient an effective amount of a composition according to claim 15.

19. A method for the treatment of a patient suffering from, or subject to, asthma comprising administering to said patient an effective amount of a composition according to claim 15.

* * * * *

UNITED STATES PATENT AND TRADEMARK OFFICE
CERTIFICATE OF CORRECTION

PATENT NO. : 6,706,738 B2
DATED : March 16, 2004
INVENTOR(S) : Clark et al.

It is certified that error appears in the above-identified patent and that said Letters Patent is hereby corrected as shown below:

<u>Title page,</u>
Item [*] Notice, should read -- Subject to any disclaimer, the term of this patent is extended of adjusted under 35 U.S.C. 154(b) by 165 days. --.

Signed and Sealed this

Second Day of May, 2006

JON W. DUDAS
*Director of the United States Patent and Trademark Office*